(12) United States Patent
Allan et al.

(10) Patent No.: US 10,383,948 B2
(45) Date of Patent: *Aug. 20, 2019

(54) ANTI-CMET ANTIBODY DRUG CONJUGATES AND METHODS FOR THEIR USE

(71) Applicants: AbbVie Inc., North Chicago, IL (US); AbbVie Biotherapeutics Inc., Redwood City, CA (US)

(72) Inventors: Christian B. Allan, San Mateo, CA (US); Mark Anderson, Grayslake, IL (US); Louie Naumovski, Los Altos Hills, CA (US); Edward B. Reilly, Libertyville, CA (US); Jieyi Wang, Belmont, CA (US)

(73) Assignees: AbbVie Inc., North Chicago, IL (US); AbbVie Biotherapeutics Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/910,788

(22) Filed: Mar. 2, 2018

(65) Prior Publication Data

US 2018/0250418 A1 Sep. 6, 2018

Related U.S. Application Data

(63) Continuation of application No. 15/597,624, filed on May 17, 2017.

(60) Provisional application No. 62/337,796, filed on May 17, 2016.

(51) Int. Cl.
| | | |
|---|---|---|
| *A61K 39/00* | (2006.01) | |
| *A61K 47/48* | (2006.01) | |
| *A61K 31/517* | (2006.01) | |
| *A61K 47/68* | (2017.01) | |
| *A61K 45/06* | (2006.01) | |

(52) U.S. Cl.
CPC ........ *A61K 47/6849* (2017.08); *A61K 31/517* (2013.01); *A61K 45/06* (2013.01); *A61K 47/6803* (2017.08); *A61K 47/6811* (2017.08)

(58) Field of Classification Search
None
See application file for complete search history.

(56) References Cited

U.S. PATENT DOCUMENTS

| 8,329,173 | B2 | 12/2012 | Goetsch |
|---|---|---|---|
| 8,545,839 | B2 | 10/2013 | Goetsch et al. |
| 8,729,249 | B2 | 5/2014 | Goetsch et al. |
| 8,741,290 | B2 | 6/2014 | Goetsch et al. |
| 8,747,850 | B2 | 6/2014 | Goetsch et al. |
| 8,765,128 | B2 | 7/2014 | Goetsch et al. |
| 8,871,909 | B2 | 10/2014 | Goetsch |
| 8,871,910 | B2 | 10/2014 | Goetsch |
| 8,889,832 | B2 | 11/2014 | Goetsch |
| 9,107,907 | B2 | 8/2015 | Goetsch |
| 9,120,852 | B2 | 9/2015 | Jouhanneaud |
| 9,469,691 | B2 | 10/2016 | Goetsch et al. |
| 2011/0239316 | A1* | 9/2011 | Goetsch ................. C07K 16/00 800/13 |
| 2014/0112911 | A9 | 4/2014 | Goetsch et al. |
| 2014/0115727 | A1 | 4/2014 | Goetsch et al. |
| 2015/0071950 | A1 | 3/2015 | Chae et al. |
| 2015/0110815 | A1 | 4/2015 | Park et al. |
| 2015/0252114 | A1 | 9/2015 | Goetsch |
| 2015/0307613 | A1 | 10/2015 | Goetsch et al. |
| 2016/0039935 | A1 | 2/2016 | Goetsch et al. |
| 2017/0218071 | A1 | 8/2017 | Goetsch et al. |
| 2018/0110875 | A1* | 4/2018 | Liu .................... A61K 47/6849 |

FOREIGN PATENT DOCUMENTS

| EP | 2415784 A1 | 2/2012 | |
|---|---|---|---|
| EP | 2415785 A1 | 2/2012 | |
| EP | 2535356 A1 | 12/2012 | |
| EP | 2535357 A1 | 12/2012 | |
| EP | 2188312 B1 | 5/2015 | |
| EP | 2575879 B1 | 4/2016 | |
| EP | 3135691 A1 | 3/2017 | |
| EP | 2370468 B1 | 4/2017 | |
| EP | 2588497 B1 | 6/2017 | |
| WO | 2009007427 A2 | 1/2009 | |
| WO | 2010064089 A1 | 6/2010 | |
| WO | 2010069765 A1 | 6/2010 | |
| WO | 2011151412 A1 | 12/2011 | |
| WO | 2012007280 A1 | 1/2012 | |
| WO | WO-2016165580 A1 * | 10/2016 | ............. A61K 38/06 |
| WO | 2017201204 A1 | 11/2017 | |

OTHER PUBLICATIONS

Al-Wadei et al. (PlosOne, 2012, 7:e29915).*
Sattler et al. (Therapeutic Advances in Medical Oncology, 2011, 3:171-184).*
Birchmeier et al., 2003 "Met, metastasis, motility and more," Nat Rev Mol Cell Biol. 4(12):915-925.
Bottaro et al., 1991 "Identification of the hepatocyte growth factor receptor as the c-met proto-oncogene product," Science 251(4995):802-804.
Burgess et al., 2006 "Fully Human Monoclonal Antibodies to Hepatocyte Growth Factor with Therapeutic Potential against Hepatocyte Growth Factor/c-Met-Dependent Human Tumors," Cancer Res. 66(3):1721-1729.
Cao et al., 2001 "Neutralizing monoclonal antibodies to hepatocyte growth factor/scatter factor (HGF/SF) display antitumor activity in animal models," Proc Natl Acad Sci USA 98(13):7443-7448.

(Continued)

*Primary Examiner* — Julie Wu
(74) *Attorney, Agent, or Firm* — Dechert LLP

(57) ABSTRACT

The present disclosure provides antibody drug conjugates that bind human cMET, their methods of making, and their uses to treat patients having cancer.

12 Claims, 30 Drawing Sheets

Specification includes a Sequence Listing.

(56) References Cited

OTHER PUBLICATIONS

Doronina et al., 2003 "Development of potent monoclonal antibody auristatin conjugates for cancer therapy," Nat Biotechnol 21(7):778-784.
Eder et al. 2009 "Novel Therapeutic Inhibitors of the c-Met Signaling Pathway in Cancer," Clin Cancer Res 15(7):2207-2214.
Gherardi et al., 2012 "Targeting MET in cancer: rationale and progress," Nat Rev Cancer 12:89-103.
Jeffrey et al. 2013 "A Potent Anti-CD70 Antibody-Drug Conjugate Combining a Dimeric Pyrrolobenzodiazepine Drug with Site-Specific Conjugation Technology," Bioconjug Chem 24(7):1256-1263.
Spigel et al., 2013 "Randoized Phase II Trial of Onartuzumab in Combination With Erlotinib in Patients With Advanced Non-Small-Cell Lung Cancer," J Clin Oncol 31(32):4105-4114.
Trusolino et al., 2002 "Scatter-factor and semaphorin receptors: cell signalling for invasive growth," Nat Rev Cancer 2(4):289-300.
Wang et al., 2017 "ABBV-399, a c-Met Antibody-Drug Conjugate that Targets Both MET-Amplified and c-Met-Overexpressing Tumors, Irrespective of MET Pathway Dependence," Clin Cancer Res 23(4):992-1000.
International Search Report from related International Application No. PCT/US2017/033176 dated Aug. 8, 2017; 5 pgs.

\* cited by examiner

Emibetuzumab (humanized IgG4)
(SEQ ID NO: 17 and 5 from US 8217148)

<u>Amino Acid Sequence (10 AA per group, 5 groups per line)</u>

Heavy Chain Variable Region (full-length sequence disclosed as SEQ ID NO: 101):
QVQLVQSGAE VKKPGASVKV SCKAS<u>GYTFT DYYMH</u>WVRQA PGQGLEWMG<u>R</u> 050
<u>VNPNRRGTTY NQKFEG</u>RVTM TTDTSTSTAY MELRSLRSDD TAVYYCAR<u>AN</u> 100
<u>WLDY</u>WGQGTT VTVSS                                        115

Light Chain Variable Region (full-length sequence disclosed as SEQ ID NO: 102):
DIQMTQSPSS LSASVGDRVT ITC<u>SVSSSVS SIYLH</u>WYQQK PGKAPKLLIY 050
<u>STSNLAS</u>GVP SRFSGSGSGT DFTLTISSLQ PEDFATYYC<u>Q VYSGYPLT</u>FG 100
GGTKVEIKR                                                 109

CDRs are <u>underlined (CDR sequences disclosed as SEQ ID NOS 130-135, respectively, in order of appearance)</u>

FIG. 1A

Onartuzumab (humanized IgG1/kappa, one-armed)
(SEQ ID NO: 14 and 12 from patent US 7476724)

<u>Amino Acid Sequence (10 AA per group, 5 groups per line)</u>

Heavy Chain Variable Region (full-length sequence disclosed as SEQ ID NO: 103):
EVQLVESGGG LVQPGGSLRL SCAAS<u>GYTFT SYWLH</u>WVRQA PGKGLEWVG<u>M</u> 050
<u>IDPSNSDTRF NPNFKD</u>RFTI SADTSKNTAY LQMNSLRAED TAVYYC<u>ATYR</u> 100
<u>SYVTPLDY</u>WG QGTLVTVSS                                   119

Light Chain Variable Region (full-length sequence disclosed as SEQ ID NO: 104):
DIQMTQSPSS LSASVGDRVT ITC<u>KSSQSLL YTSSQKNYLA</u> WYQQKPGKAP 050
KLLIY<u>WASTR</u> ESGVPSRFSG SGSGTDFTLT ISSLQPEDFA TYYC<u>QQYYAY</u> 100
<u>PWTF</u>GQGTKV EIKR                                        114

CDRs are <u>underlined (CDR sequences disclosed as SEQ ID NOS 136-141, respectively, in order of appearance)</u>

FIG. 1B huAbF46-H4 (humanized IgG1/kappa)
(SEQ ID NO: 83 and 84 from US20130089557)

<u>Amino Acid Sequence (10 AA per group, 5 groups per line)</u>

Heavy Chain Variable Region (full-length sequence disclosed as SEQ ID NO: 105):
EVQLVESGGG LVQPGGSLRL SCAASGFTFT <u>DYYMSWVRQA</u> PGKGLEWLGF 050
<u>IRNKANGYTT EYSASVKGRF</u> TISRDNSKNT LYLQMNSLRA EDTAVYYCA<u>R</u> 100
<u>DNWFAYVVGQ</u> GTLVTVSS                                   118

Light Chain Variable Region (full-length sequence disclosed as SEQ ID NO: 106):
DIQMTQSPSS LSASVGDRVT ITC<u>KSSQSLL</u> <u>ASGNQNNYLA</u> WHQQKPGKAP 050
KMLII<u>WASTR</u> VSGVPSRFSG SGSGTDFTLT ISSLQPEDFA TYYC<u>QQSYSA</u> 100
<u>PLT</u>FGQGTKV EIKR                                       114

CDRs are <u>underlined (CDR sequences disclosed as SEQ ID NOS 142-147, respectively, in order of appearance)</u>

FIG. 1C

ARGX-111 (36C4) (human IgG1/lambda)
(SEQ ID NO: 51 and 55 from US 8,637,027)

<u>Amino Acid Sequence (10 AA per group, 5 groups per line)</u>

Heavy Chain Variable Region (full-length sequence disclosed as SEQ ID NO: 107):
QVQLVESGPG LVKPSQTLSL TCAVSGGSIT <u>TNYYYWSWIR</u> QSPGKGLEWM 050
G<u>VIAYDGSTD YSPSLKSRTS</u> ISRDTSKNQF SLQLSSVTPE DTAVYYCAR<u>D</u> 100
<u>VRVIATGWAT ANALDAWGQG</u> TLVTVSS                          127

Light Chain Variable Region (full-length sequence disclosed as SEQ ID NO: 108):
QSVLTQPPSV SGSPGKTVTI SCAGTSSDVG <u>YGNYVSWYQQ</u> LPGTAPKLLI 050
F<u>AVSYRAS</u>GI PDRFSGSKSG NTAFLTISGL QSEDEADYYC <u>ASYRSSNNAA</u> 100
<u>V</u>FGGGTHLTV L                                           111

CDRs are <u>underlined (CDR sequences disclosed as SEQ ID NOS 148-153, respectively, in order of appearance)</u>

FIG. 1D

SAIT-301

Amino Acid Sequence (10 AA per group, 5 groups per line)

Heavy Chain Variable Region (full-length sequence disclosed as SEQ ID NO: 109):
EVQLVESGGG LVQPGGSLRL SCAASGFTFT <u>DYYISWVRQA</u> PGKGLEWVGF 050
<u>IRNKANGYTT EYSASVKGRF</u> TISRDDSKNS LYLQMNSLKT EDTAVYYCAR 100
<u>DNWFAY</u>WGQG TLVTVSS 117

Light Chain Variable Region (full-length sequence disclosed as SEQ ID NO: 110):
DIVMTQSPLS LPVTPGEPAS ISC<u>KSSQSLL AWSNQNNYLA</u> WYLQKPGQSP 050
QMLI<u>IWAITR</u> VGGVPDRFSG SGSGTDFTLK ISRVEAEDVG VYYC<u>QQSYSR</u> 100
<u>PYT</u>FGQGTKL EIKRT 115

CDRs are <u>underlined</u> (CDR sequences disclosed as SEQ ID NOS 154-158 and 111, respectively, in order of appearance)

FIG. 1E

ABBV-399 Process I: Comparison of Crude Conjugation Reaction Mixture with Batch HIC Treated Material ABBV-399 Process I: Comparison of Crude Conjugation Reaction Mixture with Batch HIC Treated Material ABBV-399 Process II: Comparison of Crude Conjugation
Reaction Mixture with Column HIC Treated Material ABBV-399 Process II: Comparison of Crude Conjugation
Reaction Mixture with Column HIC Treated Material Proliferation Inhibition Results with ABT-700-PBD

| Cell line | Cytotoxicity $IC_{50}$ (nM) | | |
|---|---|---|---|
| | ABBV-399 | ABT-700-PBD | MMAE/PBD |
| Hs746T (Ga, amp, high) | 0.073 | 0.018 | 4.1 |
| EBC-1 (Lu, amp, high) | 0.079 | 0.095 | 0.8 |
| H441 (Lu, high) | 0.09 | 0.01 | 9 |
| BT-20 (Br, low) | 0.23 | 0.1 | 2.3 |
| A549 (Lu, low) | 1.36 | 0.1 | 13.6 |
| U87MG (GBM, low) | 18.76 | 0.21 | 89.3 |
| M059J (GBM, low) | 3.6 | 0.02 | 180 |
| U118MG (GBM, low) | 0.54 | 0.2 | 2.7 |
| KP4 (Pa, low) | 3.84 | 0.02 | 192 |
| SW48 (CRC, low) | >20 | 0.0029 | >1000 |
| NHEK (keratinocytes) | none | none | n/a |

FIG. 5

In Vitro Activity of ABT-700 PBD in Colorectal Tumor Lines

| CRC Line | ADC and Free Drug IC₅₀s (nM) | | | | | ABBV-399 Results | | |
|---|---|---|---|---|---|---|---|---|
| | ABT-700 PBD | Ab095 PBD | Ab095 MMAF | PBD | MMAE | Max Inhib (20 nM) | IC$_{50}$ (nM) | Receptors/Cell |
| SW1116 | 0.03 | 37.4 | >133 | 0.78 | 9.92 | | | |
| HCT-116 | 0.005 | 42.6 | >133 | 0.49 | 4.81 | same as control | | ~75K |
| LoVo | 0.074 | 41.2 | >133 | 0.09 | 2.25 | same as control | | 68K |
| SK-CO-1 | ~0.001 | 9.85 | >133 | 0.02 | 0.54 | | | |
| SW620 | 0.005 | 21.3 | >133 | ~0.008 | 0.92 | same as control | | ~100K |
| CaCO2 | ambig | 41.1 | >133 | 0.42 | 2.64 | | | |
| DLD-1 | 0.004 | 21.3 | >133 | 0.14 | 46.2 | same as control | | 43K |
| Colo 201 | 0.007 | 19 | >133 | ~0.12 | 1.4 | | | |
| HCT-15 | >67 (ambig) | >133 | >133 | 0.12 | >100 | same as control | | 105K |
| RKO | 0.01 | 28.1 | >133 | ~0.006 | 0.67 | same as control | | 4k |
| HT-29 | 0.004 | 26.2 | >133 | ~0.01 | 1.1 | 70% | 9 | 161K |
| Colo 205 | 0.02 | 27.4 | >133 | <0.001 | 1.18 | | | |
| T84 | 0.1 | 53 | >133 | 0.037 | 7.64 | | | |
| SW403 | 0.006 | 11.4 | >133 | <0.001 | 0.65 | | | |
| SW1463 | 0.013 | 10.3 | >133 | 0.011 | 1.1 | | | |
| LS1034 | 0.04 | 43.6 | >133 | 0.32 | ~32 | | | |
| Colo320 DM | 0.02 | 58.1 | >133 | 0.029 | 33.9 | | | |
| Colo320 HSR | 0.04 | >133 | >133 | 0.05 | 33 | | | |
| LS174T | 0.001 | 4.6 | >133 | 1.15 | 3 | | | |
| SW48 | <0.001 | 1.9 | ~46 | <0.001 | 0.24 | same as control | | 24K |
| SW480 | 26 | 56.4 | >133 | 0.02 | 2 | | | |
| WiDr | 0.01 | 34.8 | >133 | 0.012 | 0.5 | | | |

FIG. 6A

In Vitro Activity of ABT-700 PBD in Brain Tumor Lines

| Brain Cancer Line | ADC and Free Drug IC$_{50}$s (nM) | | | | | ABBV-399 Results | | |
|---|---|---|---|---|---|---|---|---|
| | ABT-700 PBD | PBD | MMAE | Ab095 PBD | Ab095 MMAF | Max Inhib (20 nM) | IC$_{50}$ (nM) | Receptors/Cell |
| U87MG | 0.08 | 0.13 | 1.2 | 32.9 | 54.4 | 60% | 18 | 21K |
| U138MG | < 0.001 | 0.18 | 0.54 | 23.3 | 22.8 | 90% | 0.1 | 31K |
| T98G | 141 | 0.34 | 2.1 | > 133 | > 133 | same as control | | |
| U251 | < 0.007 | < 0.002 | 1.47 | 9.2 | > 133 | same as control | | |
| MO59J | < 0.001 | 0.05 | 2.3 | 26 | > 133 | 60% | 3.6 | 87K |
| MO59K | < 0.001 | 0.072 | 3.5 | 12.2 | > 133 | same as control | | |
| A172 | > 67 (ambig) | 0.41 | 2.1 | 36.4 | 49.7 | same as control | | |
| PFSK-1 | 2.45 | 0.2 | 0.68 | 4.64 | 48.7 | same as control | | |
| DBTRG-05MG | < 0.001 | 0.21 | 2.1 | 26 | > 133 | same as control | | |
| SNB-19 | 0.006 | 0.017 | 1.5 | 39.2 | 59.3 | 65% | 8 | 66K |
| SNB-75 | 28.2 | 0.015 | 1.8 | 42.6 | 91.9 | same as control | | |
| SF-539 | 0.035 | 0.015 | 3.8 | 50 | > 133 | same as control | | |
| SF-264 | 0.005 | 0.023 | 3 | 24.3 | 103 | | | |
| CHLA-03-AA | 0.97 | 0.045 | 2.8 | 14.8 | 51.5 | | | |

FIG. 7

ANTI-CMET ANTIBODY DRUG CONJUGATES AND METHODS FOR THEIR USE

CROSS REFERENCE TO RELATED APPLICATIONS

This application is a continuation of U.S. application Ser. No. 15/597,624, filed May 17, 2017, which claims the benefit of priority under 35 U.S.C. § 119(e) of U.S. Provisional Application No. 62/337,796, filed May 17, 2016, the contents of all of which are incorporated herein by reference in their entireties.

SEQUENCE LISTING

The instant application contains a Sequence Listing which has been submitted electronically in ASCII format and is hereby incorporated by reference in its entirety. Said ASCII copy, created on May 17, 2017, is named 12252_0206-00000_SL.TXT and is 96,370 bytes in size.

1. FIELD

This application pertains to, among other things, anti-cMet antibody drug conjugates ("ADCs"), compositions including the ADCs, methods of making the ADCs, methods of selecting specific patient populations for cancer treatment with a anti-cMet ADC, and methods of using the ADCs to treat cancers.

2. BACKGROUND

Oncogenic protein kinases such as cMet represent a class of biologically important targets for cancer intervention. cMet, a well characterized receptor tyrosine kinase encoded by the MET proto-oncogene, is the cell surface receptor for hepatocyte growth factor (HGF; Gherardi E, Birchmeier W, Birchmeier C et al. Targeting MET in cancer: rationale and progress. Nat Rev Can. 2012; 12:89-103). cMet overexpression occurs in approximately 30%-50% of solid tumors including non-small cell lung cancer (NSCLC), colorectal cancer (CRC), and advanced gastroesophageal cancer (AGEC) (Spigel D R, Ervin T J, Ramlau R A, et al. Randomized Phase II trial of onartuzumab in combination with erlotinib in patients with advanced non-small-cell lung cancer. J Clin Oncol. 2013; 31(32):41054114; Resnick M B, Routhier J, Konkin T et al. Epidermal growth factor receptor, cMET, B-catenin, and p53 expression as prognostic indicators in stage II colon cancer: a tissue microarray study. Clin Can Res. 2004; 10:3069-3075; Lee H E, Kim M A, Lee H S, et al. MET in gastric carcinomas: comparison between protein express and gene copy number and impact on outcome. Br J Can. 2012; 107(2):325-333).

Overexpression of cMet has been associated with poor patient outcome. Thus, there remains a need for cancer therapeutics that target solid tumor cancers characterized by overexpression of cMet.

3. SUMMARY

The therapies described herein target solid tumor cancers in which cMet is overexpressed in at least 10% of the patient population having the cancer. cMet (cellular mesenchymal-epithelial transition factor) is a cell-surface receptor tyrosine kinase that transduces signals from the extracellular matrix into the cytoplasm by binding to hepatocyte growth factor/ HGF ligand. This cell surface receptor is expressed in epithelial cells of many organs, including the liver, pancreas, prostate, kidney, muscle and bone marrow, during both embryogenesis and adulthood. cMet regulates many physiological processes including cell proliferation and survival, migration and scattering (cell-cell repulsion), tissue morphogenesis, organ regeneration, and tissue remodeling. In cancer and other pathological processes, cMet is often aberrantly activated via mutation, amplification, or protein overexpression.

Solid tumor cancers in which cMet is overexpressed in at least 10% of the patient population include lung cancer, colorectal cancer, head and neck cancer, pancreatic cancer, gastric cancer, glioblastoma, ovarian, breast, prostate, cervical, and esophageal cancer. Data presented herein demonstrate, for the first time, that antibody drug conjugates ("ADCs") that specifically target cMet overexpression have demonstrated anti-tumor activity in patients diagnosed with non-small cell lung cancer. Data demonstrating in vivo anti-tumor efficacy of anti-cMet ADCs administered as monotherapy or combination are provided in Examples 10-14 and 16, and FIGS. 8-12 and 14-18.

cMet overexpression can be defined by an immunohistorychemistry (IHC) H-score of greater than or equal to 150 when measured according to the assay of Example 17. Briefly, IHC staining protocol for cMet overexpression has been developed using the Ventana cMet CONFIRM (SP44) kit. Tissue samples are stained with the Ventana antibody and then scored by determining the percentages of target tissue cells staining at various intensity levels of low to high. FIG. 20 depicts representative H-scores using the assay described in Example 17.

Alternatively, cMet overexpressing tumor tissue using an IHC score from 0 to 3+ as described in Example 17. FIG. 19 and FIG. 21 depict representative IHC scores using the assay described in Example 17.

The anti-cMet ADCs may be administered as single therapeutic agents (monotherapy) or adjunctively with or to other anti-cancer treatments and/or therapeutic agents, typically but not necessarily those used to treat the type of cancers being treated. Indeed, data presented herein demonstrate that tumors that exhibit resistance to other targeted or non-targeted chemotherapies retain sensitivity to anti-cMet ADCs (see, e.g., Example 14 and FIGS. 12A-12C). Accordingly, the anti-cMet ADCs described herein provide significant benefits over current targeted and non-targeted approaches toward the treatment of solid tumor cancers that overexpress cMet. Adjunctive therapies and/or therapeutic agents typically will be used at their approved dose, route of administration, and frequency of administration, but may be used at lower dosages and/or less frequently. When administered as monotherapy, the anti-cMet ADC will typically be administered on a schedule that provides therapeutic benefit. It is contemplated that anti-cMet ADCs administered once a week, once every two weeks, once every three weeks, once every four weeks, once every five weeks, once every six weeks, once every seven weeks or once every eight weeks will provide therapeutic benefit, although more or less frequent administration may be beneficial. When administered adjunctive to or with another therapy and/or agent, the anti-cMet ADC may be administered before, after or concurrently with the other therapy or agent.

The anti-cMet ADCs may be administered via a variety of routes or modes of administration, including but not limited to, intravenous infusion and/or injection and subcutaneous injection. The amount administered will depend upon the route of administration, the dosing schedule, the type of cancer being treated, the stage of the cancer being treated, and other parameters such as the age and weight of the patient, as is well known in the art. Specific exemplary dosing schedules expected to provide therapeutic benefit are provided in the Detailed Description. Generally, an amount of anti-cMet ADC in the range of about 0.005 to 15 mg/kg when administered intravenously on a weekly basis from once weekly to and including once every eight weeks is expected to provide therapeutic benefit.

Accordingly, in one aspect, the present disclosure provides ADCs that specifically bind cMet ("anti-cMet ADCs"). The anti-cMet ADCs comprise cytotoxic and/or cytostatic agents linked by way of linkers to an antigen binding moiety that specifically binds cMet. In some embodiments, the antigen binding moiety is an antibody and/or an antigen binding fragment.

Antibodies and/or binding fragments composing the anti-cMet ADCs generally comprise a heavy chain comprising a variable region ($V_H$) having three complementarity determining regions ("CDRs") referred to herein (in N→C order) as $V_H$CDR#1, $V_H$CDR#2, and $V_H$CDR#3, and a light chain comprising a variable region ($V_L$) having three complementarity determining regions referred to herein (in N→C order) as $V_L$ CDR#1, $V_L$ CDR#2, and $V_L$ CDR#3. The amino acid sequences of exemplary CDRs, as well as the amino acid sequence of the $V_H$ and $V_L$ regions of the heavy and light chains of exemplary anti-cMet antibodies and/or binding fragments that can compose the anti-cMet ADCs are provided herein. Specific embodiments of anti-cMet ADCs include, but are not limited to, ABT-700 and STI-0602.

For therapeutic uses, it may be desirable to utilize anti-cMet ADCs that bind cMet with an affinity of at least 100 nM. Accordingly, in some embodiments, the anti-cMet ADCs comprise an anti-cMet and/or anti-cMet binding fragment that binds cMet with an affinity of at least about 100 nM, or even higher, for example, at least about 90 nM, 80 nM, 70 nM, 60 nM, 50 nM, 40 nM, 30 nM, 25 nM, 20 nM, 15 nM, 10 nM, 7 nM, 6 nM, 5 nM, 4 nM, 3 nM, 2 nM, 1 nM, 0.1 nM, 0.01 nM, or greater. Affinity of anti-cMet antibodies and/or binding fragments can be determined using techniques well known in the art or described herein, such as for example, ELISA, isothermal titration calorimetry (ITC), surface plasmon resonance, flow cytometry, or fluorescent polarization assay. In some embodiments, the affinity refers to apparent affinity $EC_{50}$ values, measured according to Example 5. In one embodiment, the antibody has an apparent affinity $EC_{50}$ value from lower than about 10 nanomol/L, preferably from about 1 picomol/L to 10 nanomol/L, preferably about 0.3 nanomol/L, as determined according to Example 5.

Antibodies may be in the form of full-length antibodies, bispecific antibodies, dual variable domain antibodies, multiple chain or single chain antibodies, surrobodies (including surrogate light chain construct), single domain antibodies, camelized antibodies, scFv-Fc antibodies, and the like. They may be of, or derived from, any isotype, including, for example, IgA (e.g., $IgA_1$ or $IgA_2$), IgD, IgE, IgG (e.g., $IgG_1$, $IgG_2$, $IgG_3$ or $IgG_4$), IgM, or IgY. In some embodiments, the anti-cMet antibody is an IgG (e.g., $IgG_1$, $IgG_2$, $IgG_3$ or $IgG_4$). Antibodies may be of human or non-human origin. Examples of non-human origin include, but are not limited to, mammalian origin (e.g., simians, rodents, goats, and rabbits) or avian origin (e.g., chickens). In specific embodiments, antibodies composing the anti-cMet ADCs are suitable for administration to humans, such as, for example, humanized antibodies and/or fully human antibodies.

Antigen binding fragments composing the anti-cMet ADCs may include any fragment of an antibody capable of specifically binding cMet. Specific examples of antibody binding fragments that may be included in the anti-cMet ADCs include, but are not limited to, Fab, Fab', (Fab')$_2$, Fv and scFv.

Antibodies and/or binding fragments composing the anti-cMet ADCs may include modifications and/or mutations that alter the properties of the antibodies and/or fragments, such as those that increase half-life, increase or decrease ADCC, etc., as is known in the art.

The cytotoxic and/or cytostatic agents composing the anti-cMet ADCs may be any agents known to inhibit the growth and/or replication of, and/or kill cells. Numerous agents having cytotoxic and/or cytostatic properties are known in the literature. Non-limiting examples of classes of cytotoxic and/or cytostatic agents include, by way of example and not limitation, cell cycle modulators, apoptosis regulators, kinase inhibitors, protein synthesis inhibitors, alkylating agents, DNA cross-linking agents, intercalating agents, mitochondria inhibitors, nuclear export inhibitors, topoisomerase I inhibitors, topoisomerase II inhibitors, RNA/DNA antimetabolites and antimitotic agents.

In a specific embodiment, a cytotoxic and/or cytostatic agent composing an anti-cMet ADC is a cell-permeating antimitotic agent, such as, for example, an auristatin. Specific examples of cell-permeating auristatins include, but are not limited to, dolastatin-10 and monomethyl auristatin E ("MMAE"). In another specific embodiment, a cytotoxic and/or cytostatic agent composing an anti-cMet ADC is a cell-permeating DNA cross-linking agent, such as a cell-permeating minor groove-binding DNA cross-linking agent. Specific examples of cell-permeating DNA minor groove-binding agents include, but are not limited to, pyrrolobenzodiazepines ("PBD") and PBD dimers.

The linkers linking the cytotoxic and/or cytostatic agents to the antigen binding moiety of an anti-cMet ADC may be long, short, flexible, rigid, hydrophilic or hydrophobic in nature, or may comprise segments that have different characteristics, such as segments of flexibility, segments of rigidity, etc. The linker may be chemically stable to extracellular environments, for example, chemically stable in the blood stream, or may include linkages that are not stable and release the cytotoxic and/or cytostatic agents in the extracellular milieu. In some embodiments, the linkers include linkages that are designed to release the cytotoxic and/or cytostatic agents upon internalization of the anti-cMet ADC within the cell. In some specific embodiments, the linkers includes linkages designed to cleave and/or immolate or otherwise breakdown specifically or non-specifically inside cells. A wide variety of linkers useful for linking drugs to antigen binding moieties such as antibodies in the context of ADCs are known in the art. Any of these linkers, as well as other linkers, may be used to link the cytotoxic and/or cytostatic agents to the antigen binding moiety of the anti-cMet ADCs described herein.

The number of cytotoxic and/or cytostatic agents linked to the antigen binding moiety of an anti-cMet ADC can vary (called the "drug-to-antibody ratio," or "DAR"), and will be limited only by the number of available attachments sites on the antigen binding moiety and the number of agents linked to a single linker. Typically, a linker will link a single cytotoxic and/or cytostatic agent to the antigen binding moiety of an anti-cMet ADC. In embodiments of anti-cMet ADCs which include more than a single cytotoxic and/or cytostatic agent, each agent may be the same or different. As long as the anti-cMet ADC does not exhibit unacceptable levels of aggregation under the conditions of use and/or storage, anti-cMet ADCs with DARs of twenty, or even higher, are contemplated. In some embodiments, the anti-cMet ADCs described herein may have a DAR in the range of about 1-10, 1-8, 1-6, or 1-4. In certain specific embodiments, the anti-cMet ADCs may have a DAR of 2, 3, or 4. In other specific embodiments, the anti-cMet ADCs may have an average DAR of 3.1.

4. BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 1A-1E show the amino acid sequences of several cMet antibodies.

FIGS. 2A-2B: illustrate ABBV-399 Process 1.

FIG. 5 provides proliferation inhibition results with ABBV-399 and ABT-700 PBD.

Figure 6B:
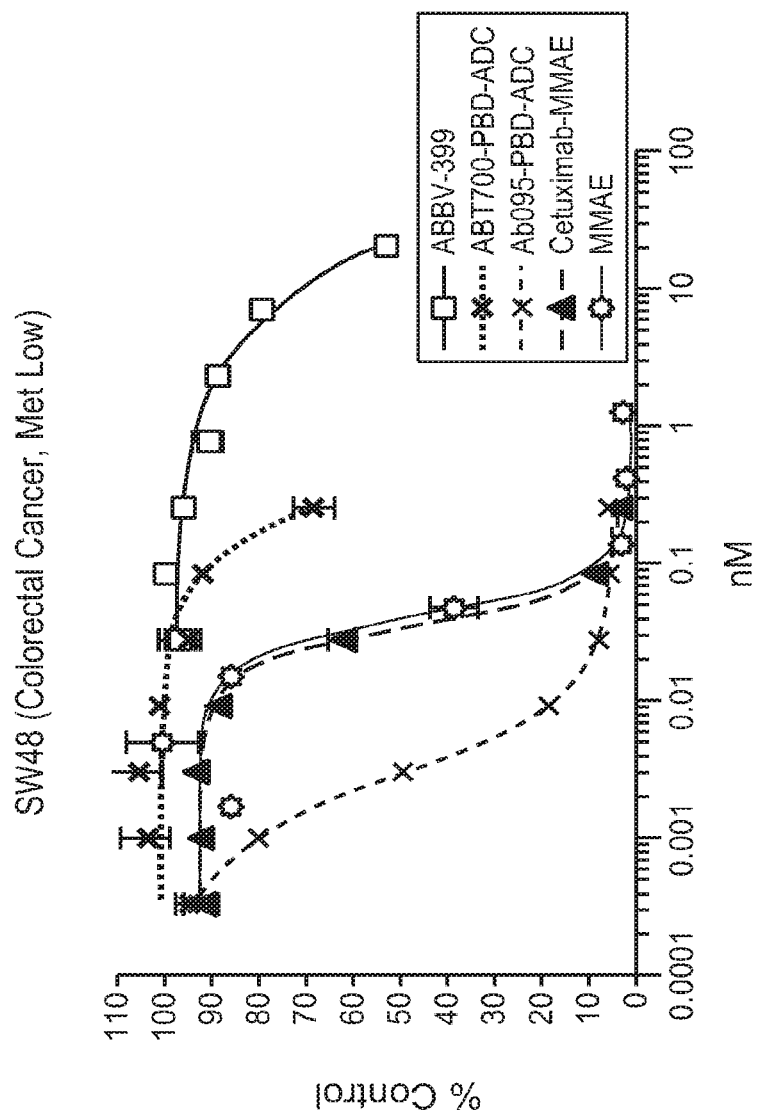

FIGS. 6A-6B show in vitro activity of ABT-700 PBD in colorectal cancer cell lines.

FIG. 7 shows in vitro activity of ABT-700 PBD in brain cancer cell lines.

Figure 8:
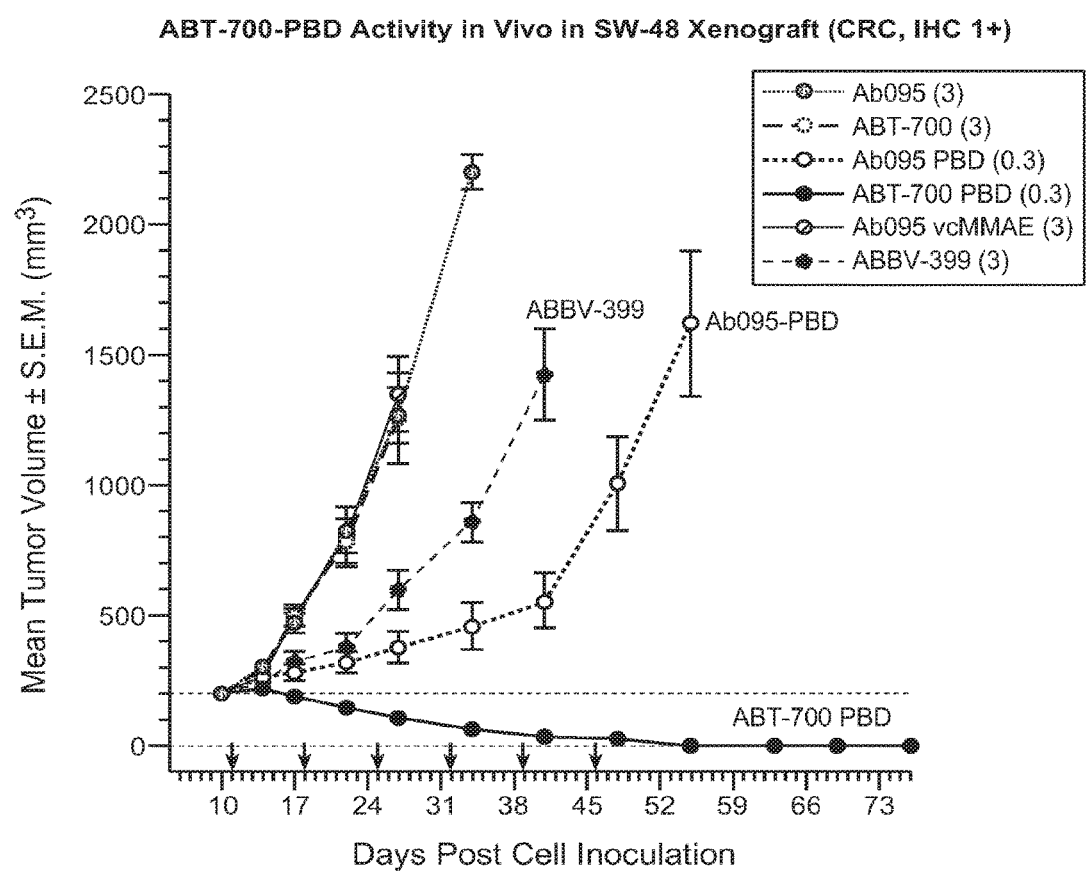

FIG. 8 shows ABT-700 PBD activity in SW48 xenografts.

Figure 9A:
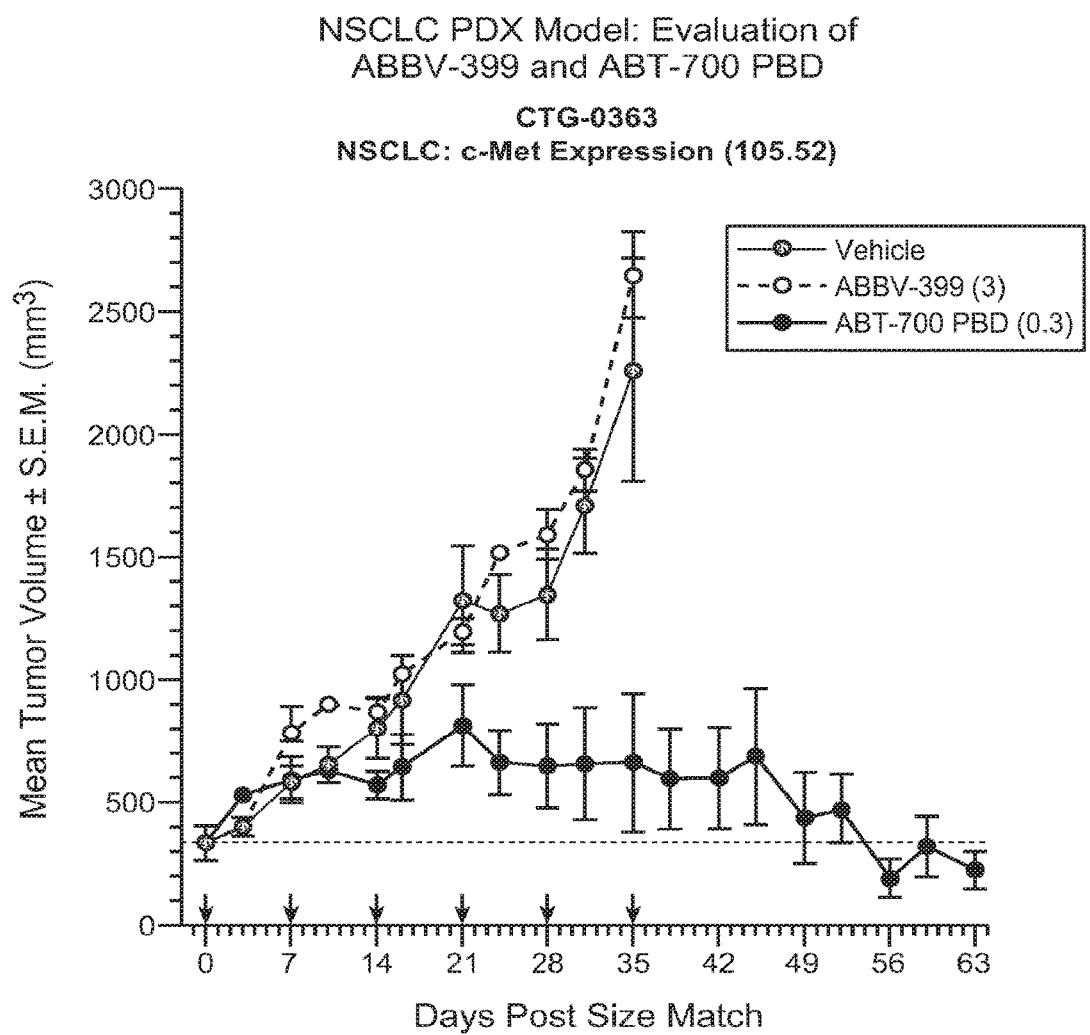
Figure 9B:
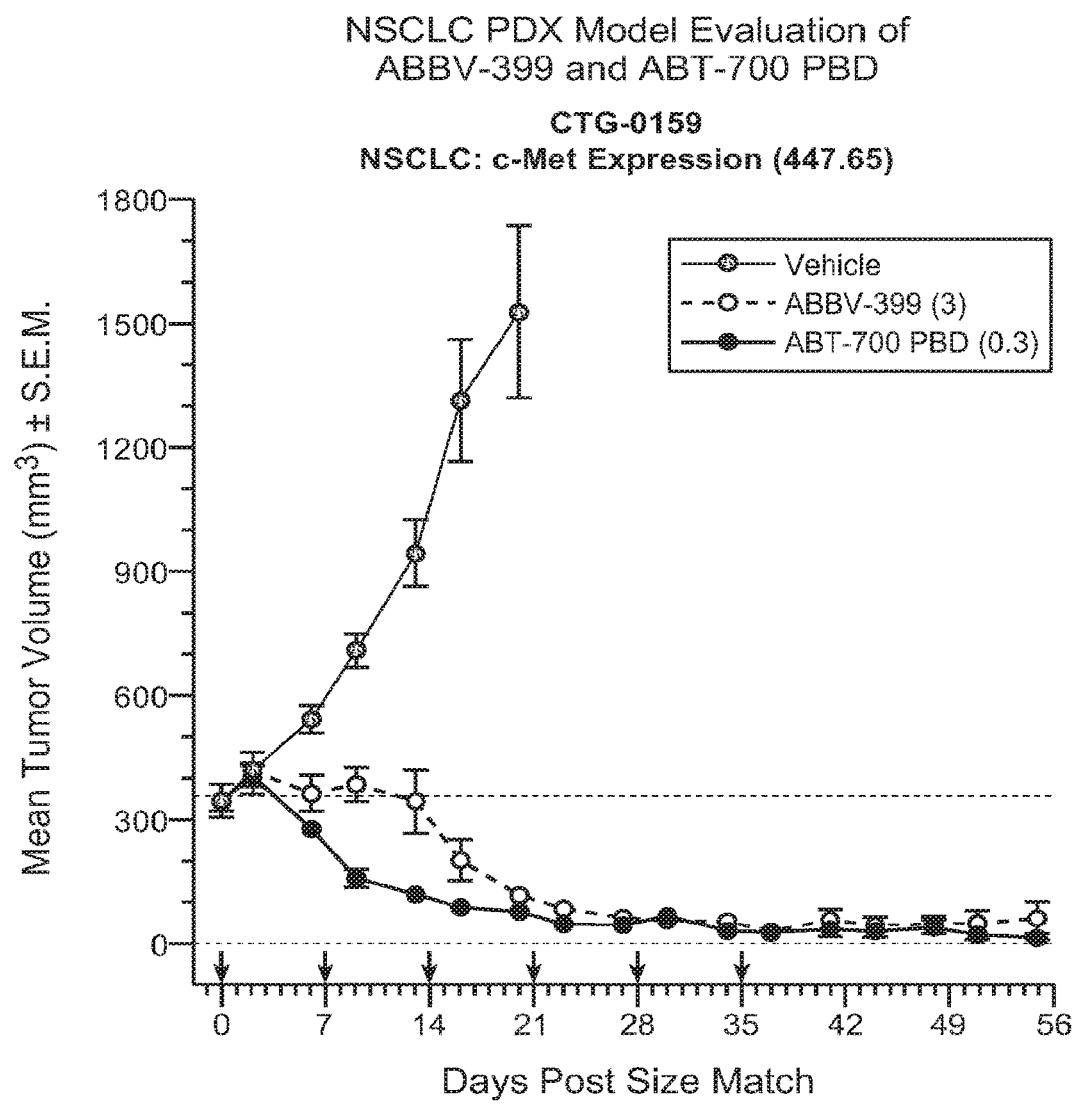
Figure 9C:
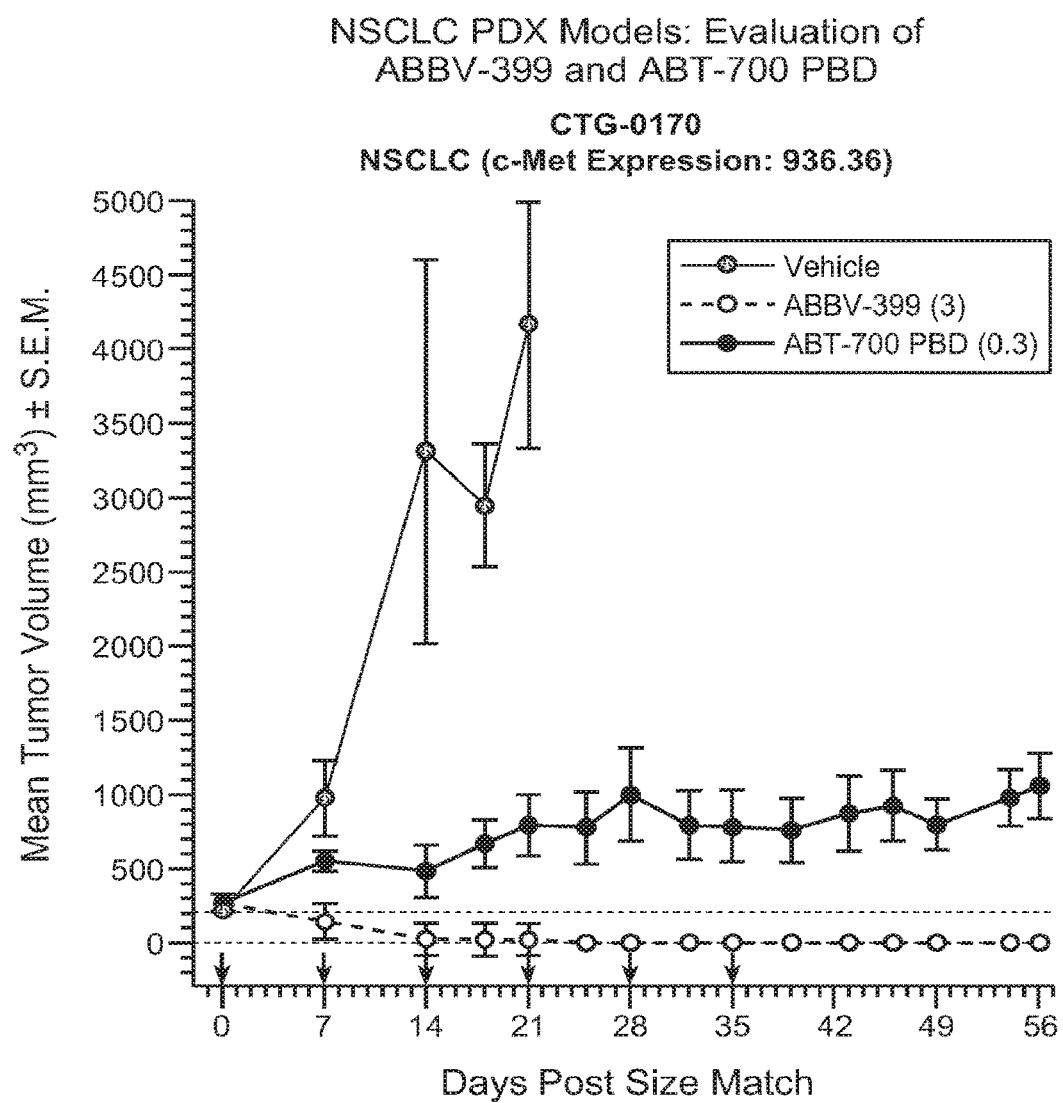

FIGS. 9A-9C show the activity of ABT-700 PBD and ABBV-399 in NSCLC patient xenografts.

Figure 10B:
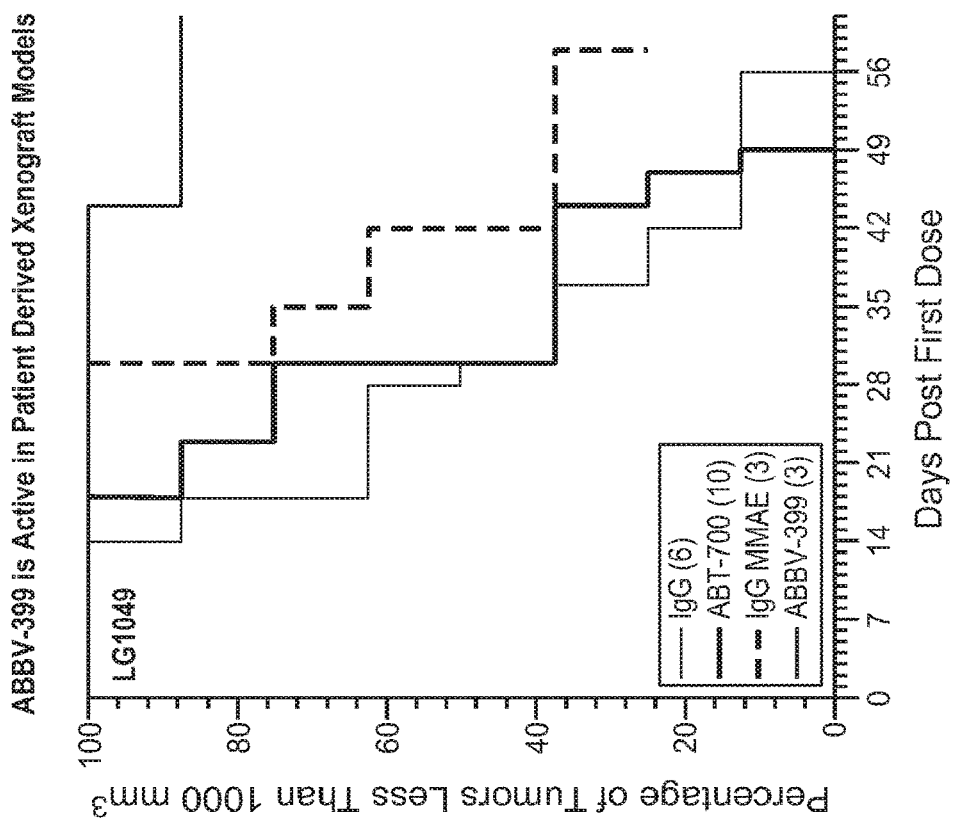
Figure 10A:
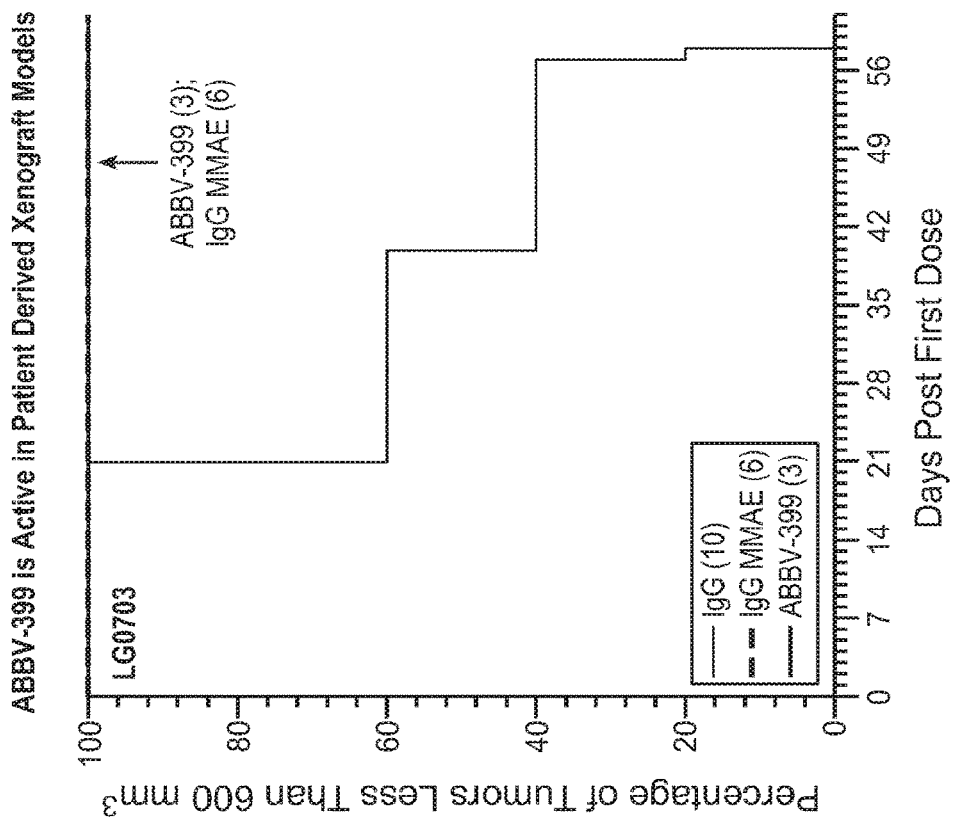

FIGS. 10A-10B show the activity of ABBV-399 in NSCLC patient xenografts using Kaplan-Meier plots.

Figure 11A:
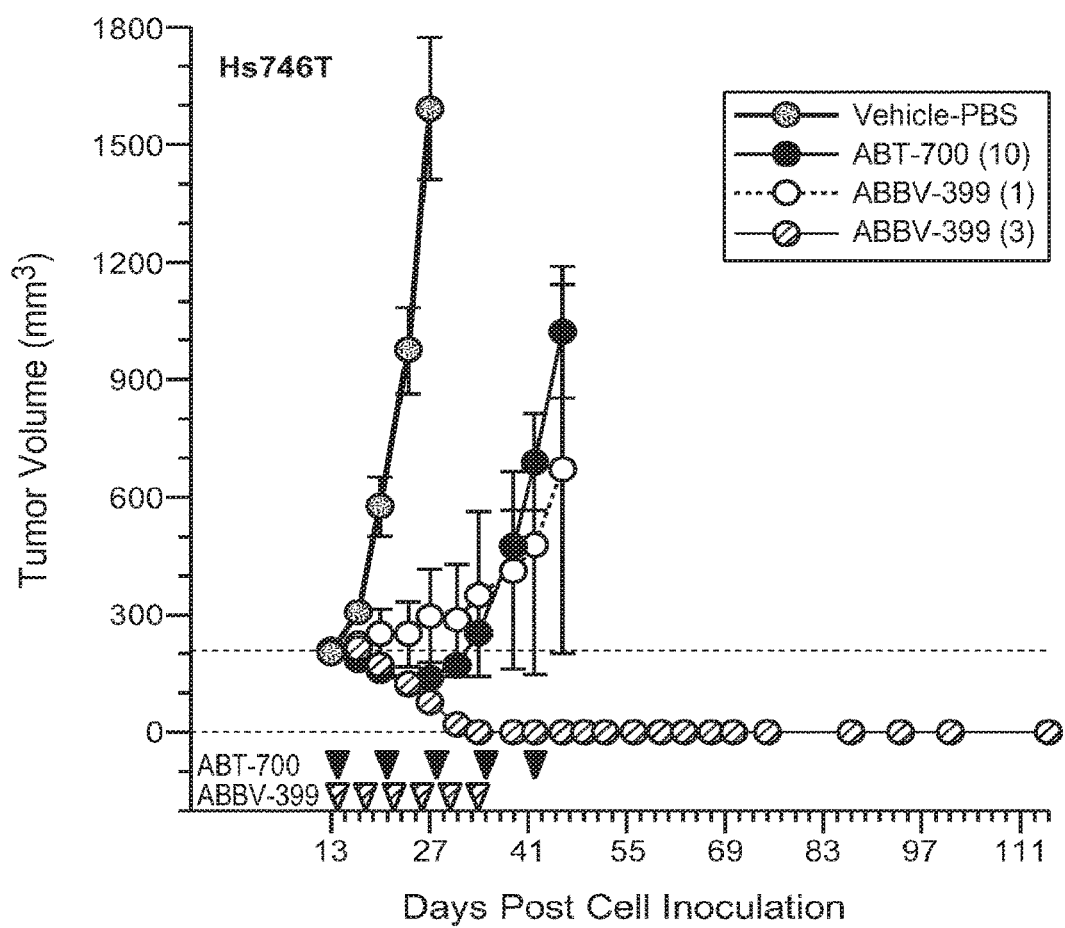
Figure 11B:
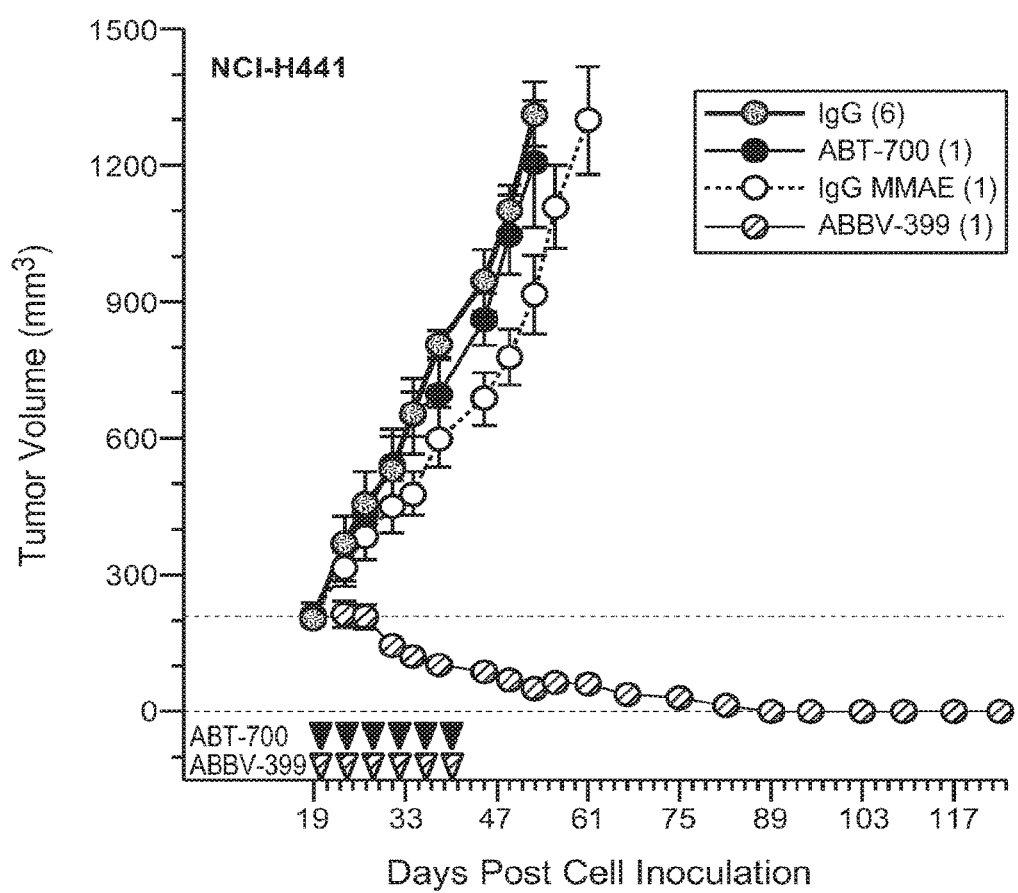
Figure 11C:
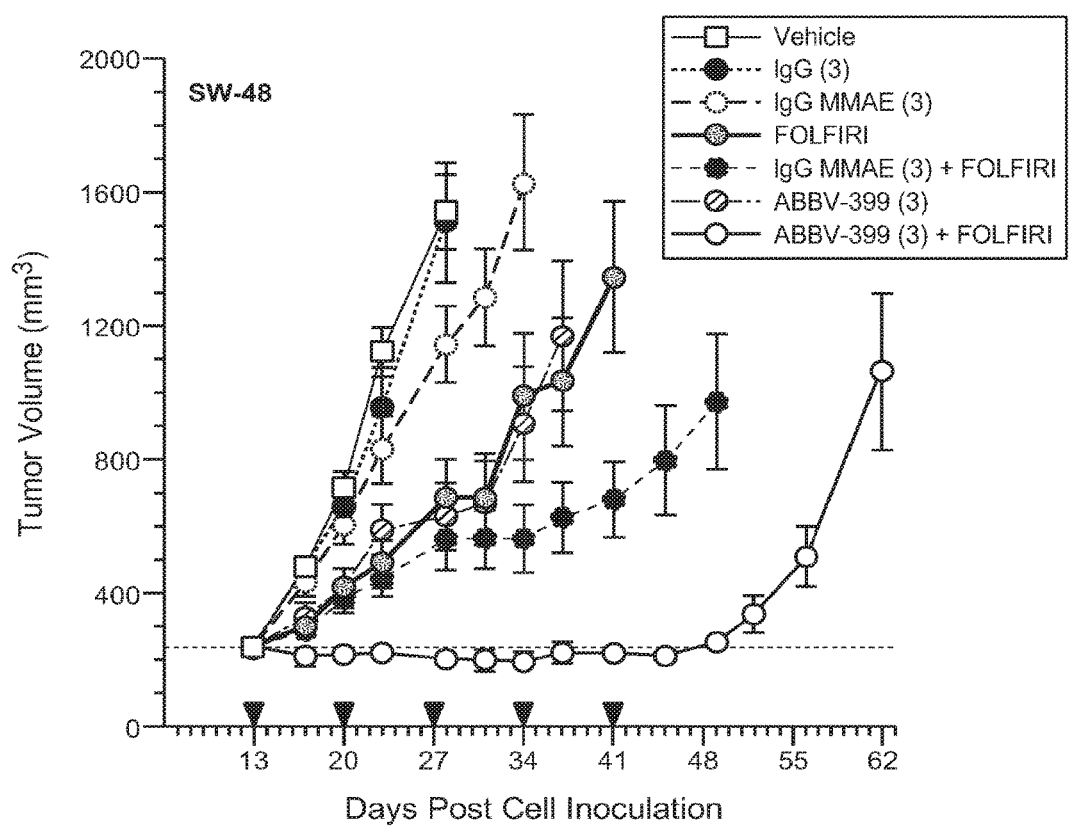

FIGS. 11A-11B compare the activity of ABT-700 versus ABBV-399 in human tumor xenografts; FIG. 11C shows the activity of ABBV-339 alone or in combination with FOL-FIRI.

Figure 12A:
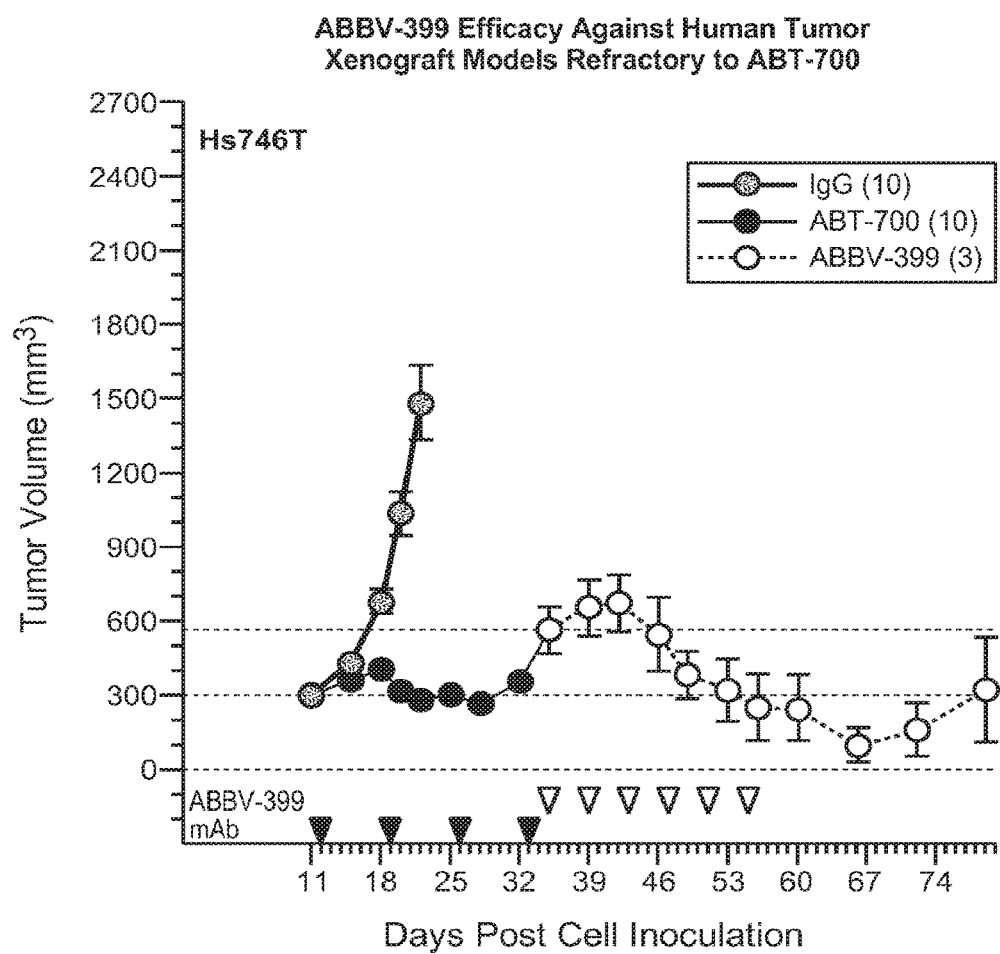
Figure 12B:
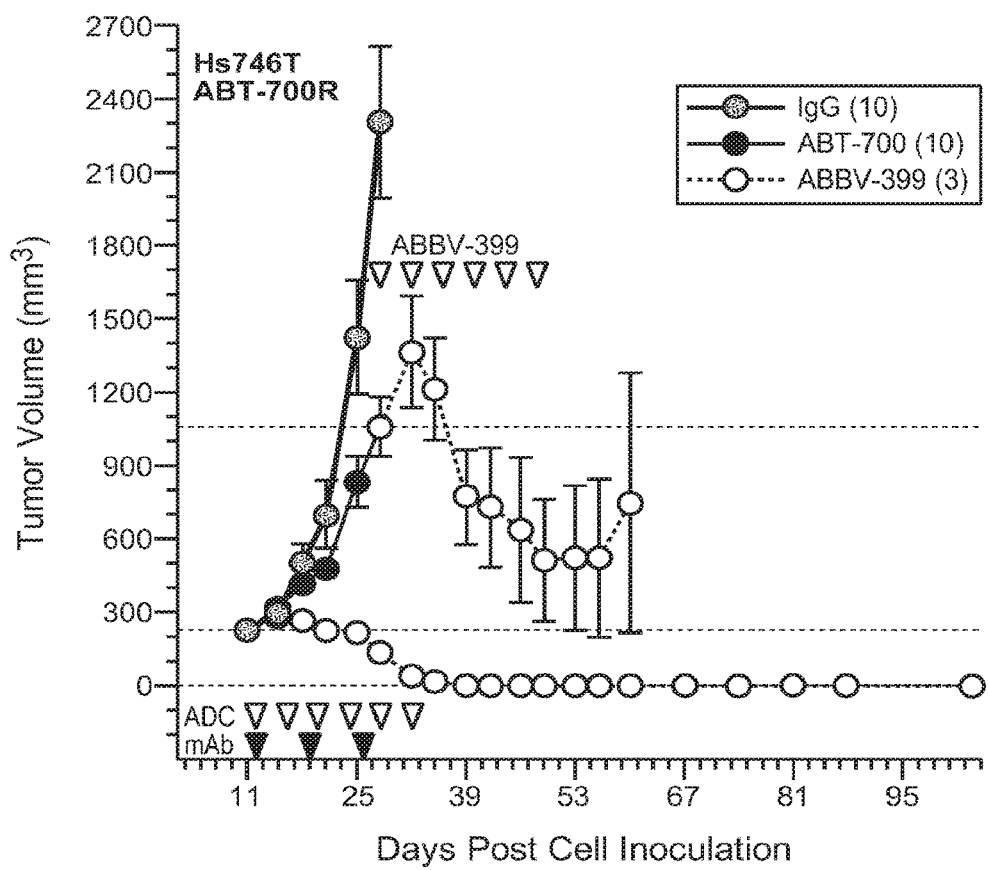
Figure 12C:
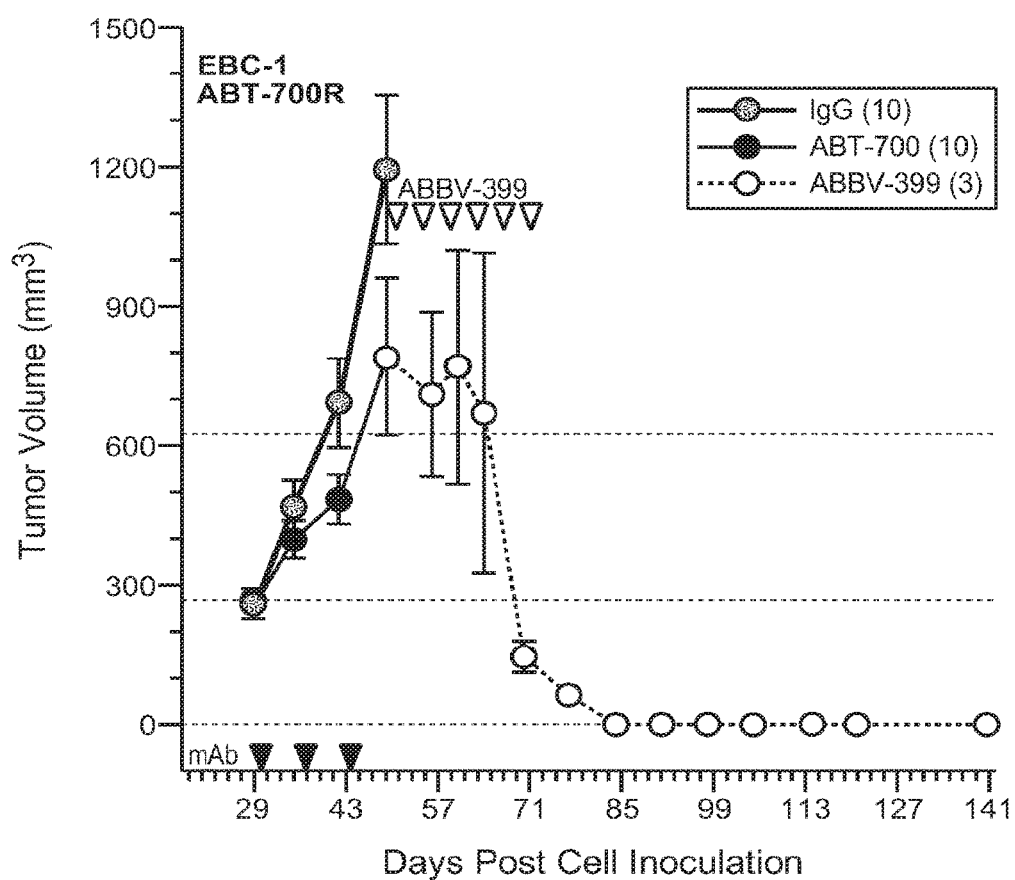

FIGS. 12A-12C depict the activity of ABBV-399 in human xenograft models refractory to ABT-700.

Figure 13:
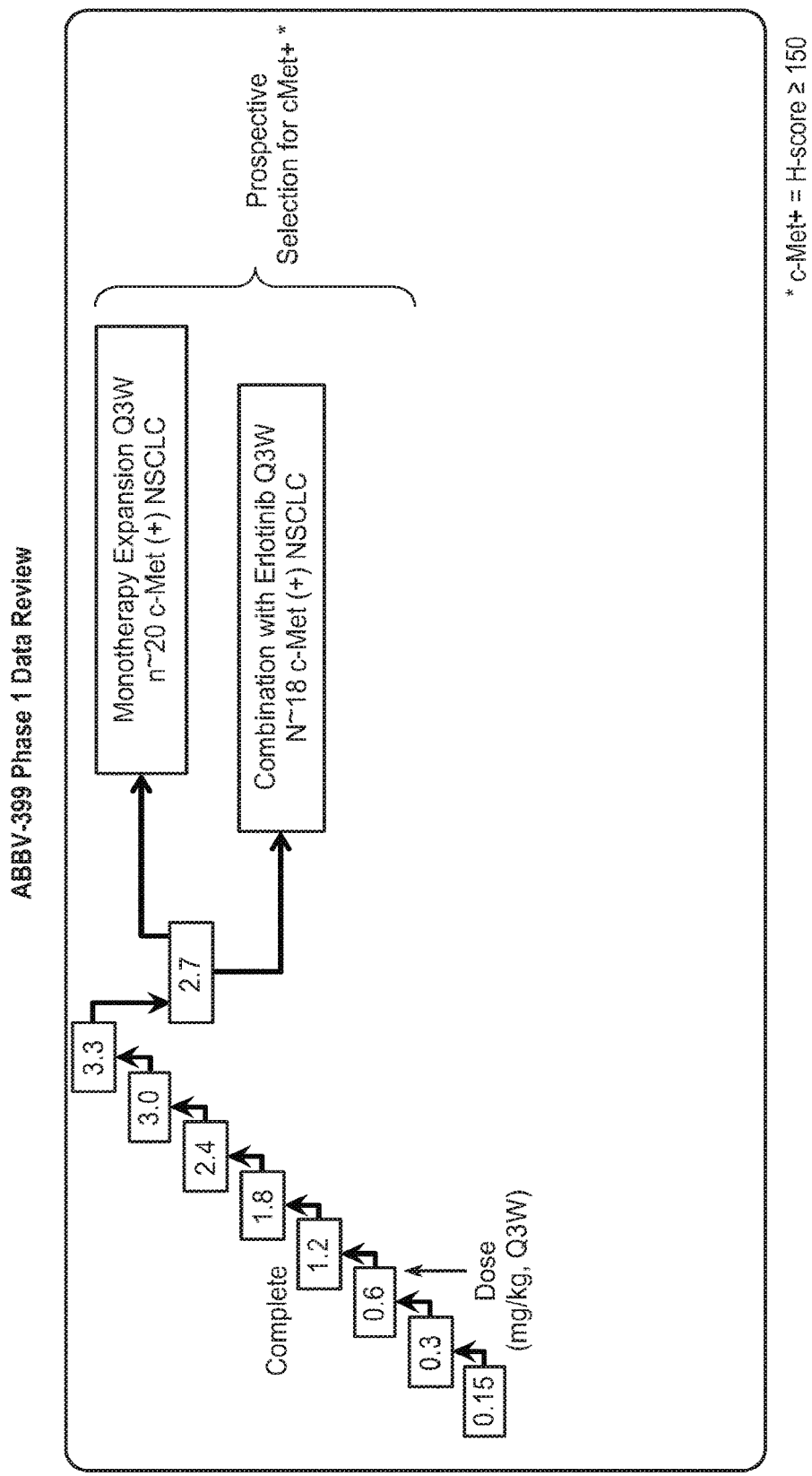

FIG. 13 provides the ABBV-399 dose escalation scheme for the monotherapy phase I trial.

Figure 14:
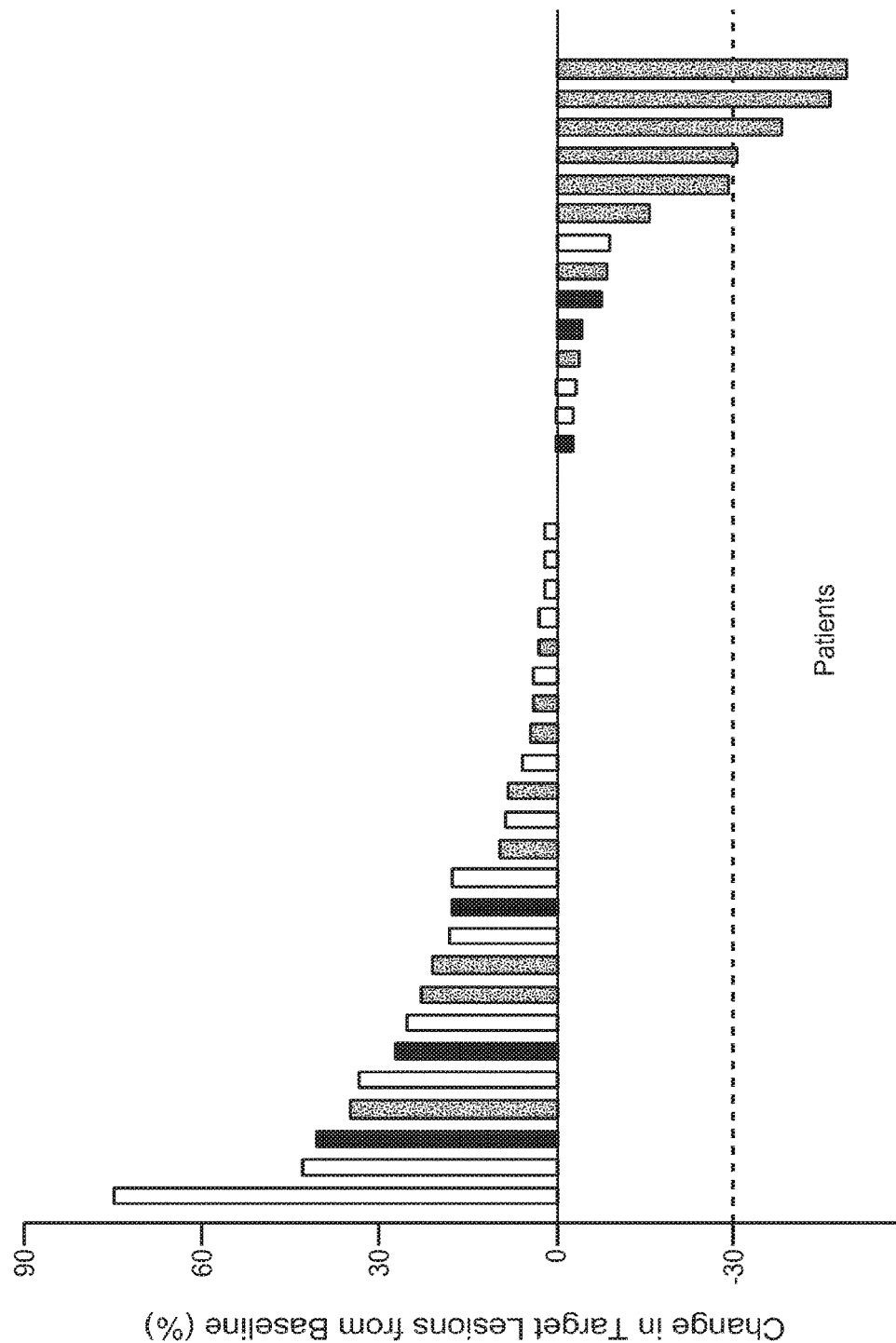

FIG. 14 provides a waterfall plot showing best percent change in target lesions.

Figure 15:
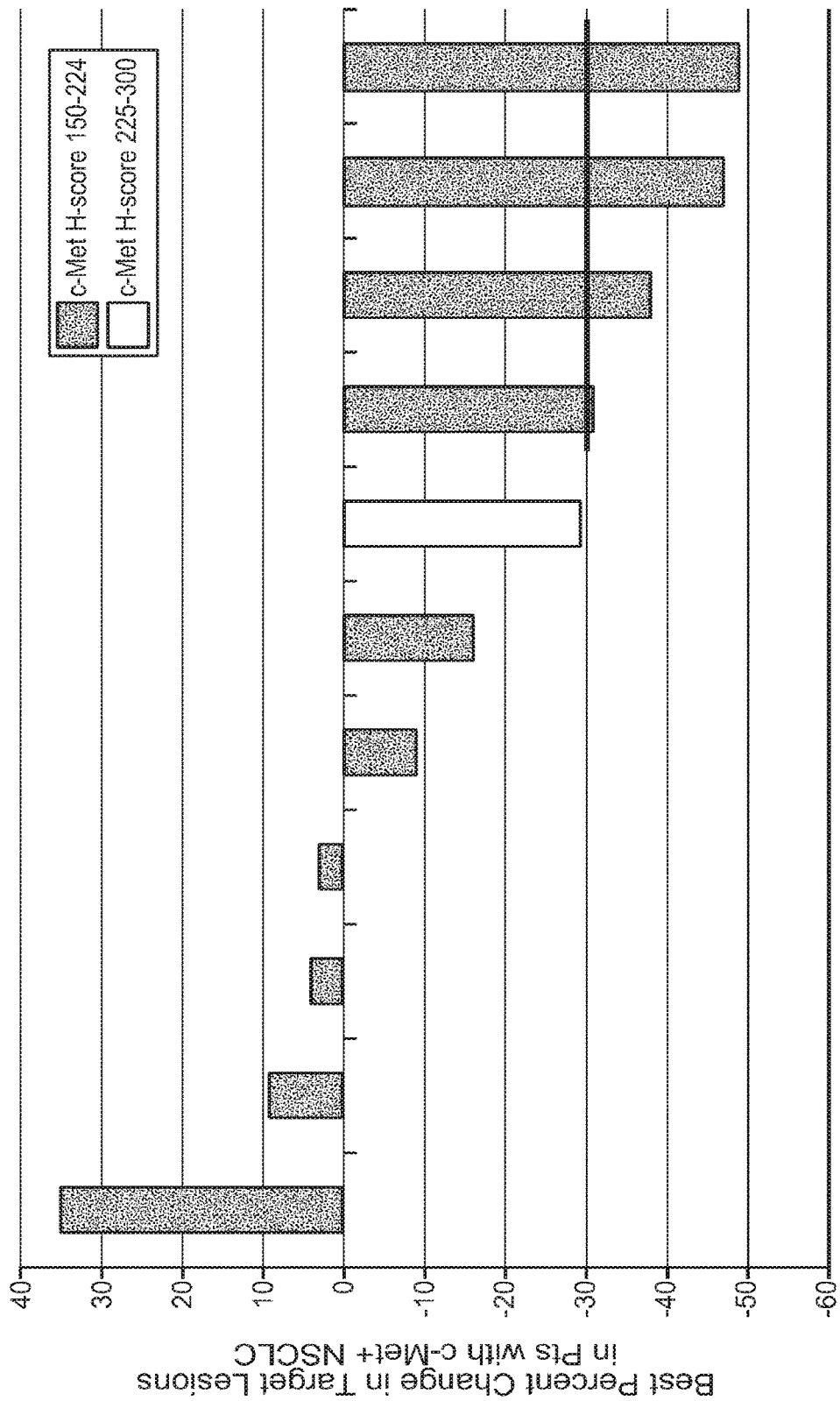

FIG. 15 provides a waterfall plot showing best percent change in target lesions/cMet levels with ABBV-399 monotherapy.

Figure 16:
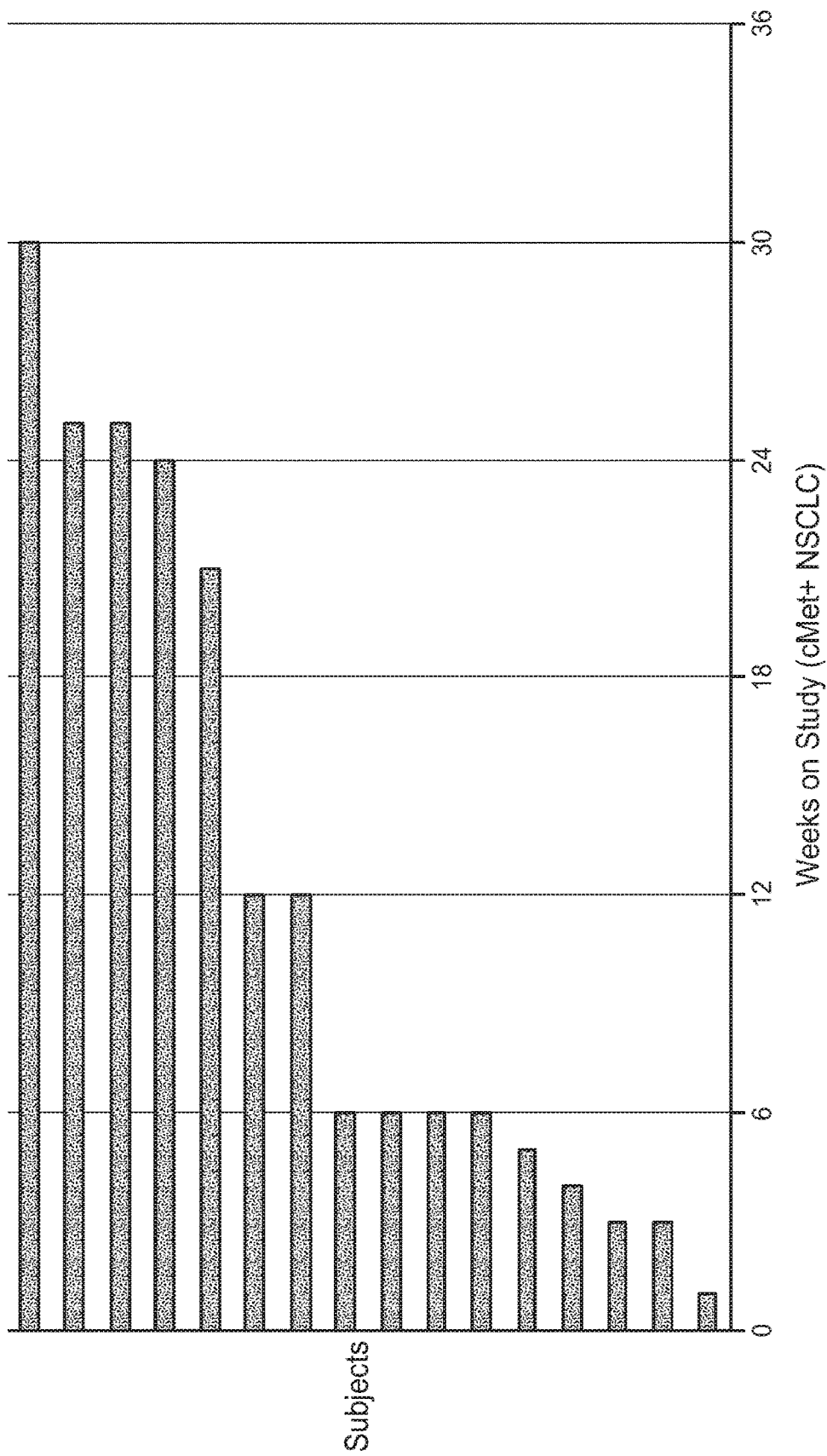

FIG. 16 shows the number of weeks before clinical progression in 16 patients treated with ABBV-399.

Figure 17:
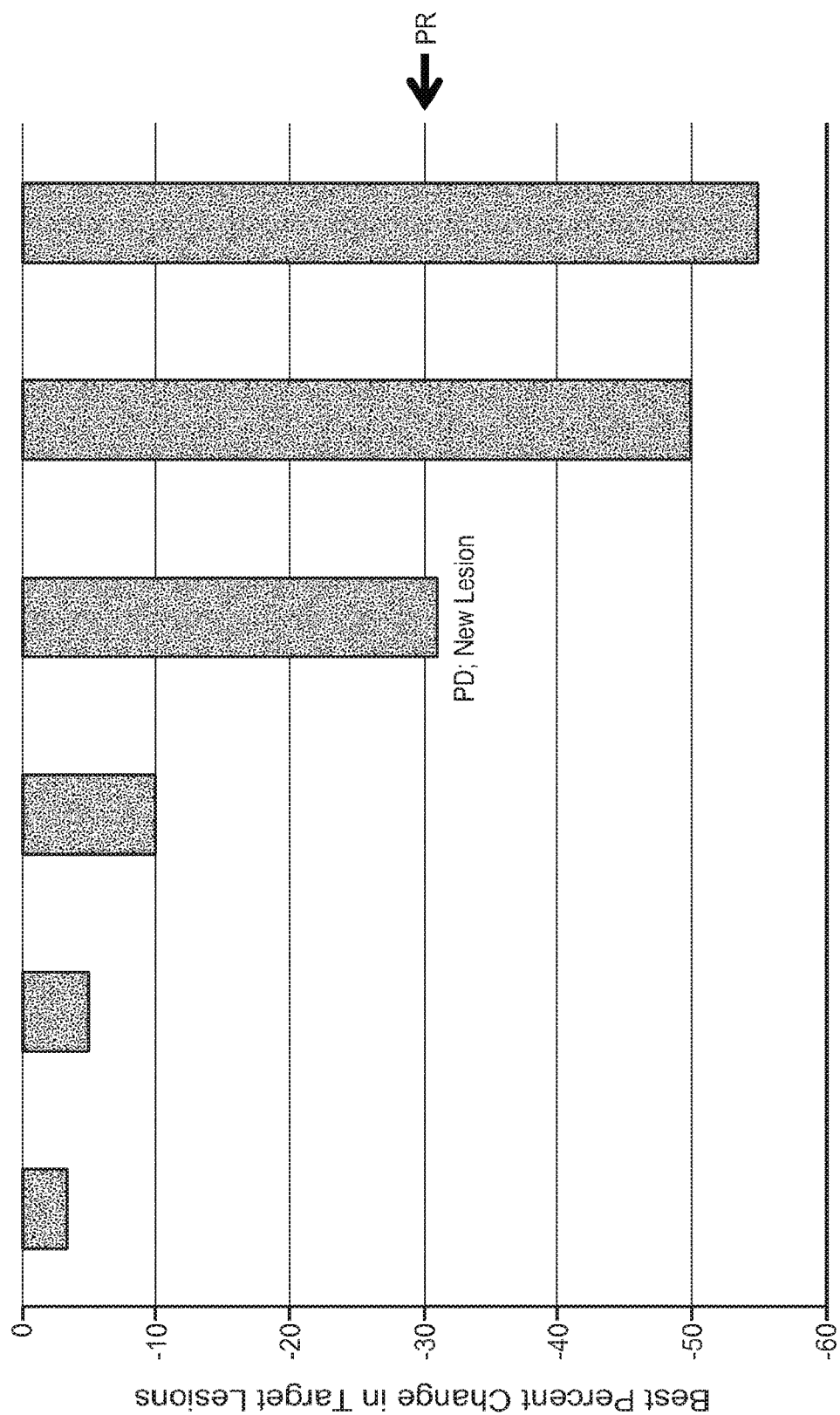

FIG. 17 is a waterfall plot showing best percent change in target lesions ABBV-399 combination with erlotinib.

Figure 18:
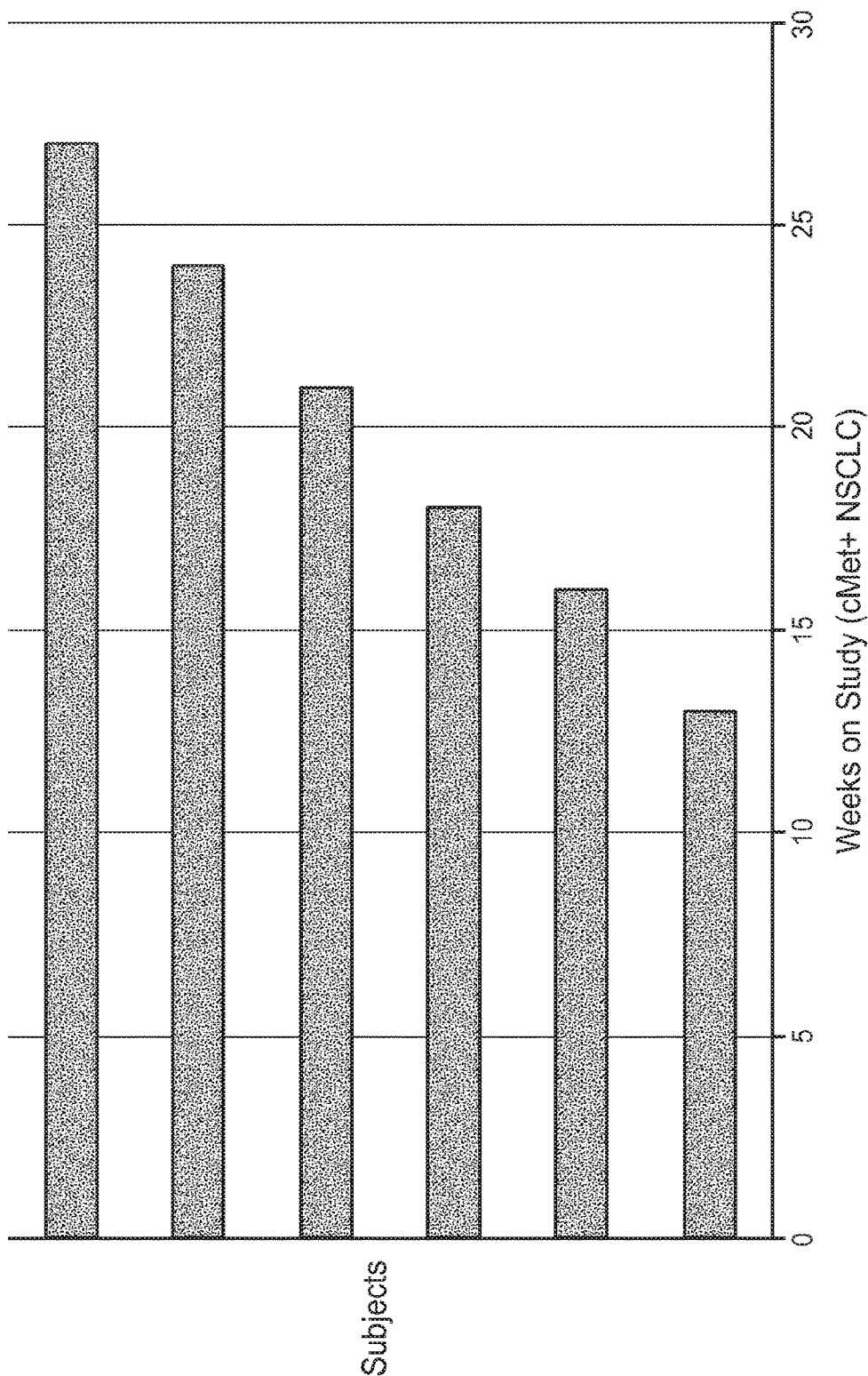

FIG. 18 shows the number of weeks before clinical progression in 6 patients treated with ABBV-399 and erlotinib.

Figure 19:
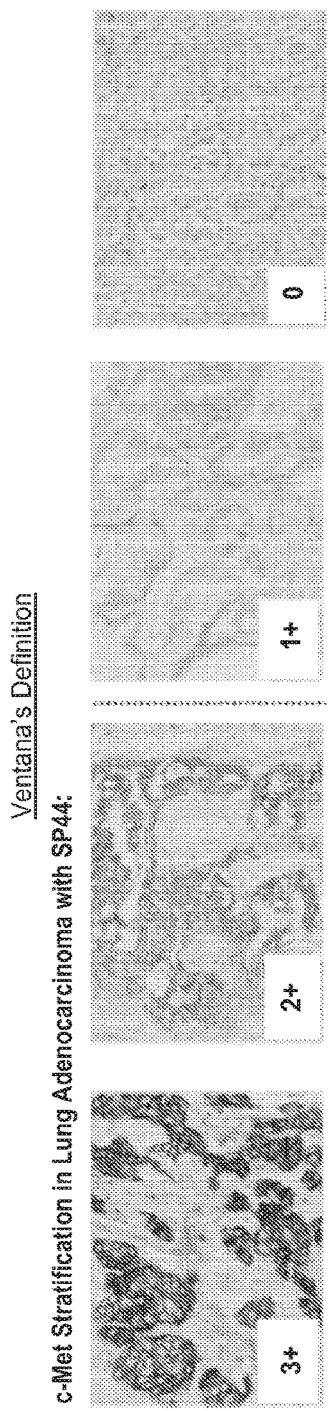

FIG. 19 illustrates the Ventana's SP44 scoring guide.

Figure 20:
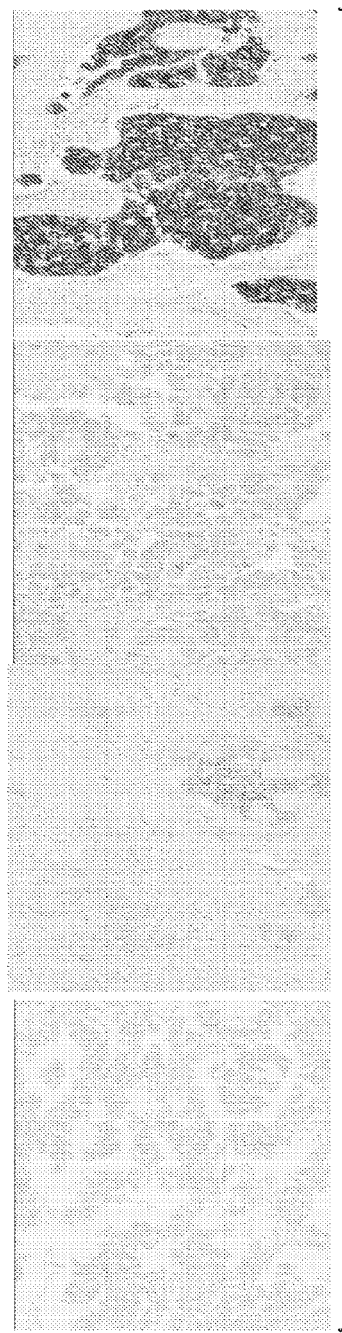

FIG. 20 illustrates patient selection based on cMet overexpression.

Figure 21:
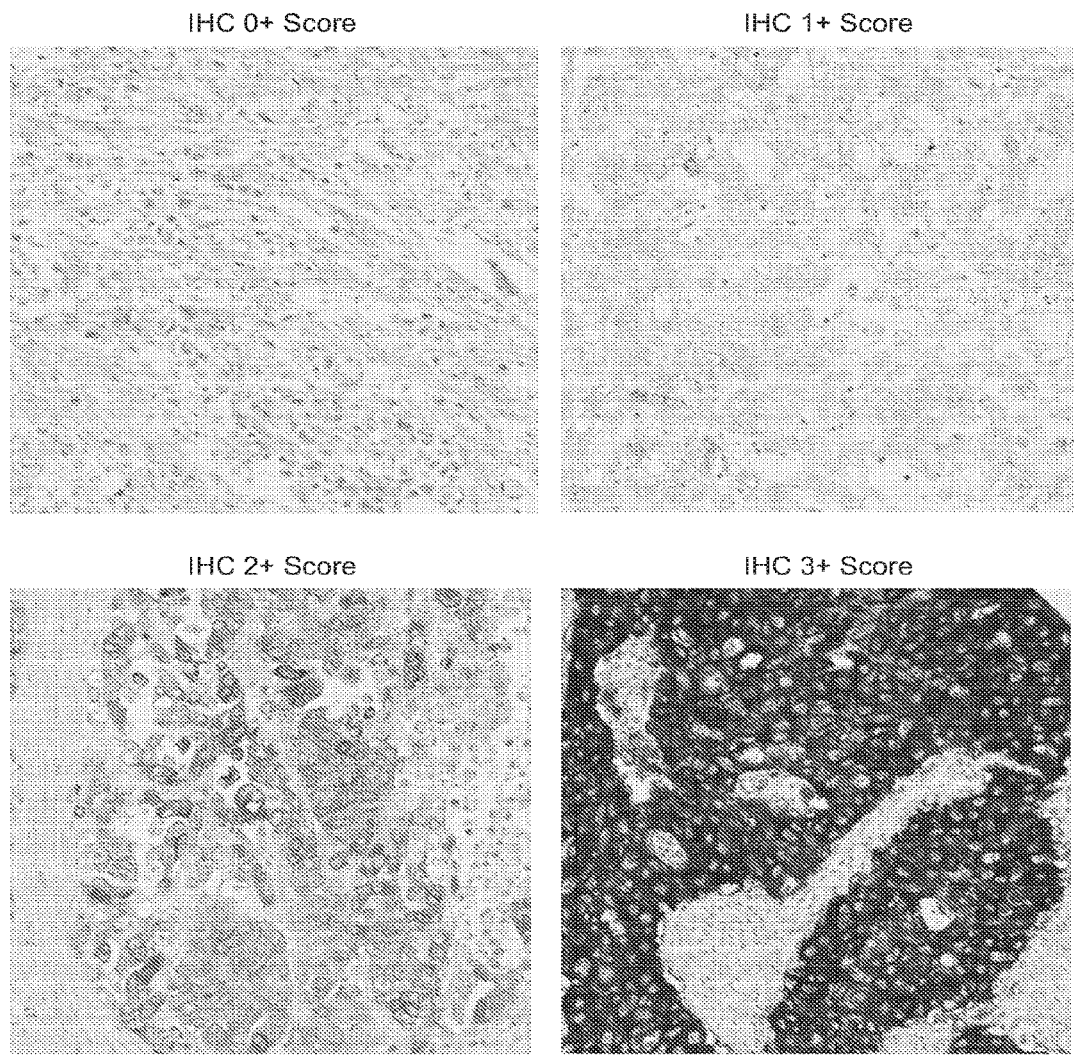

FIG. 21 provides exemplary IHC scores using the method of Example 17.

5. DETAILED DESCRIPTION

5.1. Abbreviations

The antibodies, binding fragments, ADCs and polynucleotides described herein are, in many embodiments, described by way of their respective polypeptide or polynucleotide sequences. Unless indicated otherwise, polypeptide sequences are provided in N→C orientation; polynucleotide sequences in 5'→3' orientation. For polypeptide sequences, the conventional three or one-letter abbreviations for the genetically encoded amino acids may be used, as noted in TABLE 1, below.

TABLE 1

Encoded Amino Acid Abbreviations

| Amino Acid | Three Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Certain sequences are defined by structural formulae specifying amino acid residues belonging to certain classes (e.g., aliphatic, hydrophobic, etc.). The various classes to which the genetically encoded amino acids belong as used herein are noted in TABLE 2, below. Some amino acids may belong to more than one class. Cysteine, which contains a sulfhydryl group, and proline, which is conformationally constrained, are not assigned classes.

TABLE 2

Encoded Amino Acid Classes

| Class | Amino Acids |
|---|---|
| Aliphatic | A, I, L, V |
| Aromatic | F, Y, W |
| Non-Polar | M, A, I, L, V |
| Polar | N, Q, S, T |
| Basic | H, K, R |
| Acidic | D, E |
| Small | A, G |

5.2. Definitions

Unless otherwise defined herein, scientific and technical terms used in connection with the present disclosure shall have the meanings that are commonly understood by those of ordinary skill in the art.

5.3. Antibody Drug Conjugates that Bind to cMet and cMet Overexpression Assay The present disclosure concerns antibody drug conjugates that specifically bind human cMet, compositions comprising the ADCs, anti-cMet antibodies and/or binding fragments that can comprise the ADCs, polynucleotides encoding anti-cMet antibodies and/or binding fragments that comprise the ADCs, host cells capable of producing the antibodies and/or binding fragments, methods and compositions useful for making the antibodies, binding fragments and ADCs, and various methods of using the ADCs in cancer treatment.

Data provided herein demonstrate, for the first time, that antibody drug conjugates ("ADCs") specifically targeting cMet exhibit potent antitumor effects, both alone and in combination with other targeted and non-targeted antitumor therapies, against solid tumors in which cMet is overexpressed, particularly those with an IHC-score of 2+ and 3+ when measured by immunohistochemistry with the SP44 antibody. Data demonstrating in vivo anti-tumor efficacy of ABBV-399 administered as monotherapy are provided in the Examples.

For purposes of this application, including the claims, the particular assay used in the study described herein is referred to as the "cMet ABBV-ADC staining protocol." This protocol is described in detail in Example 17 and the results are expressed in terms of H-score and may also be expressed in terms of IHC score or other scoring system well known in the art.

The H-score approach provides optimal data resolution for determining variation in intensity and tumor percentage of staining within and among tumor types. It also provides a good tool for determining thresholds for positive staining. In this method, the percentage of cells (0-100) within a tumor with staining intensities ranging from 0-3+ are provided. This protocol results in staining of the cMet protein both in the cytoplasm and in the cell surface/membrane. The staining intensity for each cell in a fixed field (typically, 100 cells) of the processed tumor biopsy is determined, and an individual value is attributed to each cell as follows, depending on the cell surface/membrane staining:

0=no staining
1+=weak staining
2+=moderate staining
3+=strong staining

To obtain an H-score, the percentage of tumor cells are multiplied by each intensity and added together. The maximum H-score is 300 if 100% of tumor cells label with 3+ intensity. The H-score is calculated as follows:

$$H\text{-score}=[1\times(\%\text{ cells }1+)+2\times(\%\text{ cells }2+)+3\times(\%\text{ cells }3+)]$$

This protocol results both in cytoplasmic and membrane cMet staining. For the H-score calculations referred to herein, membrane staining was used. The final tumor H-score (0-300) score gives more relative weight to higher-intensity membrane staining (3+ cell>2+ cell>1+ cell). FIG. 20 shows exemplary staining results for various tumor H-scores (15, 90, 180, and 290) obtained with the "cMet ABBV-ADC staining protocol."

Each tumor can also be given an IHC score of IHC 0, IHC 1+, IHC 2+, or IHC 3+. While both the IHC and H scores involve 0, 1+, 2+, and 3+ values they are not to be confused. For the H-score, 0, 1+, 2+, and 3+ values refer to the intensity of staining of an individual cell. For the IHC score, 0, 1+, 2+, and 3+ values refer to the overall staining of a particular area of the tumor sample. FIG. 21 shows exemplary staining results for various tumor IHC0/1+/2+/3+ scores obtained with the "cMet ABBV-ADC staining protocol."

For the purposes on this disclosure, and following the protocol described herein, if none of the cells in a fixed field are stained, the value attributed to the tumor is IHC 0. If the overall level of staining in a fixed field is low, the value attributed is IHC 1+. If most of the cells in a fixed field exhibit moderate staining, the value attributed is IHC 2+. If most of the cells in a fixed field exhibit strong staining, the value attributed is IHC 3+.

In another embodiment, and for the purposes on this disclosure, and following the protocol described herein, if none of the cells in a fixed field are stained, the value attributed to the tumor is IHC 0. If the overall level of staining in a fixed field is low, the value attributed is IHC 1+. If at least 15% of the cells in a fixed field exhibit moderate staining, the value attributed is IHC 2+. If at least 15% of the cells in a fixed field exhibit strong staining, the value attributed is IHC 3+.

For purposes of this disclosure, an H-score between 150 and 224 is equivalent to an IHC score of 2+ and an H-score of 225 and above is equivalent to an IHC score of 3+.

Accordingly, in one aspect, the present disclosure provides ADCs that specifically bind cMet ("anti-cMet ADCs"). The anti-cMet ADCs comprise cytotoxic and/or cytostatic agents linked by way of linkers to an antigen binding moiety that specifically binds cMet. In the case of ABBV-399, the antigen binding moiety (ABT-700) binds cMet at IPT domain 1 of human cMet. In other anti-cMet ADCs, the antigen binding moiety may be any moiety capable of specifically binding cMet. In some embodiments, the antigen binding moiety is an antibody and/or an antibody binding fragment.

In a specific embodiment, a cytotoxic and/or cytostatic agent composing an anti-cMet ADC is a cell-permeating antimitotic agent, such as, for example, an auristatin. Specific examples of cell-permeating auristatins include, but are not limited to, dolastatin-10 and monomethyl auristatin E ("MMAE"). In another specific embodiment, a cytotoxic and/or cytostatic agent composing an anti-cMet ADC is a cell-permeating DNA cross-linking agent, such as a cell-permeating minor groove-binding DNA cross-linking agent. Specific examples of cell-permeating DNA minor groove-binding agents include, but are not limited to, pyrrolobenzodiazepines ("PBD") and PBD dimers.

As will be appreciated by skilled artisans, antibodies and/or binding fragments are "modular" in nature. Throughout the disclosure, various specific embodiments of the various "modules" composing the antibodies and/or binding fragments are described. As specific non-limiting examples, various specific embodiments of $V_H$ CDRs, $V_H$ chains, $V_L$ CDRs and $V_L$ chains are described. It is intended that all of the specific embodiments may be combined with each other as though each specific combination were explicitly described individually.

The ADCs disclosed herein are also "modular" in nature. Throughout the disclosure, various specific embodiments of the "modules" composing the ADCs are described. As non-limiting examples, specific embodiments of antibodies, linkers, and cytotoxic and/or cytostatic agents that may compose the ADCs are described. It is intended that all of the specific embodiments described may be combined with each other as though each specific combination were explicitly described individually.

It will also be appreciated by skilled artisans that the various ADCs described herein may be in the form of salts, and in some specific embodiments, pharmaceutically acceptable salts. The ADCs of the disclosure that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counter ion, e.g., a halide such as a bromide, chloride, or fluoride.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, etc. Base addition salts include those derived from inorganic bases, such as ammonium and alkali or alkaline earth metal hydroxides, carbonates, bicarbonates, and the like.

5.4. Antibodies to cMet

In specific exemplary embodiments, the antigen binding moiety is an antibody or an antigen binding fragment.

As used herein, the term "antibody" (Ab) refers to an immunoglobulin molecule that specifically binds to, or is immunologically reactive with, a particular antigen—here, cMet. Antibodies comprise complementarity determining regions (CDRs), also known as hypervariable regions, in both the light chain and heavy chain variable domains. The more highly conserved portions of the variable domains are called the framework (FR). As is known in the art, the amino acid position/boundary delineating a hypervariable region of an antibody can vary, depending on the context and the various definitions known in the art. Some positions within a variable domain may be viewed as hybrid hypervariable positions in that these positions can be deemed to be within a hypervariable region under one set of criteria, while being deemed to be outside a hypervariable region under a different set of criteria. One or more of these positions can also be found in extended hypervariable regions. The variable domains of native heavy and light chains each comprise four FR regions, largely by adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies. See Kabat et al., Sequences of Proteins of Immunological Interest (National Institute of Health, Bethesda, Md. 1987). As used herein, numbering of immunoglobulin amino acid residues is done according to the immunoglobulin amino acid residue numbering system of Kabat et al. unless otherwise indicated.

Antibodies and/or binding fragments composing the anti-cMet ADCs generally comprise a heavy chain comprising a variable region ($V_H$) having three complementarity determining regions ("CDRs") referred to herein (in N→C order) as $V_H$ CDR#1, $V_H$ CDR#2, and $V_H$ CDR#3, and a light chain comprising a variable region ($V_L$) having three complementarity determining regions referred to herein (in N→C order) as $V_L$ CDR#1, $V_L$ CDR#2, and $V_L$ CDR#3. The amino acid sequences of exemplary CDRs, as well as the amino acid sequence of the $V_H$ and $V_L$ regions of the heavy and light chains of exemplary anti-cMet antibodies and/or binding fragments that can be included in antigen binding moieties composing the anti-cMet ADCs are provided herein. Specific embodiments of anti-cMet ADCs include, but are not limited to, those that comprise antibodies and/or binding fragments that include these exemplary CDRs and/or $V_H$ and/or $V_L$ sequences, as well as antibodies and/or binding fragments that compete for binding cMet with such antibodies and/or binding fragments.

Antibodies may be in the form of full-length antibodies, bispecific antibodies, dual variable domain antibodies, multiple chain or single chain antibodies, surrobodies (including surrogate light chain construct), single domain antibodies, camelized antibodies, scFv-Fc antibodies, and the like. They may be of, or derived from, any isotype, including, for example, IgA (e.g., $IgA_1$ or $IgA_2$), IgD, IgE, IgG (e.g., $IgG_1$, $IgG_2$, $IgG_3$ or $IgG_4$), IgM, or IgY. In some embodiments, the anti-cMet antibody is an IgG (e.g., $IgG_1$, $IgG_2$, $IgG_3$ or $IgG_4$). Antibodies may be of human or non-human origin. Examples of non-human origin include, but are not limited to, mammalian origin (e.g., simians, rodents, goats, and rabbits) or avian origin (e.g., chickens). In specific embodiments, antibodies composing the anti-cMet ADCs are suitable for administration to humans, such as, for example, humanized antibodies and/or fully human antibodies.

Antibodies composing anti-cMet ADCs may be polyclonal, monoclonal, genetically engineered, and/or otherwise modified in nature, including but not limited to, chimeric antibodies, humanized antibodies, human antibodies, primatized antibodies, single chain antibodies, bispecific antibodies, dual-variable domain antibodies, etc. In various embodiments, the antibodies comprise all or a portion of a constant region of an antibody. In some embodiments, the constant region is an isotype selected from: IgA (e.g., $IgA_1$ or $IgA_2$), IgD, IgE, IgG (e.g., $IgG_1$, $IgG_2$, $IgG_3$ or $IgG_4$), IgM, and IgY. In specific embodiments, antibodies composing an anti-cMet ADC comprise an $IgG_1$ constant region isotype.

The term "monoclonal antibody" as used herein is not limited to antibodies produced through hybridoma technology. A monoclonal antibody is derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof. In many uses of the present disclosure, including in vivo use of ADCs including anti-cMet antibodies in humans, chimeric, primatized, humanized, or human antibodies can suitably be used.

The term "chimeric" antibody as used herein refers to an antibody having variable sequences derived from a non-human immunoglobulin, such as a rat or a mouse antibody, and human immunoglobulin constant regions, typically chosen from a human immunoglobulin template. Methods for producing chimeric antibodies are known in the art. See, e.g., Morrison, 1985, Science 229(4719):1202-7; Oi et al., 1986, BioTechniques 4:214-221; Gillies et al., 1985, J. Immunol. Methods 125:191-202; U.S. Pat. Nos. 5,807,715; 4,816,567; and 4,816,397, which are incorporated herein by reference in their entireties.

"Humanized" forms of non-human (e.g., murine) antibodies are chimeric immunoglobulins that contain minimal sequences derived from non-human immunoglobulin. In general, a humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., 1988, Nature 332:323-7; U.S. Pat. Nos. 5,530,101; 5,585, 089; 5,693,761; 5,693,762; and U.S. Pat. No. 6,180,370 to Queen et al.; EP239400; PCT publication WO 91/09967; U.S. Pat. No. 5,225,539; EP592106; EP519596; Padlan, 1991, Mol. Immunol., 28:489-498; Studnicka et al., 1994, Prot. Eng. 7:805-814; Roguska et al., 1994, Proc. Natl. Acad. Sci. 91:969-973; and U.S. Pat. No. 5,565,332, all of which are hereby incorporated by reference in their entireties.

"Human antibodies" are antibodies having the amino acid sequence of a human immunoglobulin and include antibodies isolated from human immunoglobulin libraries or from animals transgenic for one or more human immunoglobulin and that do not express endogenous immunoglobulins. Human antibodies can be made by a variety of methods known in the art including phage display methods using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety. Human antibodies can also be produced using transgenic mice which are incapable of expressing functional endogenous immunoglobulins but which can express human immunoglobulin genes. See, e.g., PCT publications WO 98/24893; WO 92/01047; WO 96/34096; WO 96/33735; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. In addition, companies such as Medarex (Princeton, N.J.), Astellas Pharma (Deerfield, Ill.), Amgen (Thousand Oaks, Calif.) and Regeneron (Tarrytown, N.Y.) can be engaged to provide human antibodies directed against a selected antigen using technology similar to that described above. Fully human antibodies that recognize a selected epitope can be generated using a technique referred to as "guided selection." In this approach, a selected non-human monoclonal antibody, e.g., a mouse antibody, is used to guide the selection of a completely human antibody recognizing the same epitope (see, Jespers et al., 1988, Biotechnology 12:899-903).

"Primatized antibodies" comprise monkey variable regions and human constant regions. Methods for producing primatized antibodies are known in the art. See, e.g., U.S. Pat. Nos. 5,658,570; 5,681,722; and 5,693,780, which are incorporated herein by reference in their entireties.

Anti-cMet ADCs may comprise full-length (intact) antibody molecules, as well as antigen binding fragments that are capable of specifically binding cMet. Examples of antibody binding fragments include by way of example and not limitation, Fab, Fab', F(ab')$_2$, Fv fragments, single chain Fv fragments and single domain fragments.

A Fab fragment contains the constant domain of the light chain and the first constant domain ($CH_2$) of the heavy chain. Fab' fragments differ from Fab fragments by the addition of a few residues at the carboxyl terminus of the heavy chain $CH_2$ domain including one or more cysteines from the antibody hinge region. F(ab') fragments are produced by cleavage of the disulfide bond at the hinge cysteines of the F(ab')$_2$ pepsin digestion product. Additional chemical couplings of antibody fragments are known to those of ordinary skill in the art. Fab and F(ab')$_2$ fragments lack the Fc fragment of intact antibody, clear more rapidly from the circulation of animals, and may have less non-specific tissue binding than an intact antibody (see, e.g., Wahl et al., 1983, J. Nucl. Med. 24:316).

An "Fv" fragment is the minimum fragment of an antibody that contains a complete target recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Often, the six CDRs confer antigen binding specificity upon the antibody. However, in some instances even a single variable domain (or half of an Fv comprising only three CDRs specific for a target) may have the ability to recognize and bind antigen, although at a lower affinity than the entire binding site.

"Single-chain Fv" or "scFv" antibody binding fragments comprise the $V_H$ and $V_L$ domains of an antibody, where these domains are present in a single polypeptide chain. Generally, the Fv polypeptide further comprises a polypeptide linker between the $V_H$ and $V_L$ domains which enables the scFv to form the desired structure for antigen binding.

Antibodies and/or binding fragments composing the anti-cMet ADCs may include modifications and/or mutations that alter the properties of the antibodies and/or fragments, such as those that increase half-life, increase or decrease ADCC, etc., as is known in the art.

"Single domain antibodies" are composed of a single $V_H$ or $V_L$ domains which exhibit sufficient affinity to cMet. In a specific embodiment, the single domain antibody is a camelized antibody (See, e.g., Riechmann, 1999, Journal of Immunological Methods 231:25-38).

Antibodies composing the anti-cMet ADCs may also be bispecific antibodies. Bispecific antibodies comprised of monoclonal, often human or humanized, antibodies that have binding specificities for two different epitopes on the same or different antigens. In the present disclosure, one of the binding specificities can be directed towards cMet, the other can be for any other antigen, e.g., for a cell-surface protein, receptor, receptor subunit, tissue-specific antigen, virally derived protein, virally encoded envelope protein, bacterially derived protein, or bacterial surface protein, etc.

Antibodies composing anti-cMet ADCs may be derivatized. Derivatized antibodies are typically modified by glycosylation, acetylation, pegylation, phosphorylation, amidation, derivatization by known protecting/blocking groups, proteolytic cleavage, linkage to a cellular ligand or other protein. Any of numerous chemical modifications may be carried out by known techniques, including, but not limited to, specific chemical cleavage, acetylation, formylation, metabolic synthesis of tunicamycin, etc. Additionally, the derivative may contain one or more non-natural amino acids, e.g., using ambrx technology. See, e.g., Wolfson, 2006, Chem. Biol. 13(10):1011-2.

Antibodies or binding fragments composing anti-cMet ADCs may be antibodies or fragments whose sequences have been modified to alter at least one constant region-mediated biological effector function. For example, in some embodiments, an anti-cMet antibody may be modified to reduce at least one constant region-mediated biological effector function relative to the unmodified antibody, e.g., reduced binding to the Fc receptor (FcγR). FcγR binding may be reduced by mutating the immunoglobulin constant region segment of the antibody at particular regions necessary for FcγR interactions (See, e.g., Canfield and Morrison, 1991, J. Exp. Med. 173:1483-1491; and Lund et al., 1991, J. Immunol. 147:2657-2662). Reducing FcγR binding may also reduce other effector functions which rely on FcγR interactions, such as opsonization, phagocytosis and antigen-dependent cellular cytotoxicity ("ADCC").

Antibodies included in anti-cMet ADCs may have low levels of, or lack, fucose. Antibodies lacking fucose have been correlated with enhanced ADCC activity, especially at low doses of antibody. See Shields et al., 2002, J. Biol. Chem. 277:26733-26740; Shinkawa et al., 2003, J. Biol. Chem. 278:3466-73. Methods of preparing fucose-less antibodies include growth in rat myeloma YB2/0 cells (ATCC CRL 1662). YB2/0 cells express low levels of FUT8 mRNA, which encodes α-1,6-fucosyltransferase, an enzyme necessary for fucosylation of polypeptides.

Antibodies or binding fragments composing anti-cMet ADCs may include modifications that increase or decrease their binding affinities to the neonatal Fc receptor, FcRn, for example, by mutating the immunoglobulin constant region segment at particular regions involved in FcRn interactions (see, e.g., WO 2005/123780). In particular embodiments, an anti-cMet antibody of the IgG class is mutated such that at least one of amino acid residues 250, 314, and 428 of the heavy chain constant region is substituted alone, or in any combinations thereof, such as at positions 250 and 428, or at positions 250 and 314, or at positions 314 and 428, or at positions 250, 314, and 428, with substitution at positions 250 and 428 being a specific combination. For position 250, the substituting amino acid residue may be any amino acid residue other than threonine, including, but not limited to, alanine, cysteine, aspartic acid, glutamic acid, phenylalanine, glycine, histidine, isoleucine, lysine, leucine, methionine, asparagine, proline, glutamine, arginine, serine, valine, tryptophan, or tyrosine. For position 314, the substituting amino acid residue may be any amino acid residue other than leucine, including, but not limited to, alanine, cysteine, aspartic acid, glutamic acid, phenylalanine, glycine, histidine, isoleucine, lysine, methionine, asparagine, proline, glutamine, arginine, serine, threonine, valine, tryptophan, or tyrosine. For position 428, the substituting amino acid residues may be any amino acid residue other than methionine, including, but not limited to, alanine, cysteine, aspartic acid, glutamic acid, phenylalanine, glycine, histidine, isoleucine, lysine, leucine, asparagine, proline, glutamine, arginine, serine, threonine, valine, tryptophan, or tyrosine. Specific combinations of suitable amino acid substitutions are identified in TABLE 1 of U.S. Pat. No. 7,217,797, which is incorporated herein by reference. Such mutations increase binding to FcRn, which protects the antibody from degradation and increases its half-life.

An anti-cMet antibody and/or binding fragment may have one or more amino acids inserted into one or more of its hypervariable regions, for example as described in Jung & Plückthun, 1997, Protein Engineering 10:9, 959-966; Yazaki et al., 2004, Protein Eng. Des Sel. 17(5):481-9; and U.S. Pat. App. No. 2007/0280931.

Anti-cMet antibodies and/or binding fragments with high affinity for cMet may be desirable for therapeutic uses. Accordingly, the present disclosure contemplates ADCs comprising anti-cMet antibodies and/or binding fragments having a high binding affinity to cMet. In specific embodiments, the antibodies and/or binding fragments bind cMet with an affinity of at least about 100 nM, but may exhibit higher affinity, for example, at least about 90 nM, 80 nM, 70 nM, 60 nM, 50 nM, 40 nM, 30 nM, 25 nM, 20 nM, 15 nM, 10 nM, 7 nM, 6 nM, 5 nM, 4 nM, 3 nM, 2 nM, 1 nM, 0.1 nM, 0.01 nM, or even higher. In some embodiments, the antibodies bind cMet with an affinity in the range of about 1 pM to about 100 nM, or an affinity ranging between any of the foregoing values.

Affinity of antibodies and/or binding fragments for cMet can be determined using techniques well known in the art or described herein, such as for example, but not by way of limitation, ELISA, isothermal titration calorimetry (ITC), surface plasmon resonance, flow cytometry or fluorescent polarization assays. In one embodiment, affinity refers to apparent affinity EC50 values measured according to Example 5.

In the context of this disclosure, anti-cMet antibodies can serve at least two different purposes. In some embodiments, the anti-cMet antibodies are used for diagnostic purposes, assisting in and guiding patient selection. For example, these anti-cMet antibodies can be used for immunohistochemistry assays of tumor biopsies obtained from the patients to be treated or under treatment. One of ordinary skill in the art is familiar with the techniques for selecting a particular antibody for diagnostic purposes to assay for the levels of cMet protein expression in tumor biopsies. Typically, the samples are scored under one or more scoring guides, including IHC scores of 0/1+/2+/3+ or H-scores. The disclosure details one example of such a diagnostic assay that is commercially available from Ventana. The Ventana antibody SP44, and antibodies with similar properties can be made or acquired from other vendors and the protocol adjusted so that the method has the same or better diagnostic power as the Ventana assay. In addition, anti-cMet antibodies other than SP44 can also be used for this purpose. One of ordinary skill in the art would know how to properly adjust the protocol to a new antibody in order to obtain a diagnostic test for cMet expression levels. Companion diagnostics exist for a variety of other FDA approved cancer treatments and are within the level of ordinary skill. The FDA maintains a list of FDA-approved companion diagnostic tests at, for example, www.fda.gov/.

Examples of anti-cMet antibodies that can be used include, for example, the diagnostic antibodies disclosed in U.S. Pat. No. 8,673,302 (224D10 and 221C9) and U.S. Pat. No. 9,120,852 (227D3 and 205A5). The disclosures of each of these patents are fully incorporated herein by reference, including the amino acid sequences for the CDRs, heavy chains (full and variable regions), and light chains (full and variable regions). In one embodiment, the antibody is 227D3.

227D3 is secreted by the hybridoma deposited at the CNCM on Nov. 18, 2009, under number 1-4247.

| Antibody | CDR numbering | Heavy chain | Light chain | SEQ ID NO. |
|---|---|---|---|---|
| 227D3 | IMGT | | CDR-L1 | 159 |
| | | | CDR-L2 | 160 |
| | | | CDR-L3 | 161 |
| | | CDR-H1 | | 162 |
| | | CDR-H2 | | 163 |
| | | CDR-H3 | | 164 |
| 227D3 | Kabat | | CDR-L1 | 165 |
| | | | CDR-L2 | 166 |
| | | | CDR-L3 | 161 |
| | | CDR-H1 | | 167 |
| | | CDR-H2 | | 168 |
| | | CDR-H3 | | 169 |

In other embodiments, the anti-cMet antibodies are administered for treatment purposes, either as components of antibody drug conjugates (ADCs), or before/after/concurrently with administration of the ADCs.

5.6.1 ABT-700 and Related Antibodies for Treatment Purposes

For purposes of the antibodies of this section, the CDRs have been identified according to the IMGT numbering system.

ABBV-399 is an ADC comprised of the cMet targeting antibody ABT-700 (PR-1266688, h224G11) conjugated to the potent cytotoxin MMAE through a valine citrulline (vc) linker. The ADC binds to cMet on the surface of tumor cells, is internalized, and then releases MMAE leading to the inhibition of microtubule function and the disruption of critical cellular processes and death. ABBV-399 is potently cytotoxic to cancer cells with overexpress cMet or amplified MET and demonstrates antitumor activity in human tumor xenografts. Activity of ABBV-399 against ABT-700-refractory tumors has also been demonstrated (see e.g., Example 14).

ABT-700

ABT-700 is a humanized version of mouse monoclonal antibody 224G11, which was first disclosed and embodimented in U.S. Pat. No. 8,329,173. ABT-700 is a "humanized" recombinant IgG 1K (disclosed as 224G11 [TH7 Hz3] in U.S. Pat. No. 8,741,290) that targets a unique epitope of cMet located within the immunoglobulin-plexin-transcription factor homology (IPT) domain 1, resulting in blockade of both HGF-dependent and HGF-independent cMet signaling. ABT-700 competes for binding to cMet with antibodies directed against SEMA blade 5 (and vice versa), but not with antibodies directed against blades 1-3 or IPT 2-3. In contrast, 5D5 (the bivalent progenitor of one armed onartuzumab, discussed below) binds to blade 5 of the SEMA domain.

The cMet-ADCs of this disclosure encompass any antibody that comprises a heavy chain comprising CDR-H1, CDR-H2 and CDR-H3 comprising respectively the amino acid sequence SEQ ID Nos. 1, 2 and 3; and a light chain comprising CDR-L1, CDR-L2 and CDR-L3 comprising respectively the amino acid sequence SEQ ID Nos. 5, 6, and 7, according to U.S. Pat. No. 8,741,290. These are the CDRs of the original murine 224G11 antibody, as defined based on the IMGT numbering system.

As defined under the IMGT nomenclature, the CDR sequences of ABT-700 comprise the following sequences:

```
CDR-H1:
                                           (SEQ ID NO: 72)
GYIFTAYT

CDR-H2:
                                           (SEQ ID NO: 73)
IKPNNGLA

CDR-H3:
                                           (SEQ ID NO: 74)
ARSEITTEFDY

CDR-L1:
                                           (SEQ ID NO: 75)
ESVDSYANSF

CDR-L2:
                                           (SEQ ID NO: 76)
RAS

CDR-L3:
                                           (SEQ ID NO: 77)
QQSKEDPLT
```

In one embodiment, the heavy chain variable region of 224G11 [TH7 Hz3] comprises SEQ ID No. 4 of U.S. Pat. No. 8,741,290:

```
                                           (SEQ ID NO: 78)
QVQLVQSGAEVKKPGASVKVSCKASGYIFTAYTMHWVRQAPGQGLEWMGW

IKPNNGLANYAQKFQGRVTMTRDTSISTAYMELSRLRSDDTAVYYCARSE

ITTEFDYWGQGTLVTVSS;
``` and the light chain variable region comprises SEQ ID No. 10 of U.S. Pat. No. 8,741,290: DIVMTQSPDSLAVSLGERATINCKSSESVDSYANSFLHWYQQKPGQPPK LLIYRASTRESGVPDRFSGSGSGTDFTLTISSLQAEDVAVYYCQQSKED PLTFGGGTKVEIKR (SEQ ID NO: 79)

In another embodiment, the heavy chain variable region of 224G11 [TH7 Hz3] comprises:

```
                                           (SEQ ID NO: 80)
QVQLVQSGAEVKKPGASVKVSCKASGYIFTAYTMHWVRQAPGQGLEWMG

WIKPNNGLANYAQKFQGRVTMTRDTSISTAYMELSRLRSDDTAVYYCAR

SEITTEFDYWGQGTLVTVSS;
``` and the light chain variable region comprises:

```
                                           (SEQ ID NO: 81)
DIVMTQSPDSLAVSLGERATINCKSSESVDSYANSFLHWYQQKPGQPPK

LLIYRASTRESGVPDRFSGSGSGTDFTLTISSLQAEDVAVYYCQQSKED

PLTFGGGTKVEIK
```

In another embodiment, the antibody [224G11] [TH7 Hz3] comprises a complete heavy chain comprising the amino acid sequence SEQ ID No. 37 of U.S. Pat. No. 8,741,290 and a complete light chain comprising the amino acid sequence SEQ ID No. 40 of U.S. Pat. No. 8,741,290. The modified hinge region has the sequence of SEQ ID NO: 170.

In some embodiments, the anti-cMet antibody comprises a heavy chain variable region comprising SEQ ID No. 4 of U.S. Pat. No. 8,741,290:

QVQLVQSGAEVKKPGASVKVSCKASGYIFTAYTM-HWVRQAPGQGLEWMG WIKPNNGLANYAQK-FQGRVTMTRDTSISTAYMELSRLRSDDTAVYYCAR SEITTEFDYWGQGTLVTVSS (SEQ ID NO: 78) linked to any heavy chain constant region;

and a light chain variable region comprising SEQ ID No. 10 of U.S. Pat. No. 8,741,290: DIVMTQSPDSLAVSLGER-ATINCKSSESVDSYANSFLHWYQQKPGQPPK LLI-YRASTRESGVPDRFSGSGSGTDFTLTISSLQAEDVA-VYYCQQSKED PLTFGGGTKVEIKR (SEQ ID NO: 79) linked to any light chain constant region. Examples of suitable heavy and light chain constant regions are provided below.

In some embodiments, the anti-cMet antibody comprises a heavy chain variable region comprising SEQ ID No. 4 of U.S. Pat. No. 8,741,290:

QVQLVQSGAEVKKPGASVKVSCKASGYIFTAYTM-HWVRQAPGQGLEWMG WIKPNNGLANYAQK-FQGRVTMTRDTSISTAYMELSRLRSDDTAVYYCAR SEITTEFDYWGQGTLVTVSS (SEQ ID NO: 80) linked to any heavy chain constant region;

and a light chain variable region comprising: DIVMTQSPDSLAVSLGERATINCKSSESVDSYANSFL-HWYQQKPGQPPK LLIYRASTRESGVPDRFSGSGS-GTDFTLTISSLQAEDVAVYYCQQSKED PLTFGGGTK-VEIK (SEQ ID NO: 81) linked to any light chain constant region. Examples of suitable heavy and light chain constant regions are provided below.

In some embodiments, an anti-cMet antibody and/or binding fragment composing an anti-cMet ADC is an IgG₁.

In some embodiments, an anti-cMet antibody composing an anti-cMet ADC comprises a heavy chain having a constant region comprising or consisting of:

(SEQ ID NO: 82)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDCHCPPCPAPELLGGPSVF LFPPKPKDTLMISRTPEVTCVVVDVSH

EDPEVKFNWYVDGVEVHNAKTKPREEQYNSTYRVVSVLTVLHQ DWLNGK

EYKCKVSNKALPAPIEKTISKAKGQPREPQVYTLPPSREEMTKNQVSLTC

LVKG FYPSDIAVEWESNGQPENNYKTTPPVLDSDGSFFLYSKLTVDKSR

WQQGNVFSCSVMHEALHNHYTQKSLSLSPG

In some embodiments, an anti-cMet antibody composing an anti-cMet ADC comprises a light chain having a constant region comprising or consisting of:

(SEQ ID NO: 83)
RTVAAPSVFIFPPSDEQLKSGTASVVCLLNNFYPREAKVQWKVDNALQSG

NSQESVTEQ DSKDSTYSLS STLTLSKADYEKHKVYACEVTHQGLSSPV

TKSFNRGEC

In some embodiments, an anti-cMet antibody composing an anti-cMet ADC comprises a heavy chain having a constant region comprising or consisting of:

(SEQ ID NO: 84)
ASTKGPSVFPLAPSSKSTSGGTAALGCLVKDFPEPVTVSWNSGALTSGVH

TFPAVLQSSGL YSLSSVVTVPSSSLGTQTYICNVNHKPSNTKVDKRVEP

KSCDCHCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKEY

KCKVSNKALPAPIEKTISKAKGQPREPQVYTLPPSREEMTKNQVSLTCLV

KGFYPSDIAVEWESNGQPENNYKTTPPVLDSDGSFFLYSKLTVDKSRWQQ

GNVFSCSVMHEALHNHYTQKSLSLSPGK and a light chain having a constant region comprising or consisting of:

(SEQ ID NO: 85)
TVAAPSVFIFPPSDEQLKSGTASVVCLLNNFYPREAKVQWKVDNALQSGN

SQESVTEQ DSKDSTYSLS STLTLSKADYEKHKVYACEVTHQGLSSPVT

KSFNRGEC

In some embodiments, the heavy chain of an anti-cMet antibody (ABT-700) composing an anti-cMet ADC comprises or consists of (constant regions are bold; CDRs are underlined (Kabat-numbered CDR sequences disclosed as SEQ ID NOS 112-114, respectively, in order of appearance)):

```
(full-length sequence disclosed as SEQ ID NO: 86)
QVQLVQSGAE VKKPGASVKV SCKASGYIFT AYTMHWVRQA PGQGLEWMGW      050

IKPNNGLANY AQKFQGRVTM TRDTSISTAY MELSRLRSDD TAVYYCARSE      100

ITTEFDYWGQ GTLVTVSSAS TKGPSVFPLA PSSKSTSGGT AALGCLVKDY      150

FPEPVTVSWN SGALTSGVHT FPAVLQSSGL YSLSSVVTVP SSSLGTQTYI      200

CNVNHKPSNT KVDKRVEPKS CDCHCPPCPA PELLGGPSVF LFPPKPKDTL      250

MISRTPEVTC VVVDVSHEDP EVKFNWYVDG VEVHNAKTKP REEQYNSTYR      300

VVSVLTVLHQ DWLNGKEYKC KVSNKALPAP IEKTISKAKG QPREPQVYTL      350

PPSREEMTKN QVSLTCLVKG FYPSDIAVEW ESNGQPENNY KTTPPVLDSD      400

GSFFLYSKLT VDKSRWQQGN VFSCSVMHEA LHNHYTQKSL SLSPG           445
``` and the light chain comprises or consists of CDR sequences disclosed as SEQ ID NOS 115-117, respectively, in order of appearance):

```
(full-length sequence disclosed as SEQ ID NO: 87)
DIVMTQSPDS LAVSLGERAT INCKSSESVD SYANSFLHWY QQKPGQPPKL      050

LIYRASTRES GVPDRFSGSG SGTDFTLTIS SLQAEDVAVY YCQQSKEDPL      100

TFGGGTKVEI KRTVAAPSVF IFPPSDEQLK SGTASVVCLL NNFYPREAKV      150

QWKVDNALQS GNSQESVTEQ DSKDSTYSLS STLTLSKADY EKHKVYACEV      200

THQGLSSPVT KSFNRGEC                                         218
```

In some embodiments, the heavy chain of an anti-cMet antibody composing an anti-cMet ADC comprises or consists of a variable region (amino acids 1-118 of SEQ ID NO: 88), a constant region (shown in bold) and CDRs (underlined; CDR sequences disclosed as SEQ ID NOS 118-120, respectively, in order of appearance):

(full-length heavy chain sequence disclosed as SEQ ID NO: 88)
```
QVQLVQSGAE VKKPGASVKV SCKASGYIFT AYTMHWVRQA PGQGLEWMGW    050

IKPNNGLANY AQKFQGRVTM TRDTSISTAY MELSRLRSDD TAVYYCARSE    100

ITTEFDYWGQ GTLVTVSSAS TKGPSVFPLA PSSKSTSGGT AALGCLVKDY    150

FPEPVTVSWN SGALTSGVHT FPAVLQSSGL YSLSSVVTVP SSSLGTQTYI    200

CNVNHKPSNT KVDKRVEPKS CDCHCPPCPA PELLGGPSVF LFPPKPKDTL    250

MISRTPEVTC VVVDVSHEDP EVKFNWYVDG VEVHNAKTKP REEQYNSTYR    300

VVSVLTVLHQ DWLNGKEYKC KVSNKALPAP IEKTISKAKG QPREPQVYTL    350

PPSREEMTKN QVSLTCLVKG FYPSDIAVEW ESNGQPENNY KTTPPVLDSD    400

GSFFLYSKLT VDKSRWQQGN VFSCSVMHEA LHNHYTQKSL SLSPGK        446
``` and the light chain comprises or consists of a variable region (amino acids 1-110 in SEQ ID NO: 89), a constant region (shown in bold), and CDR sequences (underlined and disclosed as SEQ ID NOS 121-123, respectively, in order of appearance):

(full-length light chain sequence disclosed as SEQ ID NO: 89)
```
DIVMTQSPDS LAVSLGERAT INCKSSESVD SYANSFLHWY QQKPGQPPKL    050

LIYRASTRES GVPDRFSGSG SGTDFTLTIS SLQAEDVAVY YCQQSKEDPL    100

TFGGGTKVEI KRTVAAPSVF IFPPSDEQLK SGTASVVCLL NNFYPREAKV    150

QWKVDNALQS GNSQESVTEQ DSKDSTYSLS STLTLSKADY EKHKVYACEV    200

THQGLSSPVT KSFNRGEC                                      218
```

In one embodiment, the antibody is ABT-700 and the heavy chain is encoded by the following nucleotide sequence (full-length sequence disclosed as SEQ ID NO: 90):

ATGGGATGGTCTTGGATCTTTCTGCTGTTTCTGTCTGGTACTGCTGGTGT

GCTGAGCcaggtccagctggtgcaatccggcgcagaggtgaagaagccag gcgcttccgtgaaggtgagctgtaaggcctct<u>ggctacatcttcacagca</u>

<u>tacaccatgcac</u>tgggtgaggcaagctcctgggcagggactggagtggat ggga<u>tggattaaacccaacaatgggctggccaactacgcccagaaattcc</u>

<u>agggt</u>agggtcactatgacaagggataccagcatcagcaccgcatatatg gagctgagcaggctgaggtctgacgacactgctgtctattattgcgccag <u>gagcgaaattacaacagaattcgattac</u>gggggcagggcaccctggtga ccgtgtcctctgccagcaccaagggcccaagcgtgttccccctggccccc agcagcaagagcaccagcggcggcacagccgccctgggctgcctggtgaa ggactacttccccgagcccgtgaccgtgtcctggaacagcggagccctca cttctggagttcataccttcccagcagtattgcagagcagtggcctgtat tcactgtcttccgtcgtaacagttccatcctccagcctcgggacacagac ttacatttgtaacgtgaatcacaagcctagcaacaccaaggtcgacaaga gagttgaaccaaagagttgtgattgccactgtcctccctgcccagctcct gagctgcttggcggtcccagtgtcttcttgtttccccctaaacccaaga caccctgatgatctcaaggactcccgaggtgacatgcgtggtggtggatg tgtctcatgaggacccagaggtgaagttcaactggtacgtggacggcgtg gaggtgcacaacgccaagaccaagcccagagaggagcagtacaacagcac ctacagggtggtgtccgtgctgaccgtgctgcaccaggactggctgaacg gcaaggagtacaagtgtaaggtgtccaacaaggccctgccagccccaatc gaaaagaccatcagcaaggccaagggccagccaagagagccccaggtgta caccctgccacccagcagggaggagatgaccaagaaccaggtgtccctga cctgtctggtgaagggcttctacccaagcgacatcgccgtggagtgggag agcaacggccagcccgagaacaactacaagaccacccccccagtgctgga cagcgacggcagcttcttcctgtacagcaagctgaccgtggacaagagca gatggcagcagggcaacgtgttcagctgctccgtgatgcacgaggccctg cacaaccactacacccagaagagcctgagcctgtcccccaggctga Secretion signal peptide in bold CAPITAL letters.
Includes final stop codon (TGA)
Constant region is bold
CDRs are underlined (CDR sequences disclosed as SEQ ID NOS 124-126, respectively, in order of appearance)

In one embodiment, the antibody is ABT-700 and the light chain is encoded by the following nucleotide sequence (full-length sequence disclosed as SEQ ID NO: 91):

ATGGAAACTGATACACTGCTGCTGTGGGTCCTGCTGCTGTGGGTCCCTGG

AAGCACAGGGgacattgtgatgacccagtctcccgatagcctggccgtgt ccctgggcgagagggctaccatcaactgt<u>aaaagctccgaatctgtggac</u>

<u>tcttacgcaaacagctttctgcac</u>tggtatcagcaaaagccaggccaacc

-continued

```
tccaaagctgctgatttacagggcttctaccagggagagcggcgtgcccg ataggttcagcggatctggcagcggcaccgactttacactgaccatctcc agcctgcaggccgaagatgtggcagtctattactgccagcagtccaagga ggaccccctgactttcgggggtggtactaaagtggagatcaagcgtacgg tggccgctcccagcgtgttcatcttcccccaagcgacgagcagctgaag agcggcaccgccagcgtggtgtgtctgctgaacaacttctaccccaggga ggccaaggtgcagtggaaggtggacaacgccctgcagagcggcaacagcc aggagagcgtcaccgagcaggacagcaaggactccacctacagcctgagc agcaccctgaccctgagcaaggccgactacgagaagcacaaggtgtacgc ctgtgaggtgacccaccagggcctgtccagccccgtgaccaagagcttca acaggggcgagtgctga
```

Secretion signal peptide in bold CAPITAL letters.

Includes final stop codon (tga)

Constant region is bold

CDRs are underlined (CDR sequences disclosed as SEQ ID NOS 127-129, respectively, in order of appearance)

In one embodiment, herein referred to as ABBV399, the antibody heavy chain sequence is represented by SEQ ID NO:88, the light chain sequence is represented by SEQ ID NO:89 conjugated to monomethyl auristatin E (MMAE) through a valine citrulline (vc) linker.

The sequence of ABT-700 PBD, comprising the sequence of ABT-700 carrying a S238C mutation (also referred to herein as ABT-700 (S238C)-PBD) according to Kabat numbering, is as follows (CDRs are underlined; the numbering system is Kabat; and the S238C mutation is represented by C (bold, italics, and underlined):

Amino Acid Sequence (10 AA Per Group, 5 Groups Per Line)

Heavy Chain (SEQ ID NO: 171) (Underlined CDR Sequences Disclosed as SEQ ID NOS 173-175, Respectively, in Order of Appearance):

```
QVQLVQSGAE VKKPGASVKV SCKASGYIFT AYTMHWVRQA PGQGLEWMGW      50

IKPNNGLANY AQKFQGRVTM TRDTSISTAY MELSRLRSDD TAVYYCARSE    100

ITTEFDYWGQ GTLVTVSSAS TKGPSVFPLA PSSKSTSGGT AALGCLVKDY    150

FPEPVTVSWN SGALTSGVHT FPAVLQSSGL YSLSSVVTVP SSSLGTQTYI    200

CNVNHKPSNT KVDKRVEPKS CDCHCPPCPA PELLGGPCVF LFPPKPKDTL    250

MISRTPEVTC VVVDVSHEDP EVKFNWYVDG VEVHNAKTKP REEQYNSTYR    300

VVSVLTVLHQ DWLNGKEYKC KVSNKALPAP IEKTISKAKG QPREPQVYTL    350

PPSREEMTKN QVSLTCLVKG FYPSDIAVEW ESNGQPENNY KTTPPVLDSD    400

GSFFLYSKLT VDKSRWQQGN VFSCSVMHEA LHNHYTQKSL SLSPG         445
```

Light Chain (SEQ ID NO: 172) (Underlined CDR Sequences Disclosed as SEQ ID NOS 176-178, Respectively, in Order of Appearance):

```
DIVMTQSPDS LAVSLGERAT INCKSSESVD SYANSFLHWY QQKPGQPPKL     50

LIYRASTRES GVPDRFSGSG SGTDFTLTIS SLQAEDVAVY YCQQSKEDPL    100

TFGGGTKVEI KRTVAAPSVF IFPPSDEQLK SGTASVVCLL NNFYPREAKV    150

QWKVDNALQS GNSQESVTEQ DSKDSTYSLS STLTLSKADY EKHKVYACEV    200

THQGLSSPVT KSFNRGEC                                      218
```

Accordingly, the antibody ABT-700 PBD comprises two PBD drug-linker molecules conjugated to a cys engineered mAb ABT-700 (S238C), and has a heavy chain of SEQ ID NO: 171 and a light chain of SEQ ID NO: 172.

In one embodiment, the C-terminal lysine amino acid on the heavy chain of 224G11 [TH7 Hz3] was engineered out to eliminate heterogeneity at the C-terminus due to incomplete cleavage of the lysine. In ABT-700, the heavy chain is post-translationally modified by addition of N-linked glycans to asparagine-296. The major glycans are fucosylated biantennary oligosaccharides containing zero, one, or two galactose residues. In addition, at the N-terminus of the heavy chain is a glutamine residue, which can undergo spontaneous cyclization to form a pyroglutamate residue.

The original murine 224G11 antibody has been further chimerized and humanized. The chimerization and humanization processes are described in detail in U.S. Pat. No. 8,741,290 and those process are incorporated herein by reference in their entirety, as are the descriptions of the biological and structural properties of all of the antibodies described therein. During the humanization process of the murine 224G11 antibody, the chimeric form of 224G11 Mab (224G11chim/IgG1), meaning variable domain (VH+VL) from m224G11 combined with human constant domain IgG1/kappa yielded strong (17% of maximal HGF effect) agonist activity associated with a reduced antagonist efficacy (54% inhibition of HGF maximal effect compared to the m224G11 that yields 75% inhibition of HGF maximum effect). Three humanized forms of 224G11 Mab, [224G11] Hz1/IgG1, [224G11]Hz2/IgG1 and [224G11]Hz3/IgG1, also constructed on a human IgG1/kappa backbone, yielded also decreased antagonist efficacy and significant agonist activity (11 to 24% of maximal HGF level) as compared to mouse 224G11.

The hinges of some of the humanized forms of the 224G11 antibody were modified, as described in detail in the U.S. Pat. No. 8,741,290, and incorporated herein by reference. The resulting antibodies, whose ADCs are also within the scope of this disclosure, included 224G11 [TH7Hz3].

The antibody h224G11/ABT-700 refers to the humanized form 224G11 [TH7 Hz3]. This antibody represents the ABT-700 antibody that is part of the ABBV-399 of this disclosure. The biological activities of the antibody ABT-700, or h224G11, were extensively characterized in U.S. Pat. No. 8,741,290. Its biological characterizations therein are incorporated herein by reference in their entireties. The entire description of U.S. Pat. No. 8,741,290 is incorporated herein by reference.

Exemplary versions of other chimerized and humanized versions of 224G11 antibody drug conjugates that fall within the scope of this disclosure are those referred to in the U.S. Pat. No. 8,741,290 as the antibodies [224G11] [IgG2Hz1], [224G11] [IgG2Hz2]; [224G11] [IgG2Hz3]; [224G11] [TH7Hz1]; [224G11] [TH7z2]; [224G11] [TH7Hz3]; [224G11] [IgG2chim]; [224G11][TH7chim]; [224G11] [C1]; [224G11] [C2]; [224G11] [C3]; [224G11] [C5]; [224G11] [C6]; [224G11][C7]; [224G11] [C8]; and [224G11] [C9].

Other examples include the antibodies [224G11] [Δ1-3]; [224G11] [C7Δ6]; [224G11][C6Δ9]; [224G11] [C2Δ5-7]; [224G11] [C5Δ2-6]; [224G11] [C9Δ2-7]; [224G11] [Δ5-6-7-8]; [224G11][IgG1/IgG2]; [224G11] [IgG2Hz1]; [224G11] [IgG2Hz2]; [224G11] [IgG2Hz3]; [224G11] [TH7Hz1]; [224G11] [TH7Hz2]; [224G11] [TH7Hz3]; [224G11] [TH7chim]; [224G11][MHchim]; [224G11] [MUP9Hchim]; and [224G11] [MMCHchim].

In both of these series of antibodies, the first bracket refers to the name of the antibody that is modified (i.e., 224G11) and the second bracket identifies the specific modification of the antibody, most of which correspond to changes to the hinge region, according to the IMGT unique numbering for C-domains. The symbol Δ means deletion. The specific details of each modification can be found in U.S. Pat. No. 8,741,290.

Accordingly, in some embodiments, an anti-cMet antibody and/or binding fragment comprising an anti-cMet ADC is suitable for administration to humans. In a specific embodiment, the anti-cMet antibody is humanized.

In some embodiments, anti-cMet antibodies and/or binding fragments comprising an anti-anti-cMet ADC compete for binding cMet on cells expressing cMet, or the immunoglobulin-plexin-transcription factor homology (IPT) of human cMet, or to Met-Fc or engineered/recombinant cMet in solid phase, in in vitro assays with a reference antibody. The reference antibody may be any antibody that specifically binds the immunoglobulin-plexin-transcription factor homology (IPT) of human cMet. In one specific embodiment, the reference antibody is mouse 224G11. In another specific embodiment, the reference antibody is ABT-700.

Assays for competition include, but are not limited to, a radioactive material labeled immunoassay (RIA), an enzyme-linked immunosorbant assay (ELISA), a sandwich ELISA, flow cytometry assays and surface plasmon resonance assays. A preferred method is that described in Basilico C, Hultberg A, Blanchetot C, de Jonge N, Festjens E, Hanssens V, Osepa S I, De Boeck G, Mira A, Cazzanti M, Morello V, Dreier T, Saunders M, de Haard H, Michieli P. Four individually druggable MET hotspots mediate HGF-driven tumor progression. J Clin Invest. 2014 July; 124(7): 3172-86. doi: 10.1172/JCI72316. Epub 2014 May 27.

In one exemplary embodiment of conducting an antibody competition assay between a reference antibody and a test antibody (irrespective of species or isotype), one may first label the reference with a detectable label, such as a fluorophore, biotin or an enzymatic, or radioactive label to enable subsequent detection. In this case, cells expressing cMet or the extracellular domain of cMet (or a subpart thereof), are incubated with unlabeled test antibody, labeled reference antibody is added, and the intensity of the bound label is measured. If the test antibody competes with the labeled reference antibody by binding to the same, proximal or overlapping epitope, the intensity of the detection signal will be decreased relative to a control reaction carried out without test antibody.

In a specific embodiment of this assay, the concentration of labeled reference antibody that yields 80% of maximal binding ("$conc_{80\%}$") under the assay conditions (e.g., a specified density of cells or a specified concentration of cMet/cMet extracellular domain or subpart thereof) is first determined, and a competition assay is carried out with 10× $concentration_{80\%}$ of unlabeled test antibody and $conc_{80\%}$ of labeled reference antibody.

In another exemplary embodiment of conducting a flow cytometry competition assay, cells expressing cMet are incubated with a titration series of antibodies comprising increasing concentrations of unlabeled test antibody versus fluorescently labeled anti-cMet reference antibody. The labeled reference anti-cMet antibody is used at a fixed concentration X (for example, X=1 µg/ml) and the unlabeled test antibody is used in a range of concentrations (for example, from $10^{-4}$X to 100X). Cells or cMet/cMet extracellular domain or subpart thereof is incubated with both unlabeled test antibody and labeled reference antibody concurrently. Flow cytometry data is normalized relative to fluorescently labeled reference antibody alone, where the fluorescence intensity of a sample carried out without unlabeled test antibody is assigned 100% binding. If a test antibody competes for binding cMet with the labeled reference antibody, an assay carried out with equal concentration of each (for example, 1 µg/mL of unlabeled test antibody and 1 µg/mL of labeled reference antibody) will yield an approximately 50% reduction in fluorescence intensity as compared to the 100% control, indicating approximately 50% binding. Use of a labeled reference antibody at a concentration of X and unlabeled test antibody that competes for binding cMet at a concentration of 10X would yield an approximately 90% reduction in binding as compared to the 100% control, indicating approximately 10% binding.

The inhibition can be expressed as an inhibition constant, or $K_i$, which is calculated according to the following formula:

$$K_i = IC_{50}/(1+[\text{reference Ab concentration}]/K_d),$$

where $IC_{50}$ is the concentration of test antibody that yields a 50% reduction in binding of the reference antibody and $K_d$ is the dissociation constant of the reference antibody, a measure of its affinity for cMet. Antibodies that compete with reference cMet antibodies can have a $K_i$ from 10 pM to 100 nM under assay conditions described herein.

In various embodiments, a test antibody is considered to compete with a reference antibody if it decreases binding of the reference antibody to cells expressing cMet or cMet/cMet extracellular domain or subpart thereof by at least about 20% or more, for example, by at least about 20%, 30%, 40%, 50%, 60%, 70%, 80%, 90%, 95% or even more, or by a percentage ranging between any of the foregoing values, at a reference antibody concentration that is 80% of maximal binding under the specific assay conditions used, and a test antibody concentration that is 10-fold higher than the reference antibody concentration.

In various embodiments of a flow cytometry competition assay, a test antibody is considered to compete with a reference antibody if it decreases binding of the reference antibody to cells expressing cMet by at least about 20% or more, for example, by at least about 20%, 30%, 40%, 50%, 60%, 70%, 80%, 90%, 95% or even more, or by a percentage ranging between any of the foregoing values, at a concentration of test antibody that is 10× greater than that of the reference antibody.

Detection of expression of cMet generally involves contacting a biological sample (cells, tissue, or body fluid of an individual) with one or more anti-cMet antibodies (optionally conjugated to detectable moiety), and detecting whether or not the sample is positive for cMet expression, or whether the sample has altered (e.g., reduced or increased) expression as compared to a control sample. Methods for doing so are well known to one of ordinary skill in the art, including those described in the Examples.

5.6.2. Some Other Exemplary cMet Antibodies

Another anti-cMet antibody that can be used according to this disclosure has been named 227H1, comprises a heavy chain comprising CDR-H1, CDR-H2 and CDR-H3 comprising respectively the amino acid sequence SEQ ID Nos. 4, 5 and 6; and a light chain comprising CDR-L1, CDR-L2 and CDR-L3 comprising respectively the amino acid sequence SEQ ID Nos. 13, 11 and 14 of U.S. Pat. No. 8,329,173 (SEQ ID NOS 4, 5, 6, 13, 11 and 14, respectively, of this application). These antibodies have been described in detail in U.S. Pat. No. 8,329,173, and their descriptions are incorporated herein by reference in their entireties. The Sequence Listing submitted concurrently with this application includes SEQ ID NOS 1-71 from U.S. Pat. No. 8,329,173 as SEQ ID NOS 1-71.

In one embodiment, the antibody 227H1 comprises a heavy chain comprising the amino acid sequence SEQ ID No. 19 and a light chain comprising the amino acid sequence SEQ ID No. 22 of U.S. Pat. No. 8,329,173 (SEQ ID NOS 19 and 20, respectively, of this application). These antibodies have been described in detail in U.S. Pat. No. 8,329,173, and their descriptions are incorporated herein by reference in their entireties.

Another anti-cMet antibody that can be used according to this disclosure has been named 223C4, comprises a heavy chain comprising CDR-H1, CDR-H2 and CDR-H3 comprising respectively the amino acid sequence SEQ ID Nos. 7, 8 and 9; and a light chain comprising CDR-L1, CDR-L2 and CDR-L3 comprising respectively the amino acid sequence SEQ ID Nos. 15, 16 and 17 of U.S. Pat. No. 8,329,173 (SEQ ID NOS 7, 8, 9, 15, 16 and 17, respectively, of this application). These antibodies have been described in detail in U.S. Pat. No. 8,329,173, and their descriptions are incorporated herein by reference in their entireties.

In one embodiment, the antibody 223C4 comprises a heavy chain comprising the amino acid sequence SEQ ID No. 20 and a light chain comprising the amino acid sequence SEQ ID No. 23 of U.S. Pat. No. 8,329,173 (SEQ ID NOS 20 and 23, respectively). These antibodies have been described in detail in U.S. Pat. No. 8,329,173, and their descriptions are incorporated herein by reference in their entireties.

Another anti-cMet antibody that can be used according to this disclosure has been named 11E1, comprises a heavy chain comprising CDR-H1, CDR-H2 and CDR-H3 comprising respectively the amino acid sequence SEQ ID Nos. 56, 57 and 58; and a light chain comprising CDR-L1, CDR-L2 and CDR-L3 comprising respectively the amino acid sequence SEQ ID Nos. 59, 60 and 61 of U.S. Pat. No. 8,329,173 (SEQ ID NOS 56, 57, 58, 59, 60 and 61, respectively). These antibodies have been described in detail in U.S. Pat. No. 8,329,173, and their descriptions are incorporated herein by reference in their entireties.

In one embodiment, the antibody 11E1 comprises a heavy chain comprising the amino acid sequence SEQ ID No. 62 and a light chain comprising the amino acid sequence SEQ ID No. 63 of U.S. Pat. No. 8,329,173 (SEQ ID NOS 62 and 63, respectively). These antibodies have been described in detail in U.S. Pat. No. 8,329,173, and their descriptions are incorporated herein by reference in their entireties.

These first monoclonal antibodies disclosed above, or one of their functional fragments or derivatives, are characterized in that said antibodies are secreted by the hybridoma deposited at the Collection Nationale de Cultures de Microorganismes (CNCM, National Collection of Microorganism Cultures) (Institut Pasteur, Paris, France) on Mar. 14, 2007 under the numbers CNCM I-3724 (corresponding to 11E1), I-3731 (corresponding to 224G11), I-3732 (corresponding to 227H1) and on Jul. 6, 2007 under the number 1-3786 (corresponding to 223C4). These hybridomas consist of murine hybridomas resulting in the cellular fusion of immunized mouse splenocytes with a myeloma cell line (Sp20 Ag14).

These first antibodies, all of which were originally disclosed in U.S. Pat. No. 8,329,173, and which are covered by several patents, are thus summarized as follows (the SEQ ID NOs are the same in the '173 patent and in this application):

|  | 224G11 I-3731 | | 227H1 I-3732 | | 223C4 I-3786 | | 11E1 I-3724 | |
| --- | --- | --- | --- | --- | --- | --- | --- | --- |
|  | Prot. SEQ ID NO: | Nucl. SEQ ID NO: | Prot; SEQ ID NO: | Nucl. SEQ ID NO: | Prot. SEQ ID NO: | Nucl. SEQ ID NO: | Prot. SEQ ID NO: | Nucl. SEQ ID NO: |
| CDR-H1 | 1 | 24 | 4 | 27 | 7 | 30 | 56 | 64 |
| CDR-H2 | 2 | 25 | 5 | 28 | 8 | 31 | 57 | 65 |
| CDR-H3 | 3 | 26 | 6 | 29 | 9 | 32 | 58 | 66 |
| H. chain | 18 | 41 | 19 | 42 | 20 | 43 | 62 | 70 |
| CDR-L1 | 10 | 33 | 13 | 36 | 15 | 38 | 59 | 67 |
| CDR-L2 | 11 | 34 | 11 | 34 | 16 | 39 | 60 | 68 |
| CDR-L3 | 12 | 35 | 14 | 37 | 17 | 40 | 61 | 69 |
| L. chain | 21 | 44 | 22 | 45 | 23 | 46 | 63 | 71 |

The antibodies 224G11, 227H1, and 223C4 do not bind the SEMA domain of the cMet receptor. 11E1 is able to bind the SEMA domain.

In one embodiment, the anti-cMet antibody comprises the CDRs of the antibody STI-D0602 or STI-0602 (Sorrento Therapeutics). In another embodiment, the anti-cMet antibody is STI-D0602 or STI-0602, as described in Lingna Li, Cathrine Fells, Julia Guo, Pia Muyot, Edwige Gros, Yanliang Zhang, Yingqing Sun, Hong, Zhang, Yanwen Fu, Tong Zhu, Jian Cao, Gunnar Kaufmann, Gang Chen, Zhenwei Miao, A novel cMet targeting antibody drug conjugate for NSCLC, Abstract No. 3897, AACR Annual Meeting, April 16-20, New Orleans, USA.

In one embodiment, the anti-cMet antibody comprises the CDRs of the antibody 5D5 (Genentech) or the one-armed (monovalent) derivative onartuzumab. In one embodiment, the anti-cMet antibody is the antibody 5D5 (Genentech) or the one-armed (monovalent) derivative onartuzumab (FIG. 1B). Additional information for onartuzumab is as follows:

```
Heavy chain (SEQ ID NO: 92):
EVQLVESGGGLVQPGGSLRLSCAASGYTFTSYWLHWVRQAPGKGLEWVGM
IDPSNSDTRFNPNFKDRFTISADTSKNTAYLQMNSLRAEDTAVYYCATYR
SYVTPLDYWGQGTLVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSREEMTKNQVSLSCAVKGFYPSDIAVEWESNGQPENNYKTTPPVL
DSDGSFFLVSKLTVDKSRWQQGNVFSCSVMHEALHNHYTQKSLSLSPGK Light chain (SEQ ID NO: 93):
DIQMTQSPSSLSASVGDRVTITCKSSQSLLYTSSQKNYLAWYQQKPGKAP
KLLIYWASTRESGVPSRFSGSGSGTDFTLTISSLQPEDFATYYCQQYYAY
PWTFGQGTKVEIKRTVAAPSVFIFPPSDEQLKSGTASVVCLLNNFYPREA
KVQWKVDNALQSGNSQESVTEQDSKDSTYSLSSTLTLSKADYEKHKVYAC
EVTHQGLSSPVTKSFNRGEC Hinge-CH2-CH3 (SEQ ID NO: 94):
DKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLWCLVK
GFYPSDIAVEWESNGQPENNYKTTPPVLDSDGSFFLYSKLTVDKSRWQQG
NVFSCSVMHEALHNHYTQKSLSLSPGK
```

In one embodiment, the anti-cMet antibody comprises the CDRs of the antibody emibetuzumab/LY2875358. In one embodiment, the anti-cMet antibody is emibetuzumab/LY2875358 (Eli Lilly and Company, CAS Number 1365287-97-3) (FIG. 1A). Additional information for emibetuzumab is as follows:

```
Heavy Chain (SEO ID NO: 95):
QVQLVQSGAEVKKPGASVKVSCKASGYTFTDYYMHWVRQAPGQGLEWMGR
VNPNRRGTTYNQKFEGRVTMTTDTSTSTAYMELRSLRSDDTAVYYCARAN
WLDYWGQGTTVTVSSASTKGPSVFPLAPCSRSTSESTAALGCLVKDYFPE
PVTVSWNSGALTSGVHTFPAVLQSSGLYSLSSVVTVPSSSLGTKTYTCNV
DHKPSNTKVDKRVESKYGPPCPPCPAPEAAGGPSVFLFPPKPKDTLMISR
TPEVTCVVVDVSQEDPEVQFNWYVDGVEVHNAKTKPREEQFNSTYRVVSV
LTVLHQDWLNGKEYKCKVSNKGLPSSIEKTISKAKGQPREPQVYTLPPSQ
EEMTKNQVSLTCLVKGFYPSDIAVEWESNGQPENNYKTTPPVLDSDGSFF
LYSRLTVDKSRWQEGNVFSCSVMHEALHNHYTQKSLSLSLG Light Chain (SEQ ID NO: 96)
DIQMTQSPSSLSASVGDRVTITCSVSSSVSSIYLHWYQQKPGKAPKLLIY
STSNLASGVPSRFSGSGSGTDFTLTISSLQPEDFATYYCQVYSGYPLTFG
GGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQ
GLSSPVTKSFNRGEC
```

In one embodiment, the anti-cMet antibody comprises the CDRs of the antibody AbF46 or SAIT301 (Samsung Electronics). In one embodiment, the antibody is AbF46 (FIG. 1C). In another embodiment, the anti-cMet antibody is SAIT301 (FIG. 1E).

In one embodiment, the anti-cMet antibody comprises the CDRs of the antibody ARGX-111 (36C4) (arGEN-X BV). In another embodiment, the anti-cMet antibody is ARGX-111 (FIG. 1D).

In one embodiment, the anti-cMet antibody comprises the CDRs of one of the antibodies in Sym015 (Hu9006, Hu9338) (Symphogen A/S). In another embodiment, the anti-cMet antibody is Hu9006. In another embodiment, the anti-cMet antibody is Hu9338. The amino acid sequences of these antibodies, including their CDRs, are disclosed in WO2016042412.

5.5. Expression Systems and Methods of Making the Antibodies

Anti-cMet antibodies can be prepared by recombinant expression of immunoglobulin light and heavy chain genes in a host cell through methods well known to those of ordinary skill in the art. To express an antibody recombinantly, a host cell is transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Molecular Cloning; A Laboratory Manual, Second Edition (Sambrook, Fritsch and Maniatis (eds), Cold Spring Harbor, N.Y., 1989), Current Protocols in Molecular Biology (Ausubel, F. M. et al., eds., Greene Publishing Associates, 1989) and in U.S. Pat. No. 4,816,397.

To generate nucleic acids encoding such anti-cMet antibodies, DNA fragments encoding the light and heavy chain variable regions are first obtained. These DNAs can be obtained by amplification and modification of germline DNA or cDNA encoding light and heavy chain variable sequences, for example using the polymerase chain reaction (PCR). Germline DNA sequences for human heavy and light chain variable region genes are known in the art (See, e.g., the "VBASE" human germline sequence database; see also Kabat et al., 1991, Sequences of Proteins of Immunological Interest, Fifth Edition, U.S. Department of Health and Human Services, NIH Publication No. 91-3242; Tomlinson et al., 1992, J. Mol. Biol. 22T: 116-198; and Cox et al., 1994, Eur. J. Immunol. 24:827-836; the contents of each of which are incorporated herein by reference). The nucleotides encoding the antibodies 224G11, 227H1, 223C4, and 11E11 have been described in detail in U.S. Pat. No. 8,329,173, and their descriptions are incorporated herein by reference in their entireties.

Once DNA fragments encoding anti-cMet antibody-related $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($CH_1$, $CH_2$, $CH_3$ and, optionally, $CH_4$). The sequences of human heavy chain constant region genes are known in the art (See, e.g., Kabat et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an $IgG_1$, $IgG_2$, $IgG_3$, $IgG_4$, IgA, IgE, IgM or IgD constant region, but in certain embodiments is an $IgG_1$ or $IgG_4$ constant region. For a Fab fragment heavy chain gene, the $V_H$-encoding DNA can be operatively linked to another DNA molecule encoding only the heavy chain $CH_1$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (See, e.g., Kabat et al., 1991, Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but in certain embodiments is a kappa constant region. To create a scFv gene, the $V_H$- and $V_L$-encoding DNA fragments are operatively linked to another fragment encoding a flexible linker, e.g., encoding the amino acid sequence $(Gly_4\text{-}Ser)_3$ (SEQ ID NO:97), such that the $V_H$ and $V_L$ sequences can be expressed as a contiguous single-chain protein, with the $V_L$ and $V_H$ regions joined by the flexible linker (See, e.g., Bird et al., 1988, Science 242:423-426; Huston et al., 1988, Proc. Natl. Acad. Sci. USA 85:5879-5883; McCafferty et al., 1990, Nature 348:552-554).

To express the anti-cMet antibodies, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). Prior to insertion of the anti-cMet antibody-related light or heavy chain sequences, the expression vector can already carry antibody constant region sequences. For example, one approach to converting the anti-cMet monoclonal antibody-related $V_H$ and $V_L$ sequences to full-length antibody genes is to insert them into expression vectors already encoding heavy chain constant and light chain constant regions, respectively, such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel, Gene Expression Technology: Methods in Enzymology 185, Academic Press, San Diego, Calif., 1990. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al., and U.S. Pat. No. 4,968,615 by Schaffner et al.

Recombinant expression vectors of the disclosure can carry sequences in addition to the antibody chain genes and regulatory sequences, such as sequences that regulate replication of the vector in host cells (e.g., origins of replication) and selectable marker genes. Selectable marker genes facilitate selection of host cells into which the vector has been introduced (See, e.g., U.S. Pat. Nos. 4,399,216, 4,634,665 and 5,179,017, all by Axel et al.). For example, typically a selectable marker gene confers resistance to drugs, such as G418, hygromycin or methotrexate, on a host cell into which the vector has been introduced. Suitable selectable marker genes include the dihydrofolate reductase (DHFR) gene (for use in DHFR⁻ host cells with methotrexate selection/amplification) and the neo gene (for G418 selection). For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, lipofection, calcium-phosphate precipitation, DEAE-dextran transfection and the like.

It is possible to express anti-cMet antibodies composing anti-cMet ADCs in either prokaryotic or eukaryotic host cells. In certain embodiments, expression of antibodies is performed in eukaryotic cells, e.g., mammalian host cells, of optimal secretion of a properly folded and immunologically active antibody. Exemplary mammalian host cells for expressing the recombinant antibodies of the disclosure include Chinese Hamster Ovary (CHO cells) (including DHFR⁻ CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Host cells can also be used to produce portions of intact antibodies, such as Fab fragments or scFv molecules. It is understood that variations on the above procedure are within the scope of the present disclosure. For example, it can be desirable to transfect a host cell with DNA encoding either the light chain or the heavy chain (but not both) of an anti-cMet antibody.

Recombinant DNA technology can also be used to remove some or all of the DNA encoding either or both of the light and heavy chains that is not necessary for binding to cMet. The molecules expressed from such truncated DNA molecules are also encompassed by the antibodies of the disclosure.

For recombinant expression of an anti-cMet antibody, the host cell can be co-transfected with two expression vectors, the first vector encoding a heavy chain derived polypeptide and the second vector encoding a light chain derived polypeptide. The two vectors can contain identical selectable markers, or they can each contain a separate selectable marker. Alternatively, a single vector can be used which encodes both heavy and light chain polypeptides.

Once a nucleic acid encoding one or more portions of an anti-cMet antibody is obtained, further alterations or mutations can be introduced into the coding sequence, for example to generate nucleic acids encoding antibodies with different CDR sequences, antibodies with reduced affinity to the Fc receptor, or antibodies of different subclasses.

Antibodies and/or binding fragments composing anti-cMet ADCs can also be produced by chemical synthesis (e.g., by the methods described in Solid Phase Peptide Synthesis, $2^{nd}$ ed., 1984 The Pierce Chemical Co., Rockford, Ill.). Variant antibodies can also be generated using a cell-free platform, See, e.g., Chu et al., Biochemia No. 2, 2001 (Roche Molecular Biologicals) and Murray et al., 2013, Current Opinion in Chemical Biology, 17:420-426.

Once an anti-cMet antibody and/or binding fragment has been produced by recombinant expression, it can be purified by any method known in the art for purification of an immunoglobulin molecule, for example, by chromatography (e.g., ion exchange, affinity, and sizing column chromatography), centrifugation, differential solubility, or by any other standard technique for the purification of proteins. Further, the anti-cMet antibodies and/or binding fragments can be fused to heterologous polypeptide sequences described herein or otherwise known in the art to facilitate purification.

Once isolated, the anti-cMet antibody and/or binding fragment can, if desired, be further purified, e.g., by column chromatography. (see, e.g., Fisher, Laboratory Techniques In Biochemistry And Molecular Biology, Work and Burdon, eds., Elsevier, 1980), or by gel filtration chromatography on a Superdex™ 75 column (Pharmacia Biotech AB, Uppsala, Sweden).

5.6. Specific Anti-cMet Antibody Drug Conjugates

As mentioned, anti-cMet ADCs generally comprise an anti-cMet antigen binding moiety, such as an anti-cMet antibody and/or binding fragment, having one or more cytotoxic and/or cytostatic agents, which may be the same or different, linked thereto by way of one or more linkers, which may also be the same or different. Multiple different cytotoxic/cytostatic agents can be attached to each Ab to make an ADC. These agents may target two or more pathways to kill or arrest the growth of tumor cells, target multiple nodes of the same pathway, or double up on same target (i.e., inhibit growth and/or kill cells through two or more different mechanisms).

In specific embodiments, the anti-cMet ADCs are compounds according to structural formula (I):

$$[D\text{-}L\text{-}XY]_n\text{-}Ab \qquad (I)$$

or salts thereof, where each "D" represents, independently of the others, a cytotoxic and/or cytostatic agent ("drug"); each "L" represents, independently of the others, a linker; "Ab" represents an anti-cMet antigen binding moiety, such as an anti-cMet antibody or binding fragment; each "XY" represents a linkage formed between a functional group $R^x$ on the linker and a "complementary" functional group R on the antigen binding moiety; and n represents the number of drugs linked to Ab of the ADC.

Specific embodiments of various antibodies or binding fragments (Ab) that may compose ADCs according to structural formula (I) include the various embodiments of anti-cMet antibodies and/or binding fragments described above.

In some specific embodiments of the ADCs or salts of structural formula (I), each D is the same and/or each L is the same.

Specific embodiments of cytotoxic and/or cytostatic agents (D) and linkers (L) that may compose the anti-cMet ADCs, as well as the number of cytotoxic and/or cytostatic agents linked to the anti-cMet ADCs, are described in more detail below.

In a specific exemplary embodiment, the anti-cMet ADCs are compounds according to structural formula (I) in which each "D" is the same and is either a cell-permeating auristatin (for example, dolastatin-10 or MMAE) or a cell-permeating minor groove-binding DNA cross-linking agent (for example, a PBD or a PBD dimer); each "L" is the same and is a linker cleavable by a lysosomal enzyme; each "XY" is a linkage formed between a maleimide and a sulfydryl group; "Ab" is an antibody comprising six CDRs corresponding to the six CDRs of antibody ABT-700 (224G11), or an antibody that competes for binding cMet with such an antibody; and n is 2, 3 or 4. In a specific embodiment of this exemplary embodiment or the anti-cMet ADCs of structural formula (I), "Ab" is a humanized antibody, for example, a humanized antibody comprising $V_H$ and $V_L$ chains corresponding to the $V_H$ and $V_L$ chains of antibody 5D5. In another specific embodiment of the anti-cMet ADCs of structural formula (I), the Ab is the antibody STI-D0602 (Sorrento).

In a specific exemplary embodiment, the compound according to structural formula (I) has the structure of formula (IIa):

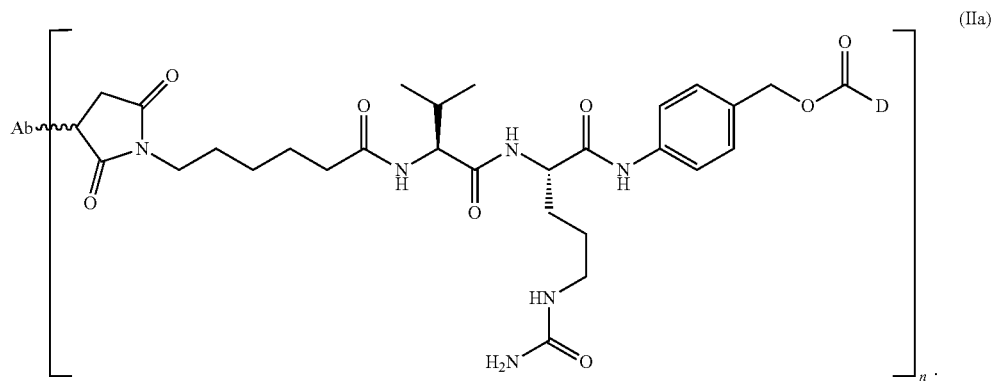

(IIa)

In one embodiment, the Ab in the compound of formula (IIa) is ABT-700.

In a specific exemplary embodiment, the compound of structural formula (I) has the following structure:

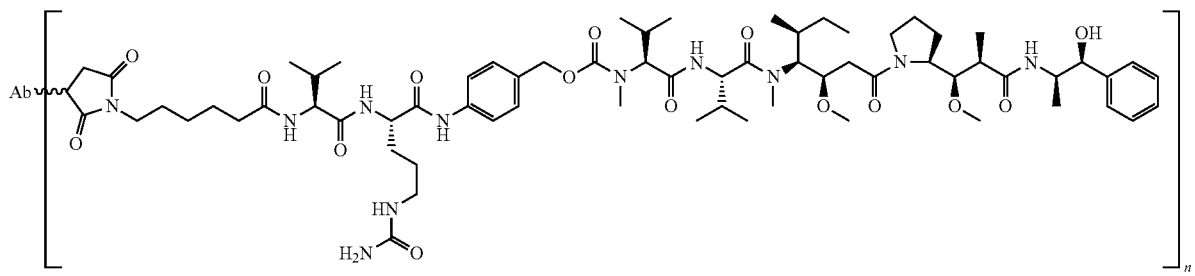

or a pharmaceutically acceptable salt thereof, wherein n has an average value ranging from 2-4, and the Ab is a full length anti-cMet antibody.

In a specific embodiment, the Ab in the compound of this particular formula is ABT-700.

In a specific embodiment, n has an average value ranging from 2-4 and Ab is a full-length anti-cMet antibody.

5.6.1. Cytotoxic and/or Cytostatic Agents

The cytotoxic and/or cytostatic agents may be any agents known to inhibit the growth and/or replication of and/or kill cells, and in particular cancer and/or tumor cells. Numerous agents having cytotoxic and/or cytostatic properties are known in the literature. Non-limiting examples of classes of cytotoxic and/or cytostatic agents include, by way of example and not limitation, radionuclides, alkylating agents, DNA cross-linking agents, DNA intercalating agents (e.g., groove binding agents such as minor groove binders), cell cycle modulators, apoptosis regulators, kinase inhibitors, protein synthesis inhibitors, mitochondria inhibitors, nuclear export inhibitors, topoisomerase I inhibitors, topoisomerase II inhibitors, RNA/DNA antimetabolites and antimitotic agents.

Specific non-limiting examples of agents within certain of these various classes are provided below.

Alkylating Agents: asaley (L-Leucine, N—[N-acetyl-4-[bis-(2-chloroethyl)amino]-DL-phenylalanyl]-, ethylester); AZQ (1,4-cyclohexadiene-1,4-dicarbamic acid, 2, 5-bis(1-aziridinyl)-3,6-dioxo-, diethyl ester); BCNU (N,N'-Bis(2-chloroethyl)-N-nitrosourea); busulfan (1,4-butanediol dimethanesulfonate); (carboxyphthalato)platinum; CBDCA (cis-(1,1-cyclobutanedicarboxylato)diammineplatinum(II)); CCNU (N-(2-chloroethyl)-N'-cyclohexyl-N-nitrosourea); CHIP (iproplatin; NSC 256927); chlorambucil; chlorozotocin (2-[[[(2-chloroethyl) nitrosoamino]carbonyl]amino]-2-deoxy-D-glucopyranose); cis-platinum (cisplatin); clomesone; cyanomorpholinodoxorubicin; cyclodisone; dianhydrogalactitol (5,6-diepoxydulcitol); fluorodopan ((5-[(2-chloroethyl)-(2-fluoroethyl)amino]-6-methyl-uracil); hepsulfam; hycanthone; indolinobenzodiazepine dimer DGN462; melphalan; methyl CCNU ((1-(2-chloroethyl)-3-(trans-4-methylcyclohexane)-1-nitrosourea); mitomycin C; mitozolamide; nitrogen mustard ((bis(2-chloroethyl) methylamine hydrochloride); PCNU ((1-(2-chloroethyl)-3-(2,6-dioxo-3-piperidyl)-1-nitrosourea)); piperazine alkylator ((1-(2-chloroethyl)-4-(3-chloropropyl)-piperazine dihydrochloride)); piperazinedione; pipobroman (N,N'-bis (3-bromopropionyl) piperazine); porfiromycin (N-methyl-mitomycin C); spirohydantoin mustard; teroxirone (triglycidylisocyanurate); tetraplatin; thio-tepa (N,N',N"-tri-1,2-ethanediylthio phosphoramide); triethylenemelamine; uracil nitrogen mustard (desmethyldopan); Yoshi-864 ((bis(3-mesyloxy propyl)amine hydrochloride).

DNA Alkylating-Like Agents: Cisplatin; Carboplatin; Nedaplatin; Oxaliplatin; Satraplatin; Triplatin tetranitrate; Procarbazine; altretamine; dacarbazine; mitozolomide; temozolomide.

Alkylating Antineoplastic Agents: Carboquone; Carmustine; Chlornaphazine; Chlorozotocin; Duocarmycin; Evofosfamide; Fotemustine; Glufosfamide; Lomustine; Mannosulfan; Nimustine; Phenanthriplatin; Pipobroman; Ranimustine; Semustine; Streptozotocin; ThioTEPA; Treosulfan; Triaziquone; Triethylenemelamine; Triplatin tetranitrate.

DNA Replication and Repair Inhibitors: Altretamine; Bleomycin; Dacarbazine; Dactinomycin; Mitobronitol; Mitomycin; Pingyangmycin; Plicamycin; Procarbazine; Temozolomide; ABT-888 (veliparib); olaparib; KU-59436; AZD-2281; AG-014699; BSI-201; BGP-15; INO-1001; ONO-2231.

Cell Cycle Modulators: Paclitaxel; Nab-Paclitaxel; Docetaxel; Vincristine; Vinblastine; ABT-348; AZD-1152; MLN-8054; VX-680; Aurora A-specific kinase inhibitors; Aurora B-specific kinase inhibitors and pan-Aurora kinase inhibitors; AZD-5438; BMI-1040; BMS-032; BMS-387; CVT-2584; flavopyridol; GPC-286199; MCS-5A; PD0332991; PHA-690509; seliciclib (CYC-202, R-roscovitine); ZK-304709; AZD4877, ARRY-520; GSK923295A.

Apoptosis Regulators: AT-101 ((-)gossypol); G3139 or oblimersen (Bcl-2-targeting antisense oligonucleotide); IPI-194; IPI-565; N-(4-(4-((4'-chloro(1,1'-biphenyl)-2-yl) methyl)piperazin-1-ylbenzoyl)-4-(((1R)-3-(dimethyl-amino)-1-((phenylsulfanyl)methyl)propyl)amino)-3-nitrobenzenesulfonamide); N-(4-(4-((2-(4-chlorophenyl)-5,5-dimethyl-1-cyclohex-1-en-1-yl)methyl)piperazin-1-yl) benzoyl)-4-(((1R)-3-(morpholin-4-yl)-1-((phenylsulfanyl) methyl)propyl)amino)-3-((trifluoromethyl)sulfonyl) benzenesulfonamide); GX-070 (Obatoclax®; 1H-Indole, 2-(2-((3,5-dimethyl-1H-pyrrol-2-yl)methylene)-3-methoxy-2H-pyrrol-5-yl)-)); HGS 1029; GDC-0145; GDC-0152; LCL-161; LBW-242; venetoclax; agents that target TRAIL or death receptors (e.g., DR4 and DR5) such as ETR2-STO1, GDC0145, HGS-1029, LBY-135, PRO-1762; drugs that target caspases, caspase-regulators, BCL-2 family members, death domain proteins, TNF family members, Toll family members, and/or NF-kappa-B proteins.

Angiogenesis Inhibitors: ABT-869; AEE-788; axitinib (AG-13736); AZD-2171; CP-547,632; IM-862; pegaptamib; sorafenib; BAY43-9006; pazopanib (GW-786034); vatalanib (PTK-787, ZK-222584); sunitinib; SU-11248; VEGF trap; vandetanib; ABT-165; ZD-6474; DLL4 inhibitors.

Proteasome Inhibitors: Bortezomib; Carfilzomib; Epoxomicin; Ixazomib; Salinosporamide A.

Kinase Inhibitors: Afatinib; Axitinib; Bosutinib; Crizotinib; Dasatinib; Erlotinib; Fostamatinib; Gefitinib; Ibrutinib; Imatinib; Lapatinib; Lenvatinib; Mubritinib; Nilotinib; Pazopanib; Pegaptanib; Sorafenib; Sunitinib; SU6656; Vandetanib; Vemurafenib; CEP-701 (lesaurtinib); XL019; INCB018424 (ruxolitinib); ARRY-142886 (selemetinib); ARRY-438162 (binimetinib); PD-325901; PD-98059; AP-23573; CCI-779; everolimus; RAD-001; rapamycin; temsirolimus; ATP-competitive TORC1/TORC2 inhibitors including PI-103, PP242, PP30, Torin 1; LY294002; XL-147; CAL-120; ONC-21; AEZS-127; ETP-45658; PX-866; GDC-0941; BGT226; BEZ235; XL765.

Protein Synthesis Inhibitors: Streptomycin; Dihydrostreptomycin; Neomycin; Framycetin; Paromomycin; Ribostamycin; Kanamycin; Amikacin; Arbekacin; Bekanamycin; Dibekacin; Tobramycin; Spectinomycin; Hygromycin B; Paromomycin; Gentamicin; Netilmicin; Sisomicin; Isepamicin; Verdamicin; Astromicin; Tetracycline; Doxycycline; Chlortetracycline; Clomocycline; Demeclocycline; Lymecycline; Meclocycline; Metacycline; Minocycline; Oxytetracycline; Penimepicycline; Rolitetracycline; Tetracycline; Glycylcyclines; Tigecycline; Oxazolidinone; Eperezolid; Linezolid; Posizolid; Radezolid; Ranbezolid; Sutezolid; Tedizolid; Peptidyl transferase inhibitors; Chloramphenicol; Azidamfenicol; Thiamphenicol; Florfenicol; Pleuromutilins; Retapamulin; Tiamulin; Valnemulin; Azithromycin; Clarithromycin; Dirithromycin; Erythromycin; Flurithromycin; Josamycin; Midecamycin; Miocamycin; Oleandomycin; Rokitamycin; Roxithromycin; Spiramycin; Troleandomycin; Tylosin; Ketolides; Telithromycin;

Cethromycin; Solithromycin; Clindamycin; Lincomycin; Pirlimycin; Streptogramins; Pristinamycin; Quinupristin/dalfopristin; Virginiamycin.

Histone Deacetylase Inhibitors: Vorinostat; Romidepsin; Chidamide; Panobinostat; Valproic acid; Belinostat; Mocetinostat; Abexinostat; Entinostat; SB939 (pracinostat); Resminostat; Givinostat; Quisinostat; thioureidobutyronitrile (Kevetrin™); CUDC-10; CHR-2845 (tefinostat); CHR-3996; 4SC-202; CG200745; ACY-1215 (rocilinostat); ME-344; sulforaphane.

Topoisomerase I Inhibitors: camptothecin; various camptothecin derivatives and analogs (for example, NSC 100880, NSC 603071, NSC 107124, NSC 643833, NSC 629971, NSC 295500, NSC 249910, NSC 606985, NSC 74028, NSC 176323, NSC 295501, NSC 606172, NSC 606173, NSC 610458, NSC 618939, NSC 610457, NSC 610459, NSC 606499, NSC 610456, NSC 364830, and NSC 606497); morpholinisoxorubicin; SN-38.

Topoisomerase II Inhibitors: doxorubicin; amonafide (benzisoquinolinedione); m-AMSA (4'-(9-acridinylamino)-3'-methoxymethanesulfonanilide); anthrapyrazole derivative ((NSC 355644); etoposide (VP-16); pyrazoloacridine ((pyrazolo[3,4,5-kl]acridine-2(6H)-propanamine, 9-methoxy-N, N-dimethyl-5-nitro-, monomethanesulfonate); bisantrene hydrochloride; daunorubicin; deoxydoxorubicin; mitoxantrone; menogaril; N,N-dibenzyl daunomycin; oxanthrazole; rubidazone; teniposide.

DNA Intercalating Agents: anthramycin; chicamycin A; tomaymycin; DC-81; sibiromycin; pyrrolobenzodiazepine derivative; SGD-1882 ((S)-2-(4-aminophenyl)-7-methoxy-8-(3-(((S)-7-methoxy-2-(4-methoxyphenyl)-5-oxo-5,11a-dihydro-1H-benzo[e]pyrrolo[1,2-a][1,4]diazepin-8-yl)oxy) propoxy)-1H-benzo[e]pyrrolo[1,2-a][1,4]diazepin-5(11aH)-one); SG2000 (SJG-136; (11aS,11a'S)-8,8'-(propane-1,3-diylbis(oxy))bis(7-methoxy-2-methylene-2,3-dihydro-1H-benzo[e]pyrrolo[1,2-a][1,4]diazepin-5 (11aH)-one)).

RNA/DNA Antimetabolites: L-alanosine; 5-azacytidine; 5-fluorouracil; acivicin; aminopterin derivative N-[2-chloro-5-[[(2, 4-diamino-5-methyl-6-quinazolinyl)methyl]amino] benzoyl]L-aspartic acid (NSC 132483); aminopterin derivative N-[4-[[(2, 4-diamino-5-ethyl-6-quinazolinyl)methyl] amino]benzoyl] L-aspartic acid; aminopterin derivative N-[2-chloro-4-[[(2, 4-diamino-6-pteridinyl)methyl]amino] benzoyl] L-aspartic acid monohydrate; antifolate PT523 ((N$^\alpha$-(4-amino-4-deoxypteroyl)-N$^\gamma$-hemiphthaloyl-L-ornithine)); Baker's soluble antifol (NSC 139105); dichlorallyl lawsone ((2-(3, 3-dichloroallyl)-3-hydroxy-1,4-naphthoquinone); brequinar; ftorafur ((pro-drug; 5-fluoro-1-(tetrahydro-2-furyl)-uracil); 5,6-dihydro-5-azacytidine; methotrexate; methotrexate derivative (N-[[4-[[(2, 4-diamino-6-pteridinyl)methyl]methylamino]-1-naphthalenyl]carbonyl] L-glutamic acid); PALA ((N-(phosphonoacetyl)-L-aspartate); pyrazofurin; trimetrexate.

DNA Antimetabolites: 3-HP; 2'-deoxy-5-fluorouridine; 5-HP; α-TGDR (α-2'-deoxy-6-thioguanosine); aphidicolin glycinate; ara C (cytosine arabinoside); 5-aza-2'-deoxycytidine; β-TGDR (β-2'-deoxy-6-thioguanosine); cyclocytidine; guanazole; hydroxyurea; inosine glycodialdehyde; macbecin II; pyrazoloimidazole; thioguanine; thiopurine.

Mitochondria Inhibitors: pancratistatin; phenpanstatin; rhodamine-123; edelfosine; d-alpha-tocopherol succinate; compound 11β; aspirin; ellipticine; berberine; cerulenin; GX015-070 (Obatoclax®; 1H-Indole, 2-(2-((3,5-dimethyl-1H-pyrrol-2-yl)methylene)-3-methoxy-2H-pyrrol-5-yl)-); celastrol (tripterine); metformin; Brilliant green; ME-344.

Antimitotic Agents: allocolchicine; auristatins, such as MMAE (monomethyl auristatin E) and MMAF (monomethyl auristatin F); halichondrin B; cemadotin; colchicine; cholchicine derivative (N-benzoyl-deacetyl benzamide); dolastatin-10; dolastatin-15; maytansine; maytansinoids, such as DM1 (N$_2$'-deacetyl-N$_2$'-(3-mercapto-1-oxopropyl)-maytansine); rhozoxin; paclitaxel; paclitaxel derivative ((2'-N-[3-(dimethylamino)propyl]glutaramate paclitaxel); docetaxel; thiocolchicine; trityl cysteine; vinblastine sulfate; vincristine sulfate.

Nuclear Export Inhibitors: callystatin A; delactonmycin; KPT-185 (propan-2-yl (Z)-3-[3-[3-methoxy-5-(trifluoromethyl)phenyl]-1,2,4-triazol-1-yl]prop-2-enoate); kazusamycin A; leptolstatin; leptofuranin A; leptomycin B; ratjadone; Verdinexor ((Z)-3-[3-[3,5-bis(trifluoromethyl)phenyl]-1,2, 4-triazol-1-yl]-N'-pyridin-2-ylprop-2-enehydrazide).

Hormonal Therapies: anastrozole; exemestane; arzoxifene; bicalutamide; cetrorelix; degarelix; deslorelin; trilostane; dexamethasone; flutamide; raloxifene; fadrozole; toremifene; fulvestrant; letrozole; formestane; glucocorticoids; doxercalciferol; sevelamer carbonate; lasofoxifene; leuprolide acetate; megesterol; mifepristone; nilutamide; tamoxifen citrate; abarelix; prednisone; finasteride; rilostane; buserelin; luteinizing hormone releasing hormone (LHRH); Histrelin; trilostane or modrastane; fosrelin; goserelin.

Any of these agents that include, or that may be modified to include, a site of attachment to an antibody and/or binding fragment may be included in an anti-cMet ADC.

Skilled artisans will also appreciate that the above mechanisms of action are not mutually exclusive, and that in some embodiments it may be desirable to utilize anti-cMet ADCs capable of exerting antitumor activity against cMet-expressing (herein referred to as cMet+ tumors) or cMet-overexpressing tumors via more than one mechanism of action. As a specific example, such an anti-cMet ADC may include a cell-permeating cytotoxic and/or cytostatic agent that is cytotoxic and/or cytostatic to both cMet+/overexpressing tumors and cMet-negative tumor cells linked to an anti-cMet antibody by way of a cleavable linker.

Accordingly, in some embodiments, the cytotoxic and/or cytostatic agents included in an anti-cMet ADC will, upon cleavage of the ADC, be able to traverse cell membranes ("cell permeable cytostatic and/or cytotoxic agents"). Specific cytotoxic and/or cytostatic agents of interest, and/or cleavage products of ADCs including such agents, may be tested for the ability to traverse cell membranes using routine methods known to those of skill in the art. Permeability (P) of molecules across a membrane can be expressed as $P=KD/\Delta x$ where K is the partition coefficient, D is the diffusion coefficient, and $\Delta x$ is the thickness of the cell membrane. The diffusion coefficient (D) is a measure of the rate of entry into the cytoplasm depending on the molecular weight or size of a molecule. K is a measure of the solubility of the substance in lipids. A low value of K describes a molecule like water that is not soluble in lipid. Graphically, it is expected that permeability (P) as a function of the partition coefficient (K) will increase linearly when D and $\Delta x$ are constants. (Walter & Gutknecht, 1986, "Permeability of small nonelectrolytes through lipid bilayer membranes," Journal of Membrane Biology 90:207-217; Diamond & Katz, 1974, "Interpretation of nonelectrolyte partition coefficients between dimyristoyl lecithin and water," Journal of Membrane Biology 17:121-154).

In a specific embodiment, the cytotoxic and/or cytostatic agent is a cell-permeable antimitotic agent.

In another specific embodiment, the cytotoxic and/or cytostatic agent is a cell-permeable auristatin, such as, for example, dolastatin-10 or MMAE.

In another specific embodiment, the cytotoxic and/or cytostatic agent is a cell-permeable minor groove-binding DNA cross-linking agent, such as, for example, a pyrrolobenzodiazepine ("PBD") dimer.

5.6.2. Linkers

In the anti-cMet ADCs described herein, the cytotoxic and/or cytostatic agents are linked to the antigen binding moiety by way of linkers. The linkers may be short, long, hydrophobic, hydrophilic, flexible or rigid, or may be composed of segments that each independently have one or more of the above-mentioned properties such that the linker may include segments having different properties. The linkers may be polyvalent such that they covalently link more than one agent to a single site on the antibody, or monovalent such that covalently they link a single agent to a single site on the antibody.

As will be appreciated by skilled artisans, the linkers link the cytotoxic and/or cytostatic agents to the antigen binding moiety by forming a covalent linkage to the cytotoxic and/or cytostatic agent at one location and a covalent linkage to the antigen binding moiety at another. The covalent linkages are formed by reaction between functional groups on the linker and functional groups on the agents and the antigen binding moiety. As used herein, the expression "linker" is intended to include (i) unconjugated forms of the linker that include a functional group capable of covalently linking the linker to a cytotoxic and/or cytostatic agent and a functional group capable of covalently linking the linker to the antigen binding moiety such as an antibody; (ii) partially conjugated forms of the linker that includes a functional group capable of covalently linking the linker to an antigen binding moiety such as an antibody and that is covalently linked to a cytotoxic and/or cytostatic agent, or vice versa; and (iii) fully conjugated forms of the linker that is covalently linked to both a cytotoxic and/or cytostatic agent and an antigen binding moiety such as an antibody. In some specific embodiments of linkers and ADCs described herein, as well as synthons used to conjugate linker-agents to antibodies, moieties comprising the functional groups on the linker and covalent linkages formed between the linker and antibody are specifically illustrated as $R^x$ and XY, respectively.

The linkers linking the cytotoxic and/or cytostatic agents to the antigen binding moiety of an anti-cMet ADC may be long, short, flexible, rigid, hydrophilic or hydrophobic in nature, or may comprise segments that have different characteristics, such as segments of flexibility, segments of rigidity, etc. The linker may be chemically stable to extracellular environments, for example, chemically stable in the blood stream, or may include linkages that are not stable and release the cytotoxic and/or cytostatic agents in the extracellular milieu. In some embodiments, the linkers include linkages that are designed to release the cytotoxic and/or cytostatic agents upon internalization of the anti-cMet ADC within the cell. In some specific embodiments, the linkers includes linkages designed to cleave and/or immolate or otherwise breakdown specifically or non-specifically inside cells. A wide variety of linkers useful for linking drugs to antigen binding moieties such as antibodies in the context of ADCs are known in the art. Any of these linkers, as well as other linkers, may be used to link the cytotoxic and/or cytostatic agents to the antigen binding moiety of the anti-cMet ADCs described herein.

The number of cytotoxic and/or cytostatic agents linked to the antigen binding moiety of an anti-cMet ADC can vary (called the "drug-to-antibody ratio," or "DAR"), and will be limited only by the number of available attachments sites on the antigen binding moiety and the number of agents linked to a single linker. Typically, a linker will link a single cytotoxic and/or cytostatic agent to the antigen binding moiety of an anti-cMet ADC. In embodiments of anti-cMet ADCs which include more than a single cytotoxic and/or cytostatic agent, each agent may be the same or different. As long as the anti-cMet ADC does not exhibit unacceptable levels of aggregation under the conditions of use and/or storage, anti-cMet ADCs with DARs of twenty, or even higher, are contemplated. In some embodiments, the anti-cMet ADCs described herein may have a DAR in the range of about 1-10, 1-8, 1-6, or 1-4. In certain specific embodiments, the anti-cMet ADCs may have a DAR of 2, 3 or 4. In certain embodiments, the anti-Cmet ADC has an average DAR of 3.1.

The linkers are preferably, but need not be, chemically stable to conditions outside the cell, and may be designed to cleave, immolate and/or otherwise specifically degrade inside the cell. Alternatively, linkers that are not designed to specifically cleave or degrade inside the cell may be used. Choice of stable versus unstable linker may depend upon the toxicity of the cytotoxic and/or cytostatic agent. A wide variety of linkers useful for linking drugs to antibodies in the context of ADCs are known in the art. Any of these linkers, as well as other linkers, may be used to link the cytotoxic and/or cytostatic agents to the antibody of the ADCs described herein.

Exemplary polyvalent linkers that may be used to link many cytotoxic and/or cytostatic agents to a single antibody molecule are described, for example, in WO 2009/073445; WO 2010/068795; WO 2010/138719; WO 2011/120053; WO 2011/171020; WO 2013/096901; WO 2014/008375; WO 2014/093379; WO 2014/093394; WO 2014/093640, the contents of which are incorporated herein by reference in their entireties. For example, the Fleximer linker technology developed by Mersana et al. has the potential to enable high-DAR ADCs with good physicochemical properties. As shown below, the Mersana technology is based on incorporating drug molecules into a solubilizing poly-acetal backbone via a sequence of ester bonds. The methodology renders highly-loaded ADCs (DAR up to 20) while maintaining good physicochemical properties.

Additional examples of dendritic type linkers can be found in US 2006/116422; US 2005/271615; de Groot et al (2003) Angew. Chem. Int. Ed. 42:4490-4494; Amir et al (2003) Angew. Chem. Int. Ed. 42:4494-4499; Shamis et al (2004) J. Am. Chem. Soc. 126:1726-1731; Sun et al (2002) Bioorganic & Medicinal Chemistry Letters 12:2213-2215; Sun et al (2003) Bioorganic & Medicinal Chemistry 11:1761-1768; King et al (2002) Tetrahedron Letters 43:1987-1990, each of which is incorporated herein by reference.

Exemplary monovalent linkers that may be used are described, for example, in Nolting, 2013, Antibody-Drug Conjugates, Methods in Molecular Biology 1045:71-100; Kitson et al., 2013, CROs/CMOs—Chemica Oggi—Chemistry Today 31(4):30-38; Ducry et al., 2010, Bioconjugate Chem. 21:5-13; Zhao et al., 2011, J. Med. Chem. 54:3606-3623; U.S. Pat. No. 7,223,837; U.S. Pat. No. 8,568,728; U.S. Pat. No. 8,535,678; and WO2004010957, each of which is incorporated herein by reference.

By way of example and not limitation, some cleavable and noncleavable linkers that may be included in the anti-cMet ADCs described herein are described below.

5.6.2.1. Cleavable Linkers

In certain embodiments, the linker selected is cleavable in vivo. Cleavable linkers may include chemically or enzymatically unstable or degradable linkages. Cleavable linkers generally rely on processes inside the cell to liberate the drug, such as reduction in the cytoplasm, exposure to acidic conditions in the lysosome, or cleavage by specific proteases or other enzymes within the cell. Cleavable linkers generally incorporate one or more chemical bonds that are either chemically or enzymatically cleavable while the remainder of the linker is noncleavable. In certain embodiments, a linker comprises a chemically labile group such as hydrazone and/or disulfide groups. Linkers comprising chemically labile groups exploit differential properties between the plasma and some cytoplasmic compartments. The intracellular conditions to facilitate drug release for hydrazone containing linkers are the acidic environment of endosomes and lysosomes, while the disulfide containing linkers are reduced in the cytosol, which contains high thiol concentrations, e.g., glutathione. In certain embodiments, the plasma stability of a linker comprising a chemically labile group may be increased by introducing steric hindrance using substituents near the chemically labile group.

Acid-labile groups, such as hydrazone, remain intact during systemic circulation in the blood's neutral pH environment (pH 7.3-7.5) and undergo hydrolysis and release the drug once the ADC is internalized into mildly acidic endosomal (pH 5.0-6.5) and lysosomal (pH 4.5-5.0) compartments of the cell. This pH dependent release mechanism has been associated with nonspecific release of the drug. To increase the stability of the hydrazone group of the linker, the linker may be varied by chemical modification, e.g., substitution, allowing tuning to achieve more efficient release in the lysosome with a minimized loss in circulation.

Hydrazone-containing linkers may contain additional cleavage sites, such as additional acid-labile cleavage sites and/or enzymatically labile cleavage sites. ADCs including exemplary hydrazone-containing linkers include the following structures:

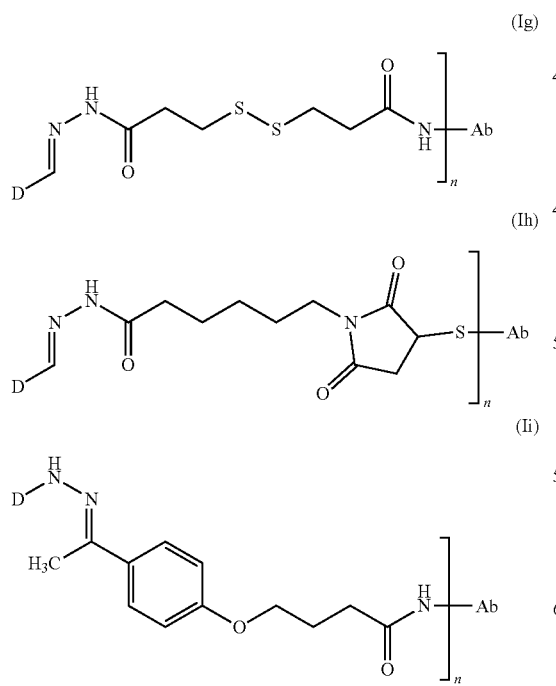

wherein D and Ab represent the cytotoxic and/or cytostatic agent (drug) and antibody, respectively, and n represents the number of drug-linkers linked to the antibody. In certain linkers such as linker (Ig), the linker comprises two cleavable groups—a disulfide and a hydrazone moiety. For such linkers, effective release of the unmodified free drug requires acidic pH or disulfide reduction and acidic pH. Linkers such as (Ih) and (Ii) have been shown to be effective with a single hydrazone cleavage site.

Other acid-labile groups that may be included in linkers include cis-aconityl-containing linkers. cis-Aconityl chemistry uses a carboxylic acid juxtaposed to an amide bond to accelerate amide hydrolysis under acidic conditions.

Cleavable linkers may also include a disulfide group. Disulfides are thermodynamically stable at physiological pH and are designed to release the drug upon internalization inside cells, wherein the cytosol provides a significantly more reducing environment compared to the extracellular environment. Scission of disulfide bonds generally requires the presence of a cytoplasmic thiol cofactor, such as (reduced) glutathione (GSH), such that disulfide-containing linkers are reasonably stable in circulation, selectively releasing the drug in the cytosol. The intracellular enzyme protein disulfide isomerase, or similar enzymes capable of cleaving disulfide bonds, may also contribute to the preferential cleavage of disulfide bonds inside cells. GSH is reported to be present in cells in the concentration range of 0.5-10 mM compared with a significantly lower concentration of GSH or cysteine, the most abundant low-molecular weight thiol, in circulation at approximately 5 µM. Tumor cells, where irregular blood flow leads to a hypoxic state, result in enhanced activity of reductive enzymes and therefore even higher glutathione concentrations. In certain embodiments, the in vivo stability of a disulfide-containing linker may be enhanced by chemical modification of the linker, e.g., use of steric hinderance adjacent to the disulfide bond.

ADCs including exemplary disulfide-containing linkers include the following structures:

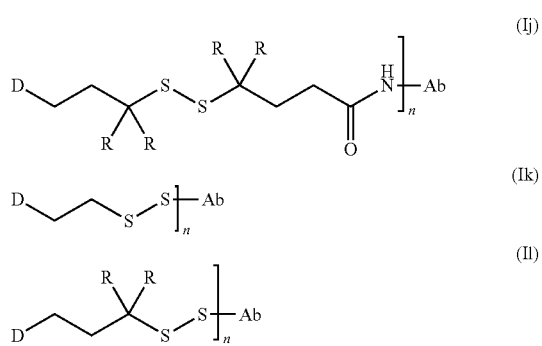

wherein D and Ab represent the drug and antibody, respectively, n represents the number of drug-linkers linked to the antibody, and R is independently selected at each occurrence from hydrogen or alkyl, for example. In certain embodiments, increasing steric hinderance adjacent to the disulfide bond increases the stability of the linker. Structures such as (Ij) and (Il) show increased in vivo stability when one or more R groups is selected from a lower alkyl such as methyl.

Another type of cleavable linker that may be used is a linker that is specifically cleaved by an enzyme. Such linkers are typically peptide-based or include peptidic regions that act as substrates for enzymes. Peptide based linkers tend to be more stable in plasma and extracellular milieu than chemically labile linkers. Peptide bonds generally have good serum stability, as lysosomal proteolytic enzymes have very low activity in blood due to endogenous inhibitors and the unfavorably high pH value of blood compared to lysosomes. Release of a drug from an antibody occurs specifically due to the action of lysosomal proteases, e.g., cathepsin and plasmin. These proteases may be present at elevated levels in certain tumor cells.

In exemplary embodiments, the cleavable peptide is selected from tetrapeptides such as Gly-Phe-Leu-Gly (SEQ ID NO:98), Ala-Leu-Ala-Leu (SEQ ID NO:99) or dipeptides such as Val-Cit, Val-Ala, Met-(D)Lys, Asn-(D)Lys, Val-(D) Asp, Phe-Lys, Ile-Val, Asp-Val, His-Val, NorVal-(D)Asp, Ala-(D)Asp, Met-Lys, Asn-Lys, Ile-Pro, Me3Lys-Pro, PhenylGly-(D)Lys, Met-(D)Lys, Asn-(D)Lys, Pro-(D)Lys, Met-(D)Lys, Asn-(D)Lys, Met-(D)Lys, Asn-(D)Lys. In certain embodiments, dipeptides are preferred over longer polypeptides due to hydrophobicity of the longer peptides.

A variety of dipeptide-based cleavable linkers useful for linking drugs such as doxorubicin, mitomycin, campotothecin, tallysomycin and auristatin/auristatin family members to antibodies have been described (see, Dubowchik et al., 1998, *J Org. Chem.* 67:1866-1872; Dubowchik et al., 1998, *Bioorg. Med. Chem. Lett.* 8(21):3341-3346; Walker et al., 2002, *Bioorg. Med. Chem. Lett.* 12:217-219; Walker et al., 2004, *Bioorg. Med. Chem. Lett.* 14:4323-4327; and Francisco et al., 2003, *Blood* 102:1458-1465, Dornina et al., 2008, Bioconjugate Chemistry 19:1960-1963, of each of which is incorporated herein by reference). All of these dipeptide linkers, or modified versions of these dipeptide linkers, may be used in the ADCs described herein. Other dipeptide linkers that may be used include those found in ADCs such as Seattle Genetics' Brentuximab Vendotin SGN-35 (Adcetris™), Seattle Genetics SGN-75 (anti-CD-70, Val-Cit-MMAF), Celldex Therapeutics glembatumumab (CDX-011) (anti-NMB, Val-Cit-MMAE), and Cytogen PSMA-ADC (PSMA-ADC-1301) (anti-PSMA, Val-Cit-MMAE).

Enzymatically cleavable linkers may include a self-immolative spacer to spatially separate the drug from the site of enzymatic cleavage. The direct attachment of a drug to a peptide linker can result in proteolytic release of an amino acid adduct of the drug, thereby impairing its activity. The use of a self-immolative spacer allows for the elimination of the fully active, chemically unmodified drug upon amide bond hydrolysis.

One self-immolative spacer is the bifunctional para-aminobenzyl alcohol group, which is linked to the peptide through the amino group, forming an amide bond, while amine containing drugs may be attached through carbamate functionalities to the benzylic hydroxyl group of the linker (PABC). The resulting prodrugs are activated upon protease-mediated cleavage, leading to a 1,6-elimination reaction releasing the unmodified drug, carbon dioxide, and remnants of the linker group. The following scheme depicts the fragmentation of p-amidobenzyl ether and release of the drug:

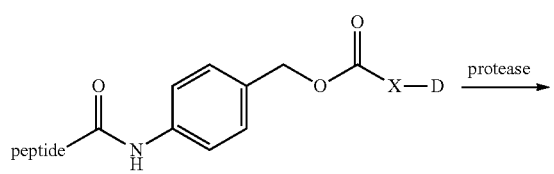

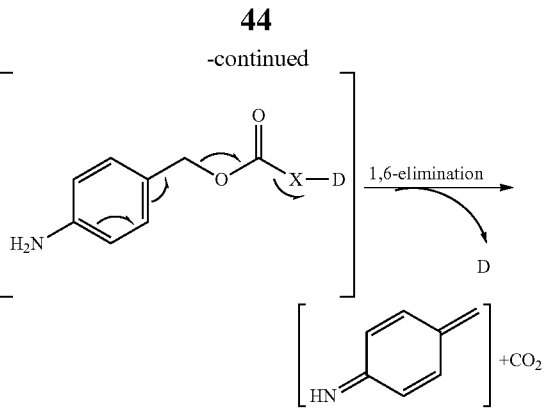

wherein X-D represents the unmodified drug.

Heterocyclic variants of this self-immolative group have also been described. See for example, U.S. Pat. No. 7,989,434, incorporated herein by reference.

In some embodiments, the enzymatically cleavable linker is a β-glucuronic acid-based linker. Facile release of the drug may be realized through cleavage of the β-glucuronide glycosidic bond by the lysosomal enzyme β-glucuronidase. This enzyme is present abundantly within lysosomes and is overexpressed in some tumor types, while the enzyme activity outside cells is low. β-Glucuronic acid-based linkers may be used to circumvent the tendency of an ADC to undergo aggregation due to the hydrophilic nature of β-glucuronides. In some embodiments, β-glucuronic acid-based linkers are preferred as linkers for ADCs linked to hydrophobic drugs. The following scheme depicts the release of the drug from and ADC containing a β-glucuronic acid-based linker:

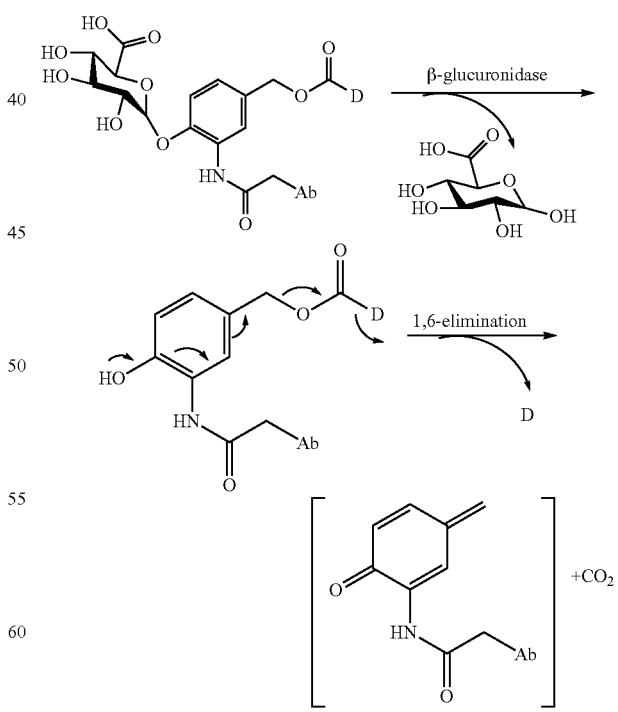

A variety of cleavable β-glucuronic acid-based linkers useful for linking drugs such as auristatins, camptothecin and doxorubicin analogues, CBI minor-groove binders, and psymberin to antibodies have been described (see, see Nolting, Chapter 5 "Linker Technology in Antibody-Drug Conjugates," In: *Antibody-Drug Conjugates: Methods in Molecular Biology*, vol. 1045, pp. 71-100, Laurent Ducry (Ed.), Springer Science & Business Medica, LLC, 2013; Jeffrey et al., 2006, *Bioconjug. Chem.* 17:831-840; Jeffrey et al., 2007, *Bioorg. Med. Chem. Lett.* 17:2278-2280; and Jiang et al., 2005, *J. Am. Chem. Soc.* 127:11254-11255, each of which is incorporated herein by reference). All of these β-glucuronic acid-based linkers may be used in the anti-cMet ADCs described herein.

Additionally, cytotoxic and/or cytostatic agents containing a phenol group can be covalently bonded to a linker through the phenolic oxygen. One such linker, described in WO 2007/089149, relies on a methodology in which a diamino-ethane "SpaceLink" is used in conjunction with traditional "PABO"-based self-immolative groups to deliver phenols. The cleavage of the linker is depicted schematically below, where D represents a cytotoxic and/or cytostatic agent having a phenolic hydroxyl group.

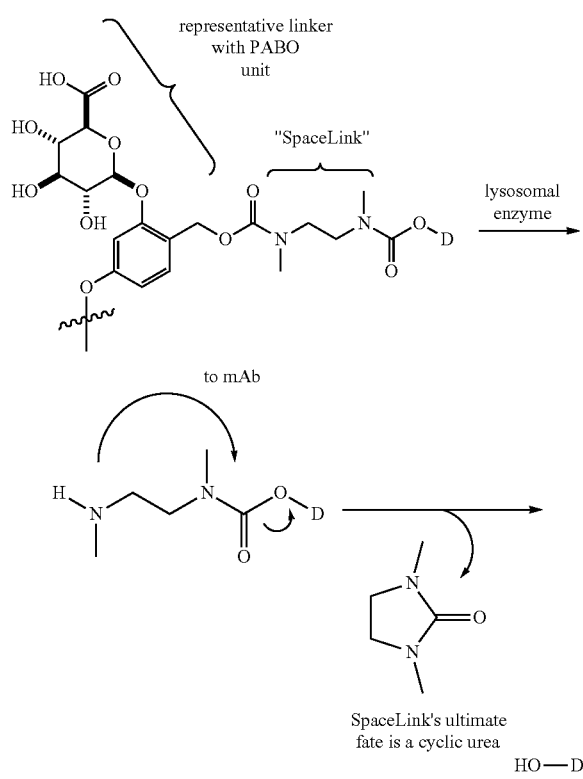

Cleavable linkers may include noncleavable portions or segments, and/or cleavable segments or portions may be included in an otherwise non-cleavable linker to render it cleavable. By way of example only, polyethylene glycol (PEG) and related polymers may include cleavable groups in the polymer backbone. For example, a polyethylene glycol or polymer linker may include one or more cleavable groups such as a disulfide, a hydrazone or a dipeptide.

Other degradable linkages that may be employed in linkers include, but are not limited to, ester linkages formed by the reaction of PEG carboxylic acids or activated PEG carboxylic acids with alcohol groups on a biologically active agent, wherein such ester groups generally hydrolyze under physiological conditions to release the biologically active agent. Hydrolytically degradable linkages include, but are not limited to, carbonate linkages; imine linkages resulting from reaction of an amine and an aldehyde; phosphate ester linkages formed by reacting an alcohol with a phosphate group; acetal linkages that are the reaction product of an aldehyde and an alcohol; orthoester linkages that are the reaction product of a formate and an alcohol; and oligonucleotide linkages formed by a phosphoramidite group, including but not limited to, at the end of a polymer, and a 5'-hydroxyl group of an oligonucleotide.

In certain embodiments, the linker comprises an enzymatically cleavable peptide moiety, for example, a linker comprising structural formula (IVa), (IVb), (IVc), or (IVd):

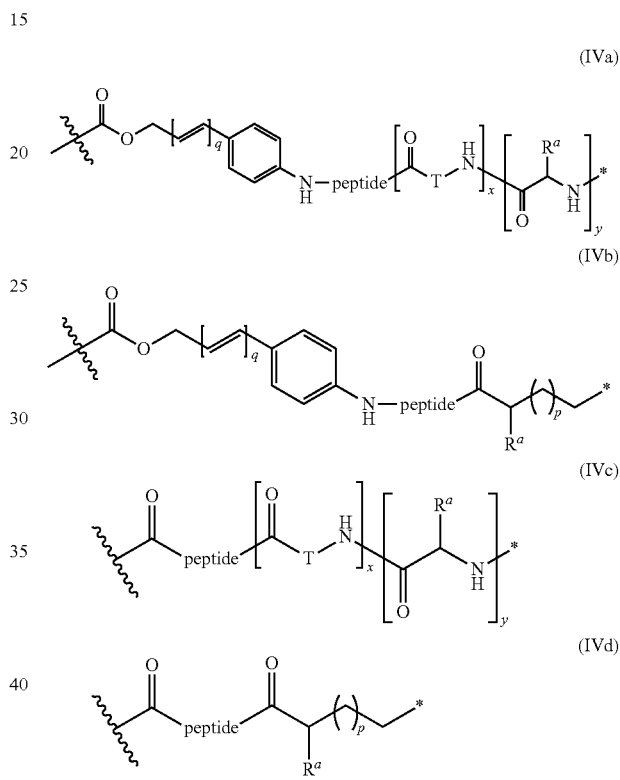

or a salt thereof, wherein:

peptide represents a peptide (illustrated C→N and not showing the carboxy and amino "termini") cleavable by a lysosomal enzyme;

T represents a polymer comprising one or more ethylene glycol units or an alkylene chain, or combinations thereof;

$R^a$ is selected from hydrogen, alkyl, sulfonate and methyl sulfonate;

p is an integer ranging from 0 to 5;

q is 0 or 1;

x is 0 or 1;

y is 0 or 1;

⨎ represents the point of attachment of the linker to a cytotoxic and/or cytostatic agent; and \* represents the point of attachment to the remainder of the linker.

In certain embodiments, the lysosomal enzyme is selected from Cathepsin B and β-glucoronidase.

In certain embodiments, the peptide is selected from a tripeptide or a dipeptide. In particular embodiments, the dipeptide is selected from: Val-Cit; Cit-Val; Ala-Ala; Ala-Cit; Cit-Ala; Asn-Cit; Cit-Asn; Cit-Cit; Val-Glu; Glu-Val;

Ser-Cit; Cit-Ser; Lys-Cit; Cit-Lys; Asp-Cit; Cit-Asp; Ala-Val; Val-Ala; Phe-Lys; Val-Lys; Ala-Lys; Phe-Cit; Leu-Cit; Ile-Cit; Phe-Arg; and Trp-Cit. In certain embodiments, the peptide is selected from: Val-Cit; Cit-Val; Ala-Ala; Ala-Cit; Cit-Ala; Asn-Cit; Cit-Asn; Cit-Cit; Val-Glu; Glu-Val; Ser-Cit; Cit-Ser; Lys-Cit; Cit-Lys; Asp-Cit; Cit-Asp; Ala-Val; and Val-Ala and salts thereof.

Specific exemplary embodiments of linkers according to structural formula (IVa) that may be included in the ADCs described herein include the linkers illustrated below (as illustrated, the linkers include a group suitable for covalently linking the linker to an antibody):

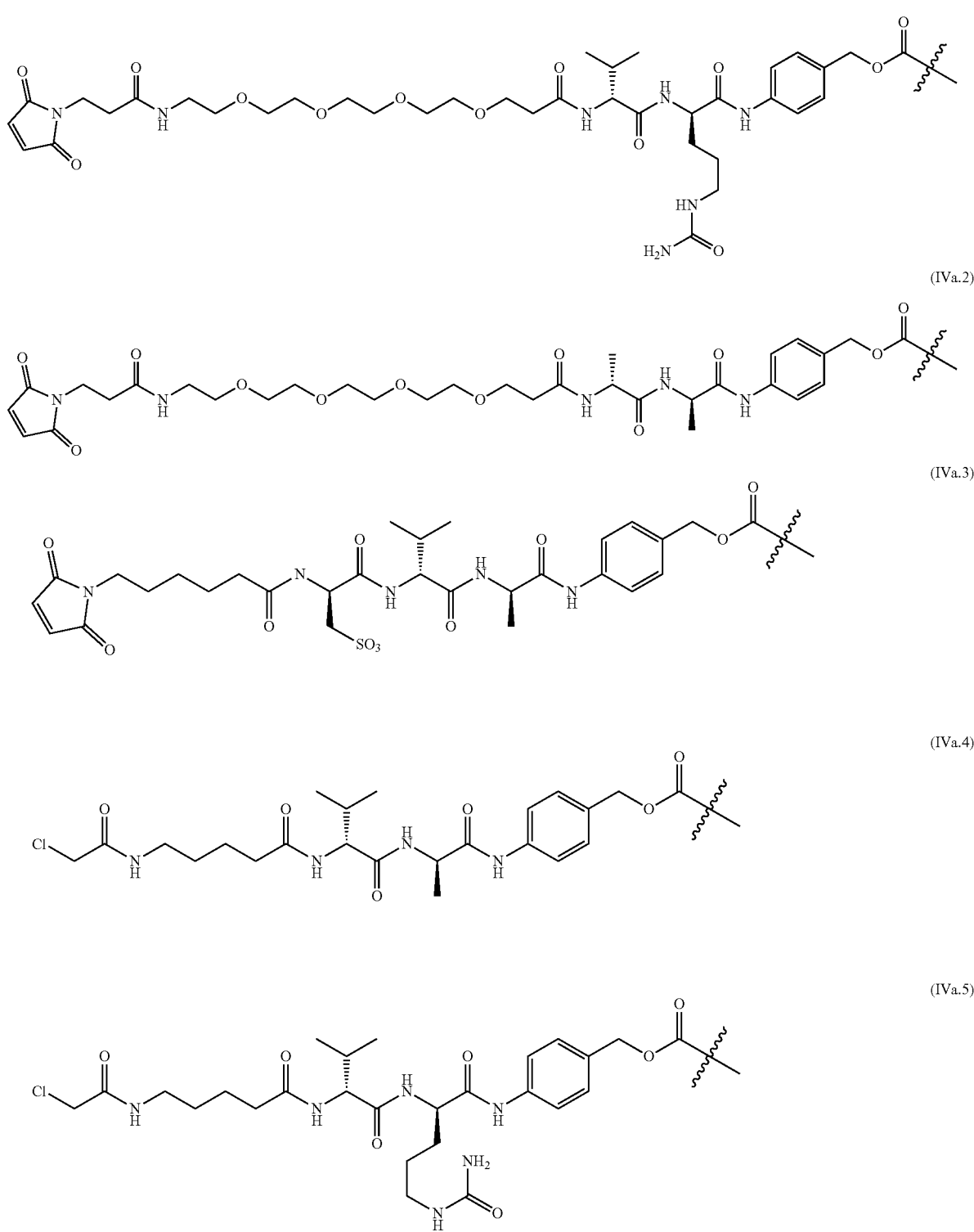

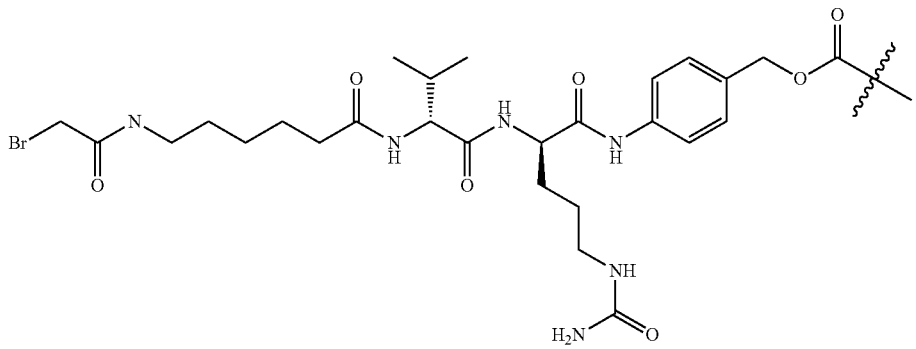
(IVa.6)
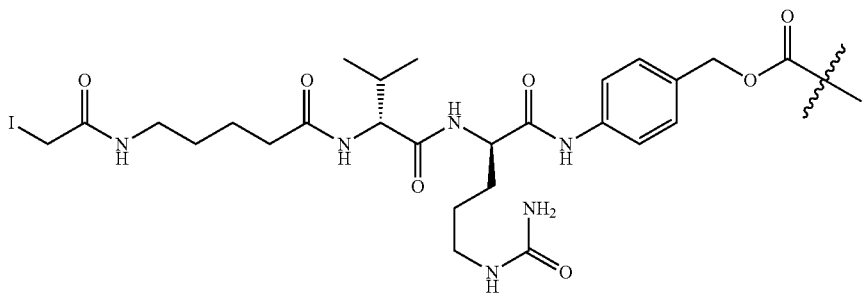
(IVa.7)
Specific exemplary embodiments of linkers according to structural formula (IVb) that may be included in the ADCs described herein include the linkers illustrated below (as illustrated, the linkers include a group suitable for covalently linking the linker to an antibody):
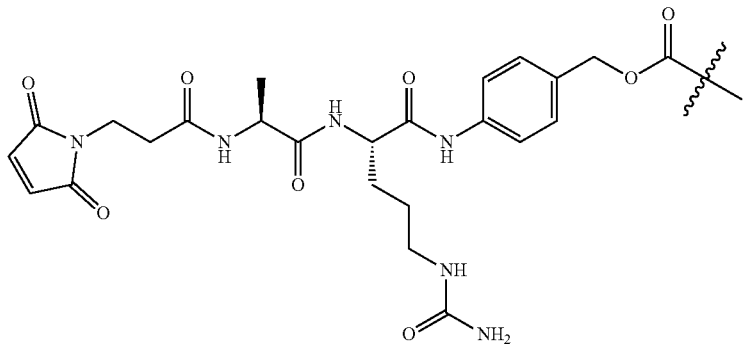
(IVb.1)
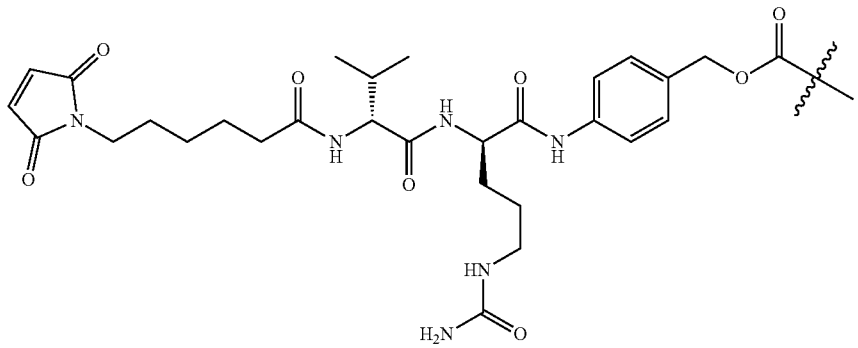
(IVb.2)

-continued
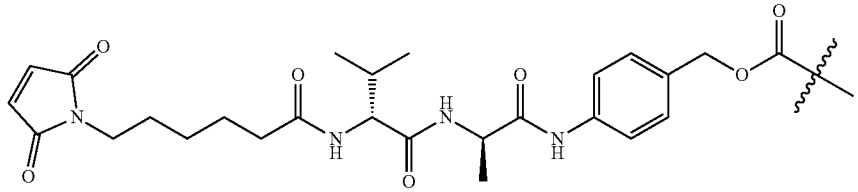
(IVb.3)
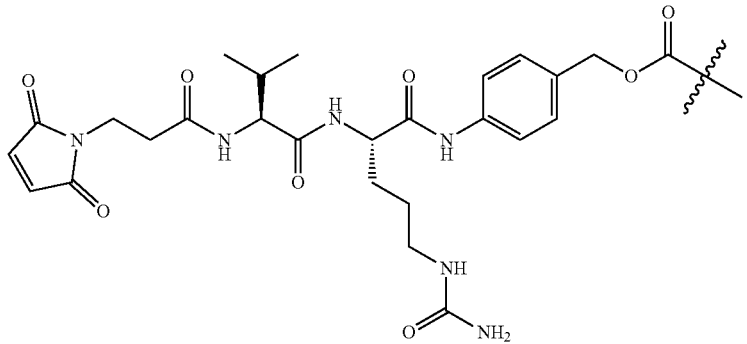
(IVb.4)
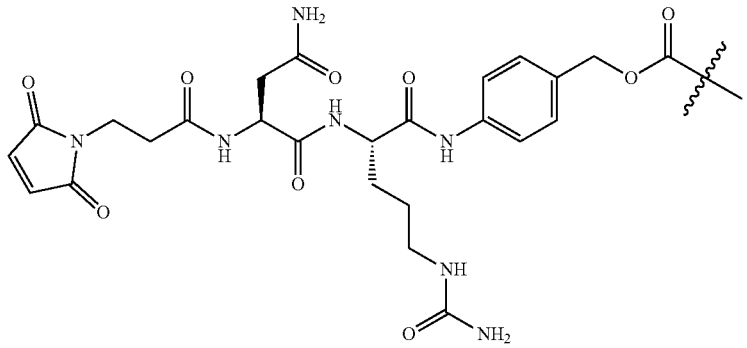
(IVb.5)
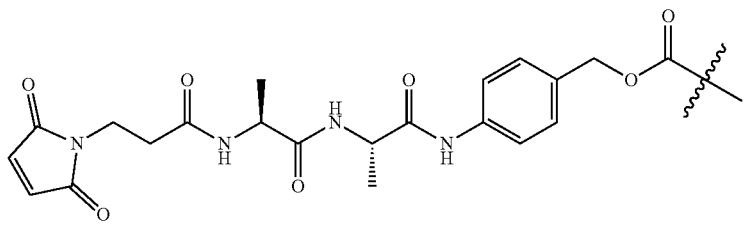
(IVb.6)
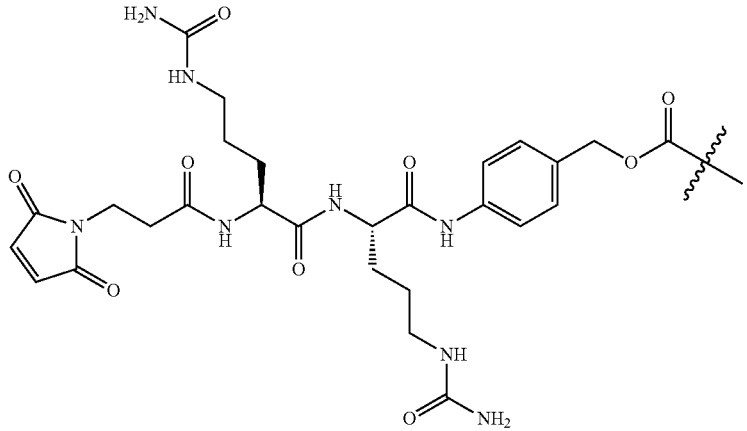
(IVb.7)

-continued
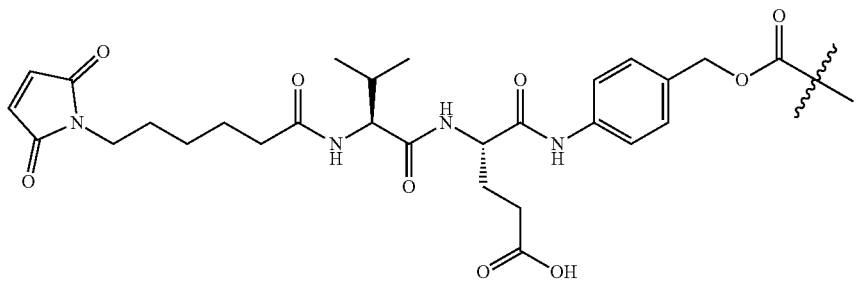
(IVb.8)
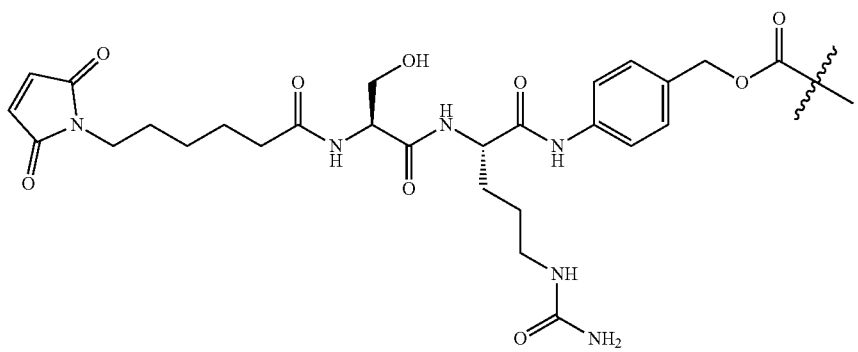
(IVb.9)
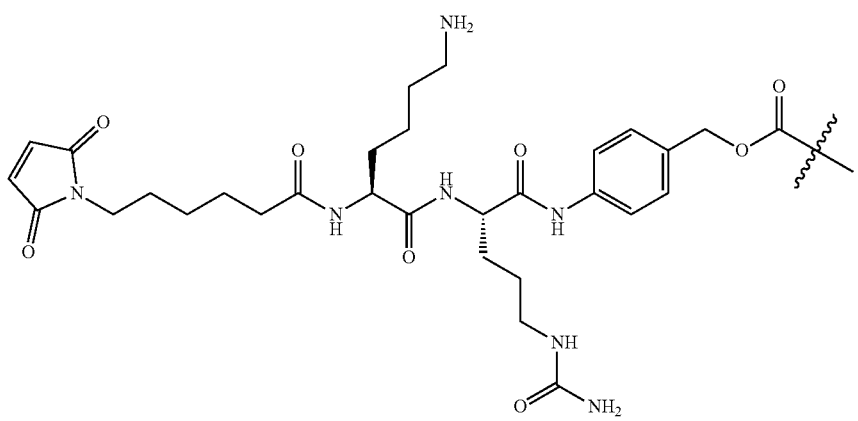
(IVb.10)
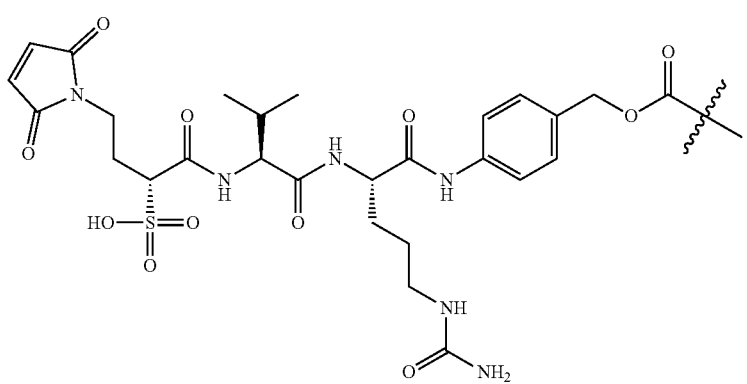
(IVb.11)

(IVb.12)
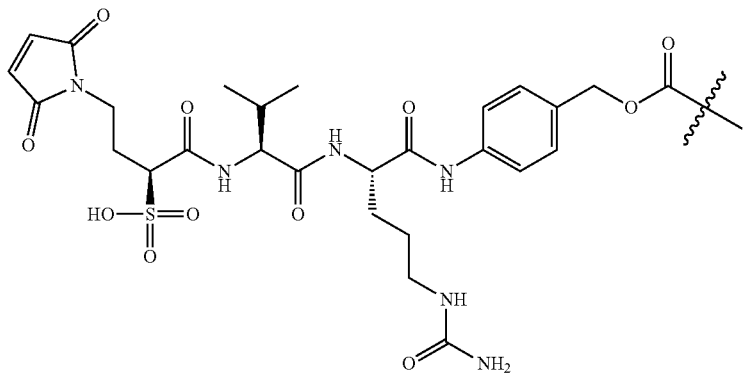
(IVb.13)
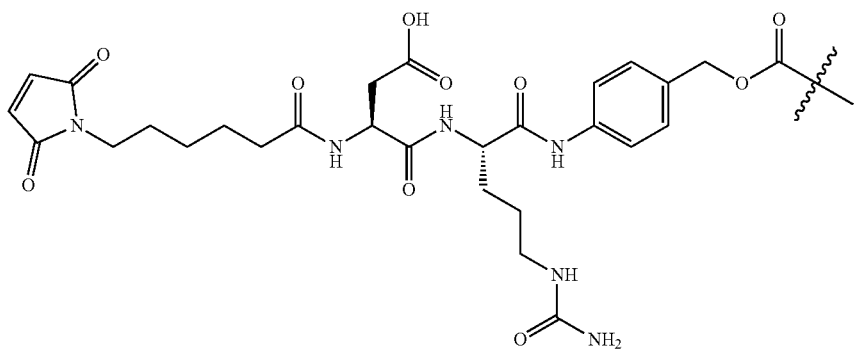
(IVb.14)
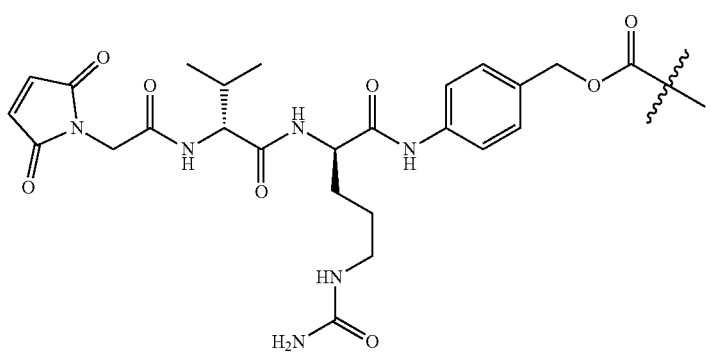
(IVb.15)
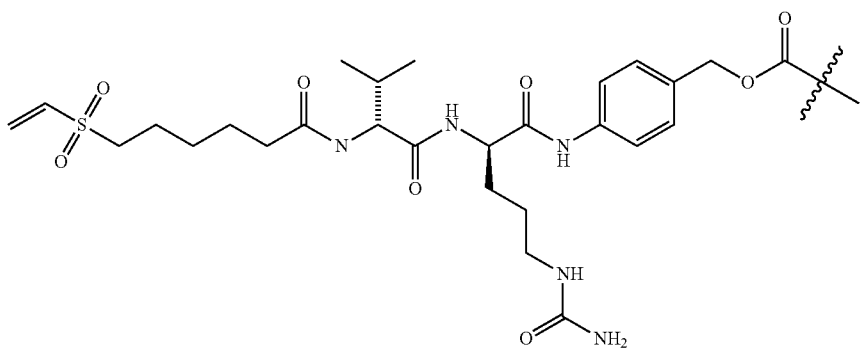

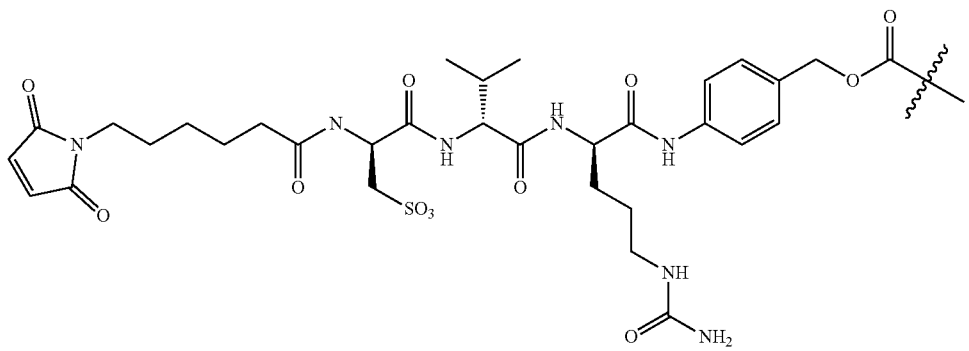
(IVb.16)
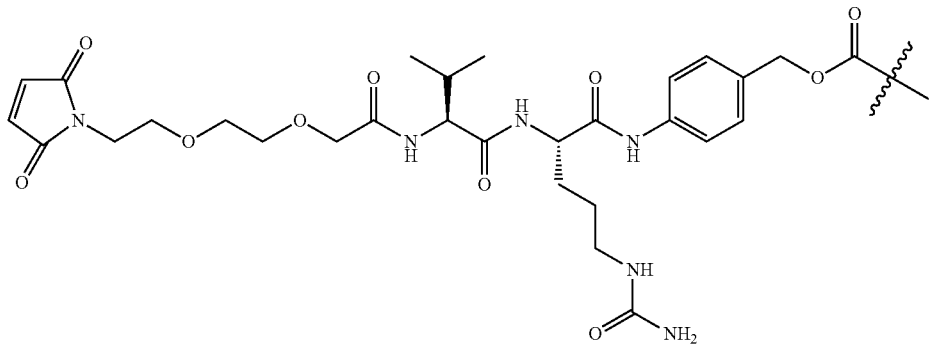
(IVb.17)
Specific exemplary embodiments of linkers according to structural formula (IVc) that may be included in the ADCs described herein include the linkers illustrated below (as illustrated, the linkers include a group suitable for covalently linking the linker to an antibody):
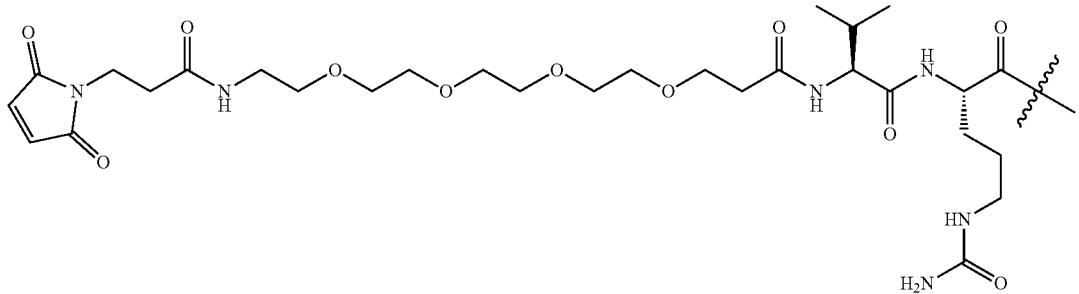
(IVc.1)
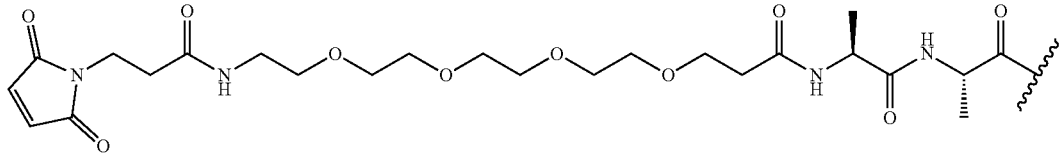
(IVc.2)
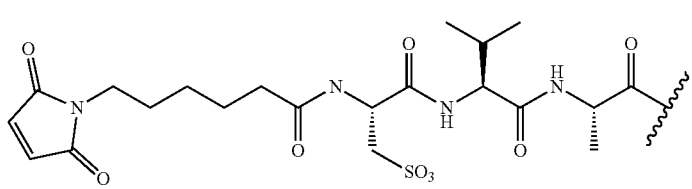
(IVc.3)

(IVc.4)
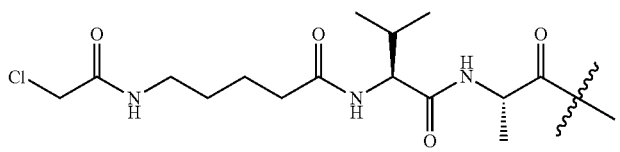
(IVc.5)
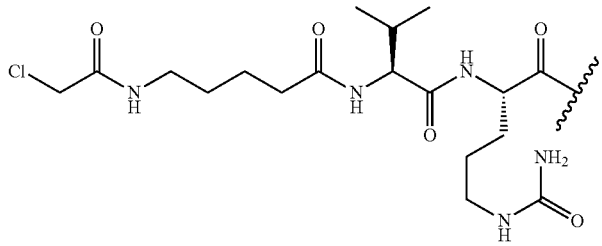
(IVc.6)
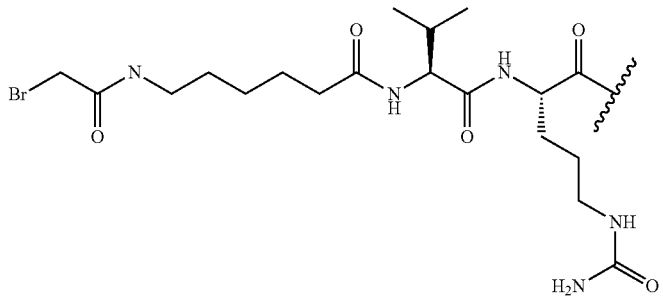
(IVc.7)
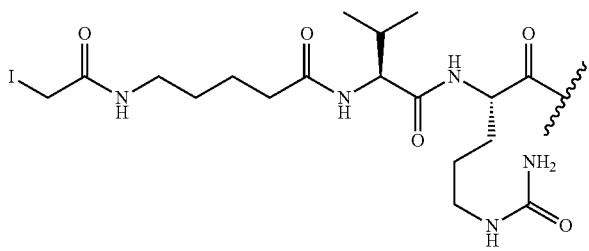
Specific exemplary embodiments of linkers according to structural formula (IVd) that may be included in the ADCs described herein include the linkers illustrated below (as illustrated, the linkers include a group suitable for covalently linking the linker to an antibody):
(IVd.1)
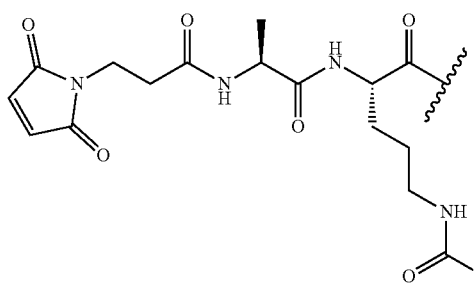
(IVd.2)
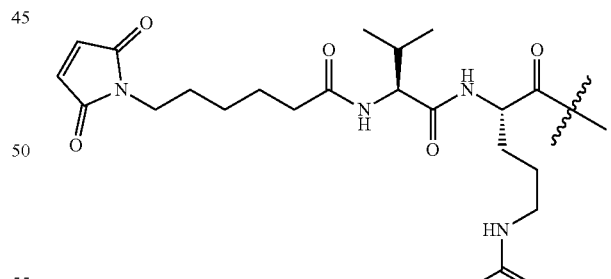
(IVd.3)
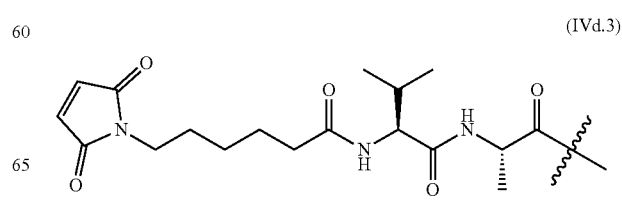

(IVd.4)
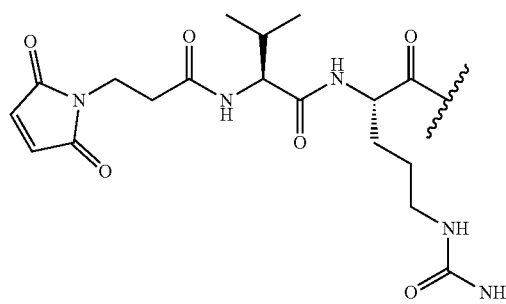
(IVd.5)
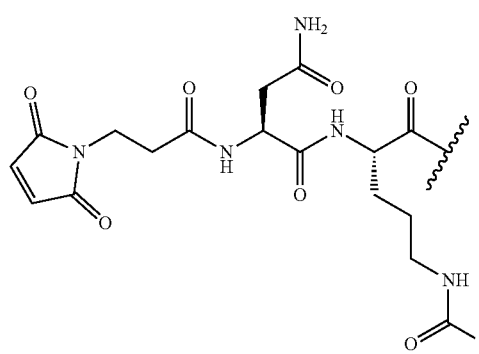
(IVd.6)
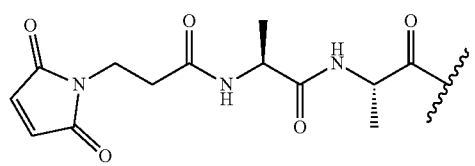
(IVd.7)
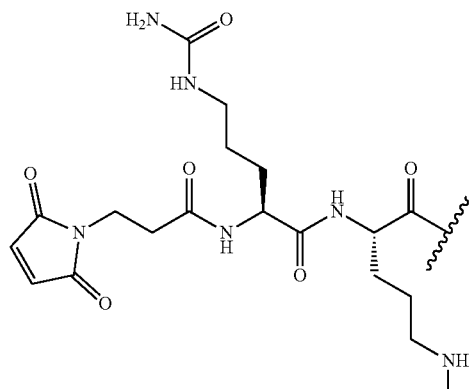
(IVd.8)
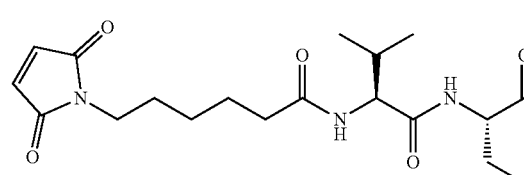
(IVd.9)
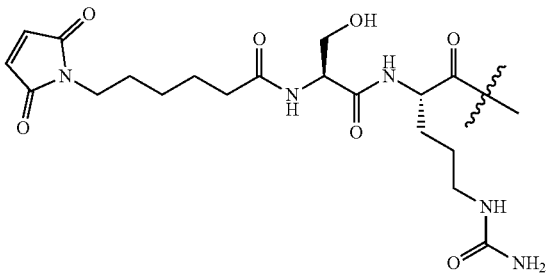
(IVd.10)
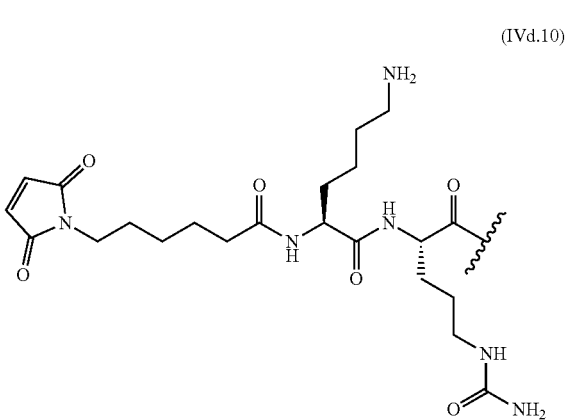
(IVd.11)
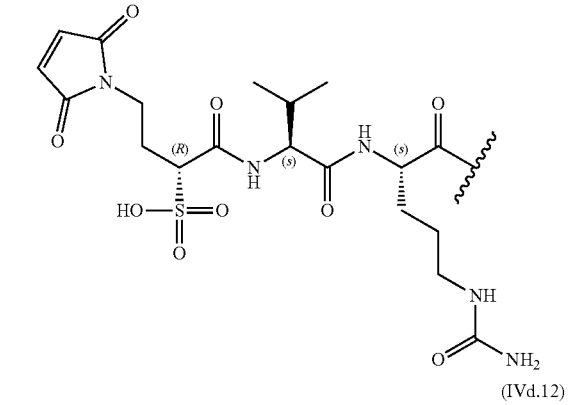
(IVd.12)
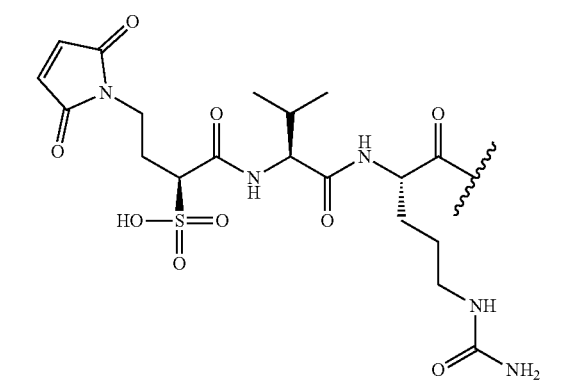

(IVd.13)
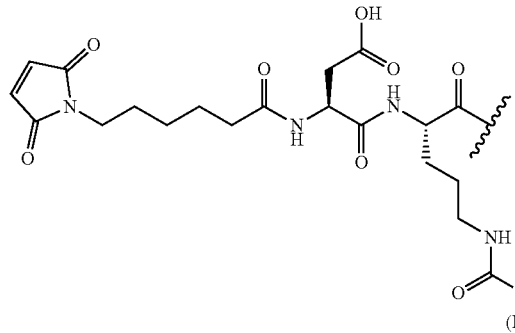

(IVd.14)
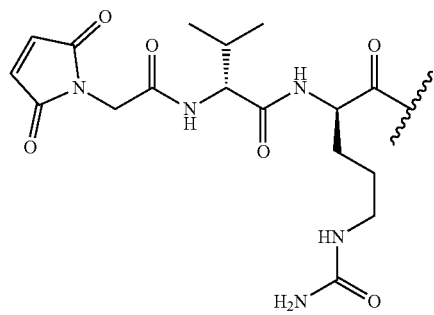

(IVd.15)
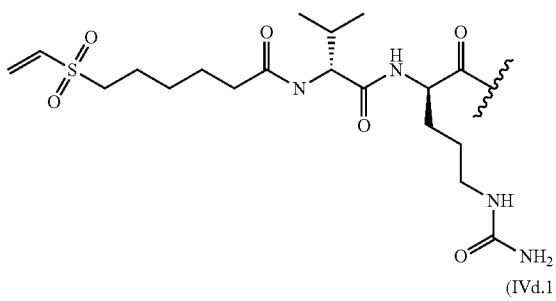

(IVd.16)
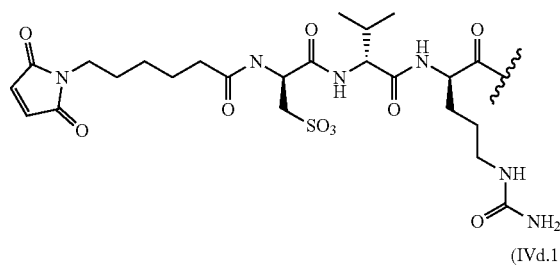

(IVd.17)
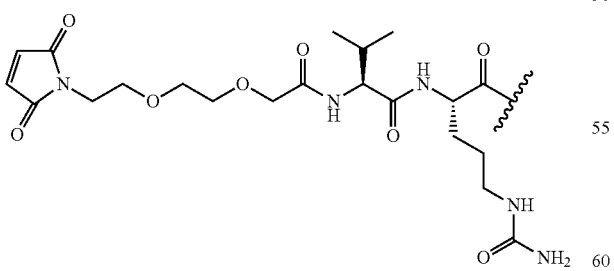

In certain embodiments, the linker comprising structural formula (IVa), (IVb), (IVc), or (IVd) further comprises a carbonate moiety cleavable by exposure to an acidic medium. In particular embodiments, the linker is attached through an oxygen to a cytotoxic and/or cytostatic agent.

5.6.2.2. Non-Cleavable Linkers

Although cleavable linkers may provide certain advantages, the linkers composing the ADC described herein need not be cleavable. For non-cleavable linkers, the release of drug does not depend on the differential properties between the plasma and some cytoplasmic compartments. The release of the drug is postulated to occur after internalization of the ADC via antigen-mediated endocytosis and delivery to lysosomal compartment, where the antibody is degraded to the level of amino acids through intracellular proteolytic degradation. This process releases a drug derivative, which is formed by the drug, the linker, and the amino acid residue to which the linker was covalently attached. The amino acid drug metabolites from conjugates with non-cleavable linkers are more hydrophilic and generally less membrane permeable, which leads to less bystander effects and less nonspecific toxicities compared to conjugates with a cleavable linker. In general, ADCs with noncleavable linkers have greater stability in circulation than ADCs with cleavable linkers. Non-cleavable linkers may be alkylene chains, or may be polymeric in nature, such as, for example, those based upon polyalkylene glycol polymers, amide polymers, or may include segments of alkylene chains, polyalkylene glycols and/or amide polymers.

A variety of non-cleavable linkers used to link drugs to antibodies have been described. See, Jeffrey et al., 2006, Bioconjug. Chem. 17; 831-840; Jeffrey et al., 2007, Bioorg. Med. Chem. Lett. 17:2278-2280; and Jiang et al., 2005, J. Am. Chem. Soc. 127:11254-11255, each of which is incorporated herein by reference. All of these linkers may be included in the ADCs described herein.

In certain embodiments, the linker is non-cleavable in vivo, for example a linker according to structural formula (VIa), (VIb), (VIc) or (VId) (as illustrated, the linkers include a group suitable for covalently linking the linker to an antibody:

(VIa)
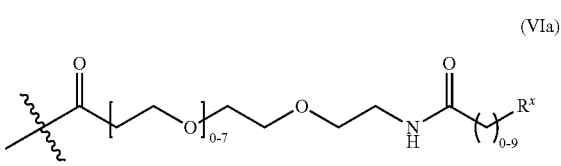

(VIb)
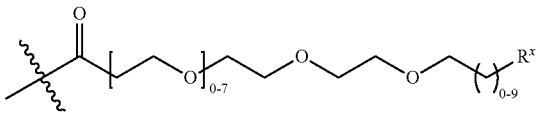

-continued

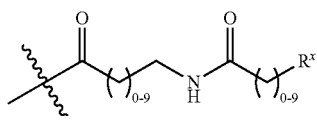
(VIc)

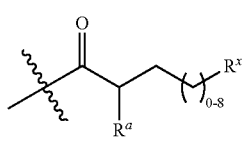
(VId)

or salts thereof, wherein:

$R^a$ is selected from hydrogen, alkyl, sulfonate and methyl sulfonate;

$R^x$ is a moiety including a functional group capable of covalently linking the linker to an antibody; and ⸓ represents the point of attachment of the linker to a cytotoxic and/or cytostatic agent.

Specific exemplary embodiments of linkers according to structural formula (VIa)-(VId) that may be included in the ADCs described herein include the linkers illustrated below (as illustrated, the linkers include a group suitable for covalently linking the linker to an antibody, and "⸓" represents the point of attachment to a cytotoxic and/or cytostatic agent):

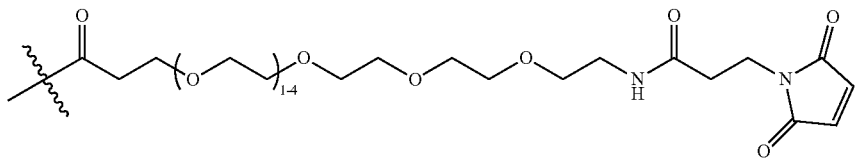
(VIa.1)

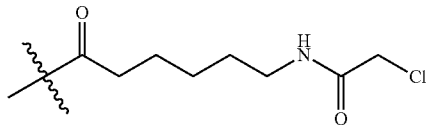
(VIc.1)

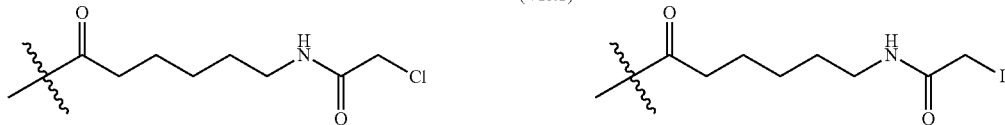
(VIc.2)

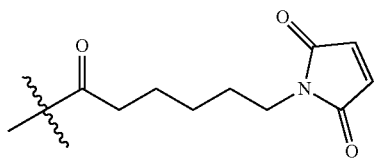
(VId.1)

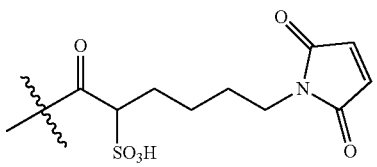
(VId.2)

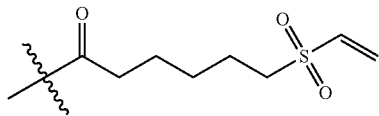
(VId.3)

5.6.2.3. Groups Used to Attach Linkers to Antibodies

A variety of groups may be used to attach linker-drug synthons to antibodies to yield ADCs. Attachment groups can be electrophilic in nature and include: maleimide groups, activated disulfides, active esters such as NHS esters and HOBt esters, haloformates, acid halides, alkyl and benzyl halides such as haloacetamides. As discussed below, there are also emerging technologies related to "self-stabilizing" maleimides and "bridging disulfides" that can be used in accordance with the disclosure. The specific group used will depend, in part, on the site of attachment to the antibody.

One example of a "self-stabilizing" maleimide group that hydrolyzes spontaneously under antibody conjugation conditions to give an ADC species with improved stability is depicted in the schematic below. See US20130309256 A1; also Lyon et al., Nature Biotech published online, doi: 10.1038/nbt.2968).

Normal System:

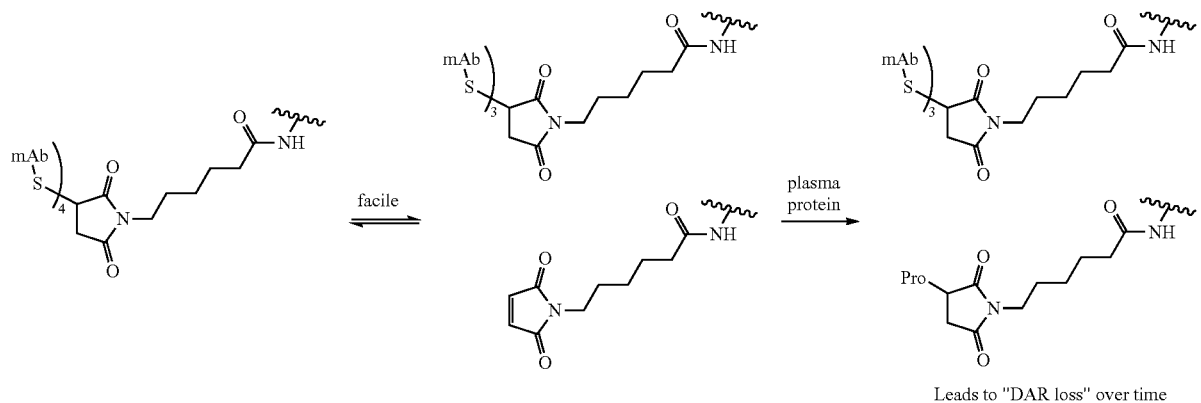

SGN MaIDPR (Maleimido Dipropylamino) System:

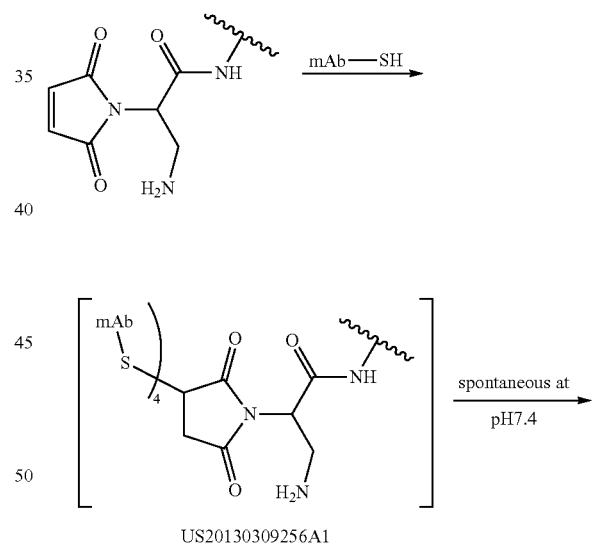

US20130309256A1

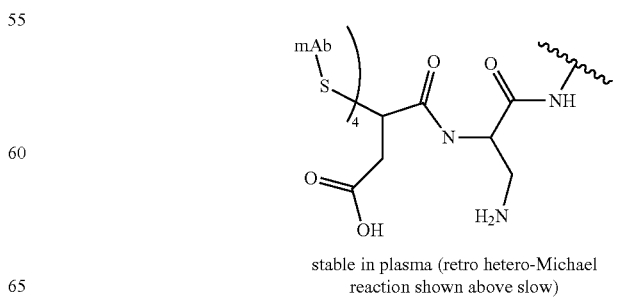

stable in plasma (retro hetero-Michael reaction shown above slow)

Polytherics has disclosed a method for bridging a pair of sulfhydryl groups derived from reduction of a native hinge disulfide bond. See, Badescu et al., 2014, Bioconjugate Chem. 25:1124-1136. The reaction is depicted in the schematic below. An advantage of this methodology is the ability to synthesize homogeneous DAR4 ADCs by full reduction of IgGs (to give 4 pairs of sulfhydryls) followed by reaction with 4 equivalents of the alkylating agent. ADCs containing "bridged disulfides" are also embodimented to have increased stability.

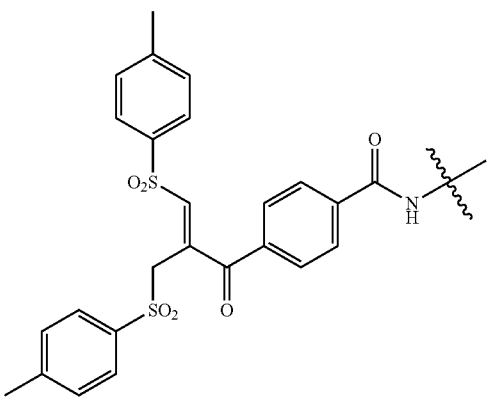

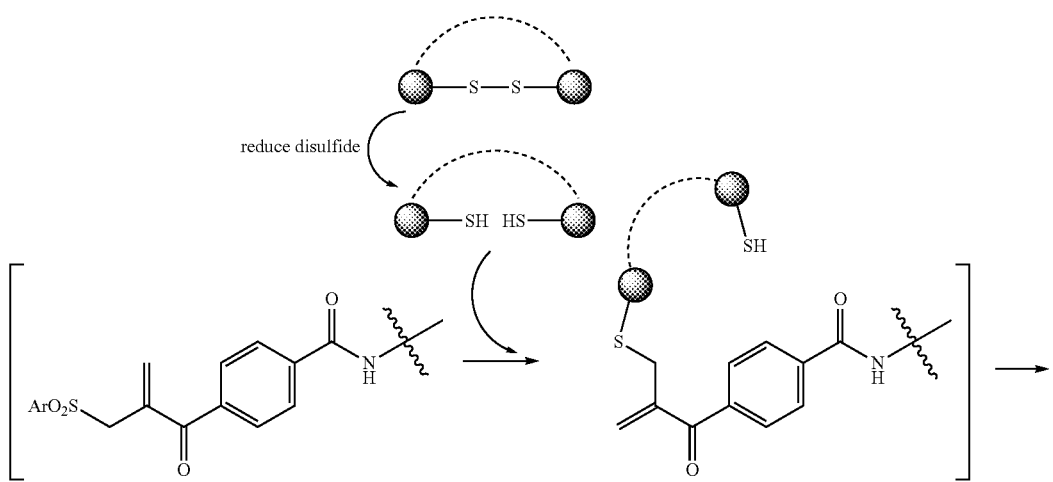

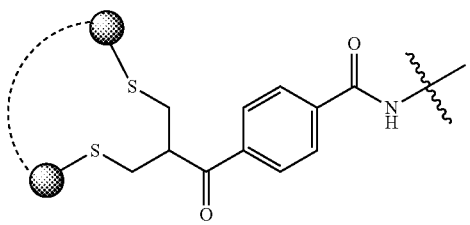

"bridged disulfide"

Similarly, as depicted below, a maleimide derivative (1, below) that is capable of bridging a pair of sulfhydryl groups has been developed. See WO2013/085925.

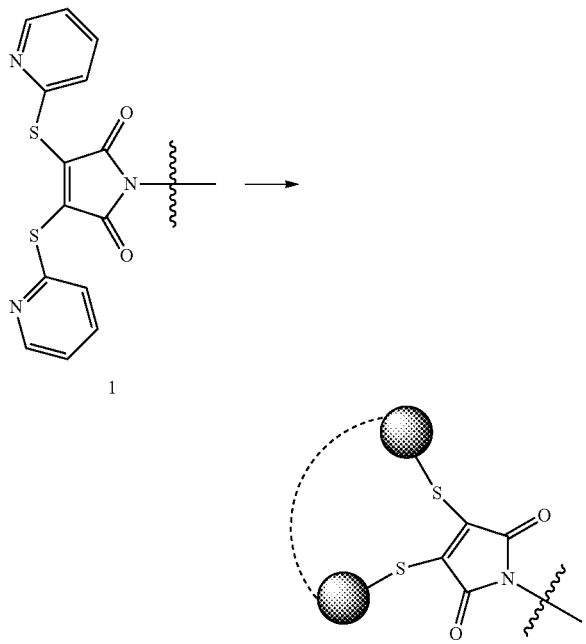

5.6.2.4. Linker Selection Considerations

As is known by skilled artisans, the linker selected for a particular ADC may be influenced by a variety of factors, including but not limited to, the site of attachment to the antibody (e.g., Lys, Cys or other amino acid residues), structural constraints of the drug pharmacophore and the lipophilicity of the drug. The specific linker selected for an ADC should seek to balance these different factors for the specific antibody/drug combination. For a review of the factors that are influenced by choice of linkers in ADCs, see Nolting, Chapter 5 "Linker Technology in Antibody-Drug Conjugates," In: *Antibody-Drug Conjugates: Methods in Molecular Biology*, vol. 1045, pp. 71-100, Laurent Ducry (Ed.), Springer Science & Business Medica, LLC, 2013.

For example, anti-cMet ADCs can effect killing of bystander cMet-negative tumor cells present in the vicinity of cMet-expressing cancer cells. The mechanism of bystander cell killing by ADCs has indicated that metabolic products formed during intracellular processing of the ADCs may play a role. Cell-permeable cytotoxic and/or cytostatic metabolites generated by metabolism of the ADCs in cMet-expressing cells appear to play a role in bystander cell killing, while non-cell-permeable metabolites, which are incapable of traversing the cell membrane and diffusing into the medium cannot effect bystander killing. In certain embodiments, the linker is selected to effect, enhance or increase the bystander killing effect of the anti-cMet ADCs.

The properties of the linker may also impact aggregation of the ADC under conditions of use and/or storage. Typically, ADCs reported in the literature contain no more than 3-4 drug molecules per antigen-binding moiety, for example, per antibody molecule (see, e.g., Chari, 2008, *Acc Chem Res* 41:98-107). Attempts to obtain higher drug-to-antibody ratios ("DAR") often failed, particularly if both the drug and the linker were hydrophobic, due to aggregation of the ADC (King et al., 2002, *J Med Chem* 45:4336-4343; Hollander et al., 2008, *Bioconjugate Chem* 19:358-361; Burke et al., 2009 *Bioconjugate Chem* 20:1242-1250). In many instances, DARs higher than 3-4 could be beneficial as a means of increasing potency. In instances where the cytotoxic and/or cytostatic agent is hydrophobic in nature, it may be desirable to select linkers that are relatively hydrophilic as a means of reducing ADC aggregation, especially in instances where DARS greater than 3-4 are desired. Thus, in certain embodiments, the linker incorporates chemical moieties that reduce aggregation of the ADCs during storage and/or use. A linker may incorporate polar or hydrophilic groups such as charged groups or groups that become charged under physiological pH to reduce the aggregation of the ADCs. For example, a linker may incorporate charged groups such as salts or groups that deprotonate, e.g., carboxylates, or protonate, e.g., amines, at physiological pH.

Exemplary polyvalent linkers that have been reported to yield DARs as high as 20 that may be used to link numerous cytotoxic and/or cytostatic agents to an antibody are described in WO 2009/073445; WO 2010/068795; WO 2010/138719; WO 2011/120053; WO 2011/171020; WO 2013/096901; WO 2014/008375; WO 2014/093379; WO 2014/093394; WO 2014/093640, the contents of which are incorporated herein by reference in their entireties.

In particular embodiments, the aggregation of the ADCs during storage or use is less than about 10% as determined by size-exclusion chromatography (SEC). In particular embodiments, the aggregation of the ADCs during storage or use is less than 10%, such as less than about 5%, less than about 4%, less than about 3%, less than about 2%, less than about 1%, less than about 0.5%, less than about 0.1%, or even lower, as determined by size-exclusion chromatography (SEC).

5.6.3. ABBV-399

As described throughout the specification, ABBV-399 is an ADC comprised of the cMet targeting antibody ABT-700 (PR-1266688, h224G11) conjugated to the potent cytotoxin monomethyl auristatin E (MMAE) through a valine citrulline (vc) linker. ABBV-399 has been used in a Phase 1 clinical trial (see Example 16) with a DAR of 3.1.

In alternative embodiments, ABBV-399 can be used at a 1:1 E2/E4 ratio, which corresponds to an average DAR of 3.0. In other words, the ABBV-399 is used as a composition comprising a 1:1 ratio of the E2 and E4 purified fractions of antibody-drug conjugate.

5.6.4. ABT-700 PBD

ABT-700 (S238C)-PBD (Kabat numbering) is the same as ABT-700 (S239C)-PBD (Eu numbering) and is comprised of two PBD drug-linker molecules conjugated to a cys engineered mAb ABT-700. The conjugation process consists of a quantitative reduction of the engineered and interchain disulfides. The reduction mixture is then purified to remove the excess reagent and its byproducts, followed by quantitative oxidation of the interchain disulfides and then conjugation with excess PBD drug-linker. After quenching, the reaction mixture is purified and buffer-exchanged to yield ABT-700 (S238C)-PBD. Reaction parameters have been identified to provide a conjugate with >80% DAR2 drug loading.

The sequence of ABT-700 PBD, which carries a S238C mutation (Kabat numbering) (equivalent to S239C mutation in Eu numbering), is as follows (CDRs are underlined; the numbering system is Kabat; and the S238C mutation is represented by C (bold, underlined, and italics):

Amino Acid Sequence (10 AA Per Group, 5 Groups Per Line)

Heavy Chain (SEQ ID NO: 171) (Underlined CDR Sequences Disclosed as SEQ ID NOS 173-175, Respectively, in Order of Appearance):

```
QVQLVQSGAE VKKPGASVKV SCKASGYIFT AYTMHWVRQA PGQGLEWMGW    50

IKPNNGLANY AQKFQGRVTM TRDTSISTAY MELSRLRSDD TAVYYCARSE   100

ITTEFDYWGQ GTLVTVSSAS TKGPSVFPLA PSSKSTSGGT AALGCLVKDY   150

FPEPVTVSWN SGALTSGVHT FPAVLQSSGL YSLSSVVTVP SSSLGTQTYI   200

CNVNHKPSNT KVDKRVEPKS CDCHCPPCPA PELLGGPCVF LFPPKPKDTL   250

MISRTPEVTC VVVDVSHEDP EVKFNWYVDG VEVHNAKTKP REEQYNSTYR   300

VVSVLTVLHQ DWLNGKEYKC KVSNKALPAP IEKTISKAKG QPREPQVYTL   350

PPSREEMTKN QVSLTCLVKG FYPSDIAVEW ESNGQPENNY KTTPPVLDSD   400

GSFFLYSKLT VDKSRWQQGN VFSCSVMHEA LHNHYTQKSL SLSPG        445
```

Light Chain (SEQ ID NO: 172) (Underlined CDR Sequences Disclosed as SEQ ID NOS 176-178, Respectively, in Order of Appearance):

```
DIVMTQSPDS LAVSLGERAT INCKSSESVD SYANSFLHWY QQKPGQPPKL    50

LIYRASTRES GVPDRFSGSG SGTDFTLTIS SLQAEDVAVY YCQQSKEDPL   100

TFGGGTKVEI KRTVAAPSVF IFPPSDEQLK SGTASVVCLL NNFYPREAKV   150

QWKVDNALQS GNSQESVTEQ DSKDSTYSLS STLTLSKADY EKHKVYACEV   200

THQGLSSPVT KSFNRGEC                                      218
```

5.7. Methods of Making Anti-cMet Antibody Drug Conjugates

The ADCs described herein may be synthesized using chemistries that are well-known. The chemistries selected will depend upon, among other things, the identity of the cytotoxic and/or cytostatic agent(s), the linker and the groups used to attach linker to the antibody. Generally, ADCs according to formula (I) may be prepared according to the following scheme:

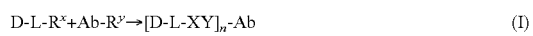

D-L-R$^x$+Ab-R$^y$→[D-L-XY]$_n$-Ab    (I)

where D, L, Ab, XY and n are as previously defined, and R$^x$ and R$^y$ represent complementary groups capable of forming covalent linkages with one another, as discussed above.

The identities of groups R$^x$ and R$^y$ will depend upon the chemistry used to link synthon D-L-W to the antibody. Generally, the chemistry used should not alter the integrity of the antibody, for example its ability to bind its target. Preferably, the binding properties of the conjugated antibody will closely resemble those of the unconjugated antibody. A variety of chemistries and techniques for conjugating molecules to biological molecules such as antibodies are known in the art and in particular to antibodies, are well-known. See, e.g., Amon et al., "Monoclonal Antibodies For Immunotargeting Of Drugs In Cancer Therapy," in: *Monoclonal Antibodies And Cancer Therapy*, Reisfeld et al. Eds., Alan R. Liss, Inc., 1985; Hellstrom et al., "Antibodies For Drug Delivery," in: *Controlled Drug Delivery*, Robinson et al. Eds., Marcel Dekker, Inc., 2nd Ed. 1987; Thorpe, "Antibody Carriers Of Cytotoxic Agents In Cancer Therapy: A Review," in: *Monoclonal Antibodies '84: Biological And Clinical Applications*, Pinchera et al., Eds., 1985; "Analysis, Results, and Future Prospective of the Therapeutic Use of Radiolabeled Antibody In Cancer Therapy," in: *Monoclonal Antibodies For Cancer Detection And Therapy*, Baldwin et al., Eds., Academic Press, 1985; Thorpe et al., 1982, *Immunol. Rev.* 62:119-58; PCT publication WO 89/12624. Any of these chemistries may be used to link the synthons to an antibody.

A number of functional groups R$^x$ and chemistries useful for linking synthons to accessible lysine residues are known, and include by way of example and not limitation NHS-esters and isothiocyanates.

A number of functional groups R$^x$ and chemistries useful for linking synthons to accessible free sulfhydryl groups of cysteine residues are known, and include by way of example and not limitation haloacetyls and maleimides.

However, conjugation chemistries are not limited to available side chain groups. Side chains such as amines may be converted to other useful groups, such as hydroxyls, by linking an appropriate small molecule to the amine. This strategy can be used to increase the number of available linking sites on the antibody by conjugating multifunctional small molecules to side chains of accessible amino acid residues of the antibody. Functional groups R$^x$ suitable for covalently linking the synthons to these "converted" functional groups are then included in the synthons.

An antibody may also be engineered to include amino acid residues for conjugation. An approach for engineering antibodies to include non-genetically encoded amino acid residues useful for conjugating drugs in the context of ADCs is described by Axup et al., 2012, *Proc Natl Acad Sci USA*. 109(40):16101-16106, as are chemistries and functional groups useful for linking synthons to the non-encoded amino acids.

Typically, the synthons are linked to the side chains of amino acid residues of the antibody, including, for example, the primary amino group of accessible lysine residues or the sulfhydryl group of accessible cysteine residues. Free sulfhydryl groups may be obtained by reducing interchain disulfide bonds.

For linkages where $R^y$ is a sulfhydryl group (for example, when $R^x$ is a maleimide), the antibody is generally first fully or partially reduced to disrupt interchain disulfide bridges between cysteine residues. Specific cysteine residues and interchain disulfide bridges that may be reduced for attachment of drug-linker synthons including a group suitable for conjugation to a sulfhydryl group for exemplary antibody ABT-700, include by way of example and not limitation, residues C221, C223, C225, and C228 on the human $IgG_1$ heavy chain, and residue C218 on the human Ig kappa light chain of the ABT-700 disclosed herein.

Cysteine residues for synthon attachment that do not participate in disulfide bridges may be engineered into an antibody by mutation of one or more codons. These unpaired cysteines provide a sulfhydryl group suitable for conjugation. Preferred positions for incorporating engineered cysteines include, by way of example and not limitation, positions S112C, S113C, A114C, S115C, A176C, S180C, S252C, V286C, V292C, S357C, A359C, S398C, S428C (Kabat numbering) on the human $IgG_1$ heavy chain and positions V110C, S114C, S121C, S127C, S168C, V205C (Kabat numbering) on the human Ig kappa light chain (see, e.g., U.S. Pat. No. 7,521,541, U.S. Pat. No. 7,855,275 and U.S. Pat. No. 8,455,622).

As will be appreciated by skilled artisans, the number of cytotoxic and/or cytostatic agents linked to an antibody molecule may vary, such that an ADC preparation may be heterogeneous in nature, where some antibodies in the preparation contain one linked agent, some two, some three, etc. (and some none). The degree of heterogeneity will depend upon, among other things, the chemistries used for linking the cytotoxic and/or cytostatic agents. For example, where the antibodies are reduced to yield sulfhydryl groups for attachment, heterogenous mixtures of antibodies having zero, 2, 4, 6 or 8 linked agents per molecule are often produced. Furthermore, by limiting the molar ratio of attachment compound, antibodies having zero, 1, 2, 3, 4, 5, 6, 7 or 8 linked agents per molecule are often produced. Thus, it will be understood that depending upon context, stated drug antibody ratios (DARs) may be averages for a collection of antibodies. For example, "DAR4" refers to an ADC preparation that has not been subjected to purification to isolate specific DAR peaks and comprises a heterogeneous mixture of ADC molecules having different numbers of cytostatic and/or cytotoxic agents attached per antibody (e.g., 0, 2, 4, 6, 8 agents per antibody), but has an average drug-to-antibody ratio of 4. Similarly, "DAR8" refers to a heterogeneous ADC preparation in which the average drug-to-antibody ratio is 8.

Heterogeneous ADC preparations may be processed, for example, by hydrophobic interaction chromatography ("HIC") to yield preparations enriched in an ADC having a specified DAR of interest (or a mixture of two or more specified DARS). Such enriched preparations are designed herein as "EX," where "E" indicates the ADC preparation has been processed and is enriched in an ADC having a specific DAR and "X" represents the number of cytostatic and/or cytotoxic agents linked per ADC molecule. Preparations enriched in a mixture of ADCs having two specific DARs are designated "EX/EY," three specific DARs "EX/EY/EZ" etc., where "E" indicates the ADC preparation has been processed to enrich the specified DARs and "X," "Y" and "Z" represent the DARs enriched. As specific examples, "E2" refers to an ADC preparation that has been enriched to contain primarily ADCs having two cytostatic and/or cytotoxic agents linked per ADC molecule. "E4" refers to an ADC preparation that has been enriched to contain primarily ADCs having four cytostatic and/or cytotoxic agents linked per ADC molecule. "E2/E4" refers to an ADC preparation that has been enriched to contain primarily two ADC populations, one having two cytostatic and/or cytotoxic agents linked per ADC molecule and another having four cytostatic and/or cytotoxic agents linked per ADC molecule.

As used herein, enriched "E" preparations will generally be at least about 80% pure in the stated DAR ADCs, although higher levels of purity, such as purities of at least about 85%, 90%, 95%, 98%, or even higher, may be obtainable and desirable. For example, an "EX" preparation will generally be at least about 80% pure in ADCs having X cytostatic and/or cytotoxic agents linked per ADC molecule. For "higher order" enriched preparations, such as, for example, "EX/EY" preparations, the sum total of ADCs having X and Y cytostatic and/or cytotoxic agents linked per ADC molecule will generally comprise at least about 80% of the total ADCs in the preparation. Similarly, in an enriched "EX/EY/EZ" preparation, the sum total of ADCs having X, Y and Z cytostatic and/or cytotoxic agents linked per ADC molecule will comprise at least about 80% of the total ADCs in the preparation.

Purity may be assessed by a variety of methods, as is known in the art. As a specific example, an ADC preparation may be analyzed via HPLC or other chromatography and the purity assessed by analyzing areas under the curves of the resultant peaks. Specific chromatography methods that may be employed to assess purity of ADC preparations are provided in Example 6.

Figure 2A:
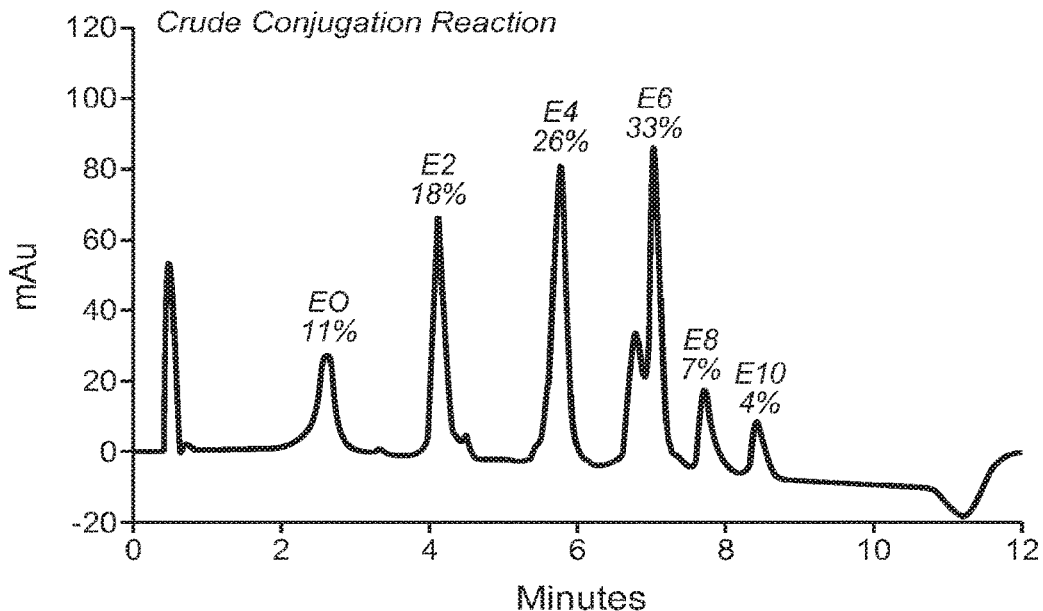
Figure 2B:
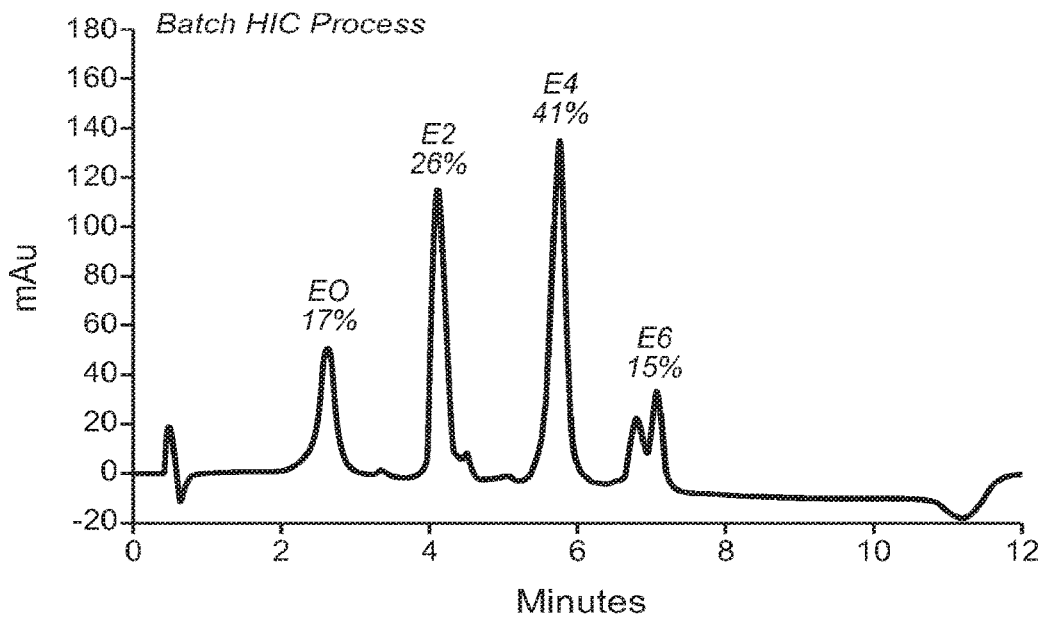
Figure 3A:
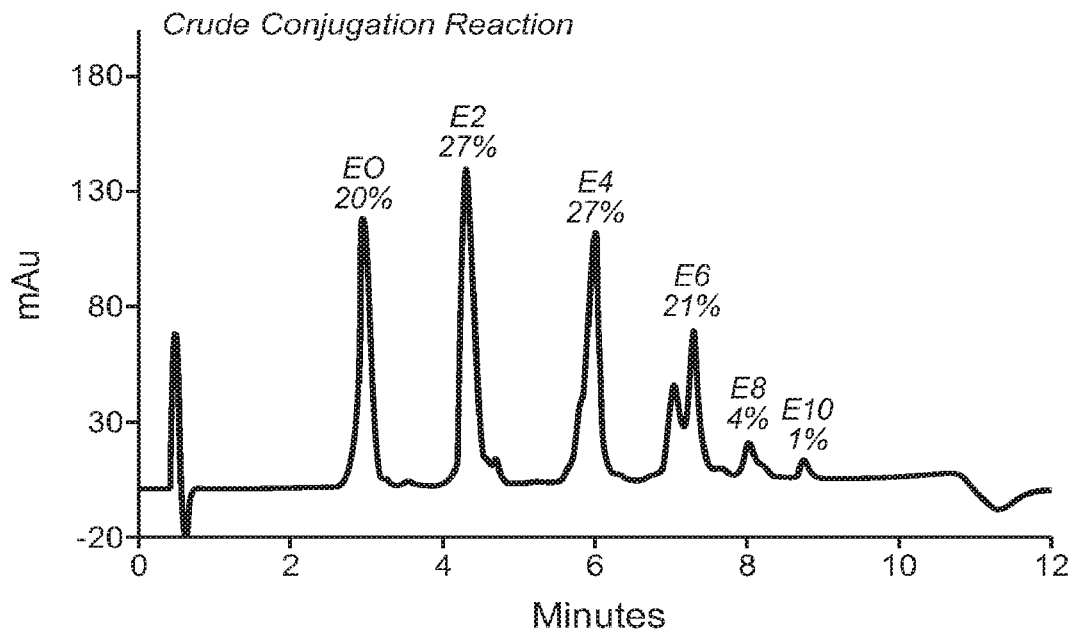
FIGS. 3A-3B illustrate ABBV-399 Process 2.
Figure 3B:
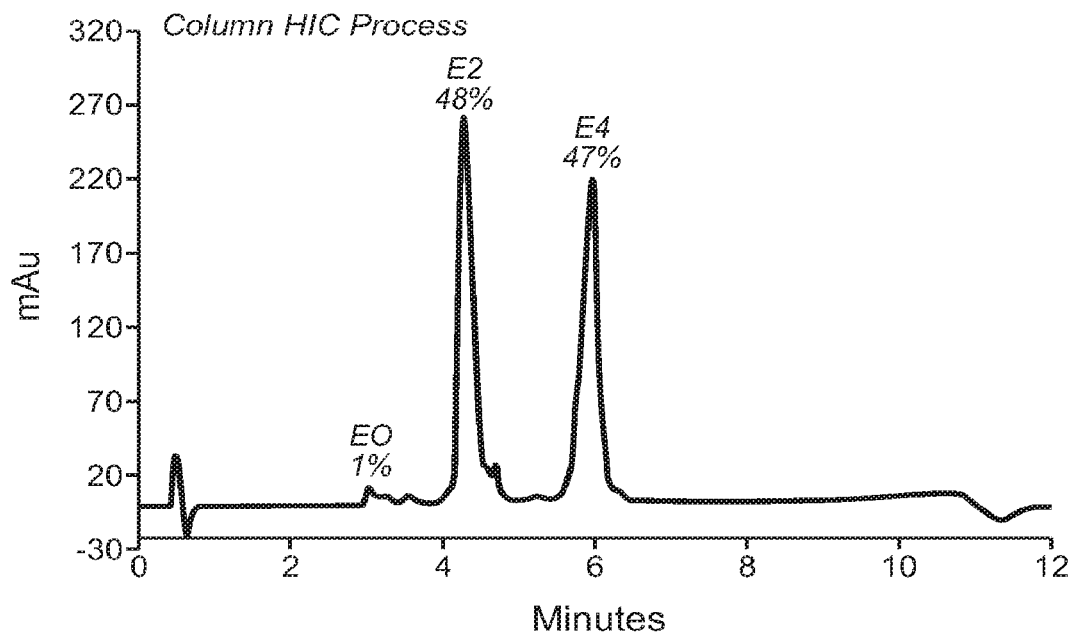
Figure 4A:
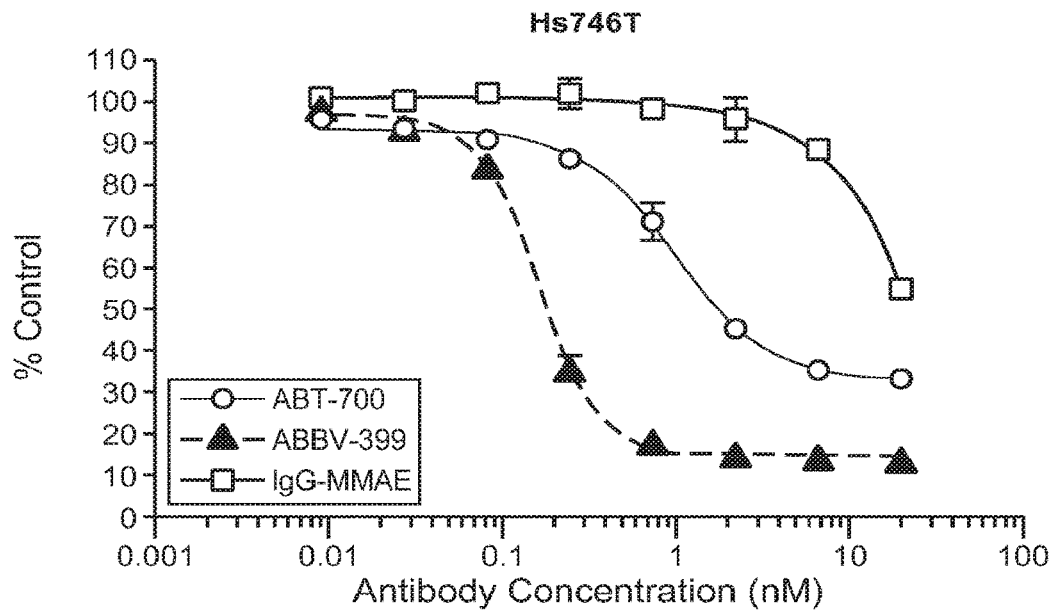
FIGS. 4A-4D depict ABBV-399 cytotoxicity in cMet expressing cell lines.
Figure 4B:
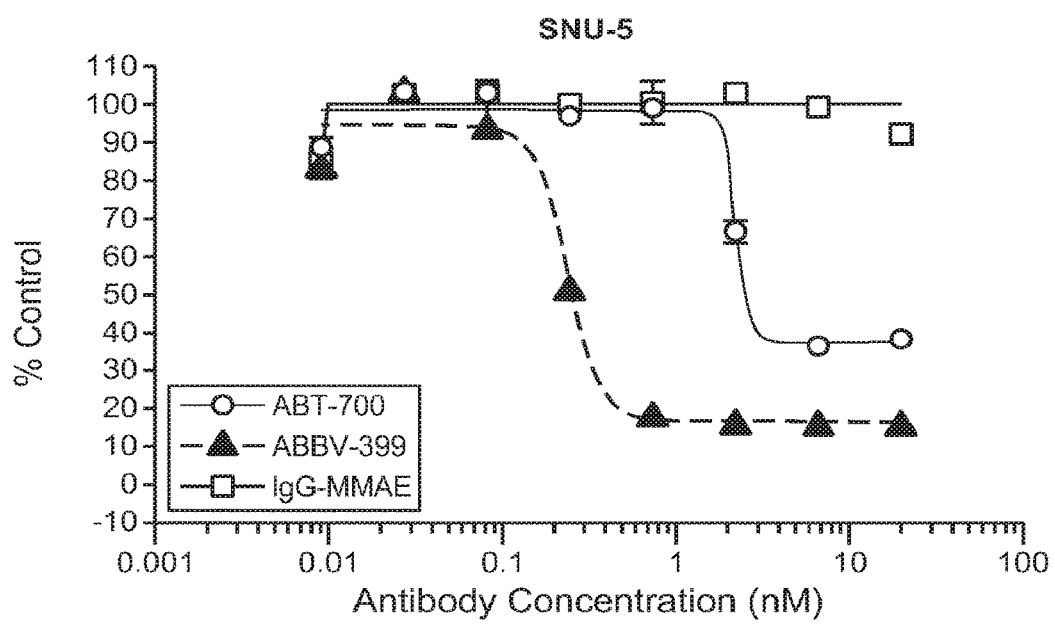
Figure 4C:
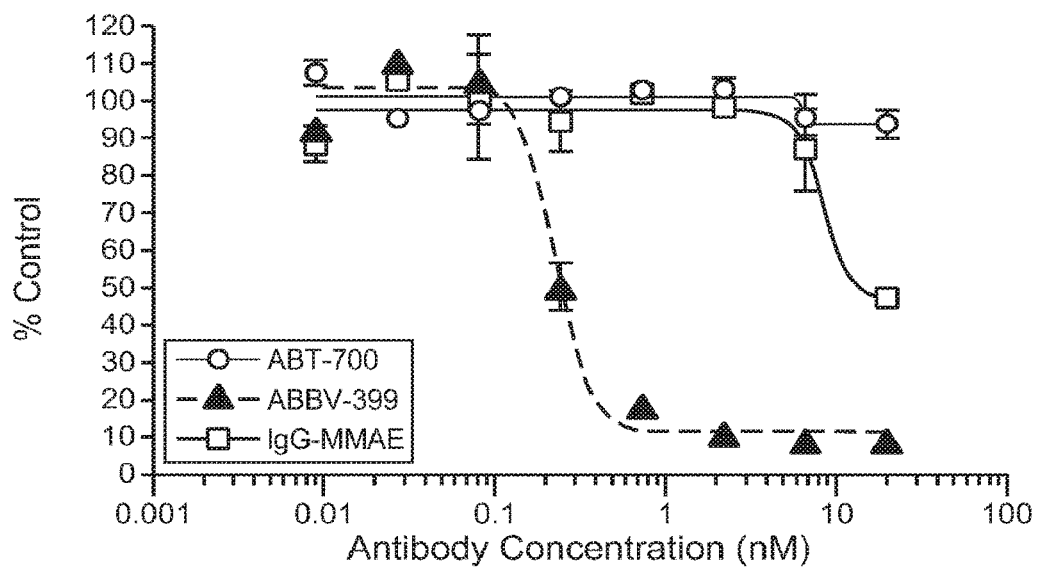
Figure 4D:
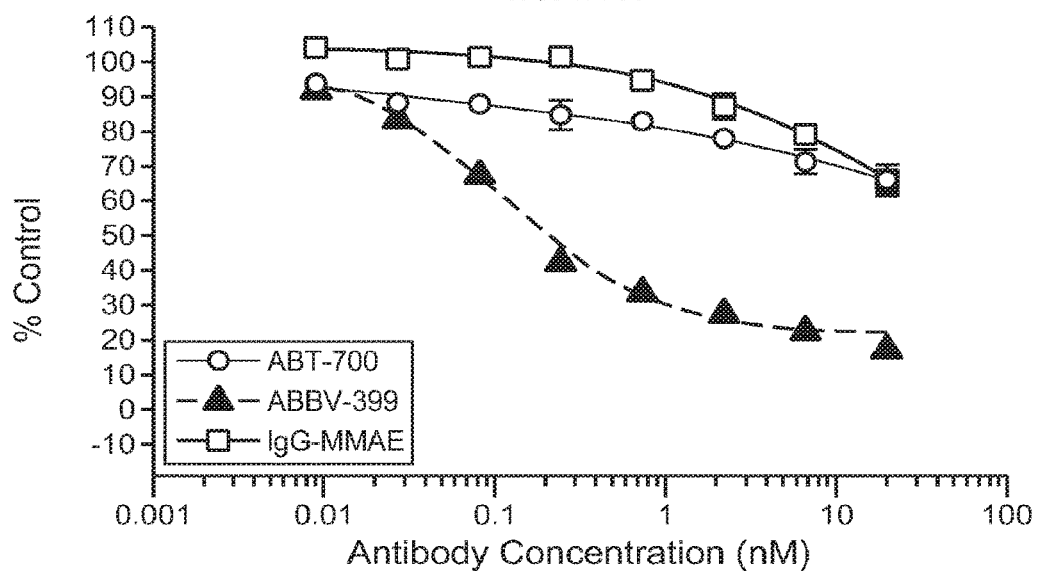

FIGS. 2A-2B illustrate Process I, which is used to obtain a DAR of 3.1. FIGS. 3A-3B illustrate Process II, which was used to obtain a 1:1 E2/E4 ratio.

Specific methods for obtaining heterogenous mixtures of ADCs comprising humanized antibody huM25 having an average DAR of 4, as well as highly purified preparations containing 2 and 4 linked agents are provided in the Examples section. These specific methods may be modified using routine skill to obtain heterogeneous and/or homogeneous ADCs comprising other anti-cMet antibodies, linkers and/or cytotoxic and/or cytostatic agents.

After conjugation of vcMMAE to ABT-700, an additional process step is used to reduce the average drug-to-antibody ratio (DAR) from approximately 5 to approximately 3, which results in a more homogeneous drug product with fewer MMAE molecules conjugated to the antibody. This strategy was implemented to reduce the number of drug molecules attached to ABBV-399, which may improve its tolerability, since high order drug molecules may contribute disproportionally to toxicity.

5.8. Compositions

The ADCs described herein may be in the form of compositions comprising the ADC and one or more carriers, excipients and/or diluents. The compositions may be formulated for specific uses, such as for veterinary uses or pharmaceutical uses in humans. The form of the composition (e.g., dry powder, liquid formulation, etc.) and the excipients, diluents and/or carriers used will depend upon the intended uses of the antibody and/or ADC and, for therapeutic uses, the mode of administration.

For therapeutic uses, the compositions may be supplied as part of a sterile, pharmaceutical composition that includes a pharmaceutically acceptable carrier. This composition can be in any suitable form (depending upon the desired method of administering it to a patient). The pharmaceutical composition can be administered to a patient by a variety of routes such as orally, transdermally, subcutaneously, intranasally, intravenously, intramuscularly, intratumorally, intrathecally, topically or locally. The most suitable route for administration in any given case will depend on the particular antibody and/or ADC, the subject, and the nature and severity of the disease and the physical condition of the subject. Typically, the pharmaceutical composition will be administered intravenously or subcutaneously.

Pharmaceutical compositions can be conveniently presented in unit dosage forms containing a predetermined amount of an antibody and/or ADC described herein per dose. The quantity of antibody and/or ADC included in a unit dose will depend on the disease being treated, as well as other factors as are well known in the art. Such unit dosages may be in the form of a lyophilized dry powder containing an amount of antibody and/or ADC suitable for a single administration, or in the form of a liquid. Dry powder unit dosage forms may be packaged in a kit with a syringe, a suitable quantity of diluent and/or other components useful for administration. Unit dosages in liquid form may be conveniently supplied in the form of a syringe pre-filled with a quantity of antibody and/or ADC suitable for a single administration.

The pharmaceutical compositions may also be supplied in bulk form containing quantities of ADC suitable for multiple administrations.

Pharmaceutical compositions may be prepared for storage as lyophilized formulations or aqueous solutions by mixing an antibody and/or ADC having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980) and Remington: The Science and Practice of Pharmacy, $22^{nd}$ Edition (Edited by Allen, Loyd V. Jr., 2012). Such additives should be nontoxic to the recipients at the dosages and concentrations employed.

Buffering agents help to maintain the pH in the range which stabilizes the protein. They may be present at a wide variety of concentrations, but will typically be present in concentrations ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium gluconate mixture, gluconic acid-sodium hydroxide mixture, gluconic acid-potassium gluconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives may be added to retard microbial growth, and can be added in amounts ranging from about 0.2%-1% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the present disclosure and include polyhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myo-inositol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-mono-thioglycerol and sodium thiosulfate; low molecular weight polypeptides (e.g., peptides of 10 residues or fewer); proteins such as human serum albumin, bovine serum albumin, gelatin or immunoglobulins; hydrophilic polymers, such as polyvinylpyrrolidone monosaccharides, such as xylose, mannose, fructose, glucose; disaccharides such as lactose, maltose, sucrose and trehalose; and trisaccacharides such as raffinose; and polysaccharides such as dextran. Stabilizers may be present in amounts ranging from 0.5 to 10 weight % per weight of ADC.

Non-ionic surfactants or detergents (also known as "wetting agents") may be added to reduce adsorption to surfaces and to help solubilize the glycoprotein as well as to protect the glycoprotein against agitation-induced aggregation, which also permits the formulation to be exposed to shear surface stress without causing denaturation of the protein. Suitable non-ionic surfactants include polysorbates (20, 80, etc.), poloxamers (184, 188 etc.), and pluronic polyols. Non-ionic surfactants may be present in a range of about 0.05 mg/mL to about 1.0 mg/mL, for example about 0.07 mg/mL to about 0.2 mg/mL.

Additional miscellaneous excipients include bulking agents (e.g., starch), chelating agents (e.g., EDTA), antioxidants (e.g., ascorbic acid, methionine, vitamin E), and cosolvents.

A specific exemplary embodiment of an aqueous composition suitable for administration via intravenous infusion comprises 20 mg/mL anti-cMet ADC, 10 mM histidine buffer, pH 6.0, 7% (w/v) sucrose, 0.03% (w/v) polysorbate 80. The composition may be in the form of a lyophilized powder that, upon reconstitution with 5.2 mL sterile water or other solution suitable for injection or infusion (for example, 0.9% saline, Ringer's solution, lactated Ringer's solution, etc.) provides the above aqueous composition. It, or other embodiments of compositions, may also be in the form of a syringe or other device suitable for injection and/or infusion pre-filled with a quantity of composition suitable for a single administration of anti-cMet ADC.

In one embodiment, the composition comprises ABBV-399 in a 1:1 ratio of purified E1 and E4 fractions. Such fractions can be obtained by any method known in the art for purifying ADCs, including the method of Examples 2 and 3. In one embodiment, the composition comprises ABBV-399 with a DAR in the range of 0-10. In another embodiment, the composition comprises ABBV-399 with a DAR in the range of 1-4. In another embodiment, the composition comprises ABBV-399 with a DAR in the range of 2-4. In another embodiment, the composition comprises ABBV-399 with a DAR of about 3.1. In another embodiment, the composition comprises ABBV-399 with a DAR of about 3.0.

5.9. Methods of Use

As discussed previously, for a variety of solid tumors, cMet is expressed/overexpressed. Data provided herein demonstrate that anti-cMet ADCs exert potent anti-tumor activity against these cMet-expressing/overexpressing tumors in vivo. Accordingly, the ADCs and/or pharmaceutical compositions comprising the ADCs may be used therapeutically to treat cMet-expressing (i.e., cMet+ tumors) and cMet-overexpressing tumors (i.e., cMet+/overexpressing tumors).

Generally, the methods involve administering to a human patient having a cMet-expressing or cMet-overexpressing tumor an amount of an anti-cMet ADC effective to provide therapeutic benefit. Any method known to one of ordinary skill in the art for assessing the presence and/or expression level of the cMet receptor protein in a cell can be used. In one embodiment, the cMet levels are membranous. In another embodiment, the cMet levels are cytoplasmic. In another embodiment, the overall cMet expression level is measured. A preferred method for determining cMet expression levels is described in detail in Example 17 and is referred to herein as the "cMet ABBV-ADC staining protocol." The H-scores (0-300) and the IHC score (0, 1+, 2+, and 3+) are assessed based on methods known to a pathologist of ordinary skill in the art. In one embodiment, patients with H-scores <150 and/or IHC scores 0 and 1+ are selected for treatment. In one embodiment, patients with H-scores ≥150 and/or IHC scores 2+ and 3+ are selected for treatment.

Patients selected for the ADC treatments of this disclosure include those with cMet-expressing and those with cMet-overexpressing tumors, which include, but are not limited to, any solid tumor (including also those that overexpress HGF and/or have abnormal activation of HGF/cMet signaling or expression). More specific examples include: lung cancers; breast cancers (e.g., invasive ductal carcinoma); head and neck cancers; pancreatic cancers; gastric carcinomas; colorectal cancers (including colorectal cancer lung metastases); ovarian cancers (e.g., serous adenocarcinoma); stomach cancers; kidney cancers (e.g., renal cell cancer such as papillary renal cell carcinoma, clear cell cancers, hereditary papillary renal cell carcinomas); adrenal cancers; gastro/oesophageal cancers; medulloblastomas; gliomas; liver cancers (e.g., hepatocellular carcinomas (including advanced, unresectable HCC)); prostate cancer (metastatic or nonmetastatic); melanomas; salivary gland tumors; sarcomas; cervical cancers; myxoid liposarcomas; adenocarcinomas of the paratyroid gland; endometrial cancers; epithelioid mesotheliomas; appendix carcinomas; goblet cell carcinomas; metastatic diffuse type gastric adenocarcinoma with signet ring features; anaplastic large cell lymphoma (ALCL); any advanced malignancy including, but not limited to, advanced, relapsed, refractory subtypes of the cancers listed herein.

Lung cancer can be classified using different systems. In one system, lung cancer includes adenocarcinoma (mixed, acinar, papillary, solid, micropapillary, lepidic nonmucinous and lepidic mucinous), squamous cell carcinoma, large cell carcinoma (e.g, non-small cell lung cancers or NSCLC (e.g., advanced or non-advanced, LCNEC, LCNEM, NSCLC—not otherwise specified (NOS)/adenosquamous carcinoma, sarcomatoid carcinoma, adenosquamous carcinoma, and large-cell neuroendocrine carcinoma); and small cell lung cancer/carcinoma or SCLC)).

Alternatively, in a different system, lung cancer can be classified into preinvasive lesions, minimally invasive adenocarcinoma, and invasive adenocarcinoma (invasive mucinous adenocarcinoma, mucinous BAC, colloid, fetal (low and high grade), and enteric).

More frequently, lung cancer may be categorized as either small cell lung cancer ("SCLC") or non-small cell lung cancer ("NSCLC"). NSCLCs may be further categorized as squamous or non-squamous. An example of a non-squamous NSCLC is adenocarcinoma.

The cancer may be newly diagnosed and naïve to treatment, or may be relapsed, refractory, or relapsed and refractory, or a metastasis or metastatic form of a cMet-expressing or of a cMet-overexpressing tumors. As demonstrated in Example 14 of this disclosure, cMet-overexpressing tumors that exhibit resistance to other targeted or non-targeted chemotherapies, retain sensitivity to ABBV-399.

Moreover, as shown in FIG. 12C, a cMet-overexpressing tumor that eventually regrew following treatment with the anti-cMet antibody ABT-700 remained sensitive to retreatment with the anti-cMet ADC, ABBV-399. Accordingly, the anti-cMet ADCs described herein provide significant benefits over current targeted and non-targeted approaches toward the treatment of cMet-overexpressing tumors.

Anti-cMet ADCs may be administered alone (monotherapy) or adjunctive to, or with, other anti-cancer therapies and/or targeted or non-targeted anti-cancer agents. When administered as anti-cMet ADC monotherapy, one or more anti-cMet ADCs may be used. In certain embodiments, an anti-cMet ADC is administered in conjunction with an anti-cMet antibody that recognizes a different epitope on cMet than that recognized by the ADC. This could be done, for example, to stimulate internalization of the cMet receptor. Alternatively, ABT-700 can be given prior to ABBV-399 (or another anti-cMet ADC) in order to "block" endogenous cMet on normal tissues in an effort to reduce possible toxicity associated with the activity of ABBV-399 on normal tissues.

In another embodiment, the anti-cMet ADC recognizes two different non-overlapping epitopes within cMet. Such ADCs, also known as ADCs carrying a bivalent biparatopic antibody, can have several advantages over monovalent antibodies. For example, they can induce cMet receptor clustering, which in turn could promote robust internalization, lysosomal trafficking, and degradation, thereby improving the release of the drug portion of the ADC into the cytoplasm as well as its availability for bystander effect.

Whether administered as monotherapy or adjunctive to, or with, other therapies or agents, an amount of anti-cMet ADC is administered such that the overall treatment regimen provides therapeutic benefit. By therapeutic benefit is meant that the use of anti-cMet ADCs to treat cancer in a patient results in any demonstrated clinical benefit compared with no therapy (when appropriate) or to a known standard of care. Clinical benefit can be assessed by any method known to one of ordinary skill in the art. In one embodiment, clinical benefit is assessed based on objective response rate (ORR) (determined using RECIST version 1.1), duration of response (DOR), progression-free survival (PFS), and/or overall survival (OS). In some embodiments, a complete response indicates therapeutic benefit. In some embodiments, a partial response indicates therapeutic benefit. In some embodiments, stable disease indicates therapeutic benefit. In some embodiments, an increase in overall survival indicates therapeutic benefit. In some embodiments, therapeutic benefit may constitute an improvement in time to disease progression and/or an improvement in symptoms or quality of life. In other embodiments, therapeutic benefit may not translate to an increased period of disease control, but rather a markedly reduced symptom burden resulting in improved quality of life. As will be apparent to those of skill in the art, a therapeutic benefit may be observed using the anti-cMet ADCs alone (monotherapy) or adjunctive to, or with, other anti-cancer therapies and/or targeted or non-targeted anti-cancer agents. Preferential methods for assessing therapeutic benefit are described in detail in the Examples, as used in a Phase 1 clinical trial with ABBV-399.

Typically, therapeutic benefit is assessed using standard clinical tests designed to measure the response to a new treatment for cancer. To assess the therapeutic benefits of the anti-cMet ADCs described herein one or a combination of the following tests can be used: (1) the Response Evaluation Criteria In Solid Tumors (RECIST) version 1.1 (for details, see Example 16), (2) the Eastern Cooperative Oncology Group (ECOG) Performance Status, (3) immune-related response criteria (irRC), (4) disease evaluable by assessment of tumor antigens, (5) validated patient reported outcome scales, and/or (6) Kaplan-Meier estimates for overall survival and progression free survival.

The ECOG Scale of Performance Status shown in TABLE 3 is used to describe a patient's level of functioning in terms of their ability to care for themselves, daily activity, and physical ability. The scale was developed by the Eastern Cooperative Oncology Group (ECOG), now part of the ECOG-ACRIN Cancer Research Group, and published in 1982.

TABLE 3

| Grade | ECOG Performance Status |
|---|---|
| 0 | Fully active, able to carry on all pre-disease performance without restriction |
| 1 | Restricted in physically strenuous activity but ambulatory and able to carry out work of a light or sedentary nature, e.g., light house work, office work |
| | Ambulatory and capable of all selfcare but unable to carry out any work activities; up and about more than 50% of waking hours |
| 3 | Capable of only limited selfcare; confined to bed or chair more than 50% of waking hours |
| 4 | Completely disabled; cannot carry on any selfcare; totally confined to bed or chair |
| 5 | Dead |

Assessment of the change in tumor burden is an important feature of the clinical evaluation of cancer therapeutics. Both tumor shrinkage (objective response) and time to the development of disease progression are important endpoints in cancer clinical trials. Standardized response criteria, known as RECIST (Response Evaluation Criteria in Solid Tumors), were published in 2000. An update (RECIST 1.1) was released in 2009. RECIST criteria are typically used in clinical trials where objective response is the primary study endpoint, as well as in trials where assessment of stable disease, tumor progression or time to progression analyses are undertaken because these outcome measures are based on an assessment of anatomical tumor burden and its change over the course of the trial. TABLE 4 provides the definitions of the response criteria used to determine objective tumor response to a study drug, such as the anti-cMet ADCs described herein.

TABLE 4

| Response | Criteria |
|---|---|
| Complete Response (CR) | Disappearance of all target lesions. Any pathological lymph nodes (whether target or non-target) must have reduction in short axis to <10 mm. |
| Partial Response (PR) | At least a 30% decrease in the sum of diameters of target lesions, taking as reference the baseline sum diameters. |
| Progressive Disease (PD) | At least a 20% increase in the sum of diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progression). |
| Stable Disease (SD) | Neither sufficient shrinkage to qualify for PR nor sufficient increase to qualify for PD, taking as reference the smallest sum diameters while on study. |

Secondary outcome measures that can be used to determine the therapeutic benefit of the anti-cMet ADCs described herein include, Objective Response Rate (ORR), Progression Free Survival (PFS), Duration of Overall Response (DOR), and Depth of Response (DpR). ORR is defined as the proportion of the participants who achieve a complete response (CR) or partial response (PR). PFS is defined as the time from the first dose date of an anti-cMet ADCs to either disease progression or death, whichever occurs first. DOR is defined as the time from the participant's initial CR or PR to the time of disease progression. DpR is defined as the percentage of tumor shrinkage observed at the maximal response point compared to baseline tumor load. Clinical endpoints for both ORR and PFS can be determined based on RECIST 1.1 criteria described above.

Another set of criteria that can be used to characterize fully and to determine response to immunotherapeutic agents, such as antibody-based cancer therapies, is the immune-related response criteria (irRC), which was developed for measurement of solid tumors in 2009, and updated in 2013 (Wolchok, et al. Clin. Cancer Res. 2009; 15(23): 7412-7420 and Nishino, et al. Clin. Cancer Res. 2013; 19(14): 3936-3943, each of which is incorporated by reference in its entirety). The updated irRC criteria are typically used to assess the effect of an immunotherapeutic agent (e.g., an anti-PD1 antibody), and defines response according to TABLE 5.

TABLE 5

| Response | Criteria |
|---|---|
| Complete Response (CR) | Disappearance of all target lesions in two consecutive observations not less than 4 weeks apart |
| Partial Response (PR) | At least a 30% decrease in the sum of the longest diameters of target lesions, taking as reference the baseline sum diameters. |
| Progressive Disease (PD) | At least a 20% increase in the sum of diameters of target lesions, taking as reference the smallest sum on study (this includes the baseline sum if that is the smallest on study). (Note: the appearance of one or more new lesions is not considered progression. The measurement of new lesions is included in the sum of the measurements). |

TABLE 5-continued

| Response | Criteria |
| --- | --- |
| Stable Disease (SD) | Neither sufficient shrinkage to qualify for PR nor sufficient increase to qualify for PD, taking as reference the smallest sum diameters while on study. |

Tumor antigens that can be used to evaluate the therapeutic benefit of the anti-cMet ADCs described herein include ApoE, CD11c, CD40, CD45 (PTPRC), CD49D (ITGA4), CD80, CSF1R, CTSD, GZMB, Ly86, MS4A7, PIK3AP1, PIK3CD, CD74, CCL5, CCR5, CXCL10, IFNG, IL10RA1, IL-6, ACTA2, COL7A1, LOX, LRRC15, MCPT8, MMP10, NOG, SERPINE1, STAT1, TGFBR1, CTSS, PGF, VEGFA, C1QA, C1QB, ANGPTL4, EGLN, ANGPTL4, EGLN3, BNIP3, AIF1, CCL5, CXCL10, CXCL11, IFI6, PLOD2, KISS1R, STC2, DDIT4, PFKFB3, PGK1, PDK1, AKR1C1, AKR1C2, CADM1, CDH11, COL6A3, CTGF, HMOX1, KRT33A, LUM, WNT5A, IGFBP3, MMP14, CDCP1, PDGFRA, TCF4, TGF, TGFB1, TGFB2, CD11b, ADGRE1 (EMR1, F4/80), CD86, CD68, MHC-Class II, CD3, HLA-DR, CD4, CD3, CD5, CD19, CD7, CD8, CD16, TCRαβ, TCRγδ, PD-1, PDL-1, CTLA-4, acid phosphatase, ACTH, alkaline phosphatase, alpha-fetoprotein CA-125, CA15-3, CA19-9, CA-195, C-212, CA-549, calcitonin, catecholamines, cathepsin-D, CEA, ERBB2 (HER2/neu), chromagranin-A, c-Myc, EGFR, ERA (estrogen receptor assay), ferritin, gastrin, 5-HIAA, hCG, alpha-HCG, beta-HCG, HVA, LDH1-5, NSE (neuron specific enolase), pancreatic polypeptide, PLAP, PLP, PRA (progesterone receptor A), proinsulin C-peptide, PSA, SMA, SCC, thyroglobulin, TDT, TPA, and alpha-TSH. These antigens can be assessed at the DNA, RNA or protein level using DNA sequencing techniques, RNA sequencing techniques, gene chip microarray, PCR based methods, flow cytometry or immunohistochemistry methods as known to experts in the art.

One exemplary therapeutic benefit resulting from the use of anti-cMet ADCs described herein to treat cMet-expressing and cMet-overexpressing tumors, whether administered as monotherapy or adjunctive to, or with, other therapies or agents, is a complete response. Another exemplary therapeutic benefit resulting from the use of anti-cMet ADCs described herein to cMet-overexpressing tumors, whether administered as monotherapy or adjunctive to, or with, other therapies or agents, is a partial response.

Validated patient reported outcome scales can also be used to denote response provided by each patient through a specific reporting system. Rather than being disease focused, such outcome scales are concerned with retained function while managing a chronic condition. One non-limiting example of a validated patient reported outcome scale is PROMIS® (Patient Reported Outcomes Measurement Information System) from the United States National Institutes of Health. For example, PROMIS® Physical Function Instrument for adult cancer patients can evaluate self-reported capabilities for the functioning of upper extremities (e.g., dexterity), lower extremities (e.g., walking or mobility), and central regions (e.g., neck, back mobility), and also includes routine daily activities, such as running errands.

Kaplan-Meier curves (Kaplan and Meier, J. Am. Stat. Assoc. 1958; 53(282): 457-481) can also be used to estimate overall survival and progression free survival for cancer patients undergoing anti-cMet antibody or ADC therapy in comparison to standard of care.

5.9.1. Adjunctive Therapies

Anti-cMet ADCs may be used adjunctive to, or with, other agents or treatments having anti-cancer properties. When used adjunctively, the anti-cMet and other agent(s) may be formulated together in a single pharmaceutical formulation, or may be formulated and administered separately, either on a single coordinated dosing regimen or on different dosing regimens. Agents administered adjunctively with anti-cMet ADCs will typically have complementary activities to the anti-cMet ADCs such that the ADCs and other agents do not adversely affect each other.

Agents that may be used adjunctively with anti-cMet ADCs include, but are not limited to, alkylating agents, angiogenesis inhibitors, antibodies, antimetabolites, antimitotics, antiproliferatives, antivirals, aurora kinase inhibitors, ALK kinase inhibitors (for example, crizotinib (XALKORI®), ceritinib (ZYKADIA®), and alectinib (ALECENSA®), apoptosis promoters (for example, Bcl-2 family inhibitors), activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNAs, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteasome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, ubiquitin ligase inhibitors, and the like, as well as combinations of one or more of these agents.

BiTE antibodies are bispecific antibodies that direct T-cells to attack cancer cells by simultaneously binding the two cells. The T-cell then attacks the target cancer cell. Examples of BiTE antibodies include adecatumumab (Micromet MT201), blinatumomab (BLINCYTO®, Amgen and Onyx Pharmaceuticals) and the like. Without being limited by theory, one of the mechanisms by which T-cells elicit apoptosis of the target cancer cell is by exocytosis of cytolytic granule components, which include perforin and granzyme B.

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site.

Alkylating agents include, but are not limited to, altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, dacarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, and trofosfamide.

Angiogenesis inhibitors include, but are not limited to, endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, and vascular endothelial growth factor receptor tyrosine kinase (VEGFR) inhibitors.

Antimetabolites include, but are not limited to, ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, and UFT.

Antivirals include, but are not limited to, ritonavir, acyclovir, cidofovir, ganciclovir, foscarnet, zidovudine, ribavirin, and hydroxychloroquine.

Aurora kinase inhibitors include, but are not limited to, ABT-348, AZD-1152, MLN-8054, VX-680, Aurora A-specific kinase inhibitors, Aurora B-specific kinase inhibitors and pan-Aurora kinase inhibitors.

Bcl-2 protein inhibitors include, but are not limited to, AT-101 ((-)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide, N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide, venetoclax and GX-070 (obatoclax).

Bcr-Abl kinase inhibitors include, but are not limited to, DASATINIB® (BMS-354825) and GLEEVEC® (imatinib).

CDK inhibitors include, but are not limited to, AZD-5438, BMI-1040, BMS-032, BMS-387, CVT-2584, flavopyridol, GPC-286199, MCS-5A, PD0332991, PHA-690509, seliciclib (CYC-202, R-roscovitine), and ZK-304709.

COX-2 inhibitors include, but are not limited to, ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, and VIOXX® (rofecoxib).

EGFR inhibitors include, but are not limited to, afatinib (GILOTRIF®), ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, PORTRAZZA® (necitumumab), TAGRISSO® (osimertinib), TYKERB® (lapatinib), TARCEVA® (erlotinib), and TAGRISSO® (osimertinib).

ErbB2 receptor inhibitors include, but are not limited to, CP-724-714, CI-1033 (canertinib), HERCEPTIN® (trastuzumab), TYKERB® (lapatinib), OMNITARG® (2C4, pertuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecific antibodies, mAB AR-209, and mAB 2B-1.

Histone deacetylase inhibitors include, but are not limited to, depsipeptide, LAQ-824, MS-275, trapoxin, suberoylanilide hydroxamic acid (SAHA), TSA, and valproic acid.

HSP-90 inhibitors include, but are not limited to, 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090, and VER49009.

Inhibitors of apoptosis proteins include, but are not limited to, HGS 1029, GDC-0145, GDC-0152, LCL-161, and LBW-242.

Activators of death receptor pathway include, but are not limited to, TRAIL, antibodies or other agents that target TRAIL or death receptors (e.g., DR4 and DR5) such as Apomab, conatumumab, ETR2-ST01, GDC0145 (lexatumumab), HGS-1029, LBY-135, PRO-1762 and trastuzumab.

Kinesin inhibitors include, but are not limited to, Eg5 inhibitors such as AZD4877, ARRY-520; and CENPE inhibitors such as GSK923295A.

JAK-2 inhibitors include, but are not limited to, CEP-701 (lesaurtinib), XL019 and INCB018424.

MEK inhibitors include, but are not limited to, ARRY-142886, ARRY-438162, PD-325901, PD-98059, and trametinib.

mTOR inhibitors include, but are not limited to, AP-23573, CCI-779, everolimus, RAD-001, rapamycin, temsirolimus, ATP-competitive TORC1/TORC2 inhibitors, including PI-103, PP242, PP30, and Torin 1.

Non-steroidal anti-inflammatory drugs include, but are not limited to, AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), and DAYPRO® (oxaprozin).

PDGFR inhibitors include, but are not limited to, C-451, CP-673 and CP-868596.

Platinum chemotherapeutics include, but are not limited to, cisplatin, ELOXATIN® (oxaliplatin) eptaplatin, lobaplatin, nedaplatin, PARAPLATIN® (carboplatin), satraplatin, and picoplatin.

Polo-like kinase inhibitors include, but are not limited to, BI-2536.

BRAF inhibitors vemurafenib, dabrafenib, cobimetinib.

Phosphoinositide-3 kinase (PI3K) inhibitors include, but are not limited to, wortmannin, LY294002, XL-147, CAL-120, ONC-21, AEZS-127, ETP-45658, PX-866, GDC-0941, BGT226, BEZ235, and XL765.

Thrombospondin analogs include, but are not limited to, ABT-510, ABT-567, ABT-898, and TSP-1.

VEGFR inhibitors include, but are not limited to, AVASTIN® (bevacizumab), ABT-869, AEE-788, ANGIOZYME™ (a ribozyme that inhibits angiogenesis (Ribozyme Pharmaceuticals (Boulder, Colo.) and Chiron (Emeryville, Calif.)), axitinib (AG-13736), AZD-2171, CP-547,632, IM-862, MACUGEN® (pegaptamib), NEXAVAR® (sorafenib, BAY43-9006), pazopanib (GW-786034), vatalanib (PTK-787, ZK-222584), SUTENT® (sunitinib, SU-11248), VEGF trap, and ZACTIMA™ (vandetanib, ZD-6474), cabozantanib (VEGFR2 and cMet inhibitor), ramucirumab (anti-VEGFR2 inhibitory mAb).

Antibiotics include, but are not limited to, intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), and zinostatin.

Topoisomerase inhibitors include, but are not limited to, aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, Onivyde™ (liposomal irinotecan), orathecin, pirarbucin, pixantrone, rubitecan, sobuzoxane, SN-38, tafluposide, and topotecan.

Antibodies include, but are not limited to, AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzumab, pertuzumab, VECTIBIX® (panitumumab) and CD20 antibodies types I and II.

Hormonal therapies include, but are not limited to, ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megestrol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), XTANDI® (enzalutamide), ZOLADEX® (fosrelin, goserelin), and ZYTIGA® (abiratenone).

Deltoids and retinoids include, but are not limited to, seocalcitol (EB 1089, CB 1093), lexacalcitrol (KH1060), fenretinide, PANRETIN® (aliretinoin), ATRAGEN® (liposomal tretinoin), TARGRETIN® (bexarotene), and LGD-1550.

PARP inhibitors include, but are not limited to, ABT-888 (veliparib), olaparib, KU-59436, AZD-2281, AG-014699, BSI-201, BGP-15, INO-1001, and ONO-2231.

Plant alkaloids include, but are not limited to, vincristine, vinblastine, vindesine, and vinorelbine.

Proteasome inhibitors include, but are not limited to, VELCADE® (bortezomib), KYPROLIS® (carfilzomib), MG132, NPI-0052, and PR-171.

Examples of immunologicals include, but are not limited to, interferons, immune checkpoint inhibitors, co-stimulatory agents, and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Immune check point inhibitors include antibodies that target PD-1 (e.g., pembrolizumab, nivolumab and pidilizumab), PD-L1 (e.g., durvalumab, atezolizumab, avelumab, MEDI4736, MSB0010718C and MPDL3280A), and CTLA4 (cytotoxic lymphocyte antigen 4; e.g., ipilimumab, tremelimumab). Co-stimulatory agents include, but are not limited to, antibodies against CD3, CD40, CD40L, CD27, CD28, CSF1R, CD137 (e.g., urelumab), B7H1, GITR, ICOS, CD80, CD86, OX40, OX40L, CD70, HLA-DR, LIGHT, LIGHT-R, TIM3, A2AR, NKG2A, TIGIT (T cell immunoreceptor with Ig and ITIM domains), VISTA (V-domain Ig suppressor of T cell activation), B7-H3, B7-H4, CD47, CD73, CD39, KIR (e.g., lirilumab), TGF-β(e.g., fresolimumab) and combinations thereof.

Other agents include, but are not limited to, ALFAFERONE® (IFN-α), BAM-002 (oxidized glutathione), BEROMUN® (tasonermin), BEXXAR® (tositumomab), CAMPATH® (alemtuzumab), dacarbazine, denileukin, epratuzumab, GRANOCYTE® (lenograstim), lentinan, leukocyte alpha interferon, imiquimod, melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (*Bacillus* Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZINBRYTA® (daclizumab high-yield process), and ZEVALIN® ($^{90}$Y-Ibritumomab tiuxetan).

Biological response modifiers are agents that modify defense mechanisms of living organisms or biological responses, such as survival, growth or differentiation of tissue cells to direct them to have anti-tumor activity and include, but are not limited to, krestin, lentinan, sizofiran, picibanil PF-3512676 (CpG-8954), and ubenimex.

Pyrimidine analogs include, but are not limited to, cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), and TROXATYL™ (triacetyluridine troxacitabine).

Purine analogs include, but are not limited to, LANVIS® (thioguanine) and PURI-NETHOL® (mercaptopurine).

Antimitotic agents include, but are not limited to, batabulin, epothilone D (KOS-862), N-(2-((4-hydroxyphenyl)amino)pyridin-3-yl)-4-methoxybenzenesulfonamide, ixabepilone (BMS 247550), TAXOL® (paclitaxel), TAXOTERE® (docetaxel), PNU100940 (109881), patupilone, XRP-9881 (larotaxel), vinflunine, and ZK-EPO (synthetic epothilone).

Ubiquitin ligase inhibitors include, but are not limited to, MDM2 inhibitors, such as nutlins, and NEDD8 inhibitors such as MLN4924.

Tyrosine Kinase inhibitors include imatinib (GLEEVEC®), dasatinib (SPRYCE®), nilotinib (TASIGNA®), bosutinib (BOSULIF®), ponatinib (ICLUSIG®), Afatinib (GIOTRIF®), Axitinib (INLYTA®), Crizotinib (XALKORI®), Erlotinib (TARCEVA®), Gefitinib (IRESSA®), Lapatinib (TYVERB®), Nilotinib (TASIGNA®), Pazopanib (VOTRIENT®), Regorafenib (STIVARGA®), Sorafenib (NEXAVAR®), Sunitinib (SUTENT®), toceranib (PALLADIA®), vatalanib, and radotinib (SUPECT®).

Anti-cMet ADCs may also be used to enhance the efficacy of radiation therapy. Examples of radiation therapy include external beam radiation therapy, internal radiation therapy (i.e., brachytherapy) and systemic radiation therapy.

Anti-cMet ADCs may be administered adjunctive to or with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGER® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOPR® (C: CYTOXAN (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL (quadrivalent human papillomavirus (Types 6, 11, 16, 18) recombinant vaccine), GASTRIMMUNE R, GENASENSE®, GMK (ganglioside conjugate vaccine), GVAX® (prostate cancer vaccine), halofuginone, histrelin, hydroxycarbamide, ibandronic acid, IGN-101, IL-13-PE38, IL-13-PE38QQR (cintredekin besudotox), IL-13-*pseudomonas* exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from *ginseng* comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces* staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), and zorubicin, as well as combinations of any of these agents.

Adjunctive therapies and/or therapeutic agents typically will be used at their approved dose, route of administration, and frequency of administration, but may be used at lower dosages and/or less frequently. When administered as monotherapy, the anti-cMet ADC will typically be administered on a schedule that generates therapeutic benefit. It is contemplated that anti-cMet ADCs administered once a week, once every two weeks, once every three weeks, once every four weeks, once every five weeks, once every six weeks, once every seven weeks or once every eight weeks will provide therapeutic benefit, although more or less frequent administration may be beneficial. When administered adjunctive to or with another therapy and/or agent, the anti-cMet ADC may be administered before treatment, after treatment or concurrently with the treatment with the other therapy or agent.

5.10. Dosages and Administration Regimens

The amount of anti-cMet ADC administered will depend upon a variety of factors, including but not limited to, the particular type of cMet+/overexpressing tumors treated, the stage of the cMet+/overexpressing tumors being treated, the mode of administration, the frequency of administration, the desired therapeutic benefit, the drug component of the ADC (e.g., MMAE versus PBD) and other parameters such as the age, weight and other characteristics of the patient, etc. Determination of dosages effective to provide therapeutic benefit for specific modes and frequency of administration is within the capabilities of those skilled in the art.

Dosages effective to provide therapeutic benefit may be estimated initially from in vivo animal models or clinical. Suitable animal models for a wide variety of diseases are known in the art.

The anti-cMet ADCs may be administered by any route appropriate to the condition to be treated. An anti-cMet ADC will typically be administered parenterally, i.e., infusion, subcutaneous, intramuscular, intravenous (IV), intradermal, intrathecal, bolus, intratumor injection or epidural ((Shire et al., 2004, *J. Pharm. Sciences* 93(6): 1390-1402)). In one embodiment, an anti-cMet ADC is provided as a lyophilized powder in a vial. The vials may contain, for example, 0.5 mg, 1 mg, 5 mg, 10 mg, 50 mg, 100 mg, or 200 mg of anti-cMet ADC. In one embodiment, prior to administration, the lyophilized powder is reconstituted with sterile water for injection (SWFI) or other suitable medium to provide a solution containing 20 mg/mL anti-cMet ADC. The resulting reconstituted solution is further diluted with saline or other suitable medium and administered via an IV infusion once every 7 days, once every 14 days, once every 21 days, or once every 28 days. In some embodiments, for the first cycle, the infusion occurs over 180 minutes, subsequent infusions are over 90 minutes. In other embodiments, the infusion occurs over 60 minutes. In some embodiments, all infusions for every cycle occur over 30 minutes.

In one exemplary embodiment, an anti-cMet ADC is administered once every 14 days at 0.15 mg/kg, 0.3 mg/kg, 0.6 mg/kg, 0.9 mg/kg, 1.2 mg/kg, 1.5 mg/kg, 1.6 mg/kg, 1.8 mg/kg, 1.9 mg/kg, 2.1 mg/kg, 2.2 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, or 6.0 mg/kg of the subject's body weight. In one embodiment, the anti-cMet ADC is administered once every 14 days at 1.6 mg/kg. In one embodiment, the anti-cMet ADC is administered once every 14 days at 1.9 mg/kg. In one embodiment, the anti-cMet ADC is administered once every 14 days at 2.2 mg/Kg. In one embodiment, the anti-cMet ADC is administered once every 14 days at 2.5 mg/Kg. In one embodiment, administration proceeds until disease progression or unacceptable toxicity.

In one embodiment, the cancer is a NSCLC adenocarcinoma, the anti-cMet ADC is ABBV-399, administered at 1.6 or 1.9 mg/kg every 14 days, and the patient has an H-score of 225 and above or an IHC score of 3+. In another embodiment, the cancer is a NSCLC squamous cell carcinoma, the anti-cMet ADC is ABBV-399, administered at 1.6 or 1.9 mg/kg every 14 days, and the patient has an H-score between 150 to 224 or an IHCscore of 2+.

In another exemplary embodiment, an anti-cMet ADC is administered once every 7 days at 0.15 mg/kg, 0.3 mg/kg, 0.45 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, or 3.0 mg/kg. In one embodiment, administration proceeds until disease progression or unacceptable toxicity.

In another exemplary embodiment, an anti-cMet ADC is administered once every 28 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. In one embodiment, administration proceeds until disease progression or unacceptable toxicity.

In another exemplary embodiment, an anti-cMet ADC is administered once every 28 days at 2.7 mg/kg. In one embodiment, administration proceeds until disease progression or unacceptable toxicity.

In another exemplary embodiment, an anti-cMet ADC is administered once every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. In one embodiment, administration proceeds until disease progression or unacceptable toxicity.

In another exemplary embodiment, an anti-cMet ADC (e.g., ABBV-399) is administered once every 21 days at 2.7 mg/kg. In one embodiment, administration proceeds until disease progression or unacceptable toxicity. In one embodiment, the cancer is a NSCLC adenocarcinoma, the anti-cMet ADC is ABBV-399, administered at 2.7 mg/kg every 21 days, and the patient has an H-score of 225 and above or an IHC score of 3+. In another embodiment, the cancer is a NSCLC squamous cell carcinoma, the anti-cMet ADC is ABBV-399, administered at 2.7 mg/kg every 21 days, and the patient has an H-score of at least 150 or greater and at least an IHCscore of 2+.

In another exemplary embodiment, an anti-cMet PBD ADC (e.g., ABT-700 PBD) is administered once every 14 days, once every 21 days, or once every 28 days, at a dose between 1.0 µg/kg to 1.0 mg/kg, 1.0 µg/kg to 500.0 µg/kg, or 5.0 µg/kg to 200.0 µg/kg of the subject's body weight. As for any other ADC, the dosage depends, for example, on the frequency of administration, condition of the patient and response to prior treatment, if any. The concentration of the ADC in a liquid formulation can be e.g., 0.01-10 mg/ml, such as 1.0 mg/ml.

In one embodiment, an anti-cMet PBD ADC (e.g., ABT-700 PBD) is administered once every 14 days, once every 21 days, or once every 28 days at 10 µg/kg, 50 µg/kg, 75 µg/kg, 100 µg/kg, 110 µg/kg, 120 µg/kg, 130 µg/kg, 140 µg/kg, 150 µg/kg, 160 µg/kg, 170 µg/kg, 180 µg/kg, 190 µg/kg, 200 µg/kg, 250 µg/kg, 300 µg/kg, 350 µg/kg, 400 µg/kg, 450 µg/kg, or 500 µg/kg. In one embodiment, the anti-cMet PBD ADC (e.g., ABT-700 PBD) is administered at 100 µg/kg. In one embodiment, the anti-cMet PBD ADC (e.g., ABT-700 PBD) is administered at 200 µg/kg. In one embodiment, the anti-cMet PBD ADC (e.g., ABT-700 PBD) is administered at 300 µg/kg. In one embodiment, the anti-cMet PBD ADC (e.g., ABT-700 PBD) is administered at 400 µg/kg.

When administered adjunctive to, or with, other agents, such as other chemotherapeutic agents, the ADCs may be administered on the same schedule as the other agent(s), or on a different schedule. When administered on the same schedule, the ADC may be administered before, after, or concurrently with the other agent. In some embodiments where an ADC is administered adjunctive to, or with, standards of care, the ADC may be initiated prior to commencement of the standard therapy, for example a day, several days, a week, several weeks, a month, or even several months before commencement of standard of care therapy.

In one set of exemplary embodiments, the additional anti-cancer agent is selected from the group consisting of cabazitaxel, colcemid, colchicine, cryptophycin, democolcine, docetaxel, nocodazole, paclitaxel, taccalonolide, taxane and vinblastine.

In one exemplary embodiment, an anti-cMet ADC is used adjunctive to afatinib (GILOTRIF®) to treat NSCLC. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. GILOTRIF® is administered at 40 mg orally once daily until disease progression or no longer tolerated by the patient. In one embodiment, the patients are selected for the first-line treatment of metastatic NSCLC with GILOTRIF® based on the presence of EGFR exon 19 deletions or exon 21 (L858R) substitution mutations in tumor specimens.

In still another exemplary embodiment, an anti-cMet ADC is used adjunctive to TARCEVA® (erlotinib) to treat non small cell lung cancer (NSCLC). The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. The recommended dose and schedule for erlotinib is 150 mg orally, once daily. The adjunctive anti-cMet ADC/erlotinib therapy is continued until disease progression or no longer tolerated by the patient.

In one embodiment, the cancer is NSCLC, the anti-cMet ADC is ABBV-399, administered at 2.7 mg/kg every 21 days, and the erlotinib is administered at 150 mg orally, once daily. The adjunctive anti-cMet ADC/erlotinib therapy is continued until disease progression or no longer tolerated by the patient. In one embodiment, the cancer is a NSCLC EGFR-mutated adenocarcinoma, the anti-cMet ADC is ABBV-399, administered at 2.7 mg/kg every 21 days, the erlotinib is administered at 150 mg orally, once daily, and the patient has an H-score of 225 and above or an IHC score of 3+.

In still another exemplary embodiment, an anti-cMet ADC is used adjunctive to IRESSA® (gefitinib) to treat non small cell lung cancer (NSCLC). The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. The recommended dose and schedule for gefitinib is 250 mg orally, once daily. The adjunctive anti-cMet ADC/gefitinib therapy is continued until disease progression or no longer tolerated by the patient.

In still another exemplary embodiment, an anti-cMet ADC is used adjunctive to afatinib to treat non small cell lung cancer (NSCLC). The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. The recommended dose and schedule for afatinib is 40 mg orally, once daily. The adjunctive anti-cMet ADC/afatinib therapy is continued until disease progression or no longer tolerated by the patient.

In still another exemplary embodiment, an anti-cMet ADC is used adjunctive to OPDIVO® (nivolumab) to treat non small cell lung cancer (NSCLC). The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. Nivolumab is administered an intravenous infusion at 3 mg/kg over 60 minutes every two weeks. The adjunctive anti-cMet ADC/nivolumab treatment is continued until disease progression or no longer tolerated by the patient.

In still another exemplary embodiment, an anti-cMet ADC is used adjunctive to OPDIVO® (nivolumab) and YERVOY® (ipilimumab) to treat non small cell lung cancer (NSCLC). The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg, for four doses with ipilimumab, then every 14 days at 0.15 mg/kg, 0.3 mg/kg, 0.6 mg/kg, 0.9 mg/kg, 1.2 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, without ipilimumab. Nivolumab is administered as an intravenous infusion at 3 mg/kg over 60 minutes every two weeks. Ipilimumab is administered intravenously at 3 mg/kg over 90 minutes every three weeks in the first four doses. The adjunctive anti-cMet ADC/nivolumab treatment is continued until disease progression or no longer tolerated by the patient.

In still another exemplary embodiment, an anti-cMet ADC can be used adjunctive to pembrolizumab (KEYTRUDA®) to treat NSCLC. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. Pembrolizumab is administered as an intravenous infusion at 2 mg/kg over 30 minutes every 3 weeks. The adjunctive anti-cMet ADC and pembrolizumab therapy is continued until disease progression or no longer tolerated by the patient.

In still another exemplary embodiment, an anti-cMet ADC is used adjunctive to cisplatin to treat NSCLC. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. Cisplatin is administered at 20 mg/m$^2$ or more, once every 3 to 4 weeks. The adjunctive anti-cMet ADC/cisplatin therapy is continued until disease progression or no longer tolerated by the patient.

In still another exemplary embodiment, an anti-cMet ADC is used adjunctive to carboplatin to treat NSCLC. The anti-cMet ADC is administered via IV infusion once every 14 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg. Carboplatin is administered at 300 mg/m$^2$ or more, once every 4 weeks. The adjunctive anti-cMet ADC/carboplatin therapy is continued until disease progression or no longer tolerated by the patient.

In still another exemplary embodiment, an anti-cMet ADC is used adjunctive to veliparib to treat NSCLC. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. Veliparib is administered orally, twice a day. The adjunctive anti-cMet ADC/veliparib therapy is continued until disease progression or no longer tolerated by the patient.

In still another exemplary embodiment, an anti-cMet ADC is used adjunctive to veliparib and pemetrexed to treat NSCLC. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. Veliparib is administered orally, twice a day. Pemetrexed is administered at 500 mg/m$^2$ intravenously every 21 days. The adjunctive anti-cMet ADC/veliparib/pemetrexed therapy is continued until disease progression or no longer tolerated by the patient.

In still another exemplary embodiment, an anti-cMet ADC is used adjunctive to cetuximab to treat NSCLC. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. Cetuximab is administered at an initial dose of 400 mg/m$^2$ over a 120-minute intravenous infusion followed by 250 mg/m$^2$ weekly infusion over 60 minutes. The adjunctive anti-cMet ADC/cetuximab therapy is continued until disease progression or no longer tolerated by the patient.

In still another exemplary embodiment, an anti-cMet ADC is used adjunctive to ipilimumab (YERVOY®) to treat NSCLC. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. Ipilimumab is administered at 3 mg/kg intravenously over 90 minutes every 3 weeks for 3 months. The anti-cMet ADC therapy is continued until disease progression or no longer tolerated by the patient.

In still another exemplary embodiment, an anti-cMet ADC is used adjunctive to radiation to treat NSCLC. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. Typically, external beam radiation therapy is applied for a few minutes up to 5 days a week for 5 to 7 weeks, but this will vary depending on the type of external beam radiation therapy that is used. The adjunctive anti-cMet ADC/radiation therapy is continued until disease progression or no longer tolerated by the patient.

In yet another exemplary embodiment, an anti-cMet ADC is used adjunctive to AVASTIN® (bevacizumab) to treat NSCLC. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. The recommended dose and schedule for bevacizumab is 10 mg/kg every 14 days or 15 mg/kg every 21 days. The adjunctive anti-cMet ADC/bevacizumab therapy is continued until disease progression or no longer tolerated by the patient.

In one exemplary embodiment, an anti-cMet ADC is used adjunctive to gemcitabine (GEMZAR®) to NSCLC cancer. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. Gemcitabine is administered by intravenous infusion at a dose of 1000 mg/m$^2$ over 30 minutes on days 1, 8, and 15 over an every 4-week schedule. Administer cisplatin intravenously at 100 mg/m$^2$ on day 1 after the infusion of gemcitabine. In another embodiment, gemcitabine is administered by intravenous infusion at a dose of 1250 mg/m$^2$ over 30 minutes on days 1 and 8 over an every 3-week schedule. Administer cisplatin intravenously at 100 mg/m$^2$ on day 1 after the infusion of gemcitabine. If myelosuppression is observed, dose modifications as provided in the prescribing information for gemcitabine may be used. The adjunctive anti-cMet ADC/gemcitabine therapy is continued until disease progression or no longer tolerated by the patient.

In one exemplary embodiment, an anti-cMet ADC is used adjunctive to gemcitabine (GEMZAR®) to treat pancreatic, ovarian, breast, or NSCLC cancer. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. In treating pancreatic cancer, gemcitabine is administered by intravenous infusion at a dose of 1000 mg/m$^2$ over 30 minutes once weekly for up to 7 weeks, followed by a week of rest from treatment. After week 8: weekly dosing on days 1, 8, and 15 of 28-day cycles. In treating ovarian cancer, gemcitabine is administered by intravenous infusion at a dose of 1000 mg/m$^2$ over 30 minutes on days 1 and 8 of each 21-day cycle, in combination with carboplatin AUC 4 intravenously after Gemzar administration on day 1 of each 21-day cycle. Refer to carboplatin prescribing information for additional information. In treating breast cancer, gemcitabine is administered by intravenous infusion at a dose of 1250 mg/m$^2$ intravenously over 30 minutes on days 1 and 8 of each 21-day cycle that includes paclitaxel. Paclitaxel should be administered at 175 mg/m2 on day 1 as a 3 hour intravenous infusion before Gemzar administration. If myelosuppression is observed, dose modifications as provided in the prescribing information for gemcitabine may be used. Subsequent cycles should consist of infusions once weekly for 3 consecutive weeks out of every 4 weeks. The adjunctive anti-cMet ADC/gemcitabine therapy is continued until disease progression or no longer tolerated by the patient.

In another exemplary embodiment, an anti-cMet ADC is used adjunctive to paclitaxel albumin-stabilized nanoparticle formulation (ABRAXANE®) to treat breast or lung cancer. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. The recommended dose and schedule for paclitaxel albumin-stabilized nanoparticle formulation is 125 mg/m$^2$ administered as an intravenous infusion over 30-40 minutes on days 1, 8, and 15 of each 28-day cycle. The adjunctive anti-cMet ADC/ABRAXANE® therapy is continued until disease progression or no longer tolerated by the patient.

In another exemplary embodiment, an anti-cMet ADC is used adjunctive to paclitaxel albumin-stabilized nanoparticle formulation (ABRAXANE®) plus gemcitabine (GEMZAR®) to treat pancreatic cancer. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. The recommended dose and schedule for paclitaxel albumin-stabilized nanoparticle formulation is 125 mg/m$^2$ administered as an intravenous infusion over 30-40 minutes on days 1, 8, and 15 of each 28-day cycle. Gemcitabine is administered by intravenous infusion at a dose of 1000 mg/m$^2$ over 30 minutes once weekly for up to 7 weeks (or until toxicity reducing or holding a dose), followed by a week of rest from treatment. Subsequent cycles should consist of infusions once weekly for 3 consecutive weeks out of every 4 weeks. The adjunctive anti-cMet ADC/ABRAXANE®/GEMZAR® therapy is continued until disease progression or no longer tolerated by the patient.

In yet another exemplary embodiment, an anti-cMet ADC is used adjunctive to AVASTIN® (bevacizumab) to treat colorectal cancer or lung or ovarian. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. The recommended dose and schedule for bevacizumab is 10 mg/kg every 14 days or 15 mg/kg every 21 days. The adjunctive anti-cMet ADC/bevacizumab therapy is continued until disease progression or no longer tolerated by the patient.

In still another exemplary embodiment, an anti-cMet ADC is used adjunctive to FOLFIRINOX (or FOLFIRI or FOLFOX or irinotecan or 5-FU or capecitabine) to treat colorectal cancer. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. FOLFIRINOX is a combination of four chemotherapy agents: fluorouracil [5-FU], leucovorin, irinotecan and oxaliplatin. In some embodiments, FOLFIRINOX is administered as follows: oxaliplatin, 85 mg/m$^2$; irinotecan, 180 mg/m$^2$; leucovorin, 400 mg/m$^2$; and fluorouracil, 400 mg/m$^2$ given as a bolus followed by 2400 mg/m$^2$ given as a 46-hour continuous infusion, every 2 weeks. The adjunctive anti-cMet ADC/FOLFIRINOX therapy is continued until disease progression or no longer tolerated by the patient.

In still another exemplary embodiment, an anti-cMet ADC is used adjunctive to Onivyde® to treat pancreatic cancer. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. Onivyde® is a liposomal irinotecan formulation. In some embodiments, Onivyde® is administered at 70 mg/m$^2$ by intravenous infusion over 90 minutes every 2 weeks. The adjunctive anti-cMet ADC/Onivyde® therapy is continued until disease progression or no longer tolerated by the patient.

In still another exemplary embodiment, an anti-cMet ADC is used adjunctive to Onivyde®, fluorouracil, and leucovorin to treat pancreatic. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. Onivyde® is a liposomal irinotecan formulation. In some embodiments, Onivyde® is administered at 70 mg/m$^2$ by intravenous infusion over 90 minutes every 2 weeks, with leucovorin 400 mg/m$^2$ and fluorouracil 2400 mg/m$^2$ over 46 hours every 2 weeks. The adjunctive anti-cMet ADC/Onivyde®/leucovorin/fluorouracil therapy is continued until disease progression or no longer tolerated by the patient.

In still another exemplary embodiment, an anti-cMet ADC is used adjunctive to nivolumab (OPDIVO®) to treat lung cancer and other cancers where nivolumab is utilized. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. Nivolumab is administered an intravenous infusion at 3 mg/kg over 60 minutes every two weeks. The adjunctive anti-cMet ADC/nivolumab therapy is continued until disease progression or no longer tolerated by the patient.

In still another exemplary embodiment, an anti-cMet ADC can be used adjunctive to pembrolizumab (KEYTRUDA®) to treat colorectal cancer. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. Pembrolizumab is administered as an intravenous infusion at 2 mg/kg over 30 minutes every 3 weeks. The adjunctive anti-cMet ADC/pembrolizumab therapy is continued until disease progression or no longer tolerated by the patient.

In one embodiment, the cancer is pancreatic cancer, the anti-cMet ADC is ABBV-399, administered at 2.7 mg/kg every 21 days, and the erlotinib is administered at 150 mg orally, once daily. The adjunctive anti-cMet ADC/erlotinib therapy is continued until disease progression or no longer tolerated by the patient.

In still another exemplary embodiment, an anti-cMet ADC is used adjunctive to doxorubicin to treat breast cancer. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. When used adjunctively with other drugs, the most commonly used dosage of doxorubicin is 40 to 60 mg/m² given as a single intravenous injection every 21 to 28 days. The adjunctive anti-cMet ADC/doxorubicin therapy is continued until disease progression or no longer tolerated by the patient.

In yet another exemplary embodiment, an anti-cMet ADC is used adjunctive to AVASTIN® (bevacizumab) to treat breast cancer. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. The recommended dose and schedule for bevacizumab is 10 mg/kg every 14 days or 15 mg/kg every 21 days. The adjunctive anti-cMet ADC/bevacizumab therapy is continued until disease progression or no longer tolerated by the patient.

In still another exemplary embodiment, an anti-cMet ADC is used adjunctive to gemcitabine to treat breast cancer. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. Gemcitabine is administered by intravenous infusion at a dose of 1000 mg/m² over 30 minutes once weekly for up to 7 weeks (or until toxicity reducing or holding a dose), followed by a week of rest from treatment. Subsequent cycles should consist of infusions once weekly for 3 consecutive weeks out of every 4 weeks. The adjunctive anti-cMet ADC/gemcitabine therapy is continued until disease progression or no longer tolerated by the patient.

In still another exemplary embodiment, an anti-cMet ADC is used adjunctive to trastuzumab (HERCEPTIN®) to treat breast cancer. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. The recommended initial loading dose for trastuzumab is 4 mg/kg administered as a 90-minute infusion. The recommended weekly maintenance dose for trastuzumab is 2 mg/kg which can be administered as a 30 minute infusion if the initial loading dose was well tolerated. The adjunctive anti-cMet ADC/trastuzumab therapy is continued until disease progression or no longer tolerated by the patient.

In still another exemplary embodiment, an anti-cMet ADC is used adjunctive to capecitabine (XELODA®) to treat breast cancer. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. Capecitabine can be administered at 1250 mg/m² twice daily for 2 weeks followed by a one week rest period in 3 week cycles. The adjunctive anti-cMet ADC/capecitabine therapy is continued until disease progression or no longer tolerated by the patient.

In still another exemplary embodiment, an anti-cMet ADC is used adjunctive to nivolumab (OPDIVO®) to treat breast cancer. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. Nivolumab is administered an intravenous infusion at 3 mg/kg over 60 minutes every two weeks. The adjunctive anti-cMet ADC/nivolumab therapy is continued until disease progression or no longer tolerated by the patient.

In still another exemplary embodiment, an anti-cMet ADC can be used adjunctive to pembrolizumab (KEYTRUDA®) to treat breast cancer. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. Pembrolizumab is administered as an intravenous infusion at 2 mg/kg over 30 minutes every 3 weeks. The adjunctive anti-cMet ADC/pembrolizumab therapy is continued until disease progression or no longer tolerated by the patient.

In still another exemplary embodiment, an anti-cMet ADC is used adjunctive to TARCEVA® (erlotinib) to treat Head and Neck cancer. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. The recommended dose and schedule for erlotinib is 150 mg orally, once daily. The adjunctive anti-cMet ADC/erlotinib therapy is continued until disease progression or no longer tolerated by the patient.

In one embodiment, the cancer is Head and Neck cancer, the anti-cMet ADC is ABBV-399, administered at 2.7 mg/kg every 21 days, and the erlotinib is administered at 150 mg orally, once daily. The adjunctive anti-cMet ADC/erlotinib therapy is continued until disease progression or no longer tolerated by the patient.

In still another exemplary embodiment, an anti-cMet ADC is used adjunctively to radiation to treat Head and Neck cancer. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. Typically, external beam radiation therapy is applied for a few minutes up to 5 days a week for 5 to 7 weeks, but this will vary depending on the type of external beam radiation therapy that is used. The adjunctive anti-cMet ADC/radiation therapy is continued until disease progression or no longer tolerated by the patient.

In yet another exemplary embodiment, an anti-cMet ADC is used adjunctive to AVASTIN® (bevacizumab) to treat Head and Neck cancer. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. The recommended dose and schedule for bevacizumab is 10 mg/kg every 14 days or 15 mg/kg every 21 days. The adjunctive anti-cMet ADC/bevacizumab therapy is continued until disease progression or no longer tolerated by the patient.

In still another exemplary embodiment, an anti-cMet ADC is used adjunctive to cetuximab to treat Head and Neck cancer. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. Cetuximab is administered at an initial dose of 400 mg/m$^2$ over a 120-minute intravenous infusion followed by 250 mg/m$^2$ weekly infusion over 60 minutes. The adjunctive anti-cMet ADC/cetuximab therapy is continued until disease progression or no longer tolerated by the patient.

In still another exemplary embodiment, an anti-cMet ADC is used adjunctive to carboplatin to treat Head and Neck cancer. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. Carboplatin is administered at 300 mg/m$^2$ or more, once every 4 weeks. The adjunctive anti-cMet ADC/carboplatin therapy is continued until disease progression or no longer tolerated by the patient.

In still another exemplary embodiment, an anti-cMet ADC is used adjunctive to nivolumab (OPDIVO®) to treat Head and Neck cancer. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. Nivolumab is administered an intravenous infusion at 3 mg/kg over 60 minutes every two weeks. The adjunctive anti-cMet ADC/nivolumab therapy is continued until disease progression or no longer tolerated by the patient.

In still another exemplary embodiment, an anti-cMet ADC can be used adjunctive to pembrolizumab (KEYTRUDA®) to treat Head and Neck cancer. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. Pembrolizumab is administered as an intravenous infusion at 2 mg/kg over 30 minutes every 3 weeks. The adjunctive anti-cMet ADC/pembrolizumab therapy is continued until disease progression or no longer tolerated by the patient.

In still another exemplary embodiment, an anti-cMet ADC is used adjunctive to cisplatin to treat Head and Neck cancer. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. The adjunctive anti-LRRC15 ADC/cisplatin therapy is continued until disease progression or no longer tolerated by the patient.

In still another exemplary embodiment, an anti-cMet ADC is used adjunctive to TARCEVA® (erlotinib) to treat Head and Neck cancer. The anti-cMet ADC (e.g., ABBV-399) is administered via IV infusion once every 14 days or every 21 days at 0.15 mg/kg, 0.3 mg/kg, 0.6 mg/kg, 0.9 mg/kg, 1.2 mg/kg, 1.5 mg/kg, 1.8 mg/kg, 2.1 mg/kg, 2.4 mg/kg, 2.7 mg/kg, 3.0 mg/kg, 3.3 mg/kg, 3.6 mg/kg, 3.9 mg/kg, 4.2 mg/kg, 4.5 mg/kg, 4.8 mg/kg, 5.1 mg/kg, 5.4 mg/kg, 5.7 mg/kg or 6.0 mg/kg, preferably once every 21 days at 2.7 mg/kg. The recommended dose and schedule for erlotinib is 150 mg orally, once daily. The adjunctive anti-cMet ADC/erlotinib therapy is continued until disease progression or no longer tolerated by the patient.

In one embodiment, the cancer is Head and Neck cancer, the anti-cMet ADC is ABBV-399, administered at 2.7 mg/kg every 21 days, and the erlotinib is administered at 150 mg orally, once daily. The adjunctive anti-cMet ADC/erlotinib therapy is continued until disease progression or no longer tolerated by the patient.

As will be appreciated by those of skill in the art, the recommended dosages for the various agents described above may need to be adjusted to optimize patient response and maximize therapeutic benefit.

In alternate embodiments, all numbers expressing quantities of ingredients, % purity, and so forth, used in this disclosure, are modified by the term "about."

5.11. Patient Selection

Patients selected for the ADC treatments of this disclosure include those with cMet-expressing tumors and those with cMet-overexpressing tumors, which include, but are not limited to, any solid tumor (including also those that overexpress HGF and/or have abnormal activation of HGF/cMet signaling or expression). Patients can be selected for treatment with the ADC treatments of this disclosure on the basis of their level of cMet, which is classified in terms of an immunohistochemistry (IHC) H-score. Details on how to quantify and qualify the level of cMet overexpression are presented in the Detailed Description (section 5.3.) and in Example 17. cMet overexpression can be defined by an IHC H-score of greater than or equal to 150 when measured according to the assay of Example 17 "cMet ABBV-ADC staining protocol." Briefly, an IHC staining protocol for cMet overexpression has been developed using the Ventana cMet CONFIRM (SP44) kit. Tissue samples are stained with the Ventana antibody and then scored by determining the percentages of target tissue cells staining at various intensity levels of low to high. FIG. 20 depicts representative H-scores using the assay described in Example 17. Alternatively, cMet overexpressing tumor tissue using an IHC score from 0 to 3+ is described in Example 21. FIG. 19 depicts representative IHC scores using the assay described in Example 21.

For purposes of this disclosure, an H-score between 150 and 224 is equivalent to an IHC score of 2+ and an H-score of 225 and above is equivalent to an IHC score of 3+. In one example, NSCLC squamous cell carcinoma patients can be selected for treatment when their cancer has an H-score of at least between 150 and 224, or an IHC score of 2+. In another example, NSCLC adenocarcinoma patients can be selected for treatment when their cancer has an H-score of 225 and above, or an IHC score of 3+.

The cancer may be newly diagnosed and naïve to treatment, or may be relapsed, refractory, or relapsed and refractory, or a metastasis or metastatic form of a cMet-expressing (herein referred to as cMet+ tumors) or cMet-overexpressing tumor, i.e., cMet+/overexpressing tumors. As demonstrated in the Examples of this disclosure, cMet+/overexpressing tumors that exhibit resistance to other targeted or non-targeted chemotherapies, retain sensitivity to ABBV-399.

The anti-cMet ADCs have myriad uses, and in one embodiment are useful therapeutically for the treatment of cMet overexpressing tumors in humans, tumors where the MET gene has been amplified; and tumors carrying mutations in or around Exon 14 of the MET gene, among others. In another embodiment, the anti-cMet ADCs are useful therapeutically for the treatment of cMet expressing tumors in humans, where cMet is not overexpressed but still expressed.

Tumors carrying EGFR Exon 19 deletions or EGFR Exon 21 mutations (L858R) are also within the scope of this disclosure. Amplification of the MET gene is considered one of the more common causes of acquired resistance in EGFR-mutant NSCLC.

Response to ABBV-399 and other cMet-ADCs disclosed herein can correlate with expression of cMet at both the protein and genomic level (e.g., amplification, Exon 14 mutations). Preferential methods for measuring both of these biomarkers are described in detail in the Examples. However, one of ordinary skill in the art would know how to use other methods to assess the same and those methods are within the scope of this disclosure.

If different results are obtained with different methods, then the results obtained with the methods described in the Examples are those to be used in determining whether a particular embodiment falls within the scope of the embodiments. For example, for evaluating expression of the cMet protein one would use the "cMet ABBV-ADC staining protocol." If the Ventana reagents used in this protocol are no longer available, another FDA-approved protocol for assessment of cMet expression levels by IHC can be used. For evaluating MET gene copy number one would use the "MET/CEP7 cMET amplification method."

MET is subject to alternative splicing. Multiple MET transcripts of different size have been identified in human cell lines and tissues. At least three 8-kb variants have been described and presumed to be generated by alternative splicing. A cMet isoform was described that lacks 18 amino acids in the extracellular region (exon 10) and is the most abundant form in a variety of tissues and cell lines. Alternative splicing of exon 14 generates another variant that has an in-frame deletion of 47 amino acids in the juxtamembrane cytoplasmic domain of the receptor. A possible mechanism of alternative splicing could be at the origin of a 85 kDa, N-terminally truncated form of MET found in malignant musculo-skeletal tumors, although this short form could also originate from alternative transcription start or proteolitic cleavage.

It has been demonstrated that MET mutants involving deletion of exon 14 stabilize the cMet receptor, resulting in a gain of function activity. MET Exon 14 contains the Cbl ubiquitin ligases site on tyrosine residue 1003 (Y1003) where ubiquitin is otherwise normally attached to the tyrosine residue and leads to the lysosomal degradation of the cMet protein. Hence, missense mutation of Y1003 residue or "skipping" of the protein region that is encoded by MET Exon 14 results in a relative over-expression of MET protein, enhanced cMet activation and subsequent oncogenesis. Inhibition by MET Tyrosine Kinase Inhibitors (TKIs) can result in clinical benefit in at least NSCLC patients harboring these MET Exon 14 alterations. Patients carrying any of these mutations can benefit from the treatments disclosed herein.

Accordingly, patients may also be selected for treatment if they carry cells with a mutation in Exon 14 of the MET gene, the result of which is an increased level of cMet protein in those cancer cells. The Examples also provide various methods for assessing this biomarker.

MET amplification is recognized as one of the potential molecular mechanisms of acquired resistance in EGFR-mutated NSCLC to EGFR-TKIs. The decision on whether or not to select a particular patient for treatment with the ADCs disclosed herein may also encompass determining whether the patient's cancer carries a deletion in Exon 19 of the Epidermal Growth Factor Receptor (EGFR), a substitution in Exon 21 (L858R), or both. Patients whose cancer carries one or both of these genomic alterations in at least some of its cells are preferentially selected for treatment with ABBV-399 or any other ADC disclosed herein. Methods for assessing these two biomarkers are provided in the Examples below.

6. EXAMPLES

The following Examples, which highlight certain features and properties of exemplary embodiments of anti-cMet ADCs and methods of using these ADS to treat patients are provided for purposes of illustration, and not limitation.

Example 1

Preparation of ABT-700

ABBV-399 (ABT-700-vcMMAE) is an antibody drug conjugate (ADC) comprised of the antibody ABT-700 conjugated to the cytotoxic microtubule inhibitor monomethyl-auristatin E (MMAE) via a cleavable valine-citrulline (vc) linker. ABT-700 is a "humanized" recombinant immunoglobulin G kappa (IgGK) that targets a unique epitope of cMet resulting in blockade of both HGF-dependent and HGF-independent cMet signaling.

ABT-700 is a humanized recombinant monoclonal antibody directed against cMet. The antibody consists of 2 identical IgG1 heavy chains of 445 amino acids paired with 2 identical light chains of 218 amino acids. The heavy chain was engineered to introduce an extra cysteine at position 223 as well as deletion of a lysine residue preceding Cys-223 and deletion of 2 threonine residues flanking His-224. In addition, the C-terminal lysine amino acid on the heavy chain was engineered to eliminate heterogeneity at the C terminus due to incomplete cleavage of the lysine. The antibody is glycosylated at asparagine 296 on each heavy chain.

The heavy chain contains 12 cysteine residues and the light chain contains 5 cysteine residues. Each heavy chain contains 4 intra-chain disulfide bridges and each light chain contains 2 intra-chain disulfide bridges. In addition, the 2 heavy chains are covalently linked by 3 inter-chain disulfide bridges. Each light chain participates in 1 disulfide bond with a heavy chain.

ABT-700 for the in vitro studies described below was prepared by routine techniques, essentially as described in U.S. Pat. No. 8,741,290. Briefly, suspension-adapted HEK293 EBNA cells (InVitrogen, US) were routinely grown in 250 ml flasks in 50 ml of serum-free medium Excell 293 (SAFC Biosciences) supplemented with 6 mM glutamine on an orbital shaker (110 rpm rotation speed). Transient transfection was performed with $2 \times 10^6$ cells/ml using linear 25 kDa polyethyleneimine (PEI) (Polysciences) prepared in water at a final concentration of 1 mg/ml mixed and plasmid DNA (final concentration of 1.25 µg/ml for heavy to light chain plasmid ratio of 1:1). At 4 hours post-transfection, the culture was diluted with one volume of fresh culture medium to achieve a final cell density of $10^6$ cells/ml. The cultivation process was monitored on the basis of cell viability and Mab production. Typically, cultures were maintained for 4 to 5 days. ABT-700 was purified using a conventional chromatography approach on a Protein A resin (GE Healthcare, US).

ABT-700 for the clinical studies described below was prepared essentially as described next. First, the plasmid pConPlusγ1fΔK/κ-hz224G11[TH7] was constructed for high-level expression of ABT-700 monoclonal antibody in CHO cells using the Glutamine Synthetase GS-CHO technology. The heavy and light chain sequences were cloned into vectors pConPlusγ1fΔK-hz224G11/TH7VH0 and pConPlusκ2-hz224G11/VL4(4-39-84) respectively, creating single-gene vectors (SGVs). The SGVs containing the heavy chain and the light chain genes were then combined, together with the Glutamine Synthetase (GS) selection gene, to generate the final double-gene vector (DGV): pConPlusγ1fΔK/κ—hz224G11[TH7]. The major components of pConPlusγ1fΔK/κ-hz224G11[TH7] include the following genes or regulatory elements in the following order: hCMV-MIE promoter, 5' UTR with intron, ABT-700 light chain coding sequence [224G11 (HzVL)], SV40 polyadenylation sequence, hCMV-MIE promoter, 5' UTR with intron, ABT-700 heavy chain coding sequence [224G11 (HzVH)], SV40 polyadenylation sequence, plasmid origin of replication, beta-lactamase, and Glutamine Synthetase cDNA with its regulatory sequences.

The expression system used for production of ABT-700 drug substance was Lonza Biologics' proprietary Glutamine Synthetase (GS) Gene Expression System in Chinese Hamster Ovary (CHO) cells. The host cell line was derived from CHO-K1SV host working cell bank designated 269-W3 (prepared from the host master cell bank 269-M).

The double-gene vector pConPlusγ1fΔK/κ-hz224G11 [TH7] was transfected into CHO-K1SV cells by electroporation and then distributed into 96-well plates. Cells expressing GS, and hence those containing the expression vector were selected by growth in protein-free and glutamine-free medium. The plates were incubated until foci of transfected cells began to appear. Only cell lines that came from wells containing single colonies (as determined by visual assessment) were progressed. Culture supernatants from wells containing single colonies were screened for antibody production using an ELISA for assembled antibody. Several clonal cell lines were established and the one showing the most consistent performance was selected for ABT-700 production. The cells were tested to confirm the quality of the mRNA and the fidelity of the coding transcripts.

A single frozen vial of cells is expanded by either shaker culture or cell bags. A larger volume of culture medium is inoculated with the expanded cultures and the cultures expanded further in a bioreactor (comprising growth medium supplemented with methionine sulphoximine) in a 5% $CO_2$, 36° C. incubator. The cultures are harvested and filtered for the removal of cells and debris. The ABT-700 is purified through a Protein A column, followed by anion exchange membrane chromatography, cation exchange column chromatography, viral filtration, ultrafiltration, and final bulk filtration. All solutions are prepared according to cGMP.

Example 2

Preparation of Heterogeneous DAR ABT700-vcMMAE ADCs

ABBV-399 is an ADC comprised of ABT-700 (an anti-cMet IgG1 antibody) conjugated to MMAE via a vc linker.

ABBV399 is derived from the conjugation of vcMMAE to inter-chain disulfide bonds in ABT-700 after mild reduction to the sulfhydryl groups. After an additional process step to remove higher order DAR species, the average DAR for ABBV-399 is approximately 3.

Two different processes, Process I (FIG. 2A and FIG. 2B) and Process II (FIG. 3A and FIG. 3B) were used to make ABBV-399 heterogeneous DAR compositions.

An ABBV399 composition heterogeneous in DAR was prepared by a two-step chemical process: disulfide reduction of ABT-700 followed by alkylation (conjugation) with maleimidocaproyl valine-citrulline ("val-cit") para-aminobenzyl alcohol ("PABA") monomethyl auristatin E (referred to herein as "vcMMAE"), illustrated below:

In the first step, a limited number of interchain disulfide bonds of ABT700 are reduced with tris(2-carboxyethyl) phosphine ("TCEP") (≥0.8 equiv). Partially-reduced ABT700 is then conjugated to vcMMAE (≥1.8 equiv) in DMSO. Residual unreacted vcMMAE is quenched with N-acetyl-L-cysteine.

FIG. 2A and FIG. 3A show chromatographic resolutions of the resultant crude ADC preparations obtained from Process I (FIG. 2A) or Process II (FIG. 3A). As can be seen, the resultant ADC preparation is a heterogeneous mixture containing antibodies having zero MMAE molecules attached ("E0" peak), two MMAE molecules attached ("E2" peak), four MMAE molecules attached ("E4" peak), six MMAE molecules attached ("E6" peak), eight MMAE molecules attached ("E8" peak), and ten MMAE molecules attached ("E10" peak). For process I, the average DAR of the crude product preparation is approximately 4.3. For process II the average DAR of the crude product preparation is approximately 3.2.

Example 3

Preparation of ABT700-vcMMAE ADCs Enriched in DAR3.1 and ABBV-399 Enriched in a 1:1 E2/E4 Ratio Preparation of ABBV-399 Enriched in DAR 3.1 Using Process I To obtain an average DAR of 3.1, as depicted in FIG. 2B, a batch chromatographic process was used. The ABBV-399 crude product solution (FIG. 2A) is diluted with a potassium phosphate buffer and treated with a HIC resin to reduce the DAR to approximately 3. The HIC resin is removed by filtration, washed with a phosphate-buffered saline solution and the wash is optionally combined with the ABBV-399 DAR 3.1 product solution.

FIG. 2B shows an analytical HIC chromatogram of the final product from process I after treatment with the HIC resin (As can be seen, the resultant ADC preparation is a heterogeneous mixture containing antibodies having zero MMAE molecules attached ("E0" peak), two MMAE molecules attached ("E2" peak), four MMAE molecules attached ("E4" peak), and six MMAE molecules attached ("E6" peak), and has an average DAR of 3.1.

Preparation of ABBV-399 Enriched in a 1:1 E2/E4 Ratio

To obtain a 1:1 E2/E4 ratio, as depicted in FIG. 3B, a column chromatographic process was used. The ABBV-399 crude product solution (FIG. 3A) is diluted with an ammonium sulfate/sodium phosphate solution to the target binding concentration. This material is loaded on the column and binds to the HIC resin. A step gradient elution using an ammonium sulfate/sodium phosphate buffer is used to enrich the antibody drug conjugates and isolate the ADC species with two or four vcMMAE molecules attached. These are eluted off the column in one peak.

FIG. 3B shows an analytical HIC chromatogram of the final product from Process II after enrichment using the HIC chromatography column. As can be seen, the resultant ADC preparation is a heterogeneous mixture containing antibodies having zero MMAE molecules attached ("E0" peak), two MMAE molecules attached ("E2" peak), and four MMAE molecules attached ("E4" peak), and has an average DAR of 3.0.

As will be shown below in Example 16, ABBV-399 has shown anti-cancer effects in a Phase I clinical trial at a dose of 2.7 mg/kg Q3W. A dose escalation to 3 mg/kg is also proposed herein to identify the maximum tolerated dose for Phase II studies keeping in mind that brentuximab vedotin and DCDT2980S (an MMAE ADC targeting CD22) have been tolerated at 1.8 and 2.4 mg/kg but not 2.7 or 3.2 mg/kg, respectively. Based on considerations of drug antibody ratio (DAR; MMAE loading per antibody molecule), ABBV-399 with a DAR of 3.1 may be potentially more tolerable than brentuximab vedotin which has an approximate DAR of 4.

Example 4

Preparation of ABT700-PBD Antibody Drug Conjugate

ABT-700 (S238C)-PBD is comprised of two PBD drug-linker molecules conjugated to cys engineered mAb ABT-700. The PBD synthon vaPBD was conjugated to the ABT-700 (S238C if using Kabat, S239C if using the EU numbering system) antibody. The conjugation process consists of a quantitative reduction of the engineered and interchain disulfides. This takes place through reduction of the interchain disulfides, quantitative oxidation, and conjugation with excess PBD drug linker. The reduction mixture is then purified to remove the excess reagent and its byproducts, followed by quantitative oxidation of the interchain disulfides and then conjugation with excess PBD drug-linker. After quenching, the reaction mixture is purified and buffer-exchanged to yield ABT-700 (S238C)-PBD. Reaction parameters have been identified to provide a conjugate with >80% DAR2 drug loading.

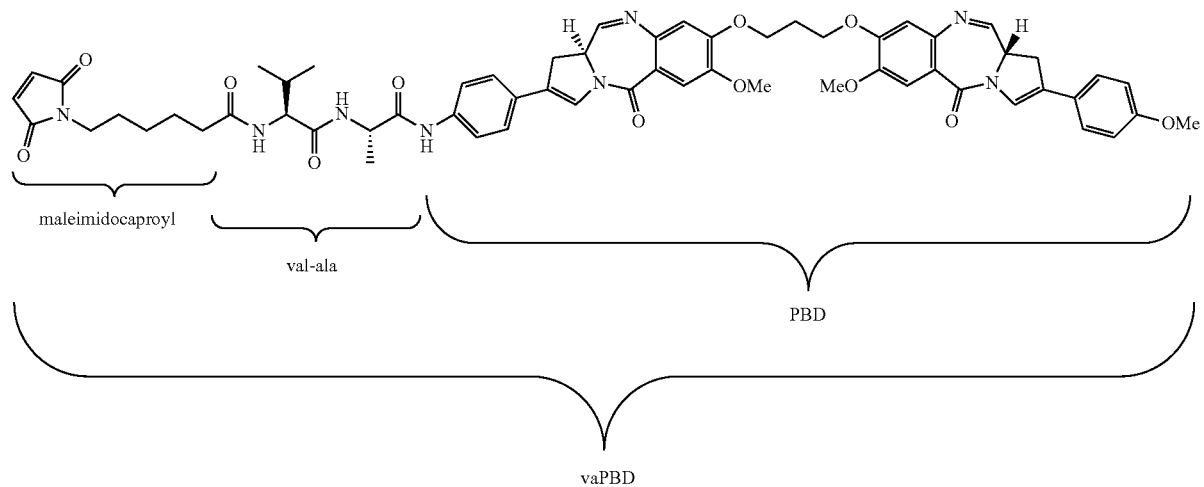 [SMILES: COc1ccc(C2=CN3C(=O)c4cc(OC)c(OCCCOc5cc6c(cc5OC)C(=O)N5C=C(c7ccc(NC(=O)[C@H](C)NC(=O)[C@@H](NC(=O)CCCCCN8C(=O)C=CC8=O)C(C)C)cc7)C[C@H]5C=N6)cc4N=C[C@@H]3C2)cc1 ; "PBD"]

Example 5

ABBV-399 Binds to Recombinant and Cellular cMet In Vitro

Binding ELISA, Cell Binding Assay and Fluorescence-Activated Cell Sorting (FACS) Analysis 96-well plates (Costar #3369) were coated with 100 μL/well of mouse anti-His antibody (Invitrogen #37-2900) at 1 μg/mL in PBS pH7.4 at 4° C. overnight, and then blocked using Superblock (Pierce, #37535) for one hour at room temperature. Plates were washed 4 times with PBST and then incubated with 100 μL of recombinant human cMet extracellular domain (rh-cMet ECD-6His) ("6His" disclosed as SEQ ID NO: 100) at 2 μg/mL in 10% Superblock in PBST for 1 h at room temperature. Plates were washed 4 times with PBST and then incubated with ABT-700 or control human IgG in serial dilutions in 10% Superblock in triplicate wells at room temperature for 1 h. Plates were washed 4 times with PBST and then incubated with 100 μL of 1:15,000 goat anti-human IgG-HRP (Thermo-scientific Pierce, Cat#31412) at room temperature for 1 h. Plates were washed 4 times in PBST and 100 μL of TMB (Pierce, #34028) was added to each well and incubated at room temperature until color developed (approximately 10 min). Reactions were stopped by addition of 2N sulfuric acid (Mallinckrodt chemicals, Cat#H381-05) and optical density (OD) was read at 450 nm.

The binding of ABBV-399 to surface cMet on a panel of human cancer cells was determined by fluorescence-assisted cell sorting (FACS) analysis. For cellular cMet binding studies, cells were harvested from flasks when approximately 80% confluent using Cell Dissociation Buffer (Invitrogen #13151-014 or #13150-016). Cells were washed once in PBS/1% FBS (FACS buffer), resuspended at 1.5-2×10⁶ cells/mL in FACS buffer and transferred to a round bottom 96-well plate (BD Falcon #3910) at 100 μL/well. Ten μL of a 10× concentration of ABT-700, ABBV-399, or controls was added and plates were incubated at 4° C. for two hours. Wells were washed twice with FACS buffer and resuspended in 50 μL of 1:500 anti-human IgG Ab (AlexaFluor 488, Invitrogen #11013) diluted in FACS buffer. Plates were incubated at 4° C. for one hour, washed twice with FACS buffer. Cells were resuspended in 100 μL of PBS/1% formaldehyde and analyzed on a Becton Dickinson LSRII flow cytometer.

ABBV-399 is reactive with the recombinant form of the human cMet extracellular domain (ECD, residues 25-932) as determined by enzyme-linked immunosorbant assay (ELISA), using a routine method for apparent affinity measurement, as known and available to one of ordinary skill in the art. ABBV-399 binds the human cMet ECD with an apparent affinity ($EC_{50}$) of 0.30 nM (TABLE 6), similar to ABT-700 ($EC_{50}$ of 0.22 nM) (TABLE 6).

ABBV-399 displayed binding affinity of 0.2 to 1.5 nM (TABLE 6) to tumor cells including NCI-H441, NCI-H292, and NCI-H1650 lung cancer cells and Hs746T, IM-95, and SNU-5 gastric cancer lines. This assay was conducted by a routine for apparent affinity measurement, as known and available to one of ordinary skill in the art.

TABLE 6

Binding affinity of ABBV-399 to recombinant and cellular cMet

|  | ABBV-399 ($EC_{50}$ nmol/L) | ABT-700 ($EC_{50}$ nmol/L) |
|---|---|---|
| cMet ECD[a] by ELISA[b] | 0.30 | 0.22 |
| Cellular cMet by FACS[c] | | |
| Hs746T | 0.4 +/− 0.1 | 0.4 +/− 0.1 |
| SNU-5 | 1.4 +/− 0.4 | 1.6 +/− 1.1 |
| IM-95 | 1.5 +/− 0.9 | 1.8 +/− 0.4 |
| NCI-H820 | 0.2 +/− 0.1 | 0.3 +/− 0.2 |
| NCI-H441 | 1.0 +/− 0.6 | 1.1 +/− 1.1 |
| NCI-H1573 | 0.6 +/− 0.1 | 0.4 +/− 0.1 |
| NCI-H1650 | 0.3 +/− 0.2 | 0.4 +/− 0.2 |

[a] Extracellular domain (residues 25-932 of cMet)
[b] $EC_{50}$ values derived from ELISA in which cMet ECD was captured on the plate via a His tag. Values are the average of six experiments.
[c] $EC_{50}$ values derived from FACS analysis of ABBV-399 on cancer cell lines. Values are the average of at least two experiments, +/− the standard deviation.

Example 6

In Vitro Potency of ABBV-399 Against Tumor Cell Lines

Cytotoxicity Assay

Tumor cells were plated at 2000-5000 cells/well in 180 μL growth medium containing 10% FBS in 96-well plates, and cultured at 37° C. in a humidified incubator with 5% C02. The following day, titrations of antibodies or ADCs in 20 μL were added and cells were incubated for 6 days. Cell viability was determined using a CellTiter-Glo Luminescent Cell Viability Assay (Promega) according to the manufacturer's instructions. A non-binding, irrelevant negative control ADC conjugated to MMAE was also included in all assays to confirm that cell killing was antigen dependent.

ABBV-399 inhibited proliferation of cancer cells that over-express cMet, including the MET-amplified cell lines Hs746T and SNU-5 gastric cancer cells (FIG. 4). As a comparison, ABT-700 inhibited proliferation of cells with MET amplification (FIG. 4A and FIG. 4B) but not cell lines without MET amplification, i.e., the NCI-H820 and NCI-H441 (FIG. 4C and FIG. 4D).

Determination of Receptor Density cMet cell surface density (antigen binding capacity per cell) was determined by indirect immunofluorescence staining of cell surface antigens on cultured cells using QIFIKIT (Dako). Briefly, cells were harvested from a culture flask as described above for FACS analysis, added to a round bottom 96-well plate at 100 μL/well and incubated at 4° C. with 3 μg/mL cMet antibody m224G11. Wells, treated with an irrelevant mouse monoclonal antibody of the same isotype mIgG1 at 3 μg/mL, were included as controls. Following a one hour incubation with primary antibody, cells were centrifuged for 3 minutes at 300×g, washed twice with FACS buffer, and incubated for one hour at 4° C. with 100 μL of the QIFIT-provided FITC conjugated antibody diluted 1:50 in FACS buffer. Cells were centrifuged for 3 minutes at 300×g, washed twice with FACS buffer, and fixed with 100 μL/well of 1% formaldehyde in PBS. For the indirect immunofluorescence staining of the QIFIKIT beads, 100 L of resuspended beads from Vial 1 and Vial 2 were added to separate wells, centrifuged for 3 min at 300×g, washed once with FACS buffer and fixed with 100 μL/well of 1% formaldehyde in PBS. Data was acquired on a Becton Dickinson LSRII flow cytometer and Geomean values for the 5 bead populations were recorded and used to calculate a standard curve based on the lot specific antibody molecules per bead. The standard curve was used to assign ABC (Antibody Binding Capacity or number of receptors) to stained cell samples.

ABBV-399 is cytotoxic to cancer cells that over-express cMet. To determine the correlation of cMet expression level to sensitivity to ABBV-399, the in vitro analysis was expanded to include a panel of 16 cell lines. These included 6 NSCLC lines (A549, NCI-H1573, NCI-H820, NCI-H441, and NCI-H1650, 4 gastro esophageal cancer lines (Hs746T, SNU-5, SNU-620, and IM-95), 2 CRC lines (SW-48 and HT-29), 2 breast cancer lines (MDA-MB-231 and MCF-7), the KP4 pancreatic cancer line, and the U-87 MG glioblastoma cancer line. Additional NSCLC cell lines (EBC-1, NCI-H226, SW900, HCC15, SK-MES-1, and NCI-H1702) were also tested and are shown in Table 7A.

TABLE 7A

|  |  | Cytotoxicity $IC_{50}$ (nM) | | |
|---|---|---|---|---|
|  | cMet receptors/cell | ABBV-399 | ABT 700-PBD | MMAE/ PBD |
| NSCLC cell line | | | | |
| H820 (Adeno) | 320,000 | 0.1 | 0.02 | 5 |
| H441 (Adeno) | 197,000 | 0.06 | 0.003 | 20 |
| H1573 (Adeno) | 116,000 | 18.3 | 0.07 | 261 |
| H1650 (Adeno) | 55,000 | 47.9 | 0.4 | 120 |
| A549 (Adeno) | 43,000 | 1.6 | 0.1 | 16 |
| EBC-1 (Squamous, amp) | 233,000 | 0.06 | 0.095 | 0.6 |
| H226 (Squamous) | 114,000 | same as control | 0.04 | n/a |
| SW900 (Squamous) | 63,000 | 7.5 | 0.02 | 375 |
| HCC15 (Squamous) | 59,000 | same as control | 0.003 | n/a |
| SK-MES-1 (Squamous) | 39,000 | same as control | 0.17 | n/a |
| H1703 (Squamous) | 23,000 | same as control | 0.7 | n/a |

TABLE 7A-continued

| | cMet receptors/cell | Cytotoxicity IC$_{50}$ (nM) | | |
| --- | --- | --- | --- | --- |
| | | ABBV-399 | ABT 700-PBD | MMAE/PBD |
| Other cell lines | | | | |
| Hs746T (Ga, amp) | 350,000 | 0.11 | 0.018 | 6.1 |
| BT-20 (Br) | 41,000 | 0.23 | 0.1 | 2.3 |
| U87MG (GBM) | 22,000 | 1.9 | 0.21 | 9 |
| M059J (GBM) | 87,000 | 3.6 | 0.03 | 120 |
| U118MG (GBM) | 12,500 | 0.54 | 0.2 | 2.7 |
| KP4 (Pa) | 15,000 | 2.9 | 0.02 | 145 |
| SW48 (CRC) | 26,000 | same as control | 0.0029 | >1000 |
| NHBE (normal bronchial epithelial) | 40,000 | none | none | n/a |

FACS analysis demonstrated that these cell lines possess a range of cMet expression levels as quantified via cMet antibody binding capacity representing the number of cell surface cMet molecules (TABLE 7B). Sensitivity to ABBV-399 in the cell proliferation assay was quantified as maximal killing and IC$_{50}$ (TABLE 7B). These data suggest that there is a threshold level of cMet expression required for significant killing by ABBV-399. Exceptions to this were the cell lines known to have an autocrine HGF loop, such as IM 95, KP4, and U-87 MG, in which lower cMet expression levels were sufficient for ABBV-399 to exert significant cytotoxicity.

TABLE 7B cMet Expression on Tumor Cells In Vitro and Sensitivity to ABBV-399

| | cMet Expression[a] | Maximal Killing[b] | ABBV-399 IC$_{50}$[c] |
| --- | --- | --- | --- |
| Lung Cancer | | | |
| A549 | 43,000 | 22% | 1.6 +/− 1.1 |
| NCI-H1573 | 115,667 | 18% | 18 +/− 14 |
| NCI-H820 | 320,000 | 87% | 0.20 +/− 0.07 |
| NCI-H441 | 197,000 | 56% | 0.06 +/− 0.05 |
| NCI-H1650 | 4,500 | 13% | 47.9 +/− 8.5 |
| EBC-1 | 233,231 | 96% | 0.06 +/− 0.03 |
| Gastric Cancer | | | |
| Hs746T | 350,000 | 87% | 0.11 +/− 0.06 |
| SNU-620 | 230,000 | 80% | 0.17 +/− 0.08 |
| SNU-5 | 291,000 | 85% | 0.28 +/− 0.07 |
| IM-95 | 21,500 | 53% | 1.7 +/− 0.9 |
| Colorectal Cancer | | | |
| SW48 | 25,500 | 0% | NA |
| HT-29 | 161,438 | 70% | 9.0 +/− 1.4 |
| Breast Cancer | | | |
| MDA-MB-231 | 30,500 | 0% | NA |
| MCF-7 | 8,300 | 0% | NA |
| Pancreatic Cancer | | | |
| KP4 | 15,300 | 53% | 2.9 +/− 1.9 |
| Glioblastoma | | | |
| U-87MG | 22,000 | 30% | 1.9 +/− 0.1 |
| Non-tumor Cell Lines | | | |
| NHBE (bronchial epithelial) | 40,085 | 10% | NA |
| HUVEC (vascular endothelial | 15,790 | 6% | NA |
| HMEC (mammary epithelial) | ND | 0% | NA |
| PrEC (prostate epithelial) | 64,853 | 0% | NA |
| NHDF (dermal fibroblasts) | 1,602 | 0% | NA |

[a]Approximate number of cMet molecules on cell surface determined by FACS analysis as antibody binding capacity for m224G11 (the murine parent of ABT-700) binding at 10 µg/mL.
[b]Relative to untreated control at ≤1 µg/mL in a six day proliferation.

Example 7

ABT700-PBD ADC Inhibits Tumor Cell Proliferation in a Broad Panel of Cell Lines

Tumor cells were plated at 2000-5000 cells/well in 180 µL growth medium containing 10% FBS in 96-well plates, and cultured at 37° C. in a humidified incubator with 5% C02. The following day, titrations of ADCs in 20 µL were added and cells were incubated for 6 days. Cell viability was determined using a CellTiter-Glo Luminescent Cell Viability Assay (Promega) according to the manufacturer's instructions. A non-binding, irrelevant negative control ADC conjugated to MMAE was also included in all assays to confirm that cell killing was antigen-dependent.

The results are shown in FIG. 5. Both cMet ADCs were active against a diverse panel of tumor types, with varying levels of cMet expression (high/low) and gene amplification (amp). The MMAE/PBD column indicates how much more MMAE ADC is required to give the same cytotoxic activity as that achieved with the PBD ADC. In most cell lines, the PBD ADC is significantly more potent than the MMAE conjugate.

Example 8

ABT700-PBD ADC is Active In Vitro Against Human Colorectal Cancer Cell Lines

Tumor cells were plated at 2000-5000 cells/well in 180 µL growth medium containing 10% FBS in 96-well plates, and cultured at 37° C. in a humidified incubator with 5% C02. The following day, titrations of ADCs and free drug (PBD and MMAE) in 20 µL were added and cells were incubated for 6 days. Cell viability was determined using a CellTiter-Glo Luminescent Cell Viability Assay (Promega) according to the manufacturer's instructions. A non-binding, irrelevant negative control ADC conjugated to MMAF (Ab095 MMAF) was also included in all assays to confirm that cell killing was antigen-dependent. The cetuximab-MMAE ADC is a positive control. Receptor density levels were calculated as described in Example 6.

The results are show in FIG. 6A and FIG. 6B. ABT700-PBD is active against a variety of colorectal cancer cell lines, including those with low levels of cMet receptors on the cell surface (e.g., SW48, FIG. 6B). A cMet gene-amplified cell line on average has 200-300K receptors per cell. The activity of the ABBV-399 ADC is also shown for comparative purposes. Where no results are entered, no activity was observed. In general, ABT700-PBD is more active than ABBV-300 in colorectal cancer cell lines.

Example 9

ABT700-PBD ADC is Active In Vitro Against Human Brain Cancer Cell Lines

Tumor cells were plated at 2000-5000 cells/well in 180 μL growth medium containing 10% FBS in 96-well plates, and cultured at 37° C. in a humidified incubator with 5% C02. The following day, titrations of ADCs and free drug (PBD and MMAE) in 20 μL were added and cells were incubated for 6 days. Cell viability was determined using a CellTiter-Glo Luminescent Cell Viability Assay (Promega) according to the manufacturer's instructions. A non-binding, irrelevant negative control ADC conjugated to MMAF (Ab095 MMAF) was also included in all assays to confirm that cell killing was antigen-dependent. Receptor density levels were calculated as described in Example 6. A cMet gene-amplified cell line on average has 200-300K receptors per cell.

The results are show in FIG. 7. ABT700-PBD is active against a variety of brain cancer cell lines, including those with low levels of cMet receptors on the cell surface (e.g., SW48, FIG. 6B). The activity of the ABBV-399 ADC is also shown for comparative purposes. Where no results are entered, no activity was observed. In general, ABT700-PBD is more active than ABBV-300 in brain cancer cell lines.

Example 10

ABT700-PBD ADC is Active In Vivo Against Human Colorectal Tumor Xenografts

The in vivo efficacy of ABT-700, ABBV-399 and ABT-700 PBD were evaluated in mice transplanted with SW-48 colorectal cells (cMet IHC 1+). The experiments were done essentially as described in Example 13 below.

ADCs or antibodies were administered every seven days at the doses shown (mg/kg). ABT-700 PBD is superior to ABBV-399 in low cMet expresser SW-48 xenografts. See FIG. 8.

Example 11

ABBV-399 and ABT700-PBD ADCs are Active In Vivo Against Human NSCLC Patient-Derived Xenografts Efficacy of ABBV-399 ABT700-PBD ADCs was determined in xenografts derived from non-small cell lung and colorectal cancer patients. Tumor fragments of 3 to 5 mm$^3$ at passage 3 (P3) were implanted subcutaneously in the right rear flank of NSG mice (The Jackson Laboratory) with a trochar. ABBV-399 and ABT-700 PBD were administered every seven days for a total of six doses. Numbers in parentheses represent dose administered in mg/kg. For all groups, tumor volumes were plotted only for the duration that allowed the full set of animal to remain on study. If animals had to be taken off study, the remaining animals were monitored for tumor growth until they reached defined end-points. Tumor growth delay (TGD) results are shown in Table 8.

| # | Indication | PDX Model | TGD[1] (%) ABBV-399 | TGD (%) ABT-700 PBD |
|---|---|---|---|---|
| 1 | Colorectal | CTG-0440 | 12 | 0 |
| 2 | Colorectal | CTG-0084 | 0 | 0 |
| 3 | Colorectal | CTG-0419 | 54 | 54 |
| 4 | Colorectal | CTG-0117 | 0 | 54 |
| 5 | Colorectal | CTG-0387 | 0 | 63 |
| 6 | Colorectal | CTG-0058 | 71 | 80 |
| 7 | Colorectal | CTG-0115 | 114 | 114 |
| 8 | Colorectal | CTG-0796 | 78 | 122 |
| 9 | Colorectal | CTG-0382 | 126 | 126 |
| 10 | Colorectal | CTG-0062 | 0 | 186 |
| 11 | Colorectal | CTG-0358 | 94 | 250 |
| 12 | Colorectal | CTG-0406 | 0 | 271 |
| 13 | Colorectal | CTG-0652 | 350 | 350 |
| 14 | NSCL | CTG-0176 | 71 | 79 |
| 15 | NSCL | CTG-0363 | 0 | 125 |
| 16 | NSCL | CTG-0164 | 25 | 136 |
| 17 | NSCL | CTG-0165 | 170 | 170 |
| 18 | NSCL | CTG-0178 | 0 | 200 |
| 19 | NSCL | CTG-0162 | 88 | 288 |
| 20 | NSCL | CTG-0159 | 288 | 288 |
| 21 | NSCL | CTG-0170 | 336 | 336 |
| 22 | NSCL | CTG-0167 | 0 | 445 |

[1]Tumor growth delay (TGD), expressed as a percentage, is the difference of the median time of the test article treated group tumors to reach 1 cm$^3$ as compared to the control group.

Graphs are shown for three different human tumor xenografts with relatively low (CTG-0363), intermediate (CTG-0159), and high (CTG-0170) levels of expression of cMet mRNA, a surrogate for cMet protein levels on the cell surface (FIG. 9A, FIG. 9B, and FIG. 9C, respectively). The tumor response to each ADC is dependent on the cMet levels. The ABT700-PBD ADC is more active than ABBV-399, at about 1/10 of the dose.

Example 12

ABBV-399 are Active In Vivo Against Human NSCLC Patient-Derived Xenografts

For the LG0703 and LG1049 patient-derived xenograft models (The Jackson Laboratory, Sacramento, Calif.), efficacy of ABBV-399 was determined in xenografts derived from non-small cell lung cancer patients. Tumor fragments of 3 to 5 mm$^3$ at passage 3 (P3) were implanted subcutaneously in the right rear flank of NSG mice (The Jackson Laboratory) with a trochar. For all groups, tumor volumes were plotted only for the duration that allowed the full set of animal to remain on study. If animals had to be taken off study, the remaining animals were monitored for tumor growth until they reached defined end-points. Efficacy is depicted on a Kaplan-Meier plot for (A) LG0703 and (B) LG1049 models as fractions reaching the indicated tumors volumes following therapy. In both models, ABBV-399 and control agents were administered every four days for a total of six doses. In the LG1049 model, ABT-700 was administered every seven days for a total of six doses. Numbers in parentheses represent dose administered in mg/kg.

The ABBV-399 ADC is more active than ABT-700 alone. See FIGS. 10A-10B.

Example 13

ABBV399, Alone and in Combination, Inhibits Tumor Growth in cMet-Overexpressing Tumors in Animal Models ABBV-399 has shown robust and reproducible antitumor effects in a variety of xenograft models including gastric cancer, NSCLC and glioblastoma multiforme models. The activity in tumors is in part based on delivery of the MMAE cytotoxic payload. In addition, ABBV-399 may also have antitumor activity through inhibition of both HGF-dependent and -independent cMet signaling and antibody mediated effector function.

The in vivo efficacy of ABBV-399 was evaluated in mice transplanted with (FIG. 11A) Hs746T gastric cancer, (FIG. 11B) NCI-H441 lung cancer cells, and (FIG. 11C) SW-40 colorectal cancer cells. Female SCID, SCID-Beige and nude mice were obtained from Charles River (Wilmington, Mass.) and housed at ten mice per cage. The body weight upon arrival was 20-22 g. Food and water were available ad libitum. Mice were acclimated to the animal facilities for a period of at least one week prior to commencement of experiments. Animals were tested in the light phase of a 12-hr light: 12-hr dark schedule (lights on at 06:00 hours). All experiments were conducted in compliance with AbbVie's Institutional Animal Care and Use Committee and the National Institutes of Health Guide for Care and Use of Laboratory Animals Guidelines in a facility accredited by the Association for the Assessment and Accreditation of Laboratory Animal Care.

To generate xenografts, a suspension of viable tumors cells mixed with an equal amount of Matrigel (BD Biosciences) was injected subcutaneously into the flank of 6- to 8-week old mice. The injection volume was 0.2 mL composed of a 1:1 mixture of S-MEM and Matrigel (BD Biosciences). Tumors were size matched at approximately 200-250 mm3 unless otherwise indicated. Therapy began the day of or 24 h after size matching the tumors. Mice weighed approximately 25 g at the onset of therapy. Each experimental group included 8-10 animals. Tumors were measured two to three times weekly. Measurements of the length (L) and width (W) of the tumor were obtained via electronic calipers and the volume was calculated according to the following equation: $V=L \times W2/2$. Mice were euthanized when tumor volume reached a maximum of 3,000 mm3 or upon presentation of skin ulcerations or other morbidities, whichever occurred first. For Hs746T, ABT-700 was administered every seven days while the ABBV-399 was administered every four days. For NCI-H441 xenografts, both ABT-700 and ABBV-399 were administered every four days for a total of six doses. Numbers in parentheses represent dose administered in mg/kg and arrows indicate days of administration. In both cancer types, the ABBV-399 ADC is more active than ABT-700 alone, and the effect is dose-dependent (FIG. 11A and FIG. 11B).

(FIG. 11C) Combination efficacy of ABBV-399 and FOLFIRI was determined using SW-48 human colorectal cancer xenografts. 5-Fluorouracil (APP Pharmaceuticals, Schaumburg, Ill.), irinotecan (Hospira, Lake Forest, Ill.) were obtained as solutions and diluted with 0.9% Sodium Chloride for Injection (USP), and leucovorin calcium (Fluka Chemical Corp., Milwaukee, Wis.) was obtained as a salt and re-constituted with saline before dosing. Standard of care agents 5-fluorouracil (50 mg/kg), and irinotecan (30 mg/kg) were administered intravenously and leucovorin (25 mg/kg) was administered orally on Q7Dx5 regimen (FOLFIRI). IgG control, Ig MMAE and ABBV-399 were administered intraperitoneally every seven days. Numbers in parentheses represent dose administered in mg/kg and arrows indicate days of administration. The ABBV-399+ FOLFIRI combination is effective in SW-48 colon cancer xenografts.

Example 14

ABBV-399 Efficacy Against Human Tumor Xenograft Models Refractory to ABT-700

ABBV-399 efficacy was evaluated in mice xenotransplanted with parental Hs746T alone (FIG. 12B) or following relapse upon treatment with ABT-700 (FIG. 12A and FIG. 12B). FIG. 12C evaluates ABBV=399 efficacy following relapse upon treatment with ABT-700 in mice senografts transplanted with EBC-1 xenograft tumors. Numbers in parentheses represent dose administered in mg/kg and arrows indicate days of administration. Tumor volumes are depicted as mean±S.E.M.

Efficacy of ABBV-399 was evaluated in a gastric carcinoma model (Hs746T) and a lung squamous cell carcinoma model (EBC-1) that were made refractory to ABT-700 by repeated exposure to the antibody in vivo (Hs746T ABT-700R and EBC-1 ABT-700R). Initially, treatment of xenografts derived from the parental Hs746T with ABT-700 resulted in tumor stasis followed by relapse (FIG. 12A; blue line). Treatment of these relapsed tumors (red line) with ABBV-399 led to regression (FIG. 12A, red line). In contrast, Hs746T ABT-700R xenografts were refractory to ABT-700 treatment with quick tumor outgrowth on therapy (FIG. 12B; blue line). When these refractory tumors reached a mean cohort size of approximately 1,000 mm$^3$, treatment with ABBV-399 resulted in tumor regression (FIG. 12B; red line) followed by eventual outgrowth. Treatment of Hs746T ABT-700R of approximately 300 mm$^3$ with ABBV-399 resulted in complete tumor regression (FIG. 12B). Similar results were observed subsequent to treatment of the ABT-700-resistant cell line EBC-1 with ABT-700 followed by ABBV-399. These results suggest that efficacy of ABBV-399 is independent of response to ABT-700, at least for cell lines with amplified cMet.

Example 15

Formulation of ABBV-399 for Clinical Use

ABBV-399 Drug Product is provided as a sterile lyophilized powder for reconstitution. Each vial contains 100 mg of ABBV-399. After reconstitution with 5.0 mL of sterile water for injection, the final concentration of ABBV-399 is 20 mg/mL. In addition to ABBV-399, the formulation contains sucrose, polysorbate 80, and is in a histidine buffer. Prior to administration, ABBV-399 is further diluted in normal saline to a concentration range between 1-10 mg/mL, depending on the weight of the subject.

Example 16

Phase I Open-Label, Dose-Escalation and Expansion Study of ABBV-399, an Antibody Drug Conjugate (ADC) Targeting cMet, in Patients (pts) with Advanced Solid Tumors 16.1. Summary An ongoing Phase 1/1b open-label study is evaluating the safety, pharmacokinetics (PK), and preliminary efficacy of ABBV-399 in subjects with advanced solid tumors. The study consists of two phases: (1) a Dose-Escalation/Expansion Phase (Monotherapy) and a Combination Therapy Phase. Subjects with advanced solid tumors with cMet overexpression, MET exon 14 mutation or MET amplification possibly including, but not limited to NSCLC, esophageal/gastric, CRC or head and neck cancer may be enrolled in the dose expansion and combination therapy phases of the study.

The monotherapy phase of the study evaluated the safety and pharmacokinetic profile of ABBV-399 when administered intravenously in approximately 24 to 42 subjects following the dose-escalation scheme depicted in FIG. 13. ABBV-399 was administered at escalating dose levels starting from 0.15 mg/kg in 21-day dosing cycles. Based on safety and PK data from dosing every 21 days, ABBV-399 will also be administered every 14 days on a 28-day schedule. Three to 6 subjects will be enrolled in each cohort and dosed once every 21 (one dose per 21-day Cycle) or 14 (2 doses per 28-day Cycle) days until disease progression or unacceptable toxicity to determine the maximum tolerated dose (MTD) or maximally administered dose (MAD). Dose limiting toxicity (DLT) definitions will be used to make decisions regarding dose-escalation. Based on available safety, PK, and pharmacodynamic (PDx) data, up to 40 subjects will be enrolled in an expansion cohort that will further evaluate ABBV-399 at a dose level which is at or below the MTD or MAD. On the dose-expansion, subjects with advanced solid tumors with cMet overexpression, MET exon 14 mutation or MET amplification will be enrolled.

In the combination therapy phase, up to 18 subjects will be enrolled into each of the combination therapy arms as described below:

Combination cohort A: Subjects eligible to receive ABBV-399 plus erlotinib

Combination cohort B: Subjects eligible to receive ABBV-399 plus cetuximab

Combination cohort C: Subjects eligible to receive ABBV-399 plus bevacizumab

Combination cohort D: Subjects eligible to receive ABBV-399 plus nivolumab

All subjects will be evaluated for safety and tolerability of the regimen, PK profile of ABBV-399 and preliminary evidence of efficacy. On the combination therapy arms, subjects with advanced solid tumors with cMet overexpression, MET exon 14 mutation or MET amplification may be enrolled. Subjects on combination arms A, B or C will be assigned to a 14-day or 21-day ABBV-399 dosing schedule whereas subjects on arm D will receive ABBV-399 on a 14-day schedule to coincide with nivolumab every 14-day dosing.

Archival tumor tissue is required for enrollment on this study. Tumor tissue will be analyzed for cMet protein, MET copy number and other biomarkers. Expression of cMet will be determined by an immunohistochemistry assay; amplification of MET will be determined by fluorescence in situ hybridization (FISH) or DNA sequencing of tumor or circulating tumor DNA.

16.2. Patient Selection: Diagnosis and Main Criteria for Inclusion/Exclusion

Some of the Criteria for Inclusion for ABBV-399 Monotherapy Dose-Escalation/Expansion:

Subject must be ≥18 years of age

Subject with advanced solid tumor including but not limited to non-small cell lung cancer (NSCLC), colorectal, breast, ovarian, esophageal/gastric and head and neck cancer.

Subject must have advanced solid tumor that is not amenable to surgical resection or other approved therapeutic options that have demonstrated clinical benefit.

For dose-expansion: Subject must have tumor with cMet overexpression, MET exon 14 mutation or MET amplification.

Subject has an Eastern Cooperative Oncology Group (ECOG) Performance Status of 0 to 2.

Subject must have measurable disease per RECIST version 1.1

Additional Inclusion Criteria for Subjects Enrolled on the Combination Therapy Phase Subjects in the combination therapy arms must meet the above inclusion criteria and be eligible to receive erlotinib, cetuximab, bevacizumab or nivolumab per most current prescribing information, or at the discretion of the Investigator.

Main Exclusion Criteria:

For all Cohorts:

Subject has received anticancer therapy including chemotherapy, immunotherapy, radiation therapy, immunotherapy, biologic, or any investigational therapy within a period of 21 days, or herbal therapy within 7 days prior to the first dose of ABBV-399.

Palliative radiation therapy for painful bone, skin or subcutaneous metastases for 10 fractions or less is not subject to a washout period.

For approved targeted small molecules, a washout period of 5 half-lives is adequate (no washout period required for subjects currently on erlotinib).

Subject has known uncontrolled metastases to the central nervous system (CNS). Subjects with brain metastases are eligible after definitive therapy provided they are asymptomatic off steroids and anticonvulsants for at least 2 weeks prior to first dose of ABBV-399.

Subject has unresolved clinically significant adverse events ≥Grade 2 from prior anticancer therapy except for alopecia or anemia.

Subject has had major surgery within 21 days prior to the first dose of ABBV-399.

Additional Exclusion Criteria for Subjects Enrolled on the Combination Therapy Phase Subjects enrolled on the combination therapy phase must satisfy the above exclusion criteria and also the following:

Subjects may not receive ABBV-399 in combination with erlotinib, cetuximab, bevacizumab or nivolumab if they have any medical condition which in the opinion of the Investigator places the subject at an unacceptably high risk for toxicities from the combination.

Subjects may not receive cetuximab if they have K-ras mutation.

Subjects may not receive bevacizumab if they have squamous NSCLC.

It is also planned that, in certain studies and for future clinical use of the anti-cMet ADCs disclosed herein, patients will be selected on the basis of their cMet expression levels (gene amplification, membrane cMet) and MET exon 14 mutation. Methods for assessing each of these markers are provided below.

16.3. Dosing Regimen

Dose-Escalation/Expansion Phase:

ABBV-399 was administered as an intravenous infusion once every 21 days until disease progression or intolerable toxicity. Dosing began at 0.15 mg/kg and escalated to 0.3, 0.6, 1.2, 1.8, 2.4, 3.0 and 3.3 mg/kg in subsequent cohorts as tolerated. Alternative doses (intermediate or higher) or dosing schedules may be employed based on clinical safety and PK data. A dose of 2.7 mg/kg was also utilized based on the clinical safety and PK data. Based on safety and PK data from dosing every 21 days, ABBV-399 will also be administered every 14-days on a 28-day schedule (starting dose of 1.6 mg/kg). ABBV-399 has been given over 30±10 minutes. It is not administered as an intravenous push or bolus.

Combination Therapy Phase:

ABBV-399 will be combined with standard doses of erlotinib, cetuximab, bevacizumab or nivolumab starting at an ABBV-399 dose level below the MTD or MAD and then escalated no higher than MTD or MAD determined in the monotherapy dose-escalation/expansion. Dose limiting toxicity definitions will apply to the dose-escalation portion of each Combination.

| | |
|---|---|
| Investigational Product: | ABBV-399 |
| Dose: | Current dose 2.7 mg/kg of ABBV-399 for every 21-day dosing |
| | 1.6 mg/kg starting dose of ABBV-399 every 14-day dosing |
| | Dose for subjects with weight >100 kg should be calculated for 100 kg |
| Mode of Administration: | IV infusion |
| Frequency of Administration | Every 21 days (21-day Cycle) or Every 14 days (28-day Cycle) |
| Reference Therapy: | Erlotinib |
| Dose: | 150 mg |
| Mode of Administration: | Oral |
| Frequency of Administration | Every day |
| Reference Therapy: | Cetuximab |
| Dose: | 400 mg/m² initial dose over 120 minutes; then 250 mg/m² over 60 minutes |
| Mode of Administration: | IV infusion |
| Frequency of Administration | Every 7 days |
| Reference Therapy: | Bevacizumab |
| Dose: | 10-15 mg/kg |
| Mode of Administration: | IV infusion |
| Frequency of Administration | Every 21 days (15 mg/kg) or every 14 days (10 mg/kg) |
| Reference Therapy: | Nivolumab |
| Dose: | 3 mg/kg |
| Mode of Administration: | IV infusion |
| Frequency of Administration | Every 14 days |
| Duration of Treatment: Subjects with clinical benefit (CR, PR or SD) will be allowed to continue study treatment with ABBV-399 until disease progression, intolerable side effects or for up to 24 months. Subjects with clinical benefit beyond 24 months and able to tolerate the drug can continue treatment on an extension study. | |

16.4. Assessments

Study visits and evaluations will be performed at Screening, and at least weekly during the first cycle and on Day 1 of each subsequent cycle. Assessments will include limited physical examination, hematology, and chemistry tests prior to all study drug dosing and at Final Visit. ECGs will be collected at Screening, Cycle 1 Day 1, Cycle 2 Day 1 and at the Final Visit. Adverse events, laboratory data and vital signs will be assessed throughout the study.

Baseline radiographic tumor assessments with CT (or MRI) of the head, chest, abdomen, and pelvis will be obtained no more than 28 days prior to Cycle 1 Day 1. CT scan (or MRI) will then be repeated approximately every 6 weeks after start of therapy to evaluate the extent of tumor burden. Radiographic tumor assessments will continue until disease progression documented by imaging, start of a new anti cancer therapy, death or withdrawal of consent. Response evaluation will be based on RECIST version 1.1. In addition, the Investigator will evaluate the subject for evidence of clinical disease progression at each visit.

16.4.1. Biomarker Assessments

Archival tumor tissue (most recent sample is preferred) is required for enrollment on this study. If a subject has local or central lab data showing cMet overexpression, MET exon 14 mutation or MET amplification and no archival tumor tissue available, the subject may be eligible after discussion with the Medical Monitor. An optional pre- and on-treatment biopsy (any time after the start of therapy) may be obtained from subjects who consent voluntarily if it is safe to do so in the judgment of the Investigator. Institutional procedures should be followed to fix and embed freshly collected tissue in paraffin. Tumor tissue will be analyzed for cMet protein, MET copy number and other biomarkers.

Expression of cMet will be determined by an immunohistochemistry assay (see Example 17); amplification of MET will be determined by fluorescence in situ hybridization (FISH) or DNA sequencing of tumor or circulating tumor DNA (see Example 18). Biospecimens will be collected at designated time points throughout the study to conduct research with the intent of identifying biomarkers associated with subject outcome or to better characterize the disease.

16.4.2 Criteria for Evaluation

Efficacy: The efficacy endpoints include objective response rate (ORR) (determined using RECIST version 1.1), progression-free survival (PFS), and duration of overall response (DOR). Radiologic assessments will consist of CT scans (or MRI in subjects who cannot tolerate contrast) and be performed approximately every 6 weeks after start of therapy to evaluate the extent of tumor burden. Radiographic tumor assessments will continue until disease progression documented by imaging, start of a new anti-cancer therapy, death or withdrawal of consentResponse evaluations will be based on Response Evaluation Criteria in Solid Tumors (RECIST) 1.1. Eisenhauer E A, Therasse P, Bogaerts B, et al. New response evaluation criteria in solid tumors: Revised RECIST guideline (version 1.1). Eur J Cancer. 2009; 45: 228-47.

Pharmacokinetic: Blood samples for assay of ABBV-399, Total ABT-700 and free MMAE drug levels will be used to evaluate PK parameters. Blood samples for antidrug antibody (ADA) and neutralizing ADA (nADA) will be collected at designated time points throughout the study and ADA/nADA will be correlated with PK and safety outcomes.

Safety: Adverse events, laboratory profiles, physical exams, and vital signs will be assessed throughout the study. Adverse events will be graded according the National Cancer Institute Common Terminology Criteria for Adverse Events (NCI CTCAE), version 4.03.

Statistical Methods:

Efficacy: Analyses of ORR, PFS, and DOR will be performed for all evaluable dosed subjects.

Pharmacokinetic: Serum concentrations of ABBV-399 and PK parameter values will be tabulated for each subject and each regimen, and summary statistics will be computed for each sampling time and each parameter.

Safety: The safety of ABBV-399 will be assessed by evaluating the study drug exposure, adverse events, serious adverse events, all deaths, as well as changes in laboratory determinations and vital sign parameters.

Efficacy

All efficacy analyses are exploratory in nature. The exploratory efficacy endpoints include objective response rate (ORR) (determined using RECIST version 1.1) progression-free survival (PFS), and duration of response (DOR).

Objective Response Rate

Objective response rate (ORR) is defined as the proportion of subjects with a confirmed partial or complete response to the treatment. The ORR for each treatment cohort will be estimated with all the sites pooled. The 2-sided 80% confidence intervals of ORR, as well as of CR and PR rates, will be provided based on the Clopper-Pearson (exact) Method.

Progression-Free Survival

For each subject, the PFS time is defined as the time from the subject's first dose of ABBV-399 to either the subject's disease progression or death, whichever occurs first. Under the situation that neither event occurs, the PFS time will be censored at the date of last disease assessment. All subjects will be followed to disease progression or up to 24 months for those who continue study drug.

The PFS time for the treatment cohorts will be summarized by Kaplan-Meier estimates. The mean and median time with 2-sided 80% confidence intervals will be calculated to describe the time-to-event distributions.

Duration of Response

The duration of response (DOR) for a subject is defined as the time from the subject's initial objective response to study drug therapy to disease progression or death, whichever occurs first. If the dates of disease progression or death are not available, the DOR will be censored at the date of last tumor assessment. The DOR will be analyzed in the same fashion as for PFS.

Tumor Assessments

Baseline radiographic tumor assessment must be performed within 28 days prior to Cycle 1 Day 1 and will consist of CT (or MRI or non-contrast CT in subjects who cannot tolerate contrast) of the head, chest, abdomen, and pelvis (and other tumor involved regions as clinically indicated). In general, imaging while on therapy with ABBV-399 will occur approximately every 6 weeks (imaging may be obtained up to 7 days prior to the next dose of drug). For the ABBV-399 combination with nivolumab, the first planned on-therapy imaging will occur at approximately 9 weeks with subsequent imaging approximately every 6 weeks. Imaging must be done prior to administering the next scheduled dose of ABBV-399. Subjects who discontinue study drug for any reason other than progressive disease demonstrated by imaging will be followed until they have progressive disease documented by imaging or start new anti-cancer therapy, death or withdraw consent. Imaging will also be performed at the Final Visit for subjects who have not had documented radiographic progression by RECIST 1.1 criteria if clinically warranted. Imaging may also be performed at other times if the Investigator suspects tumor progression. Imaging of the brain for metastatic disease will only be repeated if clinically indicated. The same imaging technique should be used throughout the study if possible. The tumor assessment performed at Screening will serve as the baseline for clinical assessment. Changes in measurable lesions over the course of therapy will be assessed using RECIST version 1.1, as described below.

RECIST (Version 1.1) Criteria for Tumor Response

Response criteria will be assessed using RECIST (version 1.1). Changes in the measurable lesions over the course of therapy must be evaluated using the criteria listed below.

a. Eligibility

Subjects with measurable disease at Baseline can have objective tumor response evaluated by RECIST criteria. Measurable disease is defined by the presence of at least one measurable lesion. If the measurable disease is restricted to a solitary lesion, its neoplastic nature should be confirmed by cytology/histology if possible.

b. Measurability

| Measurable Lesions | Lesions accurately measured in at least one dimension with a minimum size of: longest diameter ≥10 mm (CT scan slice thickness no greater than 5 mm) 10 mm caliper measurement by clinical exam |
|---|---|
| Non-Measurable Lesions | All other lesions, including small lesions (longest diameter <10 mm) as well as truly non-measurable lesions. Lesions considered truly non-measurable include: leptomeningeal disease, ascites, pleural/pericardial effusion, inflammatory breast disease, lymphangitic involvement of skin or lung and also abdominal masses that are not confirmed and followed by imaging techniques. |
| Measurable Malignant Lymph Nodes | To be considered pathologically enlarged and measurable, a lymph node must be ≥15 mm in short axis when assessed by CT scan (CT scan slice thickness recommended to be no greater than 5 mm). At baseline and in follow-up, only the short axis will be measured and followed. |
| Non-Measurable Malignant Lymph Nodes | Pathological lymph nodes with ≥10 to <15 mm short axis. |

All measurements should be taken and recorded in metric notation, using calipers if clinically assessed. All baseline evaluations should be performed as closely as possible to the beginning of treatment and not more than 4 weeks before the beginning of the treatment.

The same method of assessment and the same technique should be used to characterize each identified and reported lesion at Baseline and during follow-up.

Clinical lesions will only be considered measurable when they are superficial (e.g., skin nodules and palpable lymph nodes) and ≥10 mm diameter as assessed using calipers. For the case of skin lesions, documentation by color photography including a ruler to estimate the size of the lesion is recommended.

c. Methods of Measurement

Conventional CT should be performed with cuts of 5 mm or less in slice thickness contiguously. This applies to tumors of the chest and abdomen. A scale should be incorporated into all radiographic measurements.

Cytology and histology can be used to differentiate between partial response (PR) and complete response (CR) in rare cases.

d. Baseline Documentation of "Target" and "Non-Target" Lesions

All measurable lesions up to a maximum of 2 lesions per organ and 5 lesions in total, representative of all involved organs should be identified as target lesions and recorded and measured at Baseline. Tumor lesions situated in a previously irradiated area, or in an area subjected to other loco-regional therapy, are usually not considered measurable unless there has been demonstrated progression in the lesion.

Lymph nodes merit special mention since they are normal anatomical structures which may be visible by imaging even if not involved by tumor. Pathological nodes which are defined as measurable and may be identified as target lesions must meet the criterion of a short axis of ≥15 mm by CT scan. Only the short axis of these nodes will contribute to the baseline sum. The short axis of the node is the diameter normally used by radiologists to judge if a node is involved by solid tumor. Nodal size is normally reported as two dimensions in the plane in which the image is obtained (for CT scan this is almost always the axial plane). The smaller of these measures is the short axis. For example, an abdominal node which is reported as being 20 mm×30 mm has a short axis of 20 mm and qualifies as a malignant, measurable node. In this example, 20 mm should be recorded as the node measurement. All other pathological nodes (those with short axis ≥10 mm but <15 mm) should be considered non-target lesions. Nodes that have a short axis <10 mm are considered non-pathological and should not be recorded or followed.

A sum of diameters for all target lesions will be calculated and reported as the baseline sum of diameters. If lymph nodes are to be included in the sum, then as noted above, only the short axis is added into the sum. The baseline sum diameters will be used as reference by which to characterize the objective tumor response.

All other lesions (or sites of disease) including pathological lymph nodes should be identified as non-target lesions and should also be recorded at Baseline. Measurements of these lesions are not required, but the presence (stable, increasing or decreasing) or absence of each should be noted throughout follow-up.

e. Evaluation of Target Lesions
Complete Response (CR):
The disappearance of all target lesions. Any pathological lymph nodes (whether target or non-target) must have reduction in short axis to <10 mm.
Partial Response (PR):
At least a 30% decrease in the sum of diameters of target lesions, taking as reference the baseline sum diameters.
Progressive Disease (PD):
At least a 20% increase in the sum of the diameters of target lesions, taking as reference the smallest sum of diameters recorded since the treatment started (baseline or after) or the appearance of one or more new lesions. In addition to the relative increase of 20%, the sum must also demonstrate an absolute increase of at least 5 mm.
Stable Disease (SD):
Neither sufficient shrinkage to qualify for PR nor sufficient increase to qualify for PD, taking as reference the smallest sum of diameters since the treatment started (baseline or after).
Assessment of Target Lesions:
Lymph nodes identified as target lesions should always have the actual short axis measurement recorded (measured in the same anatomical plane as the baseline examination), even if the nodes regress to below 10 mm on study. This means that when lymph nodes are included as target lesions, the 'sum' of lesions may not be zero even if complete response criteria are met, since a normal lymph node is defined as having a short axis of <10 mm. For PR, SD and PD, the actual short axis measurement of the nodes is to be included in the sum of target lesions.

All lesions (nodal and non-nodal) recorded at Baseline should have their actual measurements recorded at each subsequent evaluation, even when very small (<5 mm). However, sometimes target lesions or lymph nodes become too small to measure. If it is in the opinion of the radiologist that the lesion has likely disappeared, the measurement should be recorded as 0 mm. If the lesion is believed to be present, but too small to measure, a default value of 5 mm should be assigned (as derived from the 5 mm CT slice thickness). The measurement of these lesions is potentially non-reproducible; therefore providing this default value will prevent false responses or progression based upon measurement error.

f. Evaluation of Non-Target Lesions
Complete Response (CR):
The disappearance of all non-target lesions and normalization of tumor marker level. All lymph nodes must be non-pathological in size (<10 mm short axis).
Non-CR/Non-PD:
Persistence of one or more non-target lesion(s) and/or maintenance of tumor marker level above the normal limits.
Progressive Disease (PD):
Unequivocal progression of existing non-target lesions.
In this setting, to achieve 'unequivocal progression' on the basis of non-target disease, there must be an overall level of substantial worsening in non-target disease such that, even in the presence of SD or PR in target disease, the overall tumor burden has increased sufficiently to merit discontinuation of therapy. A modest 'increase' in the size of one or more non-target lesions is usually not sufficient to qualify for unequivocal progression status. The designation of overall progression solely on the basis of change in non-target disease in the face of SD or PR of target disease will therefore be extremely rare.

Note: If the subject discontinues treatment for symptomatic deterioration, every effort should be made to document objective progression even after discontinuation of treatment.

New Lesions
The appearance of new malignant lesions denotes disease progression. While there are no specific criteria for the identification of new radiographic lesions, the findings of a new lesion should be unequivocal, i.e., not attributable to differences in scanning technique, timing of scanning, phase of contrast administration, change in imaging modality or finding thought to represent something other than tumor (e.g., some 'new' bone lesions may be simply healing or flare of pre-existing lesions). A lesion identified on a follow-up study in an anatomical location that was not scanned at Baseline is considered a new lesion and will indicate disease progression. An example of this is the subject who has visceral disease at Baseline and while on study has a CT or MRI brain ordered which reveals metastases. The subject's brain metastases are considered evidence of progressive disease even if he/she did not have brain imaging at Baseline.

If a new lesion is equivocal (i.e., too small to measure), continued therapy and follow-up evaluation will clarify if it represents truly new disease. If repeat scans confirm there is a new lesion, then progression should be declared using the date of the initial scan.

16.5. Results
16.5.1. ABBV-399 Monotherapy Dose-Escalation/Expansion Phase (Phase 1):
In the 3+3 dose escalation design, ABBV-399 was administered at doses ranging from 0.15 to 3.3 mg/kg once every 21 days to pts with metastatic solid tumors (NCT02099058). As depicted in FIG. 13, ABBV-399 was administered as an intravenous infusion once every 21 days until disease progression or intolerable toxicity. Dosing began at 0.15 mg/kg and escalated to 0.3, 0.6, 1.2, 1.8, 2.4, 3.0 and 3.3 mg/kg in subsequent cohorts as tolerated. A dose of 2.7 mg/kg of ABBV-399 given every 21 days was also evaluated and based on safety and PK, was chosen as the dose for the expansion cohort. Based on safety and PK data from dosing every 21 days, ABBV-399 will also be administered every 14-days on a 28-day schedule (starting dose of 1.6 mg/kg to 2.5 mg/kg in 0.3 mg/kg incremental increases, i.e., 1.6, 1.9, 2.2, and 2.5 mg/kg). For administration at 14 or 21 days, ABBV-399 will be given over 30±10 minutes. It is not administered as an intravenous push or bolus.

As of Mar. 31, 2016, 48 pts received at least 1 dose of ABBV-399. Dose-proportional increases of area under the curve for ABBV-399 and total antibody were observed after single dose administration. Half-lives for ABBV-399 and total antibody were approximately 2-4 days. Dose-limiting toxicity of febrile neutropenia occurred in 1 pt at 3 mg/kg and 1 pt (with septic shock) at 3.3 mg/kg. The best percent change in target lesions in patients with at least 1 post-baseline tumor assessment is shown in FIG. 14. As shown in FIG. 14 (and from data not shown in the figures), best responses to ABBV-399 monotherapy in all treated patients were: 3/40 (7.5%) partial response, 20/40 (50%) patients with stable disease, and 17/40 (42.5%) patients with progressive disease. RECIST data was not available for eight patients due to clinical progression (4), adverse events (2), withdrawal of consent (1) and death due to pneumonia (1). The three patients with a partial response had cMet over-expressing non-small cell lung cancer (NSCLC).

A dose of 2.7 mg/kg was chosen for dose-expansion based primarily on safety and tolerability. For enrollment in this phase of the study, NSCLC subjects were screened for cMet overexpression using an IHC assay utilizing the CONFIRM anti-total cMet (SP44) Rabbit Monoclonal Primary Antibody kit purchased from Ventana (REF #790-4430). Tissue samples were scored by determining the percentages of target tissue cells staining at various intensity levels of low to high, i.e. IHC score of 0, 1+, 2+ or 3+ or an H-score of 0 to 149, 150-224, or 225-300. The scoring can be done either manually or via the aid of a computer. Details of the IHC assay and scoring are described in Example 17. The following table shows the number of NSCLC patients prospectively screened and the H-score used to assess cMet overexpression:

| Screened | H-score 0-149 N (%) | H-score 150-224 N (%) | H-score 225-300 N (%) | Total cMet H-score ≥ 150 N (%) |
|---|---|---|---|---|
| 91 | 39 (43%) | 35 (38%) | 17 (19%) | 52 (57%) |

There were no treatment-related deaths. Treatment-related adverse events occurring in ≥10% of pts (including all dose levels and all grades) were fatigue (22.9%), nausea (20.8%), neuropathy (14.6%), decreased appetite (12.5%), vomiting (12.5%) and hypoalbuminemia (10.4%). Among 16 patients with cMet+ NSCLC treated with ABBV-399, the results from 11 are shown in FIG. 15. FIG. 15 is a waterfall plot showing the best percent change in target lesion in response to ABBV-399 monotherapy based on radiographic data. As shown in FIG. 15 (and from data not shown in the figure) 3/16 treated patients with a partial responses (19%), 6/16 treated patients with stable disease (37.5%), 2/16 treated patients with radiographic progressive disease (12.5%), and 5 patients with no available imaging due to clinical progression (3), withdrawal of consent (1) and death due to pneumonia (1).

FIG. 16 shows the number of weeks that the 16 patients were on study before clinical progression.

16.5.2. Combination Therapy Phase (Phase 1b):

Results from a NSCLC combination therapy trial using ABBV-399 at 2.7 mg/kg once every 21 days and erlotinib 150 mg administered orally every day are shown in FIG. 17 and FIG. 18. FIG. 17 is a waterfall plot showing the best percent change in target lesions for 6 patients treated with ABBV-399 and erlotinib. As shown in FIG. 17, 2/6 patients achieved a partial response, 1/6 with progressive disease as evidenced by new lesions. FIG. 18 shows the number of weeks the 6 patients were on study before clinical progression.

16.5.3. Pre-Treatment Selection for Patients Carrying cMet+ Tumors with IHC2+/3+ Scores or H-Scores ≥150 May Significantly Improve Treatment Outcome The pre-clinical results with cell lines and xenograft models suggest that those with an cMet IHC2+/IHC3+ score will be more responsive than those with IHC 0/1+. The use of companion diagnostics to aid in the pre-treatment selection of those patients with cMet IHC2/3+ or H-score ≥150 cancers would significantly improve overall treatment outcomes and spare patients from treatment that is predicted to be ineffective. As used herein, the term cMet+ encompasses all tumors that express cMet, regardless of whether or not the cMet is overexpressed. In some cMet+ embodiments, the cMet is overexpressed. In some cMet+ embodiments, the cMet is not overexpressed.

Similarly, the results of this ongoing Phase 1 clinical trial suggest that H-scores of 150 and above, are linked to and can be predictive of response to treatment with an anti-cMet ADC, including ABBV-399.

Without being bound by any theory, preliminary results suggest that tumor heterogeneity may be a limiting factor in the efficacy of ABBV-399. Among those cMet+ tumors with IHC2+ and IHC3+ scores, there are cancer cells that show none to low cMet expression. Of those, at least some of the cells that are not killed by a "bystander effect" could repopulate the tumor and impede tumor response. ABBV-399 could be combined with standard of care treatments that inhibit or kill low cMet expressing tumor cells, not limited to targeted agents like erlotinib and immunotherapies like nivolumab but also standard of care chemotherapy, preferably with non-overlapping toxicity.

Table 9 provides clinical results from the ongoing phase 1 trial correlating overall response with H score in NSCLC patients treated with ABBV-399 as a monotherapy once every two (Q2W) or three (Q3W) weeks or with ABBV-399 in combination with erlotinib. The IHC score was obtained using the protocol described in Example 17.

TABLE 9

| Subject | Dose (mg/kg) and Frequency of Administration | Tumor Histology | IHC Score | Overall Response |
|---|---|---|---|---|
| 1 | 2.7 Q3W PLUS ERLOTINIB (150 mg QD) | Adenocarcinoma | 295 | PR |
| 2 | 2.7 Q3W PLUS ERLOTINIB (150 mg QD) | adenocarcinoma | 250 | PR |
| 3 | 2.7 Q3W PLUS ERLOTINIB (150 mg QD) | adenocarcinoma | 270 | PR |
| 4 | 1.6 Q2W | adenocarcinoma | 280 | PR |
| 5 | 1.9 Q2W | adenocarcinoma | 250 | CR |
| 6 | 2.7 Q3W PLUS ERLOTINIB (150 mg QD) | adenocarcinoma | 250 | PR |
| 7 | 2.7 MG/KG Q3W | squamous cell carcinoma | 165 | PR |
| 8 | 2.7 MG/KG Q3W | squamous cell carcinoma | 185 | PR |
| 9 | 2.7 MG/KG Q3W | squamous cell carcinoma | 170 | PR |

As shown in Table 9, four patients with NSCLC adenocarcinomas treated with 2.7 mg/kg ABBV-399 once every 3 weeks (Q3W) and erlotinib having IHC scores of 225 or greater achieved partial responses (PR). Two patients with NSCLC adenocarcinomas treated once every two weeks with ABBV-399 having IHC scores of 225 or greater achieved either a partial response or a complete response. Three patients with NSCLC squamous cell carcinomas treated with 2.7 mg/kg ABBV-399 once every 3 weeks having IHC scores between 150 to 224 achieved partial responses.

Example 17 cMet Immunohistochemistry Assay and the H-Score: The "cMet ABBV-ADC Staining Protocol"

There are various methods available in the art for evaluating cMet protein expression levels by immunohistochemistry (IHC). One of ordinary skill in the art would have routinely known how to use them and adapt them to their particular study. Several vendors provide cMet staining as a fee-for-service (see, e.g., Flagship Biosciences L.L.C., ARUP Laboratories, PathGroup Inc.). In this Phase I study, cMet expression levels were evaluated using the SP44 anti-cMet mAb from Ventana Medical Systems, more specifically Ventana's CONFIRM® anti-total cMet rabbit monoclonal antibody (Ventana Medical Systems, Inc; cat no. 790-4430), in combination with a Ventana® automated slide stainer (BenchMark ULTRA®) and a Ventana ultraView® Universal DAB detection kit (cat. no. 760-500). The stainings and results were processed by Flagship Biosciences L.L.C. in collaboration with ARUP Laboratories. Positive control tissues include colon adenocarcinomas and lung adenocarcinoma. Negative control tissues include Breast ER100 control, Breast ER13781 control, and Hodgkin's lymphoma CD15-5 control. For purposes of this application, including the claims, the particular assay used in this Phase 1 study is herein referred to as the "cMet ABBV-ADC staining protocol."

Patient tumor biopsies were fixed in formalin in PBS and embedded in paraffin. Slides were cut at 4 microns, allowed to dry, and then baked for 60 minutes at 60° C. Slides were used within 2 weeks of cutting. The slides were transferred to a BenchMark ULTRA® instrument and the following parameters were selected:
Procedure: ultraView® DAB
Name: cMet CONFIRM®
Paraffin [selected]
Deparaffinization [selected]
Cell Conditioning [selected]
Conditioner #1 [selected]
[short—8 min Conditioning]
Mild CC1 [selected]
[harsh—95 min Conditioning]
Ab Incubation Temperatures [selected]
36° C. Ab [selected
Antibody [selected]
PREP KIT # [4430] ** 0 H 16 min
Counterstain [selected]
HEMATOXILIN [2021] 4 minutes
Post Counterstain [selected]
BLUING REAGENT [2037] 4 minutes When the staining was finished, the slides were removed from the instrument and rinsed with tap water. The slides were dehydrated as follows:
Immerse slides in 70% ethanol, 2 changes, 1-2 minutes each.
Immerse slides in 95% ethanol, 1-2 minutes.
Immerse slides in 99% (or absolute) ethanol, 3-5 minutes.
Clear with xylene, 3 changes, 3-5 minutes each.
After dehydration, the slides were coversliped with non-aqueous mounting medium using glass coverslips.
The following reagents were used in this automated system:
Ventana® cMet CONFIRM® Cat. No. 790-4430 (Incubation Approximately 16 Minutes at 36° C.)
One 5 ml dispenser of CONFIRM® anti-Total cMet contains approximately 48.75 µg of the recombinant rabbit monoclonal antibody SP44 (also available from other commercial vendors). The antibody is diluted in 0.05 M Tris-HCl with 1% carrier protein and 0.10% ProClin 300® (preservative). Total protein concentration of the reagent is approximately 10 mg/mL. Specific antibody concentration is approximately 9.75 µg/mL. There is no known non specific antibody reactivity observed in this product.
Ventana Ultra CC1 Buffer Cat. No. 950-224
Cell conditioning in Ultra CC1 solution was done at 64° C. for 95 minutes.
Ventana ultraView® Universtal Detection Kit cat. no. 760-500
Ventana Hematoxylin II cat. no. 760-2021
Ventana Bluing Reagent cat. no. 760-2037
H-Score and IHC Score Determinations
The processed slides were analysed by a board-certified MD pathologist. A scoring guide was used, as provided by the manufacturer (see, e.g., FIG. 19). 10-12 representative areas of each slide were used to deduce the score. Upon evaluating the cMet staining, it was determined that an H-score approach would be the best approach for quantitating cMet expression. The H-score approach provides optimal data resolution for determining variation in intensity and tumor percentage of staining within and among tumor types. It also provides a good tool for determining thresholds for positive staining. In this method, the percentage of cells (0-100) within a tumor with staining intensities ranging from 0-3+ are provided. This protocol results in staining of the cMet protein both in the cytoplasm and in the cell surface/membrane. The staining intensity for each cell in a fixed field of the processed tumor biopsy is determined, and an individual value is attributed to each cell as follows, depending on the cell surface/membrane staining:
0=no staining
1+=weak staining
2+=moderate staining
3+=strong staining
To obtain an H-score, the percentage of tumor cells are multiplied by each intensity and added together. The maximum H-score is 300 if 100% of tumor cells label with 3+ intensity. The H-score is calculated as follows:

$$H\text{-score} = [1 \times (\% \text{ cells } 1+) + 2 \times (\% \text{ cells } 2+) + 3 \times (\% \text{ cells } 3+)]$$

This protocol results both in cytoplasmic and membrane cMet staining. For the H-score calculations referred to herein, membrane staining was used. The final tumor H-score (0-300) score gives more relative weight to higher-intensity membrane staining (3+ cell>2+ cell>1+ cell).
FIG. 20 shows exemplary staining results for various tumor H-scores (15, 90, 180, and 290) obtained with the "cMet ABBV-ADC staining protocol."
Each tumor can also be given an IHC score of IHC 0, IHC 1+, IHC 2+, or IHC 3+. While both IHC scores involve 0, 1+, 2+, and 3+ values they are not to be confused. For the H-score, 0, 1+, 2+, and 3+ values refer to the intensity of staining of a particular individual cell. For the IHC score, 0, 1+, 2+, and 3+ values refer to the overall staining of a particular area of the tumor sample. FIG. 21 shows exemplary staining results for various tumor IHC0/1+/2+/3+ scores obtained with the "cMet ABBV-ADC staining protocol."

For the purposes on this disclosure, and following the protocol described herein, if none of the cells in a fixed field are stained, the value attributed to the tumor is IHC 0. If the overall level of staining in a fixed field is low, the value attributed is IHC 1+. If most of the cells in a fixed field exhibit moderate staining, the value attributed is IHC 2+. If most of the cells in a fixed field exhibit strong staining, the value attributed is IHC 3+.

In another embodiment, and for the purposes on this disclosure, and following the protocol described herein, if none of the cells in a fixed field are stained, the value attributed to the tumor is IHC 0. If the overall level of staining in a fixed field is low, the value attributed is IHC 1+. If at least 15% of the cells in a fixed field exhibit moderate staining, the value attributed is IHC 2+. If at least 15% of the cells in a fixed field exhibit strong staining, the value attributed is IHC 3+.

Example 18

Measuring MET Gene Copy Number Amplification

Amplification of the MET gene can improve patient response to cMet inhibitors, including the treatments disclosed herein. A variety of methods for measuring MET Gene Amplification have been described in the art. See, e.g., Cappuzzo F, Marchetti A, Skokan M, Rossi E, Gajapathy S, Felicioni L, et al. Increased MET gene copy number negatively affects survival of surgically resected non-small-cell lung cancer patients. J Clin Oncol 2009; 27:1667-74; Koeppen H, Yu W, Zha J, Pandita A, Penuel E, Rangell L, et al. Biomarker analyses from a placebo-controlled phase II study evaluating erlotinib {+/−} onartuzumab in advanced non-small-cell lung cancer: MET expression levels are predictive of patient benefit. Clin Cancer Res 2014; 20:4488-98.

The preferred method is described as follows and is referred herein as the "MET/CEP7 cMET amplification method." Briefly, formalin-fixed, paraffin-embedded tissue blocks, can be submitted to dual-color FISH assays using a MET/CEP7 probe cocktail prepared with a MET DNA (RP 11-95120 BAC clone) probe, or using a 319 kb probe constructed from 3 bacterial artificial chromosome (BAC) clones that spans the entire MET gene on 7q31.1, labeled with SpectrumRed and the SpectrumGreen CEP7 (Abbott Molecular). The FISH assays can be performed, for example, according a protocol previously described (Cappuzzo F, Hirsch F R, Rossi E, et al. (2005) Epidermal growth factor receptor gene and protein and gefitinib sensitivity in non-small cell lung cancer. *J Natl Cancer Inst* 97:643-655), including pretreatment with 2× sodium chloride-sodium citrate buffer at 75° C. and digestion with proteinase K for 7 to 15 minutes each, codenaturation at 85° C. for 15 minutes, hybridization for approximately 36 hours, and rapid posthybridization washes with 2× sodium chloride-sodium citrate buffer/0.4 nonyl-phenoxyl-polyethoxylethanol. Signals are enumerated in at least 50 tumor nuclei per core, using epifluorescence microscope with single interference filters sets for green (FITC), red (Texas red) and blue (DAPI) as well as dual (red/green) and triple (blue, red, green) band pass filters. For each core, the mean and standard deviation of copy number per cell of each tested DNA sequence, the percentage of cells with ≤2, 3, and ≥4 copies of the MET genes, and the ratio of MET/CEP7 (a gene located near the centrosome of the same chromosome). When heterogeneous results were detected among the three tested cores, the core with the highest mean copy number was used to represent the patient in the statistic analyses. For documentation, images were captured using a CCD camera and merged using dedicated software (CytoVision; Genetix USA, Boston, Mass.). MET can be considered amplified when the MET:CEP7 signal ratio is ≥2.0 or when this ratio is <2.0 but there are >20 copies of MET signals in more than 10% of the tumor nuclei counted, according to the criteria established by MD Anderson Pathology Department based on prior studies. Zeng, Z S, Weiser M R, Kuntz E, Chen C T, Khan S A, Forslund A, et al. cMet gene amplification is associated with advanced stage colorectal cancer and liver metastases. Cancer Lett 2008; 265:258-69. In some studies, it has been reported that the copy number of the MET gene in relation to CEP7 ranged from 2.05 to 16.14 (median 3.48).

Another cMET amplication test is a blood-based test. This can be done by any one of a variety of commercially available reagents such as, for example, Biocept Liquid Biopsy MET Amplication Test (Biocept), MET Detect-R® (Personal Genome Diagnostics), and Guardant360® (Guardant Health®).

Example 19

Assessing the Presence of Exon 14 Mutation/Skipping of the MET Gene

MET Exon 14 contains the Cbl ubiquitin ligases site on tyrosine residue 1003 (Y1003) where ubiquitin is otherwise normally attached to the tyrosine residue and leads to the lysosomal degradation of the cMet protein. Hence, missense mutation of Y1003 residue or "skipping" of the protein region that is encoded by MET Exon 14 results in a relative over-expression of MET protein, enhanced cMet activation and subsequent oncogenesis. Inhibition by MET Tyrosine Kinase Inhibitors (TKIs) can result in clinical benefit in at least NSCLC patients harboring these MET Exon 14 alterations. Patients carrying any of these mutations can benefit from the treatments disclosed herein.

Several methods are available to one or ordinary skill in the art to detect mutations in the MET gene. Because a mutation is either present or not (i.e., it is an absolute value and not a matter of degree), its detection is not assay-dependent and any method can be used to detect it in tumor samples. Multiple mutations have been described in Exon 14 of the MET gene, many of which have been summarized in Impaired cMet Receptor Degradation Mediated by MET Exon 14 Mutations in Non-Small-Cell Lung Cancer, Mark M. Awad J C O Mar. 10, 2016:879-881; published online on Jan. 19, 2016; 10.1200/JCO.2015.64.2777. This method and the methods used in references cited therein for identifying additional mutations in Exon 14 of cancer samples are incorporated herein by reference in their entireties. These methods can be used for identifying those particular mutations in cancer samples. Also, this disclosure is directed to any known mutation in the Exon 14 gene and is not limited to those exemplified herein.

Several splice mutations of Exon 14 have been identified in pulmonary adenocarcinoma. For example:

MET amplification, protein expression, and mutations in pulmonary adenocarcinoma. Park S, Koh J, Kim D W, Kim M, Keam B, Kim T M, Jeon Y K, Chung D H, Heo D S. Lung Cancer. 2015 December; 90(3):381-7. doi: 10.1016/j.lungcan.2015.10.022. Epub 2015 Oct. 27. PMID: 26791796. This method and the methods used in references cited therein for identifying additional mutations in Exon 14 of cancer samples are incorporated herein by reference in their entireties. These methods can be used for identifying those particular mutations in cancer samples.

Responses to the multitargeted MET/ALK/ROS 1 inhibitor crizotinib and co-occurring mutations in lung adenocarcinomas with MET amplification or MET exon 14 skipping mutation. Jorge S E, Schulman S, Freed J A, VanderLaan P A, Rangachari D, Kobayashi S S, Huberman M S, Costa D B. Lung *Cancer*. 2015 December; 90(3):369-74. doi: 10.1016/j.lungcan.2015.10.028. Epub 2015 Oct. 31. This method and the methods used in references cited therein for identifying additional mutations in Exon 14 of cancer samples are incorporated herein by reference in their entireties. These methods can be used for identifying those particular mutations in cancer samples.

Additional Exon 14 mutations in NSCLC can be detected by the methods described in the following references:

Next-Generation Sequencing of Pulmonary Sarcomatoid Carcinoma Reveals High Frequency of Actionable MET Gene Mutations Exon 14 Xuewen Liu, Yuxia Jia, Mark B. Stoopler, Yufeng Shen, Haiying Cheng, Jinli Chen, Mahesh Mansukhani, Sanjay Koul, Balazs Halmos, and Alain C. Borczuk, J C O Mar. 10, 2016:794-802; published online on Jul. 27, 2015. *This method and the methods used in references* cited therein for identifying additional mutations in Exon 14 of cancer samples are incorporated herein by reference in their entireties. These methods can be used for identifying those particular mutations in cancer samples.

MET Exon 14 Mutations in Non-Small-Cell Lung Cancer Are Associated With Advanced Age and Stage-Dependent MET Genomic Amplification and cMet Overexpression. Awad M M, Oxnard G R, Jackman D M, Savukoski D O, Hall D, Shivdasani P, Heng J C, Dahlberg S E, Jänne PA, Verma S, Christensen J, Hammerman P S, Sholl L M. *J Clin Oncol.* 2016 Mar. 1; 34(7):721-30. doi: 10.1200/JCO.2015.63.4600. Epub 2016 Jan. 4. This method and the methods used in references cited therein for identifying additional mutations in Exon 14 of cancer samples are incorporated herein by reference in their entireties. These methods can be used for identifying those particular mutations in cancer samples.

Another MET exon 14 deletion has been reported in gastrointestinal malignancies. Oncotarget. 2015 Sep. 29; 6(29):28211-22. doi: 10.18632/oncotarget.4721. Gastrointestinal malignancies harbor actionable MET exon 14 deletions. Lee J, Ou S H3, Lee J M, Kim H C5, Hong M6, Kim S Y1, Jang J1, Ahn S6, Kang S Y6, Lee S1, Kim S T1, Kim B4, Choi J4, Kim K A4, Lee J, Park C Park S H, Park J O, Lim H Y, Kang W K, Park K, Park Y S, Kim K M. This method and the methods used in references cited therein for identifying additional mutations in Exon 14 of cancer samples are incorporated herein by reference in their entireties. These methods can be used for identifying those particular mutations in cancer samples.

Example 20

Assessing the Presence of Exon 19 Deletions and Exon 21 (L858R) Substitutions in the EGFR Gene of Cancer Patients The two most common EGFR somatic mutations, exon 19 deletions and L858R missense mutations, have been associated with in vitro and in vivo sensitivity to treatment with the EGFR tyrosine kinase inhibitors (EGFR-TKI) gefitinib and erlotinib. These two different types of mutations are responsible for ~85% of all EGFR somatic mutations identified in patients with NSCLC. Benefits of the treatments disclosed herein can be observed in patients with Exon 19 deletions and Exon 21 L858R substitution.

Several methods have been described in the art for detection Exon 19 deletions in cancer samples. Examples of such methods, which are available to one of ordinary skill in the art are provided below. Because a mutation is either present or not (i.e., it is an absolute value and not a matter of degree), its detection is not assay-dependent and any method can be used to detect it in tumor samples.

A recent review of the literature reporting on the effect of these mutations in cancer patients is that in EGFR-TKIEGFR-tyrosine kinase inhibitor treatment in a patient with advanced non-small cell lung cancer and concurrent exon 19 and 21 EGFR mutations: A case report and review of the literature. Yang Y, Zhang B, Li R, Liu B, Wang L. Oncol Lett. 2016 May; 11(5):3546-3550. Epub 2016 Apr. 5. The method used in this report and the methods used in references cited therein for identifying Exon 19 deletions and Exon 21 (L858R) substitutions in the EGFR gene in patients' cancer samples are incorporated herein by reference in their entireties.

It has been reported that patients with NSCLC and EGFR exon 19 deletions have a longer survival following treatment with gefitinib or erlotinib compared with those with the L858R mutation. Jackman D M, Yeap B Y, Sequist L V, et al. (2006) Exon 19 deletion mutations of epidermal growth factor receptor are associated with prolonged survival in non-small cell lung cancer patients treated with gefitinib or erlotinib. Clin Cancer Res 12:3908-3914. This reference provides two different methods for detecting EGFR Exon 19 deletions and L858R mutation. These methods and the methods used in references cited therein for identifying Exon 19 deletions and Exon 21 (L858R) substitutions in the EGFR gene in patients' cancer samples are incorporated herein by reference in their entireties.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, and some are represented below, it will be appreciated that various changes can be made without departing from the spirit and scope of the invention(s).

1. A method of treating a solid tumor cancer that overexpresses cMet, comprising administering to a human subject having said cancer an anti-cMet antibody drug conjugate ("ADC") in an amount and for a period of time sufficient to provide a therapeutic benefit.

2. The method of embodiment 1 in which the cMet overexpressing cancer is of a cancer type in which cMet is overexpressed in at least about 10% of a patient population having the cancer type.

3. The method of embodiment 1 in which a biopsy of the cMet overexpressing tumor tissue from the subject has an IHC score of 2+ and/or an H-score from 150 to 224, when measured according to the cMet ABBV-ADC staining protocol.

4. The method of embodiment 1 in which a biopsy of the cMet overexpressing tumor tissue from the subject has an IHC score of 3+ and/or an H-score greater than 225, when measured according to the cMet ABBV-ADC staining protocol.

5. The method according to any one of embodiments 1-4 in which the cMet overexpressing cancer is non-small cell lung cancer ("NSCLC").

6. The method of embodiment 5, in which the NSCLC is a non-squamous NSCLC.

7. The method of embodiment 5 in which the NSCLC is squamous NSCLC.

8. The method of embodiment 5 in which the histology of the NSCLC is NSCLC—not otherwise specified (NSCLC-NOS).

9. The method of embodiment 1 in which the cancer is colorectal cancer ("CRC").

10. The method of embodiment 9 in which the histology of the CRC is not specified.

11. The method of embodiment 10 in which the CRC is an adenocarcinoma.

12. The method of embodiment 1 in which the cancer is head & neck ("H&N") cancer.

13. The method of embodiment 12 in which the histology of H&N cancer is not specified.

14. The method of embodiment 1 in which the cancer is pancreatic cancer.

15. The method of embodiment 14 in which the pancreatic cancer is an adenocarcinoma.

16. The method of embodiment 5 in which the cMet overexpressing cancer has epidermal growth factor receptor ("EGFR") exon 19 deletions or exon 21 (L858R) substitutions as detected by an FDA approved test.

17. The method of embodiment 1 in which the cMet overexpressing cancer is resistant to prior treatment with targeted and/or non-targeted chemotherapy.

18. The method of embodiment 1 in which the cMet overexpressing cancer is resistant to prior treatment with an anti-cMet antibody.

19. The method of embodiment 1 in which the anti-cMet ADC is administered as monotherapy.

20. The method of embodiment 1 in which the anti-cMet ADC is administered adjunctive to an additional anticancer agent, where the additional agent is administered according to its FDA-approved dosing regimen.

21. The method of embodiment 20 in which the additional anticancer agent is an inhibitor of epidermal growth factor receptor ("EGFR").

22. The method of embodiment 21 in which the additional anticancer agent is erlotinib.

23. The method of embodiment 20 in which the cMet overexpressing cancer has EGFR exon 19 deletions or exon 21 (L858R) substitutions as detected by an FDA-approved test and the additional anticancer agent is an inhibitor of EGFRs having such deletions or substitutions.

24. The method of embodiment 23 in which the additional anticancer agent is afatinib.

25. The method of embodiment 20 in which the cancer is NSCLC.

26. The method of embodiment 25 in which the additional anticancer agent is selected from imatinib (GLEEVEC®), dasatinib (SPRYCE®), nilotinib (TASIGNA®), bosutinib (BOSULIF®), ponatinib (ICLUSIG®), Afatinib (GIOTRIF®), Axitinib (INLYTA®), Crizotinib (XALKORI®), Erlotinib (TARCEVA®), Gefitinib (IRESSA®), Lapatinib (TYVERB®), Nilotinib (TASIGNA®), Pazopanib (VOTRIENT®), Regorafenib (STIVARGA®), Sorafenib (NEXAVAR®), Sunitinib (SUTENT®), toceranib (PALLADIA®), vatalanib, and radotinib (SUPECT®).

27. The method of embodiment 26 in which the additional anticancer agent is an inhibitor of PD1.

28. The method of embodiment 27 in which the inhibitor of PD1 is an anti-PD1 antibody.

29. The method of embodiment 28 in which the anti-PD1 antibody is nivolumab.

30. The method of any one of embodiments 1-29 in which the anti-cMet ADC is administered in an amount ranging from about 0.15 mg/kg to about 3.3 mg/kg once every three weeks.

31. The method of embodiment 30 in which the anti-cMet ADC is administered in an amount of about 2.7 mg/kg.

32. The method of any one of embodiments 1-29 in which the anti-cMet ADC is administered in an amount ranging from about 0.15 mg/kg to about 3.3 mg/kg once every two weeks.

33. The method of embodiment 32 in which the anti-cMet ADC is administered in an amount of about 1.6 mg/kg once every two weeks.

34. The method of embodiment 32 in which the anti-cMet ADC is administered in an amount of about 1.9 mg/kg once every two weeks.

35. The method of any one of embodiments 1-34 in which the anti-cMet ADC comprises an anti-cMet antibody linked to a cytostatic and/or cytotoxic agent by way of a linker.

36. The method of embodiment 35 in which the anti-cMet antibody is a full-length antibody.

37. The method of embodiment 35 in which the anti-cMet antibody is internalized and has an apparent affinity $EC_{50}$ value lower than about 10 nanomol/L, preferably from about 1 picomol/L to 10 nanomol/L.

38. The method of embodiment 35 in which the anti-cMet antibody binds human cMet in vitro with an apparent affinity $EC_{50}$ value of about 0.3 nmol/L.

39. The method of embodiment according to any one of embodiments 35 through 38 in which the anti-cMet antibody comprises a $V_H$ chain comprising three CDRs, namely $V_H$ CDR #1 (SEQ ID NO: 112), $V_H$ CDR #2 (SEQ ID NO: 113) and $V_H$ CDR #3 (SEQ ID NO: 114); a $V_L$ chain comprising three CDRs, namely $V_L$ CDR #1 (SEQ ID NO: 115), $V_L$ CDR #2 (SEQ ID NO: 116) and $V_L$ CDR #3 (SEQ ID NO: 117); and a modified hinge region of SEQ ID NO: 170.

40. The method of embodiment 39 in which the anti-cMet antibody is an IgG1.

41. The method of embodiment 38 in which the anti-cMet antibody comprises a $V_H$ chain of SEQ ID NO: 78; a $V_L$ chain of SEQ ID NO: 79; and a modified hinge region of SEQ ID NO: 170.

42. The method of embodiment 41 in which the anti-cMet antibody is an IgG1.

43. The method of embodiment 39 in which the anti-cMet antibody comprises a heavy chain of SEQ ID NO: 86 and a light chain of SEQ ID NO: 87.

44. The method of embodiment 39 in which the anti-cMet antibody is ABBV399.

45. The method of embodiment 39 in which the anti-cMet antibody comprises a heavy chain of SEQ ID NO: 171 and a light chain of SEQ ID NO: 172.

46. The method of embodiment 39 in which the anti-cMet antibody is ABT-700 (S238C)-PBD.

47. The method of embodiment 38 in which the anti-cMet antibody comprises the six CDRs of the antibody STI-D0602/STI-0602.

48. The method of embodiment 47 in which the anti-cMet antibody is an IgG1.

49. The method of embodiment 35 in which the anti-cMet antibody comprises a $V_H$ chain of STI-D0602/STI-0602 and a $V_L$ chain of STI-D0602/STI-0602.

50. The method of embodiment 49 in which the anti-cMet antibody is an IgG1.

51. The method of embodiment 35 in which the linker is cleavable by a lysosomal enzyme.

52. The method of embodiment 51 in which the lysosomal enzyme is Cathepsin B.

53. The method of embodiment 52 in which the linker comprises a segment according to one or more of structural formulae (IVa), (IVb), (IVc) and (IVd):

p is an integer ranging from 0 to 5;
q is 0 or 1;
x is 0 or 1;
y is 0 or 1;

✻ represents the point of attachment of the linker to the cytotoxic and/or cytostatic agent; and represents the point of attachment to the remainder of the linker.

54. The method of embodiment 53 in which peptide is selected from the group consisting of Val-Cit; Cit-Val; Ala-Ala; Ala-Cit; Cit-Ala; Asn-Cit; Cit-Asn; Cit-Cit; Val-Glu; Glu-Val; Ser-Cit; Cit-Ser; Lys-Cit; Cit-Lys; Asp-Cit; Cit-Asp; Ala-Val; and Val-Ala and salts thereof.

55. The method of embodiment 51 in which the lysosomal enzyme is β-glucuronidase.

56. The method of embodiment 35 in which the anti-cMet ADC has an average drug-to-antibody ratio ("DAR") in the range of 0-10.

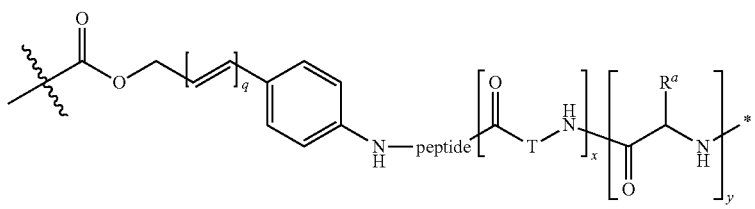 (IVa)

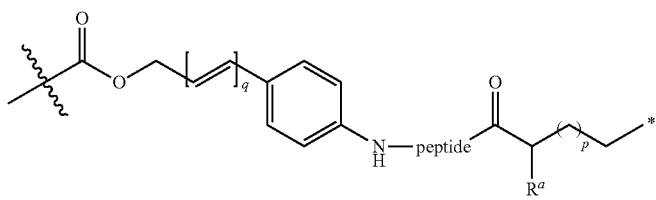 (IVb)

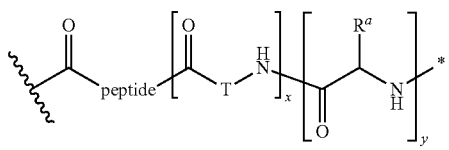 (IVc)

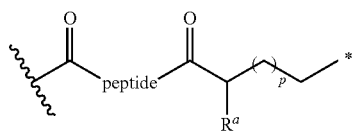 (IVd)

or a salt thereof, in which:

peptide represents a peptide (illustrated C→N and not showing the carboxy and amino "termini") cleavable by Cathepsin B;

T represents a polymer comprising one or more ethylene glycol units or an alkylene chain, or combinations thereof;

$R^a$ is selected from hydrogen, alkyl, sulfonate and methyl sulfonate;

57. The method of embodiment 35 in which the anti-cMet ADC has an average drug-to-antibody ratio ("DAR") in the range of 1-4.

58. The method of embodiment 57 in which the anti-cMet ADC has a DAR in the range of 2-4.

59. The method of embodiment 57 in which the anti-cMet ADC has a DAR of about 3.1.

60. The method of embodiment 57 in which the anti-cMet ADC has an about 1:1 ratio of E2 and E4 ADC.

61. The method of embodiment 57 in which the anti-cMet ADC has a DAR of 3.0.

62. The method of embodiment 35 in which the cytostatic and/or cytotoxic agent is a microtubule inhibitor.

63. The method of embodiment 62 in which the microtubule inhibitor is an auristatin.

64. The method of embodiment 63 in which the auristatin is MMAE or MMAF.

65. The method of embodiment 63 in which the auristatin is MMAE.

66. The method of embodiment 35 in which the anti-cMet ADC is a compound according to structural formula (I):

[D-L-XY-]$_n$-Ab  (I)

or a salt thereof, in which:
D is the cytotoxic and/or cytostatic agent;
L is the linker;
Ab is the anti-cMet antibody;
XY represents a covalent linkage linking linker L to antibody Ab; and
n has a value ranging from 2 to 8.

67. The method of embodiment 66 in which n has a value of 2, 3 or 4.

68. The method of embodiment 66 in which XY is a linkage formed with an amino group on anti-cMet antibody Ab.

69. The method of embodiment 66 in which XY is an amide or a thiourea.

70. The method of embodiment 66 in which XY is a linkage formed with a sulfhydryl group on anti-cMet antibody Ab.

71. The method of embodiment 66 in which XY is a thioether.

72. The method of embodiment 66 in which the compound according to structural formula (I) has the structure of formula (IIa):

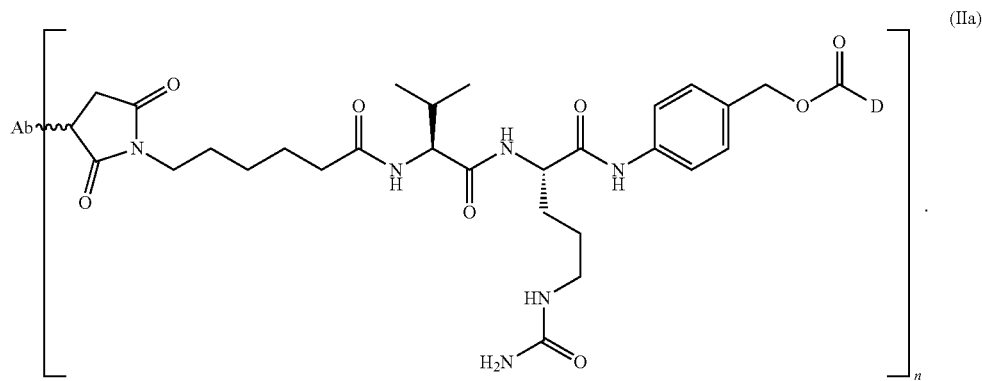

73. The method of embodiment 72 in which anti-cMet antibody Ab is ABT-700.

74. The method of embodiment 66 in which the compound of structural formula (I) has the following structure:

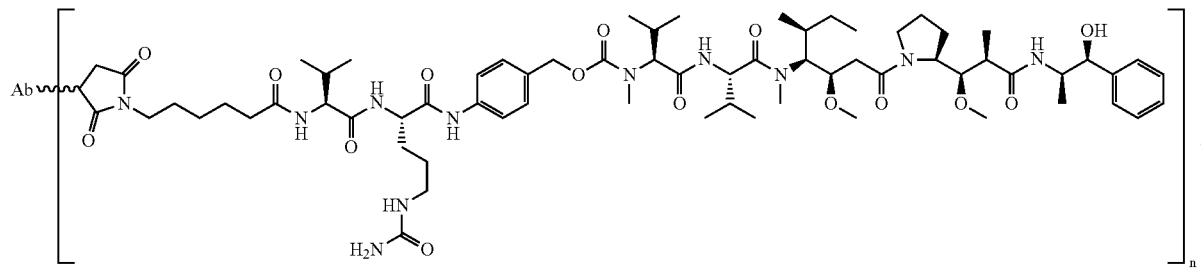

75. The method of embodiment 74 in which anti-cMet antibody Ab is ABT-700.

76. The method of embodiment 66 in which the compound according to structural formula (I) has the structure of formula (IIb):

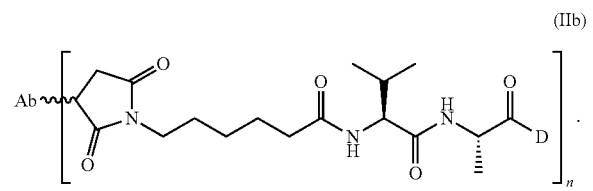

77. The method of embodiment 76 in which anti-cMet antibody Ab is ABT-700.

78. The method of embodiment 66 in which the compound according to structural formula (I) has the following structure:

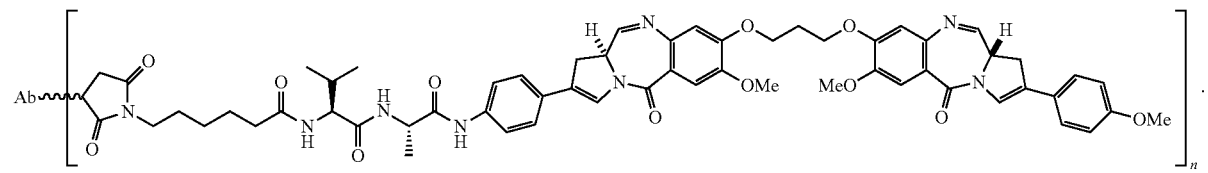

79. The method of embodiment 78 in which anti-cMet antibody Ab is ABT-700.

80. A method of treating a human patient diagnosed with non-small cell lung cancer ("NSCLC") comprising administering to the patient an anti-cMet antibody drug conjugate ("ADC") in an amount and for a period of time sufficient to provide therapeutic benefit.

81. The method of embodiment 80 in which the NSCLC tumor tissue has an immunohistochemistry ("IHC") H-score of greater than or equal to 150 when measured according to the cMet ABBV-ADC staining protocol or an IHC score of 2+.

82. The method of embodiment 80 in which the NSCLC tumor tissue has an immunohistochemistry ("IHC") H-score of greater than 225 when measured according to the cMet ABBV-ADC staining protocol or an IHC score of 3+.

83. The method of embodiment 80 in which the NSCLC tumor tissue has an IHC score of 2+ and/or an H-score from 150 to 224, when measured according to the cMet ABBV-ADC staining protocol.

84. The method of embodiment 80 in which the NSCLC tumor tissue has an IHC score of 3+ and/or an H-score greater than 225, when measured according to the cMet ABBV-ADC staining protocol.

85. The method according to any one of embodiments 80, 81, and 94 in which the NSCLC is a non-squamous cell carcinoma.

86. The method according to any one of embodiments 80, 81, and 83 in which the NSCLC is a squamous cell carcinoma.

87. The method of embodiment 80 in which the histology of the NSCLC is NSCLC—not otherwise specified (NSCLC-NOS).

88. The method of embodiment 80 in which the NSCLC tumor has epidermal growth factor receptor ("EGFR") exon 19 deletions or exon 21 (L858R) substitutions as detected by an FDA-approved test such as Cobas® EGFR Mutation Test v2 or the Therascreen® EGFR RGQ PCR Kit.

89. The method according to any one of embodiments 80 through 88 in which the NSCLC tumor is resistant to prior treatment with a microtubule inhibitor.

90. The method according to any one of embodiments 80 through 89 in which the NSCLC tumor is resistant to prior treatment with an anti-cMet antibody.

91. The method according to any one of embodiments 80 through 90 in which the anti-cMet ADC is administered as monotherapy.

92. The method according to any one of embodiments 80 through 91 in which the anti-cMet ADC is administered adjunctive to an additional anticancer agent, where the additional agent is administered according to its FDA-approved dosing regimen.

93. The method of embodiment 92 in which the additional anticancer agent is an inhibitor of epidermal growth factor receptor ("EGFR").

94. The method of embodiment 93 in which the additional anticancer agent is erlotinib, administered once daily.

95. The method of embodiment 92 in which the NSCLC tumor has EGFR exon 18 deletions or exon 21 (L858R) substitutions as detected by an FDA-approved test and the additional anticancer agent is an inhibitor of EGFRs having such deletions or substitutions.

96. The method of embodiment 95 in which the additional anticancer agent is afatinib.

97. The method of embodiment 92 in which the additional anticancer agent is a microtubule inhibitor.

98. The method of embodiment 97 in which the additional anticancer agent is selected from the group consisting of cabazitaxel, colcemid, colchicine, cryptophycin, democolcine, docetaxel, nocodazole, paclitaxel, taccalonolide, taxane and vinblastine.

99. The method of embodiment 92 in which the additional anticancer agent is an inhibitor of PD1.

100. The method of embodiment 99 in which the inhibitor of PD1 is an anti-PD1 antibody.

101. The method of embodiment 100 in which the anti-PD1 antibody is nivolumab.

102. The method of any one of embodiments 80 through 101 in which the anti-cMet ADC is administered in an amount ranging from about 0.15 mg/kg to about 3.3 mg/kg, once every 3 weeks.

103. The method of embodiment 102 in which the anti-cMet ADC is administered in an amount of about 2.7 mg/kg once every 3 weeks.

104. The method of any one of embodiments 80 through 101 in which the anti-cMet ADC is administered in an amount ranging from about 0.15 mg/kg to about 3.3 mg/kg, once every 2 weeks.

105. The method of embodiment 104 in which the anti-cMet ADC is administered in an amount of about 1.6 mg/kg, once every 2 weeks. Add dependent to 1.9

106. The method of embodiment 104 in which the anti-cMet ADC is administered in an amount of about 1.9 mg/kg, once every 2 weeks.

107. The method of any one of embodiments 80 through 105 in which the anti-cMet ADC comprises an anti-cMet antibody linked to a cytostatic and/or cytotoxic agent by way of a linker.

108. The method of embodiment 107 in which the anti-cMet antibody is a full-length antibody.

109. The method of embodiment 108 in which the anti-cMet antibody is internalized and has an apparent affinity $EC_{50}$ value lower than about 10 nanomol/L, preferably from about 1 picomol/L to 10 nanomol/L.

110. The method of embodiment 109 in which the anti-cMet antibody binds human cMet in vitro with an apparent affinity $EC_{50}$ value of about 0.3 nmol/L.

111. The method of embodiment according to any one of embodiments 107 through 110 in which the anti-cMet antibody comprises a $V_H$ chain comprising three CDRs, namely $V_H$ CDR #1 (SEQ ID NO: 112), $V_H$ CDR #2 (SEQ ID NO: 113) and $V_H$ CDR #3 (SEQ ID NO: 114); a $V_L$ chain comprising three CDRs, namely $V_L$ CDR #1 (SEQ ID NO:

116. The method of embodiment 111 in which the anti-cMet antibody comprises a heavy chain of SEQ ID NO: 171 and a light chain of SEQ ID NO: 172.

117. The method of embodiment 110 in which the anti-cMet antibody comprises comprises the six CDRs of the antibody STI-D0602/STI-0602.

118. The method of embodiment 117 in which the anti-cMet antibody is an IgG1.

119. The method of embodiment 104 in which the anti-cMet antibody comprises a $V_H$ chain of STI-D0602/STI-0602 and a $V_L$ chain of STI-D0602/STI-0602.

120. The method of embodiment 119 in which the anti-cMet antibody is an IgG1.

121. The method of embodiment 107 in which the linker is cleavable by a lysosomal enzyme.

122. The method of embodiment 121 in which the lysosomal enzyme is Cathepsin B.

123. The method of embodiment 122 in which the linker comprises a segment according to one or more of structural formulae (IVa), (IVb), (IVc) and (IVd):

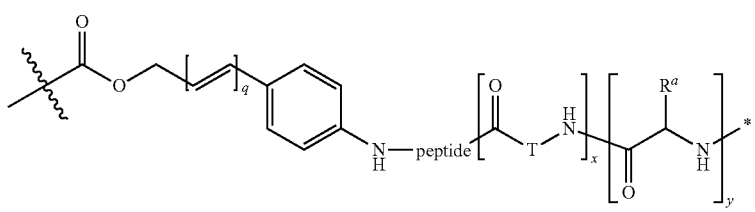

(IVa)

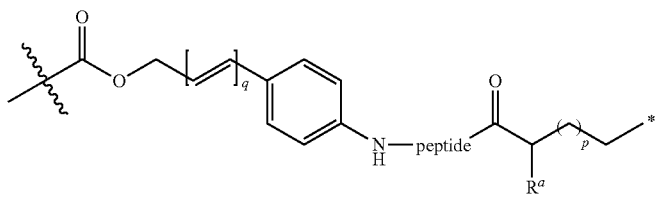

(IVb)

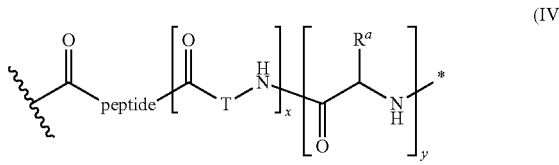 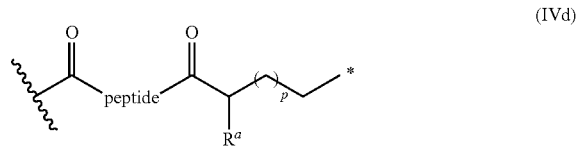

(IVc) (IVd)

115), $V_L$ CDR #2 (SEQ ID NO: 116) and $V_L$ CDR #3 (SEQ ID NO: 117); and a modified hinge region of SEQ ID NO: 170.

112. The method of embodiment 111 in which the anti-cMet antibody is an IgG1.

113. The method of embodiment 111 in which the anti-cMet antibody comprises a $V_H$ chain of SEQ ID NO: 78; a $V_L$ chain of SEQ ID NO: 79; and a modified hinge region of SEQ ID NO: 170.

114. The method of embodiment 113 in which the anti-cMet antibody is an IgG1.

115. The method of embodiment 111 in which the anti-cMet antibody comprises a heavy chain of SEQ ID NO: 86 and a light chain of SEQ ID NO: 87.

or a salt thereof, in which:
peptide represents a peptide (illustrated C→N and not showing the carboxy and
amino "termini") cleavable by Cathepsin B;
T represents a polymer comprising one or more ethylene glycol units or an
alkylene chain, or combinations thereof;
$R^a$ is selected from hydrogen, alkyl, sulfonate and methyl sulfonate;
p is an integer ranging from 0 to 5;
q is 0 or 1;
x is 0 or 1;
y is 0 or 1;
* represents the point of attachment of the linker to the cytotoxic and/or cytostatic agent; and

* represents the point of attachment to the remainder of the linker.

124. The method of embodiment 123 in which peptide is selected from the group consisting of Val-Cit; Cit-Val; Ala-Ala; Ala-Cit; Cit-Ala; Asn-Cit; Cit-Asn; Cit-Cit; Val-Glu; Glu-Val; Ser-Cit; Cit-Ser; Lys-Cit; Cit-Lys; Asp-Cit; Cit-Asp; Ala-Val; and Val-Ala and salts thereof.

125. The method of embodiment 121 in which the lysosomal enzyme is β-glucuronidase.

126. The method of embodiment 107 in which the anti-cMet ADC has an average drug-to-antibody ratio ("DAR") in the range of 0-10.

127. The method of embodiment 107 in which the anti-cMet ADC has an average drug-to-antibody ratio ("DAR") in the range of 1-4.

128. The method of embodiment 127 in which the anti-cMet ADC has a DAR in the range of 2-4.

129. The method of embodiment 127 in which the anti-cMet ADC has a DAR of about 3.1.

130. The method of embodiment 127 in which the anti-cMet ADC has an about 1:1 ratio of E2 and E4 ADC.

131. The method of embodiment 127 in which the anti-cMet ADC has a DAR of 3.0.

132. The method according to any one of embodiments 107 through 131 in which the cytostatic and/or cytotoxic agent is a microtubule inhibitor.

133. The method of embodiment 132 in which the microtubule inhibitor is an auristatin.

134. The method of embodiment 133 in which the auristatin is MMAE or MMAF.

135. The method of embodiment 134 in which the auristatin is MMAE.

136. The method according to any one of embodiments 107 through 135 in which the anti-cMet ADC is a compound according to structural formula (I):

[D-L-XY-]$_n$-Ab     (I)

or a salt thereof, in which:
D is the cytotoxic and/or cytostatic agent;
L is the linker;
Ab is the anti-cMet antibody;
XY represents a covalent linkage linking linker L to antibody Ab; and
n has a value ranging from 2 to 8.

137. The method of embodiment 136 in which n has a value of 2, 3 or 4.

138. The method of embodiment 136 in which XY is a linkage formed with an amino group on anti-cMet antibody Ab.

139. The method of embodiment 136 in which XY is an amide or a thiourea.

140. The method of embodiment 136 in which XY is a linkage formed with a sulfhydryl group on anti-cMet antibody Ab.

141. The method of embodiment 136 in which XY is a thioether.

142. The method of embodiment 136 in which the compound according to structural formula (I) has the structure of formula (IIa):

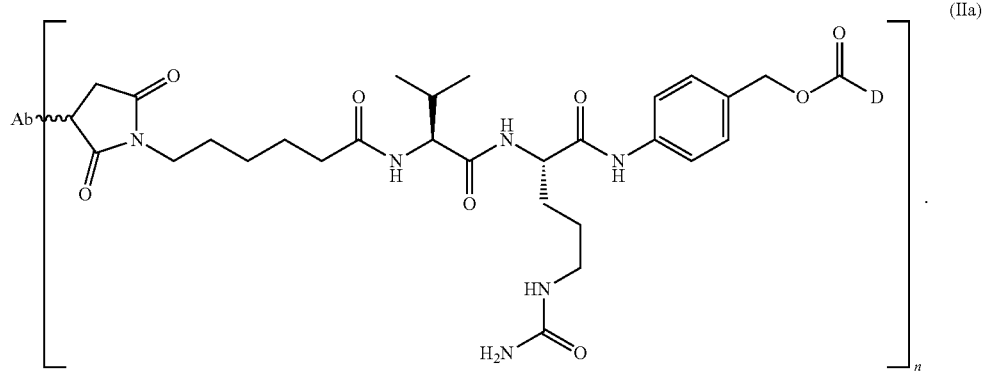

143. The method of embodiment 142 in which anti-cMet antibody Ab is ABT-700.

144. The method of embodiment 136 in which the compound of structural formula (I) has the following structure:

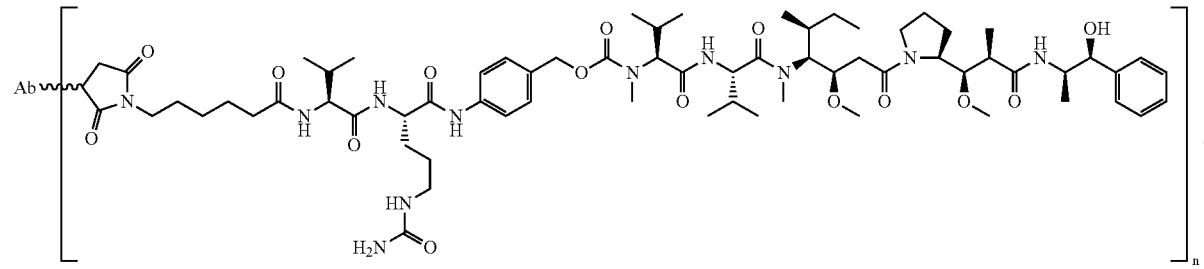

145. The method of embodiment 144 in which anti-cMet antibody Ab is ABT-700.

146. The method of embodiment 136 in which the compound according to structural formula (I) has the structure of formula (IIb):

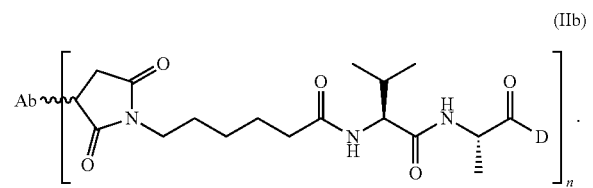

(IIb)

147. The method of embodiment 146 in which anti-cMet antibody Ab is ABT-700.

148. The method of embodiment 136 in which the compound according to structural formula (I) has the following structure:

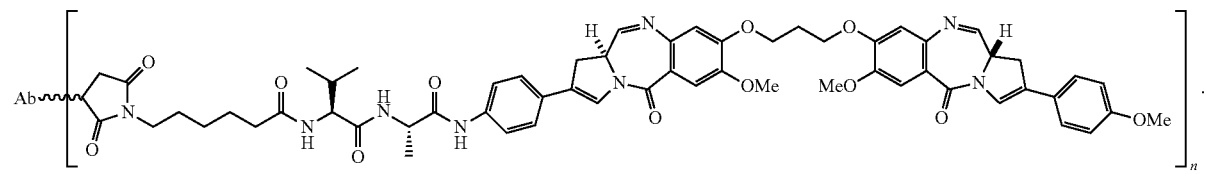

149. The method of embodiment 148 in which anti-cMet antibody Ab is ABT-700.

150. A method of treating a human subject having a NSCLC tumor with an IHC score of at least 2+ in at least one tumor biopsy from the subject, comprising administering to the subject an anti-cMet ADC in an amount of about 2.7 mg/kg once every two weeks or once every 3 weeks, in which the anti-cMet ADC is a compound according to the following structure:

or a pharmaceutically acceptable salt thereof, in which n has a value ranging from 2-4 and Ab is a full-length anti-cMet antibody.

151. The method of embodiment 150 in which the anti-cMet antibody is ABT-700.

152. The method of embodiment 151 in which the anti-cMet ADC is administered as monotherapy.

153. The method of embodiment 150 in which the anti-cMet ADC is administered adjunctive to an additional anticancer agent.

154. The method of embodiment 153 in which the additional anticancer agent is erlotinib.

155. The method of embodiment 153 in which the additional anticancer agent is Nivolumab.

156. The method of embodiment 153 in which the NSCLC tumor has EGFR exon 19 deletions or exon 21 (L858R) substitutions as detected by an FDA-approved test and the additional anticancer agent is afatinib.

157. The method of anyone of embodiments 1-34 in which the drug is a pyrrolobenzodiazepine (PBD), preferably PBD ((S)-2-(4-aminophenyl)-7-methoxy-8-(3-(((S)-7-methoxy-2-(4-methoxyphenyl)-5-oxo-5,11a-dihydro-1H-benzo[e]pyrrolo[1,2-a][1,4]diazepin-8-yl)oxy)propoxy)-1H-benzo[e]pyrrolo[1,2-a][1,4]diazepin-5(11aH)-one); SG2000 (SJG-136; (11aS,11a'S)-8,8'-(propane-1,3-diylbis(oxy))bis(7-methoxy-2-methylene-2,3-dihydro-1H-benzo[e]pyrrolo[1,2-a][1,4]diazepin-5(11aH)-one)) (or SGD-1882).

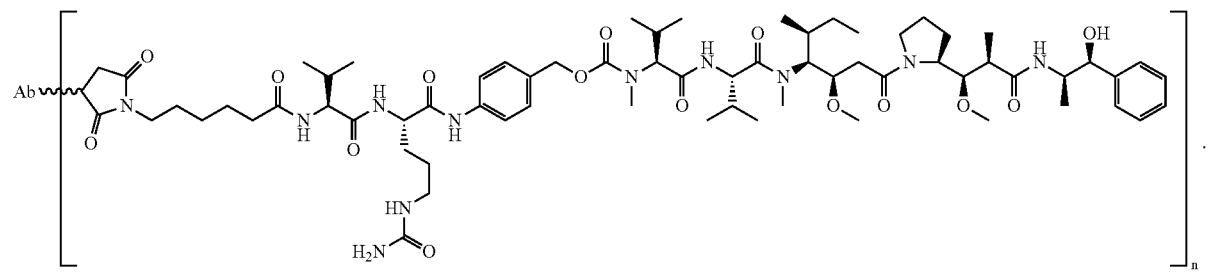

158. The method of anyone of embodiments 35 through 56 and 62 in which the drug is a pyrrolobenzodiazepine (PBD), preferably SGD-1882.

159. The method of anyone of embodiments 66 through 71 and 76 through 78 in which the drug is a pyrrolobenzodiazepine (PBD), preferably SGD-1882.

160. The method according to embodiment 66, in which the compound of formula I has the following structure:

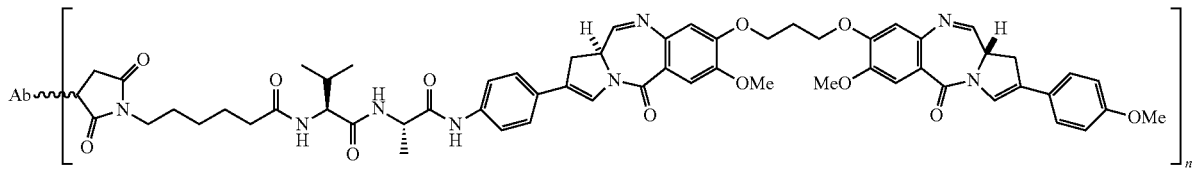

in which Ab is the antibody and n is 2.

161. The method according to embodiment 160, in which the antibody is ABT-700 or ABT-700 (S238C).

162. The method according to anyone of embodiments 80 through 131 in which the drug is a pyrrolobenzodiazepine (PBD), preferably SGD-1882.

163. The method according to embodiment 107 in which the cytostatic and/or cytotoxic agent is a DNA minor grove binding crosslinking agent.

164. The method according to embodiment 163, in which the DNA minor grove binding crosslinking agent is a pyrrolobenzodiazepine (PBD), preferably SGD-1882.

165. The method according to embodiment 107 in which the cMet ADC is the compound of formula

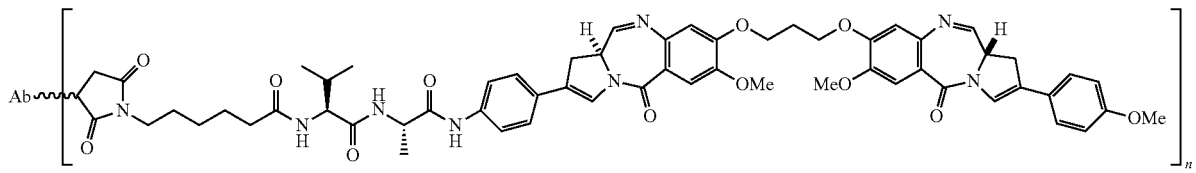

in which Ab is ABT-700 or ABT-700 (S238C) and n is 2.

166. A method of treating a human subject having a NSCLC tumor with an IHC score of at least 2+ in at least one tumor biopsy from the subject, comprising administering to the subject an anti-cMet ADC in an amount of about 2.7 mg/kg once every two weeks or once every 3 weeks, in which the anti-cMet ADC is a compound according to the following structure:

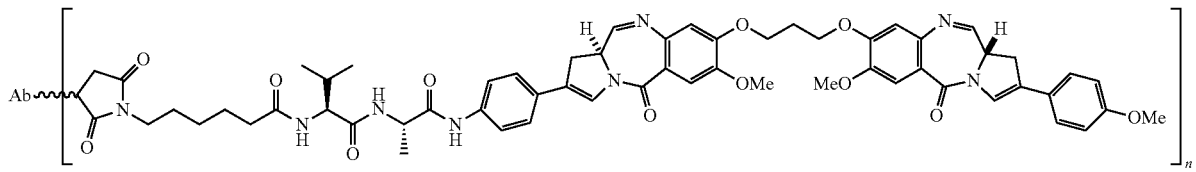

or a pharmaceutically acceptable salt thereof, in which n is 2 and Ab is a full-length anti-cMet antibody.

167. The method of embodiment 166 in which the anti-cMet antibody is ABT-700 or ABT-700 (S238C).

168. The method of embodiment 167 in which the anti-cMet ADC is administered as monotherapy.

169. The method of embodiment 166 in which the anti-cMet ADC is administered adjunctive to an additional anticancer agent.

170. The method of embodiment 169 in which the additional anticancer agent is erlotinib.

171. The method of embodiment 169 in which the additional anticancer agent is Nivolumab.

172. The method of embodiment 169 in which the NSCLC tumor has EGFR exon 19 deletions or exon 21 (L858R) substitutions as detected by an FDA-approved test and the additional anticancer agent is afatinib.

173. A method of treating a human subject having a NSCLC adenocarcinoma, comprising administering to the subject ABBV-399 once every 3 weeks in an amount of about 2.7 mg/kg, in which the adenocarcinoma has an H-score of at least 225.

174. A method of treating a human subject having a NSCLC adenocarcinoma, comprising administering to the subject ABBV-399 once every 3 weeks in an amount of about 2.7 mg/kg, in which the adenocarcinoma has an IHC score of 3+.

175. The method according to any one of embodiments 173 and 174, in which ABBV-399 is administered adjunctive to erlotinib, in which the erlotinib is administered once daily at 150 mg.

176. A method of treating a human subject having a NSCLC squamous cell carcinoma, comprising administering to the subject ABBV-399 once every 2 weeks in an amount of about 1.6 mg/kg, in which the squamous cell carcinoma has an H-score of from 150 to 224.

177. A method of treating a human subject having a NSCLC adenocarcinoma, comprising administering to the subject ABBV-399 once every 2 weeks in an amount of about 1.6 mg/kg, in which the adenocarcinoma has an IHC score of 2+.

178. A method of treating a human subject having a NSCLC squamous cell carcinoma, comprising administering to the subject ABBV-399 once every 2 weeks in an amount of about 1.9 mg/kg, in which the squamous cell carcinoma has an H-score of from 150 to 224.

179. A method of treating a human subject having a NSCLC squamous cell carcinoma, comprising administering to the subject ABBV-399 once every 2 weeks in an amount of about 1.9 mg/kg, in which the squamous cell carcinoma has an IHC score of 2+.

180. A method of treating a human subject having a NSCLC adenocarcinoma, comprising administering to the subject ABT-700 (S238C)-PBD once every 3 weeks in an amount of about 2.7 mg/kg, in which the adenocarcinoma has an H-score of at least 225.

181. A method of treating a human subject having a NSCLC adenocarcinoma, comprising administering to the subject ABT-700 (S238C)-PBD once every 3 weeks in an amount of about 2.7 mg/kg, in which the adenocarcinoma has an IHC score of 3+.

182. The method according to any one of embodiments 180 and 181, in which ABT-700 (S238C)-PBD is administered adjunctive to erlotinib, in which the erlotinib is administered once daily at 150 mg.

183. A method of treating a human subject having a NSCLC squamous cell carcinoma, comprising administering to the subject ABT-700 (S238C)-PBD once every 2 weeks in an amount of about 1.6 mg/kg, in which the squamous cell carcinoma has an H-score of from 150 to 224.

184. A method of treating a human subject having a NSCLC squamous cell carcinoma, comprising administering to the subject ABT-700 (S238C)-PBD once every 2 weeks in an amount of about 1.6 mg/kg, in which the squamous cell carcinoma has an IHC score of 2+.

185. A method of treating a human subject having a NSCLC squamous cell carcinoma, comprising administering to the subject ABT-700 (S238C)-PBD once every 2 weeks in an amount of about 1.6 mg/kg, in which the squamous cell carcinoma has an H-score of from 150 to 224.

186. A method of treating a human subject having a NSCLC squamous cell carcinoma, comprising administering to the subject ABT-700 (S238C)-PBD once every 2 weeks in an amount of about 1.9 mg/kg, in which the squamous cell carcinoma has an IHC score of 2+.

We claim:

1. A method of treating a non-small cell lung cancer ("NSCLC") that overexpresses cMet, comprising administering to a human subject having said NSCLC an anti-cMet antibody drug conjugate ("ADC"), wherein the drug conjugate is monomethyl auristatin E ("MMAE"), and the ADC has the following structure:

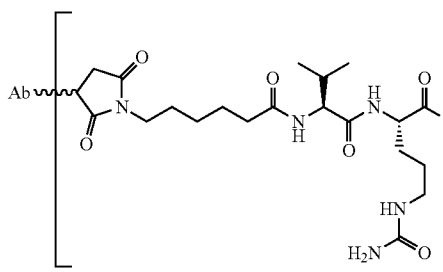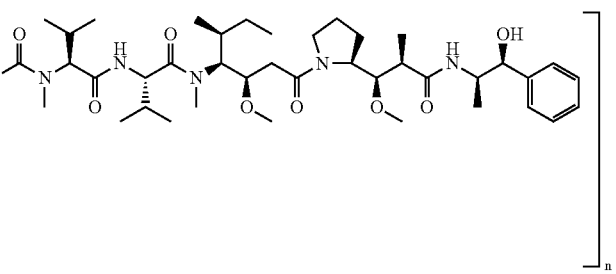

wherein Ab is an anti-cMet antibody comprising a VH chain comprising three CDRs, namely VH CDR #1 (SEQ ID NO:112), VH CDR #2 (SEQ ID NO:113) and VH CDR #3 (SEQ ID NO: 114); a VL chain comprising three CDRs, namely VL CDR #1 (SEQ ID NO: 115), VL CDR #2 (SEQ ID NO: 116) and VL CDR #3 (SEQ ID NO: 117); and a modified hinge region of SEQ ID NO: 170, n has a value ranging from 2 to 8, and attachment to the Ab is via a thioether linkage formed with a sulfhydryl group of a cysteine residue, and,
wherein said NSCLC has a biopsy IHC score of 2+ to 3+.

2. The method of claim 1, in which the anti-cMet antibody comprises a VH chain of SEQ ID NO: 78; a VL chain of SEQ ID NO: 79.

3. The method of claim 1, in which the anti-cMet antibody comprises a heavy chain of SEQ ID NO: 86 and a light chain of SEQ ID NO: 87.

4. The method of claim 1 in which the ADC has a drug antibody ratio ("DAR") of about 3.1.

5. The method of claim 1 in which the ADC has about a 1:1 ratio of E2 and E4.

6. The method of claim 1, in which the NSCLC is squamous NSCLC.

7. The method of claim 6, in which a biopsy of the squamous NSCLC tumor tissue has an IHC score of 2+ and/or an H-score from 150 to 224.

8. The method of claim 1, in which the cMet overexpressing NSCLC cancer is an adenocarcinoma.

9. The method of claim 8, in which a biopsy of the adenocarcinoma tumor tissue has an IHC score of 3+ and/or an H-score greater than 225.

10. The method of claim 1 in which the anti-cMet ADC is administered adjunctive to an additional anticancer agent.

11. The method of claim 10 in which the additional anticancer agent is an inhibitor of epidermal growth factor receptor ("EGFR").

12. The method of claim 11 in which the additional anticancer agent is erlotinib.

* * * * *

SEQUENCE LISTING

```
<160> NUMBER OF SEQ ID NOS: 178

<210> SEQ ID NO 1
<211> LENGTH: 8
<212> TYPE: PRT
<213> ORGANISM: Mus musculus

<400> SEQUENCE: 1

Gly Tyr Ile Phe Thr Ala Tyr Thr
1               5

<210> SEQ ID NO 2
<211> LENGTH: 8
<212> TYPE: PRT
<213> ORGANISM: Mus musculus

<400> SEQUENCE: 2

Ile Lys Pro Asn Asn Gly Leu Ala
1               5

<210> SEQ ID NO 3
<211> LENGTH: 11
<212> TYPE: PRT
<213> ORGANISM: Mus musculus

<400> SEQUENCE: 3

Ala Arg Ser Glu Ile Thr Thr Glu Phe Asp Tyr
1               5                   10

<210> SEQ ID NO 4
<211> LENGTH: 8
<212> TYPE: PRT
<213> ORGANISM: Mus musculus

<400> SEQUENCE: 4

Gly Tyr Ser Phe Thr Asp Tyr Thr
1               5

<210> SEQ ID NO 5
```

```
<211> LENGTH: 8
<212> TYPE: PRT
<213> ORGANISM: Mus musculus

<400> SEQUENCE: 5

Ile Asn Pro Tyr Asn Gly Gly Thr
1               5

<210> SEQ ID NO 6
<211> LENGTH: 11
<212> TYPE: PRT
<213> ORGANISM: Mus musculus

<400> SEQUENCE: 6

Ala Arg Glu Glu Ile Thr Lys Asp Phe Asp Phe
1               5                   10

<210> SEQ ID NO 7
<211> LENGTH: 8
<212> TYPE: PRT
<213> ORGANISM: Mus musculus

<400> SEQUENCE: 7

Gly Tyr Thr Phe Thr Asp Tyr Asn
1               5

<210> SEQ ID NO 8
<211> LENGTH: 8
<212> TYPE: PRT
<213> ORGANISM: Mus musculus

<400> SEQUENCE: 8

Ile Asn Pro Asn Asn Gly Gly Thr
1               5

<210> SEQ ID NO 9
<211> LENGTH: 14
<212> TYPE: PRT
<213> ORGANISM: Mus musculus

<400> SEQUENCE: 9

Ala Arg Gly Arg Tyr Val Gly Tyr Tyr Tyr Ala Met Asp Tyr
1               5                   10

<210> SEQ ID NO 10
<211> LENGTH: 10
<212> TYPE: PRT
<213> ORGANISM: Mus musculus

<400> SEQUENCE: 10

Glu Ser Val Asp Ser Tyr Ala Asn Ser Phe
1               5                   10

<210> SEQ ID NO 11
<211> LENGTH: 3
<212> TYPE: PRT
<213> ORGANISM: Mus musculus

<400> SEQUENCE: 11

Arg Ala Ser
1

<210> SEQ ID NO 12
<211> LENGTH: 9
<212> TYPE: PRT
```

```
<213> ORGANISM: Mus musculus

<400> SEQUENCE: 12

Gln Gln Ser Lys Glu Asp Pro Leu Thr
1               5

<210> SEQ ID NO 13
<211> LENGTH: 10
<212> TYPE: PRT
<213> ORGANISM: Mus musculus

<400> SEQUENCE: 13

Glu Ser Ile Asp Thr Tyr Gly Asn Ser Phe
1               5                   10

<210> SEQ ID NO 14
<211> LENGTH: 9
<212> TYPE: PRT
<213> ORGANISM: Mus musculus

<400> SEQUENCE: 14

Gln Gln Ser Asn Glu Asp Pro Phe Thr
1               5

<210> SEQ ID NO 15
<211> LENGTH: 6
<212> TYPE: PRT
<213> ORGANISM: Mus musculus

<400> SEQUENCE: 15

Glu Asn Ile Tyr Ser Asn
1               5

<210> SEQ ID NO 16
<211> LENGTH: 3
<212> TYPE: PRT
<213> ORGANISM: Mus musculus

<400> SEQUENCE: 16

Ala Ala Thr
1

<210> SEQ ID NO 17
<211> LENGTH: 9
<212> TYPE: PRT
<213> ORGANISM: Mus musculus

<400> SEQUENCE: 17

Gln His Phe Trp Gly Pro Pro Tyr Thr
1               5

<210> SEQ ID NO 18
<211> LENGTH: 118
<212> TYPE: PRT
<213> ORGANISM: Mus musculus

<400> SEQUENCE: 18

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Ile Phe Thr Ala Tyr
                20                  25                  30

Thr Met His Trp Val Arg Gln Ser Leu Gly Glu Ser Leu Asp Trp Ile
            35                  40                  45
```

Gly Gly Ile Lys Pro Asn Asn Gly Leu Ala Asn Tyr Asn Gln Lys Phe
    50                  55                  60

Lys Gly Lys Ala Thr Leu Thr Val Asp Lys Ser Ser Thr Ala Tyr
65                  70                  75                  80

Met Asp Leu Arg Ser Leu Thr Ser Glu Asp Ser Ala Val Tyr Tyr Cys
                    85                  90                  95

Ala Arg Ser Glu Ile Thr Thr Glu Phe Asp Tyr Trp Gly Gln Gly Thr
                100                 105                 110

Ala Leu Thr Val Ser Ser
            115

<210> SEQ ID NO 19
<211> LENGTH: 118
<212> TYPE: PRT
<213> ORGANISM: Mus musculus

<400> SEQUENCE: 19

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Asp Tyr
                20                  25                  30

Thr Leu Asn Trp Val Lys Gln Ser His Gly Lys Thr Leu Glu Trp Ile
            35                  40                  45

Gly Leu Ile Asn Pro Tyr Asn Gly Gly Thr Thr Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Glu Glu Ile Thr Lys Asp Phe Asp Phe Trp Gly Gln Gly Thr
                100                 105                 110

Thr Leu Thr Val Ser Ser
            115

<210> SEQ ID NO 20
<211> LENGTH: 121
<212> TYPE: PRT
<213> ORGANISM: Mus musculus

<400> SEQUENCE: 20

Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
                20                  25                  30

Asn Met Asp Trp Val Lys Gln Ser His Gly Met Ser Leu Glu Trp Ile
            35                  40                  45

Gly Asp Ile Asn Pro Asn Asn Gly Gly Thr Ile Phe Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Gly Arg Tyr Val Gly Tyr Tyr Tyr Ala Met Asp Tyr Trp Gly
                100                 105                 110

Gln Gly Thr Ser Val Thr Val Ser Ser
            115                 120

<210> SEQ ID NO 21
<211> LENGTH: 111
<212> TYPE: PRT
<213> ORGANISM: Mus musculus

<400> SEQUENCE: 21

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Ala Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Val Ala Thr Tyr Tyr Cys Gln Gln Ser Lys
                85                  90                  95

Glu Asp Pro Leu Thr Phe Gly Ser Gly Thr Lys Leu Glu Met Lys
            100                 105                 110

<210> SEQ ID NO 22
<211> LENGTH: 111
<212> TYPE: PRT
<213> ORGANISM: Mus musculus

<400> SEQUENCE: 22

Gly Ile Val Leu Thr Gln Ser Pro Ala Ser Leu Ala Val Ser Leu Gly
1               5                   10                  15

Gln Arg Ala Thr Ile Ser Cys Arg Val Ser Glu Ser Ile Asp Thr Tyr
            20                  25                  30

Gly Asn Ser Phe Ile His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Ser Ala Thr Tyr Tyr Cys Gln Gln Ser Asn
                85                  90                  95

Glu Asp Pro Phe Thr Phe Gly Ser Gly Thr Lys Leu Glu Met Lys
            100                 105                 110

<210> SEQ ID NO 23
<211> LENGTH: 107
<212> TYPE: PRT
<213> ORGANISM: Mus musculus

<400> SEQUENCE: 23

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Val Asp Gly Val Pro Ser Arg Phe Ser Gly
    50                  55                  60

Ser Gly Ser Gly Thr Gln Tyr Ser Leu Lys Ile Asn Ser Leu Gln Ser

```
            65                  70                  75                  80
        Glu Asp Phe Gly Ser Tyr Tyr Cys Gln His Phe Trp Gly Pro Pro Tyr
                        85                  90                  95
        Thr Phe Gly Gly Gly Thr Lys Leu Glu Ile Lys
                       100                 105
```

<210> SEQ ID NO 24
<211> LENGTH: 24
<212> TYPE: DNA
<213> ORGANISM: Mus musculus

<400> SEQUENCE: 24
ggatacatat tcactgcata cacc                                            24

<210> SEQ ID NO 25
<211> LENGTH: 24
<212> TYPE: DNA
<213> ORGANISM: Mus musculus

<400> SEQUENCE: 25
attaaaccaa acaatggtct tgct                                            24

<210> SEQ ID NO 26
<211> LENGTH: 33
<212> TYPE: DNA
<213> ORGANISM: Mus musculus

<400> SEQUENCE: 26
gcaagatctg agattacgac ggaatttgac tac                                  33

<210> SEQ ID NO 27
<211> LENGTH: 24
<212> TYPE: DNA
<213> ORGANISM: Mus musculus

<400> SEQUENCE: 27
ggttattcat tcactgacta cacc                                            24

<210> SEQ ID NO 28
<211> LENGTH: 24
<212> TYPE: DNA
<213> ORGANISM: Mus musculus

<400> SEQUENCE: 28
attaatcctt acaatggtgg tact                                            24

<210> SEQ ID NO 29
<211> LENGTH: 33
<212> TYPE: DNA
<213> ORGANISM: Mus musculus

<400> SEQUENCE: 29
gcaagagagg aaattacgaa ggactttgat ttc                                  33

<210> SEQ ID NO 30
<211> LENGTH: 24
<212> TYPE: DNA
<213> ORGANISM: Mus musculus

<400> SEQUENCE: 30
ggatacacat tcactgacta caac                                            24

```
<210> SEQ ID NO 31
<211> LENGTH: 24
<212> TYPE: DNA
<213> ORGANISM: Mus musculus

<400> SEQUENCE: 31
attaatccta acaatggtgg tact                                          24

<210> SEQ ID NO 32
<211> LENGTH: 42
<212> TYPE: DNA
<213> ORGANISM: Mus musculus

<400> SEQUENCE: 32
gcaagaggga ggtatgttgg ttactactat gctatggact ac                      42

<210> SEQ ID NO 33
<211> LENGTH: 30
<212> TYPE: DNA
<213> ORGANISM: Mus musculus

<400> SEQUENCE: 33
gaaagtgttg atagttatgc caatagtttt                                    30

<210> SEQ ID NO 34
<211> LENGTH: 9
<212> TYPE: DNA
<213> ORGANISM: Mus musculus

<400> SEQUENCE: 34 cgtgcatcc                                                            9

<210> SEQ ID NO 35
<211> LENGTH: 27
<212> TYPE: DNA
<213> ORGANISM: Mus musculus

<400> SEQUENCE: 35
cagcaaagta aggaggatcc tctcacg                                       27

<210> SEQ ID NO 36
<211> LENGTH: 30
<212> TYPE: DNA
<213> ORGANISM: Mus musculus

<400> SEQUENCE: 36
gaaagtattg atacttatgg caatagtttt                                    30

<210> SEQ ID NO 37
<211> LENGTH: 27
<212> TYPE: DNA
<213> ORGANISM: Mus musculus

<400> SEQUENCE: 37
cagcaaagta atgaggatcc attcacg                                       27

<210> SEQ ID NO 38
<211> LENGTH: 18
<212> TYPE: DNA
<213> ORGANISM: Mus musculus

<400> SEQUENCE: 38
gagaatattt acagtaat                                                 18
```

<210> SEQ ID NO 39
<211> LENGTH: 9
<212> TYPE: DNA
<213> ORGANISM: Mus musculus

<400> SEQUENCE: 39 gctgcaaca                                                                  9

<210> SEQ ID NO 40
<211> LENGTH: 27
<212> TYPE: DNA
<213> ORGANISM: Mus musculus

<400> SEQUENCE: 40
caacattttt ggggtcctcc gtacacg                                             27

<210> SEQ ID NO 41
<211> LENGTH: 354
<212> TYPE: DNA
<213> ORGANISM: Mus musculus

<400> SEQUENCE: 41
gaggtccagc tgcaacagtc tggacctgag ctggtgaagc ctggggcttc agtgaagata         60
tcctgcaaga cttctggata catattcact gcatacacca tgcactgggt gaggcagagc        120
cttggagaga gccttgactg gattggaggt attaaaccaa acaatggtct tgctaactac        180
aaccagaagt tcaagggcaa ggccacattg actgtagaca gtcctccag cacagcctac         240 atggacctcc gcagcctgac atctgaggat tctgcagtct attactgtgc aagatctgag        300
attacgacgg aatttgacta ctggggccaa ggcaccgctc tcacagtctc ctca              354

<210> SEQ ID NO 42
<211> LENGTH: 354
<212> TYPE: DNA
<213> ORGANISM: Mus musculus

<400> SEQUENCE: 42
gaggtccagc tgcaacagtc tggacctgaa ctggtgaagc ctggagcttc aatgaagatt         60
tcctgcaagg cttctggtta ttcattcact gactacaccc tgaactgggt gaagcagagc        120
catggaaaga cccttgagtg gattggactt attaatcctt acaatggtgg tactacctac        180
aaccagaagt tcaagggcaa ggccacatta actgtagaca gtcatccag cacagcctac         240 atggagctcc tcagtctgac atctgaggac tctgcagtct attactgtgc aagagaggaa        300
attacgaagg actttgattt ctggggccaa ggcaccactc tcacagtctc ctca              354

<210> SEQ ID NO 43
<211> LENGTH: 363
<212> TYPE: DNA
<213> ORGANISM: Mus musculus

<400> SEQUENCE: 43
gaggtcctgc tgcaacagtc tggacctgag ctggtgaagc ctggggcttc agtgaagata         60
ccctgcaagg cttctggata cacattcact gactacaaca tggactgggt gaagcagagc        120
catggaatga gccttgagtg gattggagat attaatccta caatggtgg tactatcttc         180 aaccagaagt tcaagggcaa ggccacattg actgtagaca gtcctccag cacagcctac         240 atggagctcc gcagcctgac atctgaggac actgcagtct attactgtgc aagagggagg        300
tatgttggtt actactatgc tatggactac tggggtcaag aacctcagt caccgtctcc         360 tca                                                                          363

<210> SEQ ID NO 44
<211> LENGTH: 333
<212> TYPE: DNA
<213> ORGANISM: Mus musculus

<400> SEQUENCE: 44
gacattgtgc tgacccaatc tccagcttct ttggctgtgt ctctagggca gagggccacc      60
atatcctgca gagccagtga aagtgttgat agttatgcca atagttttat gcactggtac     120
cagcagaaac caggacagcc acccaaactc ctcatctatc gtgcatccaa cctagaatct     180
gggatccctg ccaggttcag tggcagtggg tctaggacag acttcaccct caccattaat     240
cctgtggagg ctgatgatgt tgcaacctat tactgtcagc aaagtaagga ggatcctctc     300
acgttcggct cggggacaaa attggaaatg aaa                                  333

<210> SEQ ID NO 45
<211> LENGTH: 333
<212> TYPE: DNA
<213> ORGANISM: Mus musculus

<400> SEQUENCE: 45
ggcattgtgt tgacccaatc tccagcttct ttggctgtgt ctctaggaca gagggccacc      60
atatcctgca gagtcagtga aagtattgat acttatggca atagttttat acactggtac     120
cagcagaaac caggacagcc acccaaactc ctcatctatc gtgcatccaa cctagaatct     180
gggatccctg ccaggttcag tggcagtggg tctaggacag acttcaccct caccattaat     240
cctgtggagg ctgatgattc tgcaacctat tactgtcagc aaagtaatga ggatccattc     300
acgttcggct cggggacaaa gttggaaatg aaa                                  333

<210> SEQ ID NO 46
<211> LENGTH: 321
<212> TYPE: DNA
<213> ORGANISM: Mus musculus

<400> SEQUENCE: 46
gacatccaga tgactcagtc tccagcctcc ctatctgtat ctgtgggaga aactgtcacc      60
atcacatgtc gagcaagtga gaatatttac agtaatttag catggtatca gcagaaacag     120
ggaaaatctc ctcagctcct ggtctatgct gcaacaaact tagtagatgg tgtgccatca     180
aggttcagtg gcagtggatc aggcacacag tattccctca agatcaacag cctgcagtct     240
gaagattttg ggagttatta ctgtcaacat ttttggggtc ctccgtacac gttcggaggg     300
gggaccaagc tggagataaa g                                               321

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      primer for housekeeping gene Ribosomal protein,
      large, P0 (RPL0)

<400> SEQUENCE: 47
gaaactctgc attctcgctt cctg                                            24

<210> SEQ ID NO 48

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer for housekeeping gene Ribosomal protein,
      large, P0 (RPL0)

<400> SEQUENCE: 48
aggactcgtt tgtacccgtt ga                                            22

<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: Synthetic
      primer for housekeeping gene Ribosomal protein,
      large, P0 (RPL0)

<400> SEQUENCE: 49
tgcagattgg ctacccaact gttgca                                        26

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      primer for HGF

<400> SEQUENCE: 50
aacaatgcct ctggttcc                                                 18

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer for HGF

<400> SEQUENCE: 51
cttgtagctg cgtcctttac                                               20

<210> SEQ ID NO 52
<211> LENGTH: 27
<212> TYPE: DNA
<213> ORGANISM: Artificial Sequence
<220> FEATURE:
<223> OTHER INFORMATION: Description of Artificial Sequence: Synthetic
      probe for HGF

<400> SEQUENCE: 52
ccttcaatag catgtcaagt ggagtga                                       27

<210> SEQ ID NO 53
<211> LENGTH: 28
<212> TYPE: DNA
<213> ORGANISM: Artificial Sequence
<220> FEATURE:
<223> OTHER INFORMATION: Description of Artificial Sequence: Synthetic
      primer for c-Met

<400> SEQUENCE: 53
cattaaagga gacctcacca tagctaat                                      28
```

```
<210> SEQ ID NO 54
<211> LENGTH: 22
<212> TYPE: DNA
<213> ORGANISM: Artificial Sequence
<220> FEATURE:
<223> OTHER INFORMATION: Description of Artificial Sequence: Synthetic
      primer for c-Met

<400> SEQUENCE: 54
cctgatcgag aaaccacaac ct                                                22

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: Synthetic
      probe for c-Met

<400> SEQUENCE: 55
catgaagcga ccctctgatg tccca                                             25

<210> SEQ ID NO 56
<211> LENGTH: 8
<212> TYPE: PRT
<213> ORGANISM: Mus musculus

<400> SEQUENCE: 56

Gly Tyr Thr Phe Thr Ser Tyr Trp
1               5

<210> SEQ ID NO 57
<211> LENGTH: 8
<212> TYPE: PRT
<213> ORGANISM: Mus musculus

<400> SEQUENCE: 57

Ile Asn Pro Thr Thr Gly Ser Thr
1               5

<210> SEQ ID NO 58
<211> LENGTH: 11
<212> TYPE: PRT
<213> ORGANISM: Mus musculus

<400> SEQUENCE: 58

Ala Ile Gly Gly Tyr Gly Ser Trp Phe Ala Tyr
1               5                   10

<210> SEQ ID NO 59
<211> LENGTH: 7
<212> TYPE: PRT
<213> ORGANISM: Mus musculus

<400> SEQUENCE: 59

Ser Ser Val Ser Ser Thr Tyr
1               5

<210> SEQ ID NO 60
<211> LENGTH: 3
<212> TYPE: PRT
<213> ORGANISM: Mus musculus

<400> SEQUENCE: 60

Thr Thr Ser
1
```

<210> SEQ ID NO 61
<211> LENGTH: 9
<212> TYPE: PRT
<213> ORGANISM: Mus musculus

<400> SEQUENCE: 61

His Gln Trp Ser Ser Tyr Pro Phe Thr
1               5

<210> SEQ ID NO 62
<211> LENGTH: 118
<212> TYPE: PRT
<213> ORGANISM: Mus musculus

<400> SEQUENCE: 62

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Trp Met Asn Trp Val Lys Gln Arg Pro Gly Gln Gly Leu Glu Trp Ile
        35                  40                  45

Gly Tyr Ile Asn Pro Thr Thr Gly Ser Thr Asp Tyr Asn Gln Lys Leu
    50                  55                  60

Lys Asp Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Ile Gly Gly Tyr Gly Ser Trp Phe Ala Tyr Trp Gly Gln Gly Thr
            100                 105                 110

Leu Val Thr Val Ser Ala
        115

<210> SEQ ID NO 63
<211> LENGTH: 108
<212> TYPE: PRT
<213> ORGANISM: Mus musculus

<400> SEQUENCE: 63

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Ser Ser Thr
            20                  25                  30

Tyr Leu Tyr Trp Tyr Gln Gln Lys Pro Gly Ser Ser Pro Lys Leu Trp
        35                  40                  45

Ile Tyr Thr Thr Ser Ile Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Thr Glu Asp Ala Ala Ser Tyr Phe Cys His Gln Trp Ser Ser Tyr Pro
                85                  90                  95

Phe Thr Phe Gly Ser Gly Thr Lys Leu Asp Ile Lys
            100                 105

<210> SEQ ID NO 64
<211> LENGTH: 24
<212> TYPE: DNA
<213> ORGANISM: Mus musculus

<400> SEQUENCE: 64
ggctacactt ttacttccta ctgg                                              24

<210> SEQ ID NO 65
<211> LENGTH: 24
<212> TYPE: DNA
<213> ORGANISM: Mus musculus

<400> SEQUENCE: 65 attaaccota ccactggttc tact                                              24

<210> SEQ ID NO 66
<211> LENGTH: 33
<212> TYPE: DNA
<213> ORGANISM: Mus musculus

<400> SEQUENCE: 66
gcaataggag gatatgggtc ctggtttgct tac                                    33

<210> SEQ ID NO 67
<211> LENGTH: 21
<212> TYPE: DNA
<213> ORGANISM: Mus musculus

<400> SEQUENCE: 67
tcaagtgtaa gttccaccta c                                                 21

<210> SEQ ID NO 68
<211> LENGTH: 9
<212> TYPE: DNA
<213> ORGANISM: Mus musculus

<400> SEQUENCE: 68 accacatcc                                                                9

<210> SEQ ID NO 69
<211> LENGTH: 27
<212> TYPE: DNA
<213> ORGANISM: Mus musculus

<400> SEQUENCE: 69
catcagtgga gtagttaccc attcacg                                           27

<210> SEQ ID NO 70
<211> LENGTH: 354
<212> TYPE: DNA
<213> ORGANISM: Mus musculus

<400> SEQUENCE: 70
caggtccagc ttcagcagtc tggggctgaa ctggcaaaac ctggggcctc agtgaagatg        60
tcctgcaagg cttctggcta cacttttact tcctactgga tgaactgggt gaaacagagg       120
cctggacagg gtctggaatg gattggatac attaacccta ccactggttc tactgactac       180
aatcagaagt taaggacaa ggccacattg actgcagaca atcctccaa cacagcctac        240 atgcaactga gcagcctgac atctgaggac tctgcagtct attactgtgc aataggagga       300
tatgggtcct ggtttgctta ctgggggccaa gggactctgg tcactgtctc tgca            354

<210> SEQ ID NO 71
<211> LENGTH: 324
<212> TYPE: DNA
<213> ORGANISM: Mus musculus

<400> SEQUENCE: 71

```
caaattgttc tcacccagtc tccagcaatc atgtctgcat ctcctgggga gaaggtcacc      60
ttgacctgca gtgccagctc aagtgtaagt tccacctact tgtactggta ccagcagaag     120
ccaggatcct cccccaaact ctggatttat accacatcca tcctggcttc tggagtccct     180
gctcgcttca gtggcagtgg gtctgggacc tcttactctc tcacaatcag cagcatggag     240
actgaagatg ctgcctctta tttctgccat cagtggagta gttacccatt cacgttcggc     300
tcggggacaa agttggacat aaaa                                             324
```

<210> SEQ ID NO 72
<211> LENGTH: 8
<212> TYPE: PRT
<213> ORGANISM: Mus musculus

<400> SEQUENCE: 72

Gly Tyr Ile Phe Thr Ala Tyr Thr
1               5

<210> SEQ ID NO 73
<211> LENGTH: 8
<212> TYPE: PRT
<213> ORGANISM: Mus musculus

<400> SEQUENCE: 73

Ile Lys Pro Asn Asn Gly Leu Ala
1               5

<210> SEQ ID NO 74
<211> LENGTH: 11
<212> TYPE: PRT
<213> ORGANISM: Mus musculus

<400> SEQUENCE: 74

Ala Arg Ser Glu Ile Thr Thr Glu Phe Asp Tyr
1               5                   10

<210> SEQ ID NO 75
<211> LENGTH: 10
<212> TYPE: PRT
<213> ORGANISM: Mus musculus

<400> SEQUENCE: 75

Glu Ser Val Asp Ser Tyr Ala Asn Ser Phe
1               5                   10

<210> SEQ ID NO 76
<211> LENGTH: 3
<212> TYPE: PRT
<213> ORGANISM: Mus musculus

<400> SEQUENCE: 76

Arg Ala Ser
1

<210> SEQ ID NO 77
<211> LENGTH: 9
<212> TYPE: PRT
<213> ORGANISM: Mus musculus

<400> SEQUENCE: 77

Gln Gln Ser Lys Glu Asp Pro Leu Thr

-continued

```
<210> SEQ ID NO 78
<211> LENGTH: 118
<212> TYPE: PRT
<213> ORGANISM: Mus musculus

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ala Tyr
            20                  25                  30

Thr Met His Trp Val Arg Gln Ala Pro Gly Gln Gly Leu Glu Trp Met
        35                  40                  45

Gly Trp Ile Lys Pro Asn Asn Gly Leu Ala Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Glu Ile Thr Thr Glu Phe Asp Tyr Trp Gly Gln Gly Thr
            100                 105                 110

Leu Val Thr Val Ser Ser
        115

<210> SEQ ID NO 79
<211> LENGTH: 112
<212> TYPE: PRT
<213> ORGANISM: Mus musculus

<400> SEQUENCE: 79

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Asp Ser Tyr
            20                  25                  30

Ala Asn Ser Phe Leu His Trp Tyr Gln Gln Lys Pro Gly Gln Pro Pro
        35                  40                  45

Lys Leu Leu Ile Tyr Arg Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Asp Pro Leu Thr Phe Gly Gly Gly Thr Lys Val Glu Ile Lys Arg
            100                 105                 110

<210> SEQ ID NO 80
<211> LENGTH: 118
<212> TYPE: PRT
<213> ORGANISM: Mus musculus

<400> SEQUENCE: 80

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ala Tyr
            20                  25                  30

Thr Met His Trp Val Arg Gln Ala Pro Gly Gln Gly Leu Glu Trp Met
        35                  40                  45
```

```
Gly Trp Ile Lys Pro Asn Asn Gly Leu Ala Asn Tyr Ala Gln Lys Phe
            50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Glu Ile Thr Thr Glu Phe Asp Tyr Trp Gly Gln Gly Thr
            100                 105                 110

Leu Val Thr Val Ser Ser
        115

<210> SEQ ID NO 81
<211> LENGTH: 111
<212> TYPE: PRT
<213> ORGANISM: Mus musculus

<400> SEQUENCE: 81

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Asp Ser Tyr
            20                  25                  30

Ala Asn Ser Phe Leu His Trp Tyr Gln Gln Lys Pro Gly Gln Pro Pro
        35                  40                  45

Lys Leu Leu Ile Tyr Arg Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Asp Pro Leu Thr Phe Gly Gly Gly Thr Lys Val Glu Ile Lys
            100                 105                 110

<210> SEQ ID NO 82
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Cys His Cys Pro Pro Cys Pro Ala
            100                 105                 110

Pro Glu Leu Leu Gly Gly Pro Ser Val Phe Leu Phe Pro Pro Lys Pro
        115                 120                 125
```

```
Lys Asp Thr Leu Met Ile Ser Arg Thr Pro Glu Val Thr Cys Val Val
        130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
        195                 200                 205

Leu Pro Ala Pro Ile Glu Lys Thr Ile Ser Lys Ala Lys Gly Gln Pro
210                 215                 220

Arg Glu Pro Gln Val Tyr Thr Leu Pro Pro Ser Arg Glu Glu Met Thr
225                 230                 235                 240

Lys Asn Gln Val Ser Leu Thr Cys Leu Val Lys Gly Phe Tyr Pro Ser
                245                 250                 255

Asp Ile Ala Val Glu Trp Glu Ser Asn Gly Gln Pro Glu Asn Asn Tyr
            260                 265                 270

Lys Thr Thr Pro Pro Val Leu Asp Ser Asp Gly Ser Phe Phe Leu Tyr
        275                 280                 285

Ser Lys Leu Thr Val Asp Lys Ser Arg Trp Gln Gln Gly Asn Val Phe
290                 295                 300

Ser Cys Ser Val Met His Glu Ala Leu His Asn His Tyr Thr Gln Lys
305                 310                 315                 320

Ser Leu Ser Leu Ser Pro Gly
                325

<210> SEQ ID NO 83
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 84
<211> LENGTH: 327
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 84

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Arg
                85                  90                  95

Val Glu Pro Lys Ser Cys Asp Cys His Cys Pro Pro Cys Pro Ala Pro
            100                 105                 110

Glu Leu Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325
```

<210> SEQ ID NO 85
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 85

Thr Val Ala Ala Pro Ser Val Phe Ile Phe Pro Pro Ser Asp Glu Gln

```
          1               5                  10                 15
Leu Lys Ser Gly Thr Ala Ser Val Val Cys Leu Leu Asn Asn Phe Tyr
                20                  25                 30

Pro Arg Glu Ala Lys Val Gln Trp Lys Val Asp Asn Ala Leu Gln Ser
            35                  40                 45

Gly Asn Ser Gln Glu Ser Val Thr Glu Gln Asp Ser Lys Asp Ser Thr
 50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
                100                 105

<210> SEQ ID NO 86
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ala Tyr
                20                  25                  30

Thr Met His Trp Val Arg Gln Ala Pro Gly Gln Gly Leu Glu Trp Met
            35                  40                  45

Gly Trp Ile Lys Pro Asn Asn Gly Leu Ala Asn Tyr Ala Gln Lys Phe
 50                 55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Glu Ile Thr Thr Glu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Cys His
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255
```

```
Glu Val Thr Cys Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445

<210> SEQ ID NO 87
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Asp Ser Tyr
            20                  25                  30

Ala Asn Ser Phe Leu His Trp Tyr Gln Gln Lys Pro Gly Gln Pro Pro
        35                  40                  45

Lys Leu Leu Ile Tyr Arg Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Asp Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175
```

```
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 88
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ala Tyr
            20                  25                  30

Thr Met His Trp Val Arg Gln Ala Pro Gly Gln Gly Leu Glu Trp Met
        35                  40                  45

Gly Trp Ile Lys Pro Asn Asn Gly Leu Ala Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Glu Ile Thr Thr Glu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Cys His
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
```

```
            305                 310                 315                 320
Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 89
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Asp Ser Tyr
            20                  25                  30

Ala Asn Ser Phe Leu His Trp Tyr Gln Gln Lys Pro Gly Gln Pro Pro
        35                  40                  45

Lys Leu Leu Ile Tyr Arg Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Asp Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 90
<211> LENGTH: 1395
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 90

```
atgggatggt cttggatctt tctgctgttt ctgtctggta ctgctggtgt gctgagccag      60
gtccagctgg tgcaatccgg cgcagaggtg aagaagccag gcgcttccgt gaaggtgagc     120
tgtaaggcct ctggctacat cttcacagca tacaccatgc actgggtgag gcaagctcct     180
gggcagggac tggagtggat gggatggatt aaacccaaca tgggctggc caactacgcc      240
cagaaattcc agggtagggt cactatgaca agggatacca gcatcagcac cgcatatatg     300
gagctgagca ggctgaggtc tgacgacact gctgtctatt attgcgccag gagcgaaatt     360
acaacagaat tcgattactg ggggcagggc accctggtga ccgtgtcctc tgccagcacc     420
aagggcccaa gcgtgttccc cctggccccc agcagcaaga gcaccagcgg cggcacagcc     480
gccctgggct gcctggtgaa ggactacttc cccgagcccg tgaccgtgtc ctggaacagc     540
ggagccctca cttctggagt tcataccttc ccagcagtat tgcagagcag tggcctgtat     600
tcactgtctt ccgtcgtaac agttccatcc tccagcctcg gcacagac ttacatttgt       660
aacgtgaatc acaagcctag caacaccaag gtcgacaaga gagttgaacc aaagagttgt     720
gattgccact gtcctccctg cccagctcct gagctgcttg gcggtcccag tgtcttcttg     780
tttccccta aacccaaaga caccctgatg atctcaagga ctcccgaggt gacatgcgtg     840
gtggtggatg tgtctcatga ggacccgag gtgaagttca actggtacgt ggacggcgtg      900
gaggtgcaca acgccaagac caagcccaga gaggagcagt acaacagcac ctacagggtg     960
gtgtccgtgc tgaccgtgct gcaccaggac tggctgaacg gcaaggagta caagtgtaag    1020
gtgtccaaca aggccctgcc agccccaatc gaaaagacca tcagcaaggc caagggccag    1080
ccaagagagc cccaggtgta caccctgcca cccagcaggg aggagatgac caagaaccag    1140
gtgtccctga cctgtctggt gaagggcttc tacccaagcg acatcgccgt ggagtgggag    1200
agcaacggcc agcccgagaa caactacaag accccccccc cagtgctgga cagcgacggc    1260
agcttcttcc tgtacagcaa gctgaccgtg gacaagagca gatggcagca gggcaacgtg    1320
ttcagctgct ccgtgatgca cgaggccctg cacaaccact acacccagaa gagcctgagc    1380
ctgtccccag gctga                                                     1395
```

<210> SEQ ID NO 91
<211> LENGTH: 717
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 91

```
atggaaactg atacactgct gctgtgggtc ctgctgctgt gggtccctgg aagcacaggg      60
gacattgtga tgacccagtc tcccgatagc ctggccgtgt ccctgggcga gagggctacc     120
atcaactgta aaagctccga atctgtggac tcttacgcaa acagctttct gcactggtat     180
cagcaaaagc caggccaacc tccaaagctg ctgatttaca gggcttctac cagggagagc     240
ggcgtgcccg ataggttcag cggatctggc agcggcaccg actttacact gaccatctcc     300
```

```
agcctgcagg ccgaagatgt ggcagtctat tactgccagc agtccaagga ggaccccctg    360
actttcgggg gtggtactaa agtggagatc aagcgtacgg tggccgctcc cagcgtgttc    420
atcttccccc caagcgacga gcagctgaag agcggcaccg ccagcgtggt gtgtctgctg    480
aacaacttct accccaggga ggccaaggtg cagtggaagg tggacaacgc cctgcagagc    540
ggcaacagcc aggagagcgt caccgagcag gacagcaagg actccaccta cagcctgagc    600
agcaccctga ccctgagcaa ggccgactac gagaagcaca aggtgtacgc ctgtgaggtg    660
acccaccagg gcctgtccag ccccgtgacc aagagcttca caggggcga gtgctga       717
```

<210> SEQ ID NO 92
<211> LENGTH: 449
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 92

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
        35                  40                  45

Gly Met Ile Asp Pro Ser Asn Ser Asp Thr Arg Phe Asn Pro Asn Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Ser
            355                 360                 365

Cys Ala Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 93
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
                20                  25                  30

Ser Ser Gln Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190
```

```
Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 94
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 95
<211> LENGTH: 441
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30
```

```
Tyr Met His Trp Val Arg Gln Ala Pro Gly Gln Gly Leu Glu Trp Met
        35                  40                  45
Gly Arg Val Asn Pro Asn Arg Gly Thr Thr Tyr Asn Gln Lys Phe
 50                  55                  60
Glu Gly Arg Val Thr Met Thr Thr Asp Thr Ser Thr Ser Thr Ala Tyr
 65                  70                  75                  80
Met Glu Leu Arg Ser Leu Arg Ser Asp Thr Ala Val Tyr Tyr Cys
                 85                  90                  95
Ala Arg Ala Asn Trp Leu Asp Tyr Trp Gly Gln Gly Thr Thr Val Thr
                100                 105                 110
Val Ser Ser Ala Ser Thr Lys Gly Pro Ser Val Phe Pro Leu Ala Pro
                115                 120                 125
Cys Ser Arg Ser Thr Ser Glu Ser Thr Ala Ala Leu Gly Cys Leu Val
                130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
                180                 185                 190
Thr Lys Thr Tyr Thr Cys Asn Val Asp His Lys Pro Ser Asn Thr Lys
                195                 200                 205
Val Asp Lys Arg Val Glu Ser Lys Tyr Gly Pro Pro Cys Pro Pro Cys
                210                 215                 220
Pro Ala Pro Glu Ala Ala Gly Gly Pro Ser Val Phe Leu Phe Pro Pro
225                 230                 235                 240
Lys Pro Lys Asp Thr Leu Met Ile Ser Arg Thr Pro Glu Val Thr Cys
                245                 250                 255
Val Val Val Asp Val Ser Gln Glu Asp Pro Glu Val Gln Phe Asn Trp
                260                 265                 270
Tyr Val Asp Gly Val Glu Val His Asn Ala Lys Thr Lys Pro Arg Glu
                275                 280                 285
Glu Gln Phe Asn Ser Thr Tyr Arg Val Val Ser Val Leu Thr Val Leu
                290                 295                 300
His Gln Asp Trp Leu Asn Gly Lys Glu Tyr Lys Cys Lys Val Ser Asn
305                 310                 315                 320
Lys Gly Leu Pro Ser Ser Ile Glu Lys Thr Ile Ser Lys Ala Lys Gly
                325                 330                 335
Gln Pro Arg Glu Pro Gln Val Tyr Thr Leu Pro Pro Ser Gln Glu Glu
                340                 345                 350
Met Thr Lys Asn Gln Val Ser Leu Thr Cys Leu Val Lys Gly Phe Tyr
                355                 360                 365
Pro Ser Asp Ile Ala Val Glu Trp Glu Ser Asn Gly Gln Pro Glu Asn
                370                 375                 380
Asn Tyr Lys Thr Thr Pro Pro Val Leu Asp Ser Asp Gly Ser Phe Phe
385                 390                 395                 400
Leu Tyr Ser Arg Leu Thr Val Asp Lys Ser Arg Trp Gln Glu Gly Asn
                405                 410                 415
Val Phe Ser Cys Ser Val Met His Glu Ala Leu His Asn His Tyr Thr
                420                 425                 430
Gln Lys Ser Leu Ser Leu Ser Leu Gly
                435                 440
```

<210> SEQ ID NO 96
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Ser Val Ser Ser Ser Val Ser Ser Ile
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Val Tyr Ser Gly Tyr Pro
                85                  90                  95

Leu Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Gly Gly Gly Ser Gly Gly Gly Ser Gly Gly Gly Gly Ser
1               5                   10                  15

<210> SEQ ID NO 98
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Phe Leu Gly

```
<210> SEQ ID NO 99
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ala Leu Ala Leu
1

<210> SEQ ID NO 100
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 100

His His His His His His
1               5

<210> SEQ ID NO 101
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Arg Val Asn Pro Asn Arg Arg Gly Thr Thr Tyr Asn Gln Lys Phe
    50                  55                  60

Glu Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Asn Trp Leu Asp Tyr Trp Gly Gln Gly Thr Thr Val Thr
            100                 105                 110

Val Ser Ser
        115

<210> SEQ ID NO 102
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Asp Ile Gln Met Thr Gln Ser Pro Ser Ser Leu Ser Ala Ser Val Gly
1               5                   10                  15
```

```
Asp Arg Val Thr Ile Thr Cys Ser Val Ser Ser Ser Val Ser Ser Ile
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Val Tyr Ser Gly Tyr Pro
                85                  90                  95

Leu Thr Phe Gly Gly Gly Thr Lys Val Glu Ile Lys Arg
            100                 105

<210> SEQ ID NO 103
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
        35                  40                  45

Gly Met Ile Asp Pro Ser Asn Ser Asp Thr Arg Phe Asn Pro Asn Phe
50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser
        115

<210> SEQ ID NO 104
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Thr
            20                  25                  30

Ser Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
50                  55                  60

Pro Ser Arg Phe Ser Gly Ser Gly Ser Gly Thr Asp Phe Thr Leu Thr
65                  70                  75                  80
```

```
Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys Arg

<210> SEQ ID NO 105
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Asn Trp Phe Ala Tyr Val Val Gly Gln Gly Thr
            100                 105                 110

Leu Val Thr Val Ser Ser
        115

<210> SEQ ID NO 106
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Ala Ser
            20                  25                  30

Gly Asn Gln Asn Asn Tyr Leu Ala Trp His Gln Gln Lys Pro Gly Lys
        35                  40                  45

Ala Pro Lys Met Leu Ile Ile Trp Ala Ser Thr Arg Val Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Tyr Ser Ala Pro Leu Thr Phe Gly Gln Gly Thr Lys Val Glu Ile
            100                 105                 110

Lys Arg

<210> SEQ ID NO 107
```

<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gln Val Gln Leu Val Glu Ser Gly Pro Gly Leu Val Lys Pro Ser Gln
1               5                   10                  15

Thr Leu Ser Leu Thr Cys Ala Val Ser Gly Gly Ser Ile Thr Thr Asn
            20                  25                  30

Tyr Tyr Tyr Trp Ser Trp Ile Arg Gln Ser Pro Gly Lys Gly Leu Glu
        35                  40                  45

Trp Met Gly Val Ile Ala Tyr Asp Gly Ser Thr Asp Tyr Ser Pro Ser
    50                  55                  60

Leu Lys Ser Arg Thr Ser Ile Ser Arg Asp Thr Ser Lys Asn Gln Phe
65                  70                  75                  80

Ser Leu Gln Leu Ser Ser Val Thr Pro Glu Asp Thr Ala Val Tyr Tyr
                85                  90                  95

Cys Ala Arg Asp Val Arg Val Ile Ala Thr Gly Trp Ala Thr Ala Asn
            100                 105                 110

Ala Leu Asp Ala Trp Gly Gln Gly Thr Leu Val Thr Val Ser Ser
        115                 120                 125

<210> SEQ ID NO 108
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gln Ser Val Leu Thr Gln Pro Pro Ser Val Ser Gly Ser Pro Gly Lys
1               5                   10                  15

Thr Val Thr Ile Ser Cys Ala Gly Thr Ser Ser Asp Val Gly Tyr Gly
            20                  25                  30

Asn Tyr Val Ser Trp Tyr Gln Gln Leu Pro Gly Thr Ala Pro Lys Leu
        35                  40                  45

Leu Ile Phe Ala Val Ser Tyr Arg Ala Ser Gly Ile Pro Asp Arg Phe
    50                  55                  60

Ser Gly Ser Lys Ser Gly Asn Thr Ala Phe Leu Thr Ile Ser Gly Leu
65                  70                  75                  80

Gln Ser Glu Asp Glu Ala Asp Tyr Tyr Cys Ala Ser Tyr Arg Ser Ser
                85                  90                  95

Asn Asn Ala Ala Val Phe Gly Gly Gly Thr His Leu Thr Val Leu
            100                 105                 110

<210> SEQ ID NO 109
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Ile Ser Trp Val Arg Gln Ala Pro Gly Lys Gly Leu Glu Trp Val
                35                  40                  45

Gly Phe Ile Arg Asn Lys Ala Asn Gly Tyr Thr Thr Glu Tyr Ser Ala
 50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Asp Asn Trp Phe Ala Tyr Trp Gly Gln Gly Thr Leu
            100                 105                 110

Val Thr Val Ser Ser
        115

<210> SEQ ID NO 110
<211> LENGTH: 115
<212> TYPE: PRT
<213> ORGANISM: Mus musculus

<400> SEQUENCE: 110

Asp Ile Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Ala Trp
            20                  25                  30

Ser Asn Gln Asn Asn Tyr Leu Ala Trp Tyr Leu Gln Lys Pro Gly Gln
                35                  40                  45

Ser Pro Gln Met Leu Ile Ile Trp Ala Ile Thr Arg Val Gly Gly Val
 50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Ser Tyr Ser Arg Pro Tyr Thr Phe Gly Gln Gly Thr Lys Leu Glu Ile
            100                 105                 110

Lys Arg Thr
        115

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gln Gln Ser Tyr Ser Arg Pro Tyr Thr
1               5

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Tyr Ile Phe Thr Ala Tyr Thr Met His

```
<210> SEQ ID NO 113
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Trp Ile Lys Pro Asn Asn Gly Leu Ala Asn Tyr Ala Gln Lys Phe Gln
1               5                   10                  15

Gly

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ser Glu Ile Thr Thr Glu Phe Asp Tyr
1               5

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Lys Ser Ser Glu Ser Val Asp Ser Tyr Ala Asn Ser Phe Leu His
1               5                   10                  15

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Arg Ala Ser Thr Arg Glu Ser
1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Gln Ser Lys Glu Asp Pro Leu Thr
1               5

<210> SEQ ID NO 118
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 118

Gly Tyr Ile Phe Thr Ala Tyr Thr Met His
1               5                   10

<210> SEQ ID NO 119
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Trp Ile Lys Pro Asn Asn Gly Leu Ala Asn Tyr Ala Gln Lys Phe Gln
1               5                   10                  15

Gly

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ser Glu Ile Thr Thr Glu Phe Asp Tyr
1               5

<210> SEQ ID NO 121
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Lys Ser Ser Glu Ser Val Asp Ser Tyr Ala Asn Ser Phe Leu His
1               5                   10                  15

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Arg Ala Ser Thr Arg Glu Ser
1               5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gln Gln Ser Lys Glu Asp Pro Leu Thr
```

<210> SEQ ID NO 124
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
ggctacatct tcacagcata caccatgcac                                    30

<210> SEQ ID NO 125
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
tggattaaac ccaacaatgg gctggccaac tacgcccaga aattccaggg t            51

<210> SEQ ID NO 126
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
agcgaaatta caacagaatt cgattac                                       27

<210> SEQ ID NO 127
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
aaaagctccg aatctgtgga ctcttacgca aacagctttc tgcac                   45

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
agggcttcta ccagggagag c                                             21

<210> SEQ ID NO 129
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
cagcagtcca aggaggaccc cctgact                                       27

<210> SEQ ID NO 130
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Tyr Thr Phe Thr Asp Tyr Tyr Met His
1               5                   10

<210> SEQ ID NO 131
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Arg Val Asn Pro Asn Arg Arg Gly Thr Thr Tyr Asn Gln Lys Phe Glu
1               5                   10                  15

Gly

<210> SEQ ID NO 132
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ala Asn Trp Leu Asp Tyr
1               5

<210> SEQ ID NO 133
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ser Val Ser Ser Ser Val Ser Ser Ile Tyr Leu His
1               5                   10

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ser Thr Ser Asn Leu Ala Ser
1               5

<210> SEQ ID NO 135
<211> LENGTH: 9
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 135

Gln Val Tyr Ser Gly Tyr Pro Leu Thr
1               5

<210> SEQ ID NO 136
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Tyr Thr Phe Thr Ser Tyr Trp Leu His
1               5                   10

<210> SEQ ID NO 137
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Met Ile Asp Pro Ser Asn Ser Asp Thr Arg Phe Asn Pro Asn Phe Lys
1               5                   10                  15

Asp

<210> SEQ ID NO 138
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ala Thr Tyr Arg Ser Tyr Val Thr Pro Leu Asp Tyr
1               5                   10

<210> SEQ ID NO 139
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Lys Ser Ser Gln Ser Leu Leu Tyr Thr Ser Ser Gln Lys Asn Tyr Leu
1               5                   10                  15

Ala

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

```
Trp Ala Ser Thr Arg Glu Ser
1               5
```

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

```
Gln Gln Tyr Tyr Ala Tyr Pro Trp Thr
1               5
```

<210> SEQ ID NO 142
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

```
Asp Tyr Tyr Met Ser
1               5
```

<210> SEQ ID NO 143
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

```
Phe Ile Arg Asn Lys Ala Asn Gly Tyr Thr Thr Glu Tyr Ser
1               5                   10
```

<210> SEQ ID NO 144
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

```
Arg Asp Asn Trp Phe Ala Tyr
1               5
```

<210> SEQ ID NO 145
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

```
Lys Ser Ser Gln Ser Leu Leu Ala Ser Gly Asn
1               5                   10
```

<210> SEQ ID NO 146
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 146

Trp Ala Ser Thr Arg Val Ser
1               5

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gln Gln Ser Tyr Ser Ala Pro Leu Thr
1               5

<210> SEQ ID NO 148
<211> LENGTH: 7
<212> TYPE: PRT
<213> ORGANISM: Homo sapiens

<400> SEQUENCE: 148

Thr Asn Tyr Tyr Tyr Trp Ser
1               5

<210> SEQ ID NO 149
<211> LENGTH: 16
<212> TYPE: PRT
<213> ORGANISM: Homo sapiens

<400> SEQUENCE: 149

Val Ile Ala Tyr Asp Gly Ser Thr Asp Tyr Ser Pro Ser Leu Lys Ser
1               5                   10                  15

<210> SEQ ID NO 150
<211> LENGTH: 17
<212> TYPE: PRT
<213> ORGANISM: Homo sapiens

<400> SEQUENCE: 150

Asp Val Arg Val Ile Ala Thr Gly Trp Ala Thr Ala Asn Ala Leu Asp
1               5                   10                  15

Ala

<210> SEQ ID NO 151
<211> LENGTH: 14
<212> TYPE: PRT
<213> ORGANISM: Homo sapiens

<400> SEQUENCE: 151

Ala Gly Thr Ser Ser Asp Val Gly Tyr Gly Asn Tyr Val Ser
1               5                   10

<210> SEQ ID NO 152
<211> LENGTH: 7
<212> TYPE: PRT
<213> ORGANISM: Homo sapiens

<400> SEQUENCE: 152

Ala Val Ser Tyr Arg Ala Ser
1               5
```

<210> SEQ ID NO 153
<211> LENGTH: 11
<212> TYPE: PRT
<213> ORGANISM: Homo sapiens

<400> SEQUENCE: 153

Ala Ser Tyr Arg Ser Ser Asn Asn Ala Ala Val
1               5                   10

<210> SEQ ID NO 154
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Asp Tyr Tyr Ile Ser
1               5

<210> SEQ ID NO 155
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Phe Ile Arg Asn Lys Ala Asn Gly Tyr Thr Thr Glu Tyr Ser Ala Ser
1               5                   10                  15

Val Lys Gly

<210> SEQ ID NO 156
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Asp Asn Trp Phe Ala Tyr
1               5

<210> SEQ ID NO 157
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Lys Ser Ser Gln Ser Leu Leu Ala Trp Ser Asn Gln Asn Asn Tyr Leu
1               5                   10                  15

Ala

<210> SEQ ID NO 158
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 158

Trp Ala Ile Thr Arg Val Gly
1               5

<210> SEQ ID NO 159
<211> LENGTH: 11
<212> TYPE: PRT
<213> ORGANISM: Mus musculus

<400> SEQUENCE: 159

Lys Ser Leu Leu His Ser Asn Gly Ile Thr Tyr
1               5                   10

<210> SEQ ID NO 160
<211> LENGTH: 3
<212> TYPE: PRT
<213> ORGANISM: Mus musculus

<400> SEQUENCE: 160

Gln Met Ser
1

<210> SEQ ID NO 161
<211> LENGTH: 9
<212> TYPE: PRT
<213> ORGANISM: Mus musculus

<400> SEQUENCE: 161

Ala Gln Asn Leu Glu Leu Pro Tyr Thr
1               5

<210> SEQ ID NO 162
<211> LENGTH: 8
<212> TYPE: PRT
<213> ORGANISM: Mus musculus

<400> SEQUENCE: 162

Gly Phe Thr Phe Ser Ser Tyr Ala
1               5

<210> SEQ ID NO 163
<211> LENGTH: 7
<212> TYPE: PRT
<213> ORGANISM: Mus musculus

<400> SEQUENCE: 163

Ile Met Gly Gly Gly Thr Thr
1               5

<210> SEQ ID NO 164
<211> LENGTH: 15
<212> TYPE: PRT
<213> ORGANISM: Mus musculus

<400> SEQUENCE: 164

Ala Arg Gly Arg Asp Tyr Gly Ile Arg Ser Tyr Ala Met Asp Tyr
1               5                   10                  15

<210> SEQ ID NO 165
<211> LENGTH: 15
<212> TYPE: PRT
<213> ORGANISM: Mus musculus

<400> SEQUENCE: 165
```

Ser Ser Lys Ser Leu Leu His Ser Asn Gly Ile Thr Tyr Leu Tyr
1               5                   10                  15

<210> SEQ ID NO 166
<211> LENGTH: 7
<212> TYPE: PRT
<213> ORGANISM: Mus musculus

<400> SEQUENCE: 166

Gln Met Ser Asn Leu Ala Ser
1               5

<210> SEQ ID NO 167
<211> LENGTH: 4
<212> TYPE: PRT
<213> ORGANISM: Mus musculus

<400> SEQUENCE: 167

Ser Tyr Ala Met
1

<210> SEQ ID NO 168
<211> LENGTH: 16
<212> TYPE: PRT
<213> ORGANISM: Mus musculus

<400> SEQUENCE: 168

Ser Ile Met Gly Gly Gly Thr Thr Tyr Tyr Pro Asp Ser Val Lys Gly
1               5                   10                  15

<210> SEQ ID NO 169
<211> LENGTH: 13
<212> TYPE: PRT
<213> ORGANISM: Mus musculus

<400> SEQUENCE: 169

Gly Arg Asp Tyr Gly Ile Arg Ser Tyr Ala Met Asp Tyr
1               5                   10

<210> SEQ ID NO 170
<211> LENGTH: 12
<212> TYPE: PRT
<213> ORGANISM: Artificial Sequence
<220> FEATURE:
<223> OTHER INFORMATION: Description of Artificial Sequence: Synthetic
      hinge peptide derived from IgG1

<400> SEQUENCE: 170

Pro Lys Ser Cys Asp Cys His Cys Pro Pro Cys Pro
1               5                   10

<210> SEQ ID NO 171
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ala Tyr
                20                  25                  30

```
Thr Met His Trp Val Arg Gln Ala Pro Gly Gln Gly Leu Glu Trp Met
    35                  40                  45
Gly Trp Ile Lys Pro Asn Asn Gly Leu Ala Asn Tyr Ala Gln Lys Phe
 50                  55                  60
Gln Gly Arg Val Thr Met Thr Arg Asp Thr Ser Ile Ser Thr Ala Tyr
 65                  70                  75                  80
Met Glu Leu Ser Arg Leu Arg Ser Asp Asp Thr Ala Val Tyr Tyr Cys
             85                  90                  95
Ala Arg Ser Glu Ile Thr Thr Glu Phe Asp Tyr Trp Gly Gln Gly Thr
                100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Arg Val Glu Pro Lys Ser Cys Asp Cys His
    210                 215                 220
Cys Pro Pro Cys Pro Ala Pro Glu Leu Leu Gly Gly Pro Cys Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly
        435                 440                 445
```

```
<210> SEQ ID NO 172
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Val Asp Ser Tyr
            20                  25                  30

Ala Asn Ser Phe Leu His Trp Tyr Gln Gln Lys Pro Gly Gln Pro Pro
        35                  40                  45

Lys Leu Leu Ile Tyr Arg Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
                85                  90                  95

Glu Asp Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 173
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Gly Tyr Ile Phe Thr Ala Tyr Thr Met His
1               5                   10

<210> SEQ ID NO 174
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Trp Ile Lys Pro Asn Asn Gly Leu Ala Asn Tyr Ala Gln Lys Phe Gln
1               5                   10                  15
```

Gly

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ser Glu Ile Thr Thr Glu Phe Asp Tyr
1               5

<210> SEQ ID NO 176
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Lys Ser Ser Glu Ser Val Asp Ser Tyr Ala Asn Ser Phe Leu His
1               5                   10                  15

<210> SEQ ID NO 177
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Arg Ala Ser Thr Arg Glu Ser
1               5

<210> SEQ ID NO 178
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gln Gln Ser Lys Glu Asp Pro Leu Thr
1               5